United States Patent
Yasuma et al.

(10) Patent No.: US 8,957,070 B2
(45) Date of Patent: *Feb. 17, 2015

(54) GLUCOKINASE ACTIVATOR COMPOUNDS, METHODS OF ACTIVATING GLUCOKINASE AND METHODS OF TREATING DIABETES AND OBESITY

(75) Inventors: Tsuneo Yasuma, Osaka (JP); Osamu Ujikawa, Osaka (JP)

(73) Assignee: Takeda Pharmaceutical Company Limited, Osaka (JP)

(*) Notice: Subject to any disclaimer, the term of this patent is extended or adjusted under 35 U.S.C. 154(b) by 196 days.

This patent is subject to a terminal disclaimer.

(21) Appl. No.: 11/918,884

(22) PCT Filed: Apr. 20, 2006

(86) PCT No.: PCT/JP2006/308790
§ 371 (c)(1),
(2), (4) Date: Nov. 7, 2007

(87) PCT Pub. No.: WO2006/112549
PCT Pub. Date: Oct. 26, 2006

(65) Prior Publication Data
US 2009/0247746 A1    Oct. 1, 2009

(30) Foreign Application Priority Data
Apr. 20, 2005 (JP) .................. 2005-123018
Dec. 13, 2005 (JP) .................. 2005-359656

(51) Int. Cl.
| | | |
|---|---|---|
| C07D 409/12 | (2006.01) | |
| C07D 417/04 | (2006.01) | |
| C07D 498/04 | (2006.01) | |
| C07D 209/12 | (2006.01) | |
| C07D 209/42 | (2006.01) | |
| C07D 209/88 | (2006.01) | |
| C07D 213/53 | (2006.01) | |
| C07D 277/28 | (2006.01) | |
| C07D 401/04 | (2006.01) | |
| C07D 409/14 | (2006.01) | |
| C07D 413/14 | (2006.01) | |
| C07D 417/14 | (2006.01) | |
| C07D 471/04 | (2006.01) | |
| C07D 513/04 | (2006.01) | |

(52) U.S. Cl.
CPC .......... C07D 409/12 (2013.01); C07D 209/12 (2013.01); C07D 209/42 (2013.01); C07D 209/88 (2013.01); C07D 213/53 (2013.01); C07D 277/28 (2013.01); C07D 401/04 (2013.01); C07D 409/14 (2013.01); C07D 413/14 (2013.01); C07D 417/04 (2013.01); C07D 417/14 (2013.01); C07D 471/04 (2013.01); C07D 513/04 (2013.01)

USPC ........... 514/230.5; 514/235.2; 514/252.13; 514/278; 514/339; 514/365; 544/105; 544/133; 544/369; 546/19; 546/269.7; 546/277.4; 548/181

(58) Field of Classification Search
None
See application file for complete search history.

(56) References Cited

U.S. PATENT DOCUMENTS

| | | |
|---|---|---|
| 1,974,518 A | 9/1934 | Schrader et al. |
| 5,721,246 A | 2/1998 | Yoshino et al. |
| 5,767,283 A | 6/1998 | Yoshino et al. |
| 5,834,462 A | 11/1998 | Yoshino et al. |
| 5,846,969 A | 12/1998 | Yoshino et al. |
| 5,846,982 A | 12/1998 | Audia et al. |
| 5,854,274 A | 12/1998 | Yoshino et al. |
| 2002/0099068 A1 | 7/2002 | Ritzeler et al. |
| 2004/0063645 A1 | 4/2004 | Botyanszki et al. |
| 2004/0073036 A1 | 4/2004 | Marzabadi et al. |
| 2004/0102360 A1 | 5/2004 | Barnett et al. |
| 2004/0110759 A1 | 6/2004 | Ritzeler et al. |
| 2004/0186103 A1 | 9/2004 | Marzabadi et al. |
| 2005/0020602 A1* | 1/2005 | Miyoshi et al. .......... 514/252.02 |

(Continued)

FOREIGN PATENT DOCUMENTS

| | | |
|---|---|---|
| EP | 0 622 356 | 11/1994 |
| EP | 0 673 937 | 9/1995 |

(Continued)

OTHER PUBLICATIONS

Castro et al. "Novel IKK Inhibitors: Beta-Carbolines." Bioorg. Med. Chem. Lett. 13 (2003), pp. 2419-2422.*
Castro et al., Bioorg. Med. Chem. Lett. 13 (2003), pp. 2419-2422.*
Ettmayer et al. "Lessons Learned from Marketed and Investigational Prodrugs." J. Med. Chem., (2004), 47(10): 2393-2404.*
Stella, Valentino. "Prodrugs as therapeutics." Expert Opin. Ther. Patents (2004), 14(3): 277-280.*

(Continued)

*Primary Examiner* — Alicia L Otton
(74) *Attorney, Agent, or Firm* — Wenderoth, Lind & Ponack, L.L.P.

(57) ABSTRACT

The present invention provides a glucokinase activator containing a compound represented by the formula (I):

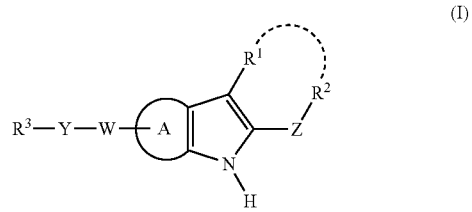

wherein each symbol is as defined in the specification, or a salt thereof or a prodrug thereof. According to the present invention, a glucokinase activator useful as a pharmaceutical agent such as agent for the prophylaxis or treatment of diabetes, obesity and the like, and the like can be provided.

9 Claims, No Drawings

(56) References Cited

U.S. PATENT DOCUMENTS

2006/0111409 A1     5/2006    Muto et al.
2007/0112005 A1*   5/2007    Chen et al. .................... 514/243

FOREIGN PATENT DOCUMENTS

| | | | | |
|---|---|---|---|---|
| EP | 1 074 542 | 2/2001 | | |
| EP | 1 258 252 | 11/2002 | | |
| EP | 1 314 733 | 5/2003 | | |
| EP | 03/035621 | 5/2003 | | |
| EP | 1 430 894 | 6/2004 | | |
| JP | 8-81441 | 3/1996 | | |
| JP | 8-231505 | 9/1996 | | |
| JP | 2000-309534 | 11/2000 | | |
| JP | 2002-167376 | 6/2002 | | |
| JP | 2003-527394 | 9/2003 | | |
| JP | 2004/536104 | 12/2004 | | |
| WO | 95/07276 | 3/1995 | | |
| WO | WO 97/21703 | * | 6/1997 | ........... C07D 401/12 |
| WO | 02/06255 | 1/2002 | | |
| WO | 02/30895 | 4/2002 | | |
| WO | 02/096910 | 12/2002 | | |
| WO | 03/087085 | 10/2003 | | |
| WO | 03/103648 | 12/2003 | | |
| WO | 2004/014851 | 2/2004 | | |
| WO | 2004/031179 | 4/2004 | | |
| WO | 2004/091664 | 10/2004 | | |
| WO | 2005/049019 | 6/2005 | | |
| WO | WO 2005/082905 | * | 9/2005 | ........... C07D 471/04 |

OTHER PUBLICATIONS

Testa, Bernard. "Prodrug research: futile or fertile?" Biochemical Pharmacology, 68 (2004): 2097-2106.*
"Type 1 diabetes." MayoClinic. See sections entitled "Causes" and "Prevention." Accessed Dec. 28, 2009.*
Wolff et al. Burgers Medicinal Chemistry and Drug Discovery. 5th ed. vol. 1: Principles and Practice. pp. 975-977.*
Supplementary Partial European Search Report completed Mar. 24, 2009 in corresponding European Application No. 06 73 2396.
Owa et al., "Synthesis and biological evaluation of N-(7-Indolyl)-3-pyridinesulfonamide derivatives as potent antitumor agents", Bioorganic & Medicinal Chemistry Letters (2002), vol. 12, pp. 2097-2100.
N. Bauman et al., "Indole-2-Carboxylic Acids, A New Class of Hypoglycemic Compounds", Biochemical Pharmacology, vol. 18, No. 5, pp. 1241-1243, 1996.
A. C. Castro et al., "Novel IKK Inhibitors: β-Carbolines", Bioorganic & Medicinal Chemistry Letters, vol. 13, No. 14, pp. 2419-2422, 2003.
A. Agarwal et al., "Synthesis and Antifungal Activity of Eudistomin N and O Analogs", Med. Chem. Res., vol. 4, No. 6, pp. 396-405, 1994.
R. Cerri et al.,"Attivita Analgesica Di Derivati Di 7-Amino-2,3-Polimetilenindoli E Loro Congeneri", Edizione Scientifica, vol. 43, No. 2, pp. 113-123, 1988.
I. Vazzana et al., "7-(N-Substituted)Amino-2,3-Polymethylene Benzofurane Derivatives with Tracheal Relaxant Activity", IL Farmaco, vol. 51, No. 10, pp. 637-642, 1996.
S. Siddiqui et al., "Some New Derivatives of Harmaline Series of Bases", Organische Chemie, vol. 41b, No. 12, pp. 1583-1586, 1986.
S. Siddiqui et al., "Some Extensions of Von Braun (BrCN) Reaction on Organic Bases Part V", Pakistan J. Sci. Ind. Res., vol. 28, No. 4, pp. 221-224, Aug. 1985.
S. Siddiqui et al., "Studies in Harmine Series of Alkaloids", Pakistan J. Sci. Ind. Res., vol. 26, No. 2, pp. 53-58, Apr. 1983.
S. Siddiqui et al., "Studies in Harmine Series of Alkaloids", Pakistan J. Sci. Ind. Res., vol. 25, No. 5, pp. 147-152, 1982.
ZCAplus AN 1983:453886 (Youji Huaxuo, 1983, 2, pp. 129-130, 128).
M. S. Joseph et a., "Synthesis and Antimicrobial Activity of Indole Isoxazolines and Isoxazole Derivatives", Indian Journal of Chemistry, vol. 43B, No. 5, pp. 964-970, May 2004.
European Patent Office Office Action (in the English language) issued Mar. 29, 2010 in European Application No. 06 732 396.
Examination Report issued Feb. 12, 2013 in corresponding European Application No. 10 174 773.1.
Yin et al., "A novel semi-quinone chalcone sharing a pyrrole ring C-glycoside from *Carthamus tinctorius*", Tetrahedron Letters, vol. 41, 2000, pp. 1955-1958.

* cited by examiner

SEQUENCE LISTING

```
<160> NUMBER OF SEQ ID NOS: 4

<210> SEQ ID NO 1
<211> LENGTH: 27
<212> TYPE: DNA
<213> ORGANISM: Artificial
<220> FEATURE:
<223> OTHER INFORMATION: Synthetic Construct; primer for cloning
      glucokinase

<400> SEQUENCE: 1
cagctctcca tccaagcagc cgttgct                                         27

<210> SEQ ID NO 2
<211> LENGTH: 21
<212> TYPE: DNA
<213> ORGANISM: Artificial
<220> FEATURE:
<223> OTHER INFORMATION: Synthetic Construct; primer for cloning
      glucokinase

<400> SEQUENCE: 2
ggcggcctgg gtcctgacaa g                                               21

<210> SEQ ID NO 3
<211> LENGTH: 69
<212> TYPE: DNA
<213> ORGANISM: Artificial
<220> FEATURE:
<223> OTHER INFORMATION: Synthetic Construct; primer for cloning
      glucokinase
```

```
<400> SEQUENCE: 3
ggatccatgc ccagaccaag atcccaactc ccacaaccca actcccaggt agagcagatc    60
ctggcagag                                                            69

<210> SEQ ID NO 4
<211> LENGTH: 24
<212> TYPE: DNA
<213> ORGANISM: Artificial
<220> FEATURE:
<223> OTHER INFORMATION: Synthetic Construct; primer for cloning
      glucokinase

<400> SEQUENCE: 4
gaattcctgg cccagcatac aggc                                           24
```

GLUCOKINASE ACTIVATOR COMPOUNDS, METHODS OF ACTIVATING GLUCOKINASE AND METHODS OF TREATING DIABETES AND OBESITY

This application is a U.S. national stage of International Application No. PCT/JP2006/308790 filed Apr. 20, 2006.

TECHNICAL FIELD

The present invention relates to a fused heterocyclic compound having a glucokinase activating action and useful as a therapeutic agent for diabetes and the like.

BACKGROUND ART

Glucokinase (sometimes to be abbreviated to as GK in the present specification) (EC2.7.1.1) is one of the four kinds of hexokinases found in mammals, and is also called hexokinase IV. GK is an enzyme that catalyzes the conversion of glucose to glucose-6-phosphate, which is the first step of glycolysis. GK is mainly present in the pancreatic β cell and the liver, and acts in the pancreatic β cell as a sensor of extracellular glucose concentration that defines the glucose-stimulated insulin secretion. In the liver, the enzyme reaction of GK becomes a rate determining factor and regulates glycogen synthesis and glycolysis. The three hexokinases (I, II, III) other than GK reach the maximum enzyme activity at a glucose concentration of 1 mM or below. In contrast, GK shows low affinity for glucose and has a Km value of 8-15 mM which is close to a physiological blood glucose level. Accordingly, GK-mediated promotion of intracellular glucose metabolism occurs, which corresponds to blood glucose changes from normal blood glucose (5 mM) to postprandial hyperglycemia (10-15 mM).

The hypothesis proposed by Matschinsky et al. in 1984 that GK acts as a glucose sensor in the pancreatic β cell and hepatocytes has been demonstrated by the analysis of glucokinase gene manipulation mouse in recent years (see The Journal of Biological Chemistry (J. Biol. Chem.), 1995, vol. 270, page 30253-30256; The Journal of Biological Chemistry (J. Biol. Chem.), 1997, vol. 272, page 22564-22569; The Journal of Biological Chemistry (J. Biol. Chem.), 1997, vol. 272, page 22570-22575; NIHONRINSHO, 2002, vol. 60, page 523-534; and Cell, 1995, vol. 83, page 69-78). That is, GK heterozygous knockout mouse showed a hyperglycemic condition, and further, a disordered glucose-stimulated insulin secretion response. GK homozygous knockout mouse dies shortly after birth with manifestations of marked hyperglycemia and urinary sugar. On the other hand, GK overexpressed mouse (hetero type) showed decreased blood glucose level, increased blood glucose clearance rate, increased liver glycogen content and the like. From these findings, it has been clarified that GK plays an important role in the systemic glucose homeostasis. In other words, decreased GK activity causes insulin secretion failure and lower liver glucose metabolism, which develops impaired glucose tolerance and diabetes. Conversely, GK activation or increased GK activity due to overexpression causes promoted insulin secretion and promoted liver glucose metabolism, which in turn increases the systemic use of glucose to improve glucose tolerance.

In addition, it has been clarified from the analysis of a report on GK gene abnormality mainly in the family of MODY2 (Maturity Onset Diabetes of the Young) that GK also acts as a glucose sensor in human, and plays a key role in glucose homeostasis (see Nature, 1992, vol. 356, page 721-722). In GK gene abnormality, due to the decreased affinity of GK for glucose (increased Km value) and decreased Vmax, the blood glucose threshold value of insulin secretion increases and the insulin secretory capacity decreases. In the liver, due to the decreased GK activity, decreased glucose uptake, promoted gluconeogenesis, decreased glycogen synthesis and liver insulin resistance are observed. On the other hand, a family with a mutation increasing the GK activity has also been found. In such family, fasting hypoglycemia associated with increased plasma insulin concentration is observed (see New England Journal Medicine, 1998, vol. 338, page 226-230).

As mentioned above, GK acts as a glucose sensor in mammals including human, and plays an important role in blood glucose regulation. On the other hand, control of blood glucose utilizing the glucose sensor system of GK is considered to open a new way to treat diabetes in many type 2 diabetes patients. Particularly, since a GK activating substance is expected to show insulin secretagogue action in the pancreatic β cell and glucose uptake promotion and glucose release suppressive action in the liver, it will be useful as a prophylactic or therapeutic drug for type 2 diabetes.

In recent years, it has been clarified that pancreatic β cell type glucokinase expresses locally in the feeding center (Ventromedial Hypothalamus: VMH) of rat brain. A subset of nerve cell present in VMH is called glucose responsive neuron, and plays an important role in the body weight control. From electrophysiological experiments, the neuron is activated in response to physiological changes in the glucose concentration (5-20 mM). However, since the glucose concentration sensor system of VHM is assumed to have a mechanism mediated by glucokinase as in the case of insulin secretion in the pancreatic β cell, separately from pancreatic β cell and the liver, a pharmaceutical agent capable of activating glucokinase of VHM has a possibility of providing not only a blood glucose corrective effect but also improvement of obesity.

As mentioned above, a pharmaceutical agent capable of activating GK is useful as a prophylactic or therapeutic drug for diabetes and chronic diabetic complications such as retinopathy, nephropathy, neuropathy, ischemic cardiac diseases, arteriosclerosis and the like, and further, as a prophylactic or therapeutic drug for obesity.

As the indole compound, the following compound has been reported.

(1) It has been reported that a compound represented by the formula:

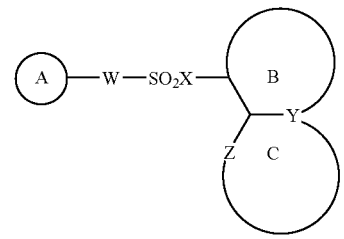

wherein ring A is an optionally substituted monocyclic or bicyclic aromatic ring;

ring B is an optionally substituted 6-membered unsaturated hydrocarbon ring or an optionally substituted 6-membered unsaturated heterocycle containing one nitrogen atom;

ring C is an optionally substituted 5-membered heterocycle containing one or two nitrogen atoms;

W is a single bond or —CH=CH—;
X is —N(R$^1$)— or an oxygen atom;
Y is a carbon atom or a nitrogen atom;
Z is —N(R$^2$)— or a nitrogen atom; and
R$^1$ and R$^2$ are the same or different and each is a hydrogen atom or a lower alkyl group,
is useful as an antitumor agent or an angiogenesis inhibitor (see WO 95/07276 and JP-A-2000-309534).

(2) It has been reported that a compound represented by the formula:

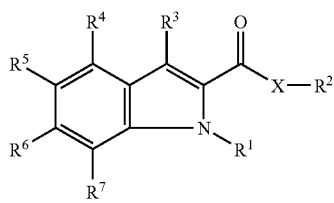

(I)

wherein
X: NR$^{33}$ (R$^{33}$: a C$_{1-8}$ alkyl group, a C$_{1-8}$ alkenyl group or a C$_{1-8}$ alkynyl group), NH, O or S; and
R$^2$: a hydrogen atom, a C$_{1-8}$ alkyl group, a C$_{1-8}$ halo alkyl group or (CH$_2$)$_n$S(=O)$_2$R$^{11}$ (n: 0 to 8; R$^{11}$: an optionally substituted C$_{5-14}$ aryl group or an optionally substituted C$_{3-11}$ hetero aryl group),
is a PPAR-γ binder, and useful for diabetes (see JP-A-2004-529855).

(3) It has been reported that a compound represented by the formula:

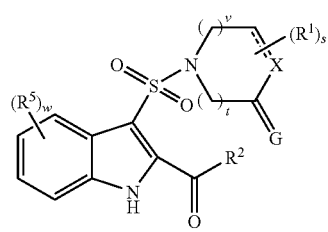

wherein
R$^2$; a hydrogen atom, an optionally substituted C$_{1-10}$ alkyl group, N(R$^4$)$_2$ or OR$^4$ (R$^4$; a hydrogen atom, a C$_{1-6}$ alkyl group, a C$_{3-10}$ cycloalkyl group, an aryl group, a heterocyclic group, CF$_3$, a C$_{2-6}$ alkenyl group or a C$_{2-6}$ alkynyl group),
is an anticancer agent, an Akt inhibitor or a tyrosine kinase inhibitor (see US-B-2004/0102360 and WO 2004/014851).

(4) It has been reported that a compound represented by the formula:

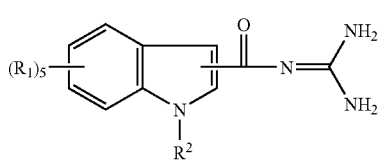

(1)

wherein
R$_1$: a hydrogen atom, an alkyl group, a cycloalkyl group, an aromatic group and the like; and R$_2$: a hydrogen atom, an alkyl group and the like, is a Na$^+$/H$^+$ exchanger inhibitor (see EP 622356 B).

(5) It has been reported that a compound represented by the formula:

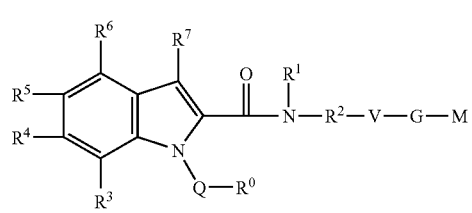

(I)

wherein
Q: a bond, CO, SO$_2$, a C$_{1-6}$ alkylene group and the like; and
R$^0$: an optionally substituted monocyclic or bicyclic 5- to 14-membered aryl group, or an optionally substituted monocyclic or bicyclic 5- to 14-membered heteroaryl group, is a FXa inhibitor (see EP 1314733 B).

(6) It has been reported that a compound represented by the formula:

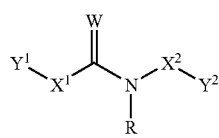

(I)

wherein
W: O or S;
R: a hydrogen atom or an alkyl group;
X$^1$ and X$^2$: an optionally substituted arylene group or an optionally substituted heteroarylene group;

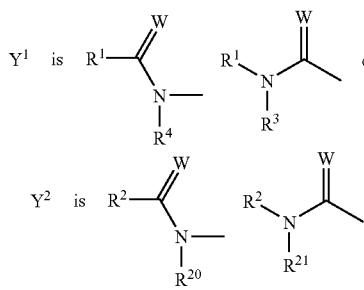

wherein
R$^3$, R$^4$, R$^{20}$ and R$^{21}$: a hydrogen atom or an alkyl group; and
R$^1$, R$^2$, R$^5$ and R$^{22}$

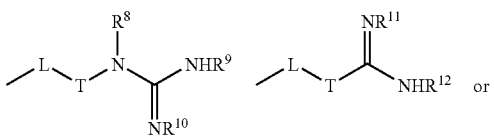

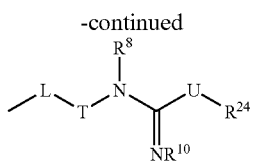

wherein $R^8$, $R^9R^{10}$, $R^{11}$ and $R^{12}$: a hydrogen atom, an alkyl group and the like; and $R^{24}$: an alkyl group etc., is an antibacterial agent or a HIV inhibitor (see US-A-2004/0063645).

(7) It has been reported that a compound represented by the formula:

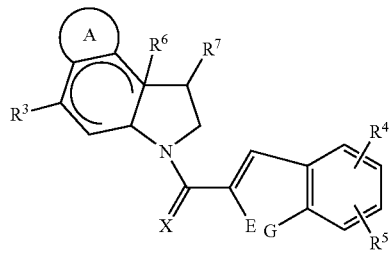

wherein

X: O, S or $NR^{23}$ ($R^{23}$: a hydrogen atom, an optionally substituted alkyl group, an optionally substituted heteroalkyl group or an acyl group);

$R^4$ and $R^5$: a hydrogen atom, an optionally substituted alkyl group, an optionally substituted heteroaryl group, $COR^{15}$ ($R^{15}$: a hydrogen atom, an optionally substituted alkyl group etc.) and the like; and E and G are bonded to form an optionally substituted aryl, an optionally substituted heteroaryl and the like, is an anticancer agent (see WO 02/096910).

(8) It has been reported that a compound represented by the formula:

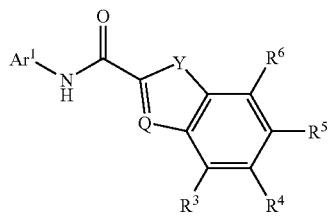

wherein $Ar^1$: an optionally substituted carbon ring;

Y: $CR^pR^v$ ($R^p$ and $R^v$: a hydrogen atom, a $C_{1-5}$ alkyl group etc.), O, $S(O)_n$ (n: 0, 1, 2), $N-R^x$ ($R^x$: a hydrogen atom, a $C_{1-5}$ alkyl group etc.) and the like; and Q: N or $CR^pR^v$, has a cytokine inhibitory activity, and is useful as an anti-inflammatory agent (see WO 03/087085).

(9) It has been reported that a compound represented by the formula:

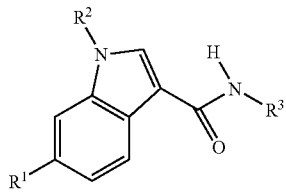

wherein $R^1$: a halogen atom, a nitro group and the like;

$R^2$: a $C_{2-5}$ alkyl group or $-CH_2-R^4$ ($R^4$: a $C_{3-6}$ cycloalkyl group);

$R^3$: an optionally substituted 5- or 6-membered aromatic heterocyclic group, is a GK activator, and useful for diabetes and the like (see WO 04/031179).

(10) A compound represented by formula:

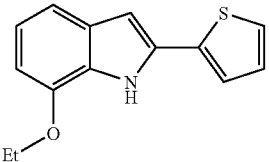 [SMILES: CCOc1cccc2cc(-c3cccs3)[nH]c12]

(see Youji Huaxue 1983, vol. 128, page 129-130) has been reported.

However, any references do not disclose that a compound represented by the following formula (I) has glucokinase activating action, or a compound represented by the following formula (II).

DISCLOSURE OF THE INVENTION

The purpose of the present invention is to provide a glucokinase activator which is useful as a pharmaceutical agent such as agents for the prophylaxis or treatment of diabetes, obesity and the like, and the like.

The present inventors have conducted intensive studies and found that a compound represented by the following formulas (I) and (II) unexpectedly has a superior glucokinase activating action as well as superior properties as a pharmaceutical product such as stability and the like, and can be a safe and useful as a pharmaceutical agent, which resulted in the completion of the present invention.

Accordingly, the present invention relates to

[1] a glucokinase activator comprising a compound represented by the formula (I):

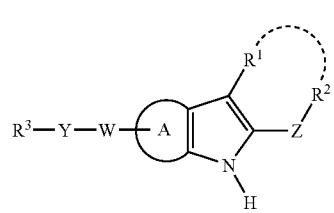

wherein ring A is an optionally substituted 6-membered ring,

W is O, $S(O)_m$ (m is 0, 1 or 2), $CR^5R^6$ ($R^5$ and $R^6$ are each independently a hydrogen atom or a $C_{1-6}$ alkyl group) or $NR^7$ ($R^7$ is a hydrogen atom or $R^{3'}$—$Y'$— ($R^{3'}$ is an optionally substituted hydrocarbon group, an optionally substituted hydroxy group, an optionally substituted mercapto group, an optionally substituted amino group or an optionally substituted heterocyclic group, and Y' is a bond, CO, $S(O)_q$ (q is 0, 1 or 2) or $CR^{8'}R^{9'}$ ($R^{8'}$ and $R^{9'}$ are each independently a hydrogen atom or a $C_{1-6}$ alkyl group))), Y is a bond, CO, $S(O)_p$ (p is 0, 1 or 2) or $CR^8R^9$ ($R^8$ and $R^9$ are each independently a hydrogen atom or a $C_{1-6}$ alkyl group), $R^3$ is an optionally substituted hydrocarbon group, an optionally substituted hydroxy group, an optionally substituted mercapto group, an optionally substituted amino group or an optionally substituted heterocyclic group, Z is a bond, CO, O, $S(O)_n$ (n is 0, 1 or 2) or $NR^{10}$ ($R^{10}$ is a hydrogen atom or a $C_{1-6}$ alkyl group), $R^1$ is a hydrogen atom, a halogen atom, an optionally substituted hydrocarbon group, an optionally substituted hydroxy group or an optionally substituted mercapto group, and $R^2$ is a hydrogen atom, an optionally substituted hydrocarbon group, an optionally substituted hydroxy group, an optionally substituted mercapto group, an optionally substituted amino group or an optionally substituted heterocyclic group, or $R^1$ and $R^2$ are bonded to each other to form an optionally substituted ring, or a salt thereof (hereinafter sometimes to be abbreviated as compound (I)) or a prodrug thereof;

[2] the glucokinase activator of the above-mentioned [1], wherein $R^7$ is a hydrogen atom or a $C_{1-6}$ alkyl group, and Y is a bond, CO, $SO_2$ or $CR^8R^9$ ($R^8$ and $R^9$ are each independently a hydrogen atom or a $C_{1-6}$ alkyl group);

[3] use of compound (I) or a prodrug thereof for the production of a glucokinase activator;

[4] a method of activating a glucokinase in a mammal, which comprises administering compound (I) or a prodrug thereof to the mammal;

[5] a compound represented by the formula (II):

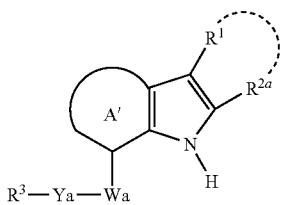

(II)

wherein
ring A' is an optionally substituted 6-membered ring,

Wa is O, $S(O)_m$ (m is 0, 1 or 2) or $NR^7$ ($R^7$ is a hydrogen atom or $R^{3'}$—$Y'$— ($R^{3'}$ is an optionally substituted hydrocarbon group, an optionally substituted hydroxy group, an optionally substituted mercapto group, an optionally substituted amino group or an optionally substituted heterocyclic group, and Y' is a bond, CO, $S(O)_q$ (q is 0, 1 or 2) or $CR^{8'}R^{9'}$ ($R^{8'}$ and $R^{9'}$ are each independently a hydrogen atom or a $C_{1-6}$ alkyl group))), Ya is CO, $S(O)_{pa}$ (pa is 0, 1 or 2) or $CR^8R^9$ ($R^8$ and $R^9$ are each independently a hydrogen atom or a $C_{1-6}$ alkyl group), $R^3$ is an optionally substituted hydrocarbon group, an optionally substituted hydroxy group, an optionally substituted mercapto group, an optionally substituted amino group or an optionally substituted heterocyclic group, $R^1$ is a hydrogen atom, a halogen atom, an optionally substituted hydrocarbon group, an optionally substituted hydroxy group or an optionally substituted mercapto group, and $R^{2a}$ is an optionally substituted non-aromatic cyclic hydrocarbon group or an optionally substituted heterocyclic group, or $R^1$ and $R^{2a}$ are bonded to each other to form an optionally substituted ring, or a salt thereof (provided that $R^3$-Ya-Wa should not be an ethoxy group) (hereinafter sometimes to be abbreviated as compound (II));

[6] compound (II) wherein $R^7$ is a hydrogen atom or a $C_{1-6}$ alkyl group, and Ya is CO, $SO_2$ or $CR^8R^9$ ($R^8$ and $R^9$ are each independently a hydrogen atom or a $C_{1-6}$ alkyl group);

[7] compound (II) wherein ring A' is an optionally substituted benzene ring or a optionally substituted pyridine ring;

[8] compound (II) wherein Wa is $NR^7$ ($R^7$ is a hydrogen atom or $R^{3'}$—$Y'$— ($R^{3'}$ is an optionally substituted hydrocarbon group, an optionally substituted hydroxy group, an optionally substituted mercapto group, an optionally substituted amino group or an optionally substituted heterocyclic group, and Y' is a bond, CO, $S(O)_q$ (q is 0, 1 or 2) or $CR^{8'}R^{9'}$ ($R^{8'}$ and $R^{9'}$ are each independently a hydrogen atom or a $C_{1-6}$ alkyl group)));

[9] compound (II) wherein Ya is $SO_2$;

[10] compound (II) wherein $R^3$ is an optionally substituted heterocyclic group;

[11] compound (II) wherein $R^1$ is a hydrogen atom;

[12] compound (II) wherein $R^{2a}$ is an optionally substituted heterocyclic group;

[13] compound (II) which is
N-[2-(4,5-dihydro-1,3-thiazol-2-yl)-1H-indol-7-yl]thiophene-2-sulfonamide;
N-[2-(4,5-dihydro-1,3-thiazol-2-yl)-5-fluoro-1H-indol-7-yl]-N-methylthiophene-2-sulfonamide;
N-[2-(4,5-dihydro-1,3-thiazol-2-yl)-5-(trifluoromethoxy)-1H-indol-7-yl]-N-methylthiophene-2-sulfonamide;
N-[4-fluoro-2-(1,3-thiazol-2-yl)-1H-indol-7-yl]-N-methylthiophene-2-sulfonamide;
N-{4-chloro-2-[5-(hydroxymethyl)-1,3-thiazol-2-yl]-1H-indol-7-yl}-N-methylthiophene-2-sulfonamide; or
4-[(2-{7-[ethyl(2-thienylsulfonyl)amino]-1H-indol-2-yl}-1,3-thiazol-5-yl)methoxy]benzoic acid;

[14] a prodrug of compound (II);

[15] a pharmaceutical agent comprising compound (II) or a prodrug thereof;

[16] The pharmaceutical agent of the above-mentioned [15], which is an agent for the prophylaxis or treatment of diabetes or obesity; and the like.

Since the glucokinase activator of the present invention has a superior activating action, it is useful as a pharmaceutical agent such as an agent for the prophylaxis or treatment of diabetes, obesity and the like, and the like.

BEST MODE FOR EMBODYING THE INVENTION

Unless otherwise specified, as the "halogen atom" in the present specification, fluorine atom, chlorine atom, bromine atom or iodine atom can be mentioned.

Unless otherwise specified, as the "$C_{1-3}$ alkylenedioxy group" in the present specification, methylenedioxy, ethylenedioxy or the like can be mentioned.

Unless otherwise specified, as the "$C_{1-6}$ alkyl group" in the present specification, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl or the like can be mentioned.

Unless otherwise specified, as the "$C_{1-6}$ alkoxy group" in the present specification, methoxy, ethoxy, propoxy, isopropoxy, butoxy, isobutoxy, sec-butoxy, tert-butoxy or the like can be mentioned.

Unless otherwise specified, as the "$C_{1-6}$ alkoxy-carbonyl group" in the present specification, methoxycarbonyl, ethoxycarbonyl, propoxycarbonyl, tert-butoxycarbonyl or the like can be mentioned.

Unless otherwise specified, as the "$C_{1-6}$ alkyl-carbonyl group" in the present specification, acetyl, propanoyl, butanoyl, isobutanoyl, pentanoyl, isopentanoyl, hexanoyl or the like can be mentioned.

Each symbol in the formulas (I) and (II) is described in detail in the following.

$R^1$ is a hydrogen atom, a halogen atom, an optionally substituted hydrocarbon group, an optionally substituted hydroxy group or an optionally substituted mercapto group.

$R^2$ is a hydrogen atom, an optionally substituted hydrocarbon group, an optionally substituted hydroxy group, an optionally substituted mercapto group, an optionally substituted amino group or an optionally substituted heterocyclic group.

Or, $R^1$ and $R^2$ are bonded to each other to form an optionally substituted ring.

$R^{2a}$ is an optionally substituted non-aromatic cyclic hydrocarbon group or an optionally substituted heterocyclic group.

Or $R^1$ and $R^{2a}$ are bonded to each other to form an optionally substituted ring.

$R^3$ is an optionally substituted hydrocarbon group, an optionally substituted hydroxy group, an optionally substituted mercapto group, an optionally substituted amino group or an optionally substituted heterocyclic group.

As the "hydrocarbon group" of the "optionally substituted hydrocarbon group" for $R^1$, $R^2$ or $R^3$, for example, a $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{4-10}$ cycloalkadienyl group, a $C_{6-14}$ aryl group, a $C_{7-13}$ aralkyl group, a $C_{8-13}$ arylalkenyl group, a $C_{3-10}$ cycloalkyl-$C_{1-6}$ alkyl group and the like can be mentioned.

As used herein, as the $C_{1-10}$ alkyl group, for example, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like can be mentioned.

As the $C_{2-10}$ alkenyl group, for example, ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like can be mentioned.

As the $C_{2-10}$ alkynyl group, for example, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like can be mentioned.

As the $C_{3-10}$ cycloalkyl group, for example, cyclopropyl, cyclobutyl, cyclopentyl, cyclohexyl, cycloheptyl, cyclooctyl and the like can be mentioned.

As the $C_{3-10}$ cycloalkenyl group, for example, 2-cyclopenten-1-yl, 3-cyclopenten-1-yl, 2-cyclohexen-1-yl, 3-cyclohexen-1-yl and the like can be mentioned.

As the $C_{4-10}$ cycloalkadienyl group, for example, 2,4-cyclopentadien-1-yl, 2,4-cyclohexadien-1-yl, 2,5-cyclohexadien-1-yl and the like can be mentioned.

The above-mentioned $C_{3-10}$ cycloalkyl group, $C_{3-10}$ cycloalkenyl group and $C_{4-10}$ cycloalkadienyl are each optionally condensed with a benzene ring to form a fused cyclic group, and as the fused cyclic group, for example, indanyl, dihydronaphthyl, tetrahydronaphthyl, fluorenyl and the like can be mentioned. In addition, as the aforementioned hydrocarbon group, a cross-linked hydrocarbon group such as bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl, norbornanyl and the like, and the like can also be mentioned.

As the $C_{6-14}$ aryl group, for example, phenyl, naphthyl, anthryl, phenanthryl, acenaphthylenyl, biphenylyl and the like can be mentioned. Of these, phenyl, 1-naphthyl, 2-naphthyl and the like are preferable.

As the $C_{7-13}$ aralkyl group, for example, benzyl, phenethyl, naphthylmethyl, biphenylylmethyl and the like can be mentioned.

As the $C_{8-13}$ arylalkenyl group, for example, styryl and the like can be mentioned.

As the $C_{3-10}$ cycloalkyl-$C_{1-6}$ alkyl group, for example, cyclohexylmethyl and the like can be mentioned.

The $C_{1-10}$ alkyl group, $C_{2-10}$ alkenyl group and $C_{2-10}$ alkynyl group exemplified as the aforementioned "hydrocarbon group" optionally have 1 to 3 substituents at substitutable positions.

As such substituents, for example, (1) a $C_{3-10}$ cycloalkyl group (e.g., cyclopropyl, cyclohexyl);

(2) a $C_{6-14}$ aryl group (e.g., phenyl, naphthyl) optionally substituted by 1 to 3 substituents selected from a $C_{1-6}$ alkyl group optionally substituted by 1 to 3 halogen atoms, a hydroxy group, a $C_{1-6}$ alkoxy group and a halogen atom;

(3) an aromatic heterocyclic group (e.g., thienyl, furyl, pyridyl, oxazolyl, thiazolyl, tetrazolyl, oxadiazolyl, pyrazinyl, quinolyl, indolyl) optionally substituted by 1 to 3 substituents selected from a $C_{1-6}$ alkyl group optionally substituted by 1 to 3 halogen atoms, a hydroxy group, a $C_{1-6}$ alkoxy group and a halogen atom;

(4) a non-aromatic heterocyclic group (e.g., tetrahydrofuryl, morpholinyl, thiomorpholinyl, piperidinyl, pyrrolidinyl, piperazinyl, dioxolyl, dioxolanyl, 1,3-dihydro-2-benzofuranyl, thiazolidinyl, thiazolinyl) optionally substituted by 1 to 3 substituents selected from a $C_{1-6}$ alkyl group optionally substituted by 1 to 3 halogen atoms, a hydroxy group, a $C_{1-6}$ alkoxy group, an oxo group and a halogen atom;

(5) an amino group optionally mono- or di-substituted by substituent(s) selected from (i) a $C_{1-6}$ alkyl group, (ii) a $C_{1-6}$ alkyl-carbonyl group, (iii) a $C_{1-6}$ alkoxy-carbonyl group, (iv) a $C_{6-14}$ aryl-carbonyl group (e.g., benzoyl), (v) a $C_{7-13}$ aralkyl-carbonyl group (e.g., benzylcarbonyl, phenethylcarbonyl), (vi) a carbamoyl group optionally mono- or di-substituted by substituent(s) selected from a $C_{1-6}$ alkyl group, a $C_{6-14}$ aryl group and a $C_{7-13}$ aralkyl group (e.g., carbamoyl, methylcarbamoyl, benzylcarbamoyl, dimethylcarbamoyl), (vii) a $C_{1-6}$ alkylsulfonyl group (e.g., methylsulfonyl, ethylsulfonyl, isopropylsulfonyl), (viii) a $C_{6-14}$ arylsulfonyl group (e.g., benzenesulfonyl, toluenesulfonyl, 1-naphthalenesulfonyl, 2-naphthalenesulfonyl), and (ix) a $C_{7-13}$ aralkylsulfonyl group (e.g., benzylsulfonyl);

(6) an amidino group;

(7) a $C_{1-6}$ alkyl-carbonyl group optionally substituted by 1 to 3 halogen atoms;

(8) a $C_{1-6}$ alkoxy-carbonyl group optionally substituted by 1 to 3 halogen atoms;

(9) an aromatic heterocyclyl-carbonyl group (e.g., thienylcarbonyl, indolylcarbonyl) optionally substituted by 1 to 3 amino groups (the amino group is each optionally mono- or di-substituted by substituent(s) selected from a $C_{1-6}$ alkyl group and an aromatic heterocyclyl-sulfonyl group (e.g., thienylsulfonyl));
(10) a non-aromatic heterocyclyl-carbonyl group (e.g., morpholinylcarbonyl);
(11) a $C_{1-6}$ alkylsulfonyl group (e.g., methylsulfonyl) optionally substituted by 1 to 3 halogen atoms;
(12) a carbamoyl group optionally mono- or di-substituted by substituent(s) selected from a $C_{1-6}$ alkyl group optionally substituted by 1 to 3 halogen atoms, a $C_{6-14}$ aryl group (e.g., phenyl), a $C_{7-13}$ aralkyl group (e.g., benzyl) and an aromatic heterocyclyl-$C_{1-6}$ alkyl group (e.g., furfuryl);
(13) a thiocarbamoyl group optionally mono- or di-substituted by $C_{1-6}$ alkyl group(s) optionally substituted by 1 to 3 halogen atoms;
(14) a sulfamoyl group optionally mono- or di-substituted by a $C_{1-6}$ alkyl group optionally substituted by 1 to 3 halogen atoms;
(15) a carboxy group;
(16) a hydroxy group;
(17) a $C_{1-6}$ alkoxy group optionally substituted by 1 to 3 substituents selected from a halogen atom, a carboxy group, a $C_{1-6}$ alkoxy group and a $C_{1-6}$ alkoxy-carbonyl group;
(18) a $C_{2-6}$ alkenyloxy group (e.g., ethenyloxy) optionally substituted by 1 or 3 halogen atoms;
(19) a $C_{3-10}$ cycloalkyloxy group (e.g., cyclohexyloxy);
(20) a $C_{7-13}$ aralkyloxy group (e.g., benzyloxy) optionally substituted by 1 or 3 halogen atoms;
(21) a $C_{6-14}$ aryloxy group (e.g., phenyloxy, naphthyloxy);
(22) a $C_{1-6}$ alkyl-carbonyloxy group (e.g., acetyloxy, tert-butylcarbonyloxy);
(23) a mercapto group;
(24) a $C_{1-6}$ alkylthio group (e.g., methylthio, ethylthio) optionally substituted by 1 to 3 substituents selected from a halogen atom and a $C_{6-14}$ aryl group;
(25) a $C_{7-20}$ aralkylthio group (e.g., benzylthio, tritylthio);
(26) a $C_{6-14}$ arylthio group (e.g., phenylthio, naphthylthio);
(27) an aromatic heterocyclethio group (e.g., tetrazolylthio) optionally substituted by 1 to 3 $C_{1-6}$ alkyl groups;
(28) a sulfo group;
(29) a cyano group;
(30) an azido group;
(31) a nitro group;
(32) a nitroso group;
(33) a halogen atom;
(34) a $C_{1-6}$ alkylsulfinyl group (e.g., methylsulfinyl);
(35) an oxo group;
(36) a $C_{3-10}$ cycloalkyl-$C_{1-6}$ alkyloxy group (e.g., cyclopropylmethyloxy);
(37) a $C_{1-3}$ alkylenedioxy group;
(38) an aromatic heterocyclyl-carbonylthio group (e.g., indolylcarbonylthio) optionally substituted by 1 to 3 amino groups (the amino group is each optionally mono- or di-substituted by substituent(s) selected from a $C_{1-6}$ alkyl group and an aromatic heterocyclyl-sulfonyl group (e.g., thienylsulfonyl));
(39) a formyl group; and the like can be mentioned.
The $C_{3-10}$ cycloalkyl group, $C_{3-10}$ cycloalkenyl group, $C_{4-10}$ cycloalkadienyl group, $C_{6-14}$ aryl group, $C_{7-13}$ aralkyl group, $C_{8-13}$ arylalkenyl group and $C_{3-10}$ cycloalkyl-$C_{1-6}$ alkyl group exemplified as the aforementioned "hydrocarbon group" optionally have 1 to 3 substituents at substitutable positions.

As such substituents, for example,
(1) those exemplified as the substituents of the aforementioned $C_{1-10}$ alkyl group and the like;
(2) a $C_{1-6}$ alkyl group optionally substituted by 1 to 3 substituents selected from
(i) a halogen atom,
(ii) a carboxy group,
(iii) a hydroxy group,
(iv) a $C_{1-6}$ alkoxy group optionally substituted by 1 to 3 substituents selected from a carboxy group and a $C_{1-6}$ alkoxy-carbonyl group,
(v) a $C_{1-6}$ alkoxy-carbonyl group,
(vi) a $C_{1-6}$ alkyl-carbonyloxy group (e.g., acetyloxy, tert-butylcarbonyloxy),
(vii) a carbamoyl group optionally mono- or di-substituted by substituent(s) selected from a $C_{1-6}$ alkylsulfonyl group and an amino group,
(viii) a aromatic heterocyclic group (e.g., thienyl, tetrazolyl),
(ix) a non-aromatic heterocyclic group (e.g., piperidino, piperazinyl, morpholinyl, dihydrooxadiazolyl, hexahydropyrazinooxazinyl (e.g., hexahydropyrazino[2,1-c][1,4]oxazinyl), 1-oxa-3,8-diazaspiro[4.5]decanyl) optionally substituted by 1 to 3 substituents selected from a $C_{1-6}$ alkyl-carbonyl group and an oxo group,
(x) an amino group optionally mono- or di-substituted by a $C_{1-6}$ alkyl group(s) (the $C_{1-6}$ alkyl group is each optionally substituted by 1 to 3 substituents selected from a non-aromatic heterocyclic group (e.g., morpholinyl), a $C_{1-6}$ alkoxy group and a $C_{1-6}$ alkylsulfonyl group),
(xi) a $C_{1-6}$ alkylsulfonyl group optionally substituted by 1 to 3 carboxy groups,
(xii) a $C_{1-6}$ alkylthio group optionally substituted by 1 to 3 substituents selected from a carboxy group, a $C_{1-6}$ alkoxy-carbonyl group, a hydroxy group and a carbamoyl group,
(xiii) a phosphono group optionally mono- or di-substituted by $C_{1-6}$ alkyl group(s),
(xiv) a non-aromatic heterocyclyl-carbonyl group (e.g., morpholinylcarbonyl),
(xv) a cyano group, and
(xvi) a $C_{6-14}$ aryloxy group optionally substituted by 1 to 3 substituents selected from a carboxy group and a $C_{1-6}$ alkoxy-carbonyl group;
(3) a $C_{2-6}$ alkenyl group (e.g., ethenyl, 1-propenyl) optionally substituted by from 1 to 3 substituents selected from a halogen atom, a carboxy group, a $C_{1-6}$ alkoxy-carbonyl group and a carbamoyl group;
(4) a $C_{7-13}$ aralkyl group (e.g., benzyl) optionally substituted 1 to 3 substituents selected from a $C_{1-6}$ alkyl group optionally substituted by 1 to 3 halogen atoms, a hydroxy group, a $C_{1-6}$ alkoxy group and a halogen atom;
and the like can be mentioned.
As the "heterocyclic group" of the "optionally substituted heterocyclic group" for $R^2$, $R^{2a}$ or $R^3$, an aromatic heterocyclic group and a non-aromatic heterocyclic group can be mentioned.
As used herein, as the aromatic heterocyclic group, for example, a 4- to 7-membered (preferably 5- or 6-membered) monocyclic aromatic heterocyclic group containing, as a ring-constituting atom besides carbon atoms, 1 to 4 heteroatoms selected from an oxygen atom, a sulfur atom and a nitrogen atom, and a fused aromatic heterocyclic group can be mentioned. As the fused aromatic heterocyclic group, for example, a group derived from a fused ring wherein a ring constituting the 4- to 7-membered monocyclic aromatic heterocyclic group and 1 or 2 rings selected from a 5- or 6-membered ring containing 1 or 2 nitrogen atoms, a 5-membered ring containing one sulfur atom, a benzene ring and the like are fused, and the like can be mentioned.

As preferable examples of the aromatic heterocyclic group, monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 4-isothiazolyl), oxazolyl (e.g., 2-oxazolyl, 4-oxazolyl, 5-oxazolyl), isoxazolyl, oxadiazolyl (e.g., 1,2,4-oxadiazol-3-yl, 1,2,4-oxadiazol-5-yl, 1,3,4-oxadiazol-2-yl), thiadiazolyl (e.g., 1,3,4-thiadiazol-2-yl, 1,2,4-thiadiazol-3-yl, 1,2,4-thiadiazol-5-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like;

fused aromatic heterocyclic groups such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxaloyl (e.g., 2-quinoxalyl, 6-quinoxalyl), benzofuryl (e.g., 2-benzofuryl, 3-benzofuryl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), imidazopyrazinyl (e.g., 1H-imidazo[4,5-b]pyrazin-2-yl), imidazothiazolyl (e.g., imidazo[2,1-b]thiazol-5-yl), pyrazolopyridinyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like;

and the like can be mentioned.

As the non-aromatic heterocyclic group, for example, a 4 to 7-membered (preferably 5- or 6-membered) monocyclic non-aromatic heterocyclic group containing, as a ring-constituting atom besides carbon atoms, 1 to 4 heteroatoms selected from an oxygen atom, a sulfur atom and a nitrogen atom, and a fused non-aromatic heterocyclic group can be mentioned. As the fused non-aromatic heterocyclic group, for example, a group derived from a fused ring wherein a ring constituting the 4- to 7-membered monocyclic non-aromatic heterocyclic group and 1 or 2 rings selected from a 5- or 6-membered ring containing 1 or 2 nitrogen atoms, a 5-membered ring containing one sulfur atom, a benzene ring and the like are fused, and the like can be mentioned.

As preferable examples of the non-aromatic heterocyclic group,
monocyclic non-aromatic heterocyclic groups such as pyrrolidinyl (e.g., 1-pyrrolidinyl), piperidinyl (e.g., piperidino, 2-piperidinyl, 3-piperidinyl, 4-piperidinyl), morpholinyl (e.g., morpholino), thiomorpholinyl (e.g., thiomorpholino), piperazinyl (e.g., 1-piperazinyl, 2-piperazinyl, 3-piperazinyl), hexamethyleneiminyl (e.g., hexamethyleneimin-1-yl), oxazolidinyl (e.g., oxazolidin-2-yl), thiazolidinyl (e.g., thiazolidin-2-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), 2-thioxo-1,3-oxazolidin-5-yl, pyranyl (e.g., 4-pyranyl), tetrahydropyranyl (e.g., 4-tetrahydropyranyl), thiopyranyl (e.g., 4-thiopyranyl), tetrahydrothiopyranyl (e.g., 4-tetrahydrothiopyranyl), 1-oxidotetrahydrothiopyranyl (e.g., 1-oxidotetrahydrothiopyran-4-yl), 1,1-dioxidotetrahydrothiopyranyl (e.g., 1,1-dioxidotetrahydrothiopyran-4-yl), pyrazolidinyl (e.g., pyrazolidin-1-yl), tetrahydropyrimidinyl, dioxanyl (e.g., 1,3-dioxan-2-yl, 1,3-dioxan-4-yl, 1,3-dioxan-5-yl, 1,4-dioxan-2-yl), dioxenyl (e.g., 4H-1,3-dioxin-2-yl, 4H-1,3-dioxin-4-yl, 4H-1,3-dioxin-5-yl, 4H-1,3-dioxin-6-yl, 2,3-dihydro-1,4-dioxin-2-yl, 2,3-dihydro-1,4-dioxin-5-yl) and the like;

fused non-aromatic heterocyclic groups such as dihydroindolyl (e.g., 2,3-dihydro-1H-isoindol-1-yl), dihydroisoindolyl (e.g., 1,3-dihydro-2H-isoindol-2-yl), dihydrobenzofuranyl (e.g., 2,3-dihydro-1-benzofuran-5-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), tetrahydrobenzofuranyl (e.g., 4,5,6,7-tetrahydro-1-benzofuran-3-yl), chromenyl (e.g., 4H-chromen-2-yl, 2H-chromen-3-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl) and the like;

and the like can be mentioned.

The "heterocyclic group" of the aforementioned "optionally substituted heterocyclic group" optionally has 1 to 3 substituents at substitutable positions. As such substituents, those exemplified as the substituents which the $C_{3-10}$ cycloalkyl group and the like exemplified as the "hydrocarbon group" of the "optionally substituted hydrocarbon group" for $R^1$, $R^2$ or $R^3$ optionally has, can be mentioned.

As the "optionally substituted hydroxy group" for $R^1$, $R^2$ or $R^3$, for example, a hydroxy group optionally substituted by a substituent selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group, a $C_{1-6}$ alkyl-carbonyl group, a 5 or 6-membered aromatic heterocyclic group, a fused aromatic heterocyclic group and the like, each of which is optionally substituted, can be mentioned.

As used herein, as the $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group and $C_{8-13}$ arylalkenyl group, those exemplified as the "hydrocarbon group" of the "optionally substituted hydrocarbon group" for $R^1$, $R^2$ or $R^3$ can be mentioned.

As the 5 or 6-membered aromatic heterocyclic group, a 5 or 6-membered cyclic group, from among the "aromatic heterocyclic groups" exemplified as the "heterocyclic group" of the "optionally substituted heterocyclic group" for $R^2$, $R^{2a}$ or $R^3$, can be mentioned.

As the fused aromatic heterocyclic group, a fused cyclic group, from among the "aromatic heterocyclic groups" exemplified as the "heterocyclic group" of the "optionally substituted heterocyclic group" for $R^2$, $R^{2a}$ or $R^3$, can be mentioned.

The aforementioned $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{8-13}$ arylalkenyl group, $C_{1-6}$ alkyl-carbonyl group, 5 or 6-membered aromatic heterocyclic group and fused aromatic heterocyclic group optionally have 1 to 3 substituents at substitutable positions.

As used herein, as the substituents of the $C_{1-10}$ alkyl group, $C_{2-10}$ alkenyl group and $C_{1-6}$ alkyl-carbonyl group, those exemplified as the substituents which the $C_{1-10}$ alkyl group and the like exemplified as the "hydrocarbon group" of the "optionally substituted hydrocarbon group" for $R^1$, $R^2$ or $R^3$ optionally has, can be mentioned.

As the substituents of the $C_{3-10}$ cycloalkyl group, $C_{3-10}$ cycloalkenyl group, $C_{6-14}$ aryl group, $C_{7-13}$ aralkyl group, $C_{8-13}$ arylalkenyl group, 5 or 6-membered aromatic heterocyclic group and fused aromatic heterocyclic group, those exemplified as the substituents which the $C_{3-10}$ cycloalkyl group and the like exemplified as the "hydrocarbon group" of the "optionally substituted hydrocarbon group" for $R^1$, $R^2$ or $R^3$ optionally has, can be mentioned.

As the "optionally substituted mercapto group" for $R^1$, $R^2$ or $R^3$, for example, a mercapto group optionally substituted by a substituent selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group, a $C_{1-6}$ alkyl-carbonyl group, a 5 or 6-membered aromatic heterocyclic group, a fused aromatic heterocyclic group and the like, each of which is optionally substituted, can be mentioned.

As the substituents, those exemplified as the substituents of the "optionally substituted hydroxy group" for $R^1$, $R^2$ or $R^3$ can be mentioned.

As the "optionally substituted amino group" for $R^2$ or $R^3$, for example, an amino group optionally mono- or di-substituted by substituent(s) selected from a $C_{1-10}$ alkyl group, a $C_{1-10}$ alkoxy group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group and a heterocyclic group, each of which is optionally substituted; an acyl group and the like, can be mentioned.

As used herein, as the $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group and $C_{8-13}$ arylalkenyl group, those exemplified as the "hydrocarbon group" of the "optionally substituted hydrocarbon group" for $R^1$, $R^2$ or $R^3$ can be mentioned.

As the heterocyclic group, those exemplified as the "heterocyclic group" of the "optionally substituted heterocyclic group" for $R^2$, $R^{2a}$ or $R^3$ can be mentioned.

As the $C_{1-10}$ alkoxy group, methoxy, ethoxy, propoxy, isopropoxy, butoxy, isobutoxy, sec-butoxy, tert-butoxy, pentyloxy, isopentyloxy, neopentyloxy, 1-ethylpropyloxy, hexyloxy, isohexyloxy, 1,1-dimethylbutyloxy, 2,2-dimethylbutyloxy, 3,3-dimethylbutyloxy, 2-ethylbutyloxy, heptyloxy, octyloxy, nonyloxy, decyloxy and the like can be mentioned.

The $C_{1-10}$ alkyl group, $C_{1-10}$ alkoxy group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{8-13}$ arylalkenyl group and heterocyclic group optionally have 1 to 3 substituents at substitutable positions.

As used herein, as the substituents of the $C_{1-10}$ alkyl group, $C_{1-10}$ alkoxy group and $C_{2-10}$ alkenyl group, those exemplified as the substituents which the $C_{1-10}$ alkyl group and the like exemplified as the "hydrocarbon group" of the "optionally substituted hydrocarbon group" for $R^1$, $R^2$ or $R^3$ optionally has, can be mentioned.

As the substituents of the $C_{3-10}$ cycloalkyl group, $C_{3-10}$ cycloalkenyl group, $C_{6-14}$ aryl group, $C_{7-13}$ aralkyl group, $C_{8-13}$ arylalkenyl group and heterocyclic group, those exemplified as the substituents which the $C_{3-10}$ cycloalkyl group and the like exemplified as the "hydrocarbon group" of the "optionally substituted hydrocarbon group" for $R^1$, $R^2$ or $R^3$ optionally has, can be mentioned.

As the "acyl group" exemplified as the substituent of the aforementioned "optionally substituted amino group", for example, a group represented by the formula: —$COR^a$, —CO—$OR^a$, —$SO_2R^a$, —$SOR^a$, —CO—$NR^{a'}R^{b'}$, —CS—$NR^{a'}R^{b'}$ or —$SO_2$—$NR^{a'}R^{b'}$ wherein $R^a$ is a hydrogen atom, an optionally substituted hydrocarbon group or an optionally substituted heterocyclic group, and $R^{a'}$ and $R^{b'}$ are the same or different and each is a hydrogen atom, an optionally substituted hydrocarbon group or an optionally substituted heterocyclic group, or $R^{a'}$ and $R^{b'}$ optionally form, together with the adjacent nitrogen atom, an optionally substituted nitrogen-containing heterocycle, and the like can be mentioned.

As the "optionally substituted hydrocarbon group" and "optionally substituted heterocyclic group" for $R^a$, $R^{a'}$ or $R^{b'}$, those similar to the "optionally substituted hydrocarbon group" for $R^1$, $R^2$ or $R^3$ and "optionally substituted heterocyclic group" for $R^2$, $R^{2a}$ or $R^3$ can be mentioned, respectively.

As the "nitrogen-containing heterocycle" of the "optionally substituted nitrogen-containing heterocycle" formed by $R^{a'}$ and $R^{b'}$ together with the adjacent nitrogen atom, for example, a 5- to 7-membered nitrogen-containing heterocycle containing, as a ring-constituting atom besides carbon atoms, at least one nitrogen atom and optionally further containing one or two heteroatoms selected from an oxygen atom, a sulfur atom and a nitrogen atom can be mentioned. As preferable examples of the nitrogen-containing heterocycle, pyrrolidine, imidazolidine, pyrazolidine, piperidine, piperazine, morpholine, thiomorpholine, oxopiperazine and the like can be mentioned.

The nitrogen-containing heterocycle optionally has 1 to 3 (preferably 1 or 2) substituents at substitutable positions. As such substituents, those exemplified as the substituents which the $C_{3-10}$ cycloalkyl group and the like exemplified as the "hydrocarbon group" of the "optionally substituted hydrocarbon group" for $R^1$, $R^2$ or $R^3$ optionally has, can be mentioned.

As preferable examples of the "acyl group",
(1) a formyl group;
(2) a carboxy group;
(3) a carbamoyl group;
(4) a $C_{1-6}$ alkyl-carbonyl group;
(5) a $C_{1-6}$ alkoxy-carbonyl group optionally substituted by 1 to 3 substituents selected from a carboxy group, a carbamoyl group, a thiocarbamoyl group, a $C_{1-6}$ alkoxy-carbonyl group and a $C_{1-6}$ alkyl-carbonyloxy group (e.g., methoxycarbonyl, ethoxycarbonyl, propoxycarbonyl, tert-butoxycarbonyl; carboxymethoxycarbonyl, carboxyethoxycarbonyl, carboxybutoxycarbonyl; carbamoylmethoxycarbonyl; thiocarbamoylmethoxycarbonyl; ethoxycarbonylmethoxycarbonyl, ethoxycarbonylethoxycarbonyl, methoxycarbonylbutoxycarbonyl, ethoxycarbonylbutoxycarbonyl; tert-butylcarbonyloxymethoxycarbonyl);
(6) a $C_{3-10}$ cycloalkyl-carbonyl group (e.g., cyclopentylcarbonyl, cyclohexylcarbonyl);
(7) a $C_{6-14}$ aryl-carbonyl group (e.g., benzoyl, 1-naphthoyl, 2-naphthoyl) optionally substituted by 1 to 3 substituents selected from a halogen atom, a cyano group, an optionally halogenated $C_{1-6}$ alkyl group (i.e., a $C_{1-6}$ alkyl group optionally substituted by 1 to 3 halogen atoms), a $C_{1-6}$ alkoxy group, a carboxy group, a $C_{1-6}$ alkoxy-carbonyl group and a carbamoyl group;
(8) a $C_{6-14}$ aryloxy-carbonyl group (e.g., phenyloxycarbonyl, naphthyloxycarbonyl) optionally substituted by 1 to 3 substituents selected from a carboxy group, a $C_{1-6}$ alkoxy-carbonyl group and a carbamoyl group;
(9) a $C_{7-13}$ aralkyloxy-carbonyl group optionally substituted by 1 to 3 substituents selected from a carboxy group, a carbamoyl group, a thiocarbamoyl group, a $C_{1-6}$ alkoxy-carbonyl group, a halogen atom, a cyano group, a nitro group, a $C_{1-6}$ alkoxy group, a $C_{1-6}$ alkylsulfonyl group and a $C_{1-6}$ alkyl group (e.g., benzyloxycarbonyl, phenethyloxycarbonyl; carboxybenzyloxycarbonyl; methoxycarbonylbenzyloxycarbonyl; biphenylylmethoxycarbonyl);

(10) a carbamoyl mono- or di-substituted by $C_{1-6}$ alkyl group(s) optionally substituted by 1 to 3 substituents selected from a halogen atom and a $C_{1-6}$ alkoxy group (e.g., methylcarbamoyl, ethylcarbamoyl, dimethylcarbamoyl, diethylcarbamoyl, ethylmethylcarbamoyl, propylcarbamoyl, isopropylcarbamoyl, butylcarbamoyl, isobutylcarbamoyl, trifluoroethylcarbamoyl, N-methoxyethyl-N-methylcarbamoyl);

(11) a $C_{1-6}$ alkylsulfonyl group optionally substituted by 1 to 3 substituents selected from a carboxy group, a carbamoyl group and a $C_{1-6}$ alkoxy-carbonyl group (e.g., methylsulfonyl, carboxymethylsulfonyl);

(12) a $C_{1-6}$ alkylsulfinyl group (e.g., methylsulfinyl);

(13) a thiocarbamoyl group;

(14) a $C_{7-13}$ aralkyl-carbonyl group (e.g., benzylcarbonyl, phenethylcarbonyl);

(15) an aromatic heterocycle (e.g., furyl, thienyl, oxazolyl, thiazolyl, isoxazolyl, isothiazolyl, pyrazolyl, pyridyl, pyrazinyl, benzofuryl, benzothienyl, quinoxalinyl)-carbonyl group (e.g., furylcarbonyl, thienylcarbonyl, thiazolylcarbonyl, pyrazolylcarbonyl, pyridylcarbonyl, pyrazinylcarbonyl, benzofurylcarbonyl, benzothienylcarbonyl, quinoxalinylcarbonyl) optionally substituted by 1 to 3 substituents selected from a $C_{1-6}$ alkyl group, a $C_{6-14}$ aryl group, a $C_{7-13}$ aralkyl group, a $C_{1-6}$ alkoxy group, a carboxy group, a $C_{1-6}$ alkoxy-carbonyl group and a carbamoyl group;

(16) a sulfamoyl group;

(17) a sulfamoyl group mono- or di-substituted by $C_{1-6}$ alkyl group(s) optionally substituted by 1 to 3 substituents selected from a halogen atom and a $C_{1-6}$ alkoxy group (e.g., methylsulfamoyl, ethylsulfamoyl, dimethylsulfamoyl); and the like can be mentioned.

The "amino group" of the aforementioned "optionally substituted amino group" is optionally substituted by an amino group optionally mono- or di-substituted by substituent(s) selected from a $C_{1-6}$ alkyl group, a $C_{1-6}$ alkyl-carbonyl group (the $C_{1-6}$ alkyl-carbonyl group is optionally substituted by 1 to 3 substituents selected from a $C_{1-6}$ alkoxy group, a $C_{1-6}$ alkoxy-carbonyl group and the like), a $C_{1-6}$ alkoxy-carbonyl-carbonyl group and the like, and the like.

Examples of the "ring" of the "optionally substituted ring" formed by $R^1$ and $R^2$, and $R^1$ and $R^{2a}$ bonded to each other include non-aromatic cyclic hydrocarbon, non-aromatic heterocycle and the like.

Examples of the non-aromatic cyclic hydrocarbon include $C_{3-10}$ cycloalkane, $C_{3-10}$ cycloalkene, $C_{4-10}$ cycloalkadiene and the like, each of which is optionally fused with benzene ring. Examples of these $C_{3-10}$ cycloalkane, $C_{3-10}$ cycloalkene and $C_{4-10}$ cycloalkadiene include the rings constituting $C_{3-10}$ cycloalkyl group, $C_{3-10}$ cycloalkenyl group and $C_{4-10}$ cycloalkadienyl group recited as examples of the "hydrocarbon group" of the "optionally substituted hydrocarbon group" for $R^1$, $R^2$ or $R^3$. Of these, cyclohexane and the like are preferable.

Examples of the non-aromatic heterocycle include the rings constituting the non-aromatic heterocyclic group recited as examples of the "heterocyclic group" of the "optionally substituted heterocyclic group" for $R^2$, $R^{2a}$ or $R^3$. Of these, piperidine and the like are preferable.

The "ring" of the aforementioned "optionally substituted ring" optionally has 1 to 3 substituents at substitutable position(s). Examples of such substituent include those recited as examples of the substituent that the $C_{3-10}$ cycloalkyl group and the like recited as examples of the "hydrocarbon group" of the "optionally substituted hydrocarbon group" for $R^1$, $R^2$ or $R^3$ optionally has.

$R^1$ is preferably hydrogen atom, halogen atom or optionally substituted hydrocarbon group, more preferably, hydrogen atom, halogen atom or $C_{1-10}$ alkyl group, still more preferably, hydrogen atom or $C_{1-10}$ alkyl group, and particularly preferably, hydrogen atom.

$R^2$ is preferably hydrogen atom, optionally substituted $C_{1-10}$ alkyl group, hydroxy group optionally substituted by a $C_{1-10}$ alkyl group, optionally substituted $C_{1-10}$ alkylthio group, optionally substituted amino group or optionally substituted heterocyclic group, more preferably, 1) a hydrogen atom;

2) a $C_{1-10}$ alkyl group optionally substituted by 1 to 3 substituents selected from
   (1) a hydroxy group,
   (2) a halogen atom,
   (3) an aromatic heterocyclyl-carbonylthio group (the aromatic heterocyclyl-carbonylthio group, preferably, is indolylcarbonylthio and the like and optionally substituted by 1 to 3 amino groups (the amino group is optionally mono- or di-substituted by substituent(s) selected from a $C_{1-6}$ alkyl group, an aromatic heterocyclyl-sulfonyl group (preferably, thienylsulfonyl etc.) and the like) and the like;

3) a hydroxy group;

4) a $C_{1-10}$ alkoxy group;

5) an amino group optionally mono- or di-substituted by substituent(s) selected from
   (1) a $C_{1-10}$ alkyl group optionally substituted by 1 to 3 substituents selected from
     (i) a halogen atom,
     (ii) a hydroxy group,
     (iii) a $C_{1-6}$ alkylthio group (the $C_{1-6}$ alkylthio group is optionally substituted by 1 to 3 $C_{6-14}$ aryl groups and the like),
     (iv) carbamoyl group (the carbamoyl group is optionally mono- or di-substituted with $C_{1-6}$ alkyl group(s) and the like),
   (2) a $C_{1-10}$ alkoxy group,
   (3) a $C_{6-14}$ aryl group,
   (4) a $C_{7-13}$ aralkyl group,
   (5) an aromatic heterocyclic group (preferably, thiazolyl, oxazolyl etc.),
   (6) an amino group optionally mono- or di-substituted by substituent(s) selected from
     (i) a $C_{1-6}$ alkyl-carbonyl group (the $C_{1-6}$ alkyl-carbonyl group is optionally substituted by 1 to 3 substituents elected from the group consisting of a $C_{1-6}$ alkoxy group, a $C_{1-6}$ alkoxy-carbonyl group and the like),
     (ii) a $C_{1-6}$ alkoxy-carbonyl-carbonyl group and the like, and the like;

6) a heterocyclic group (preferably, aromatic heterocyclic group such as pyridyl, oxadiazolyl, thiadiazolyl, thiazolyl, oxazolyl, triazolyl, tetrazolyl, benzothiazolyl and the like; non-aromatic heterocyclic group such as pyrrolidinyl, piperidinyl, oxazolinyl, thiazolinyl and the like) optionally substituted by 1 to 3 substituents selected from
   (1) a $C_{1-6}$ alkyl group optionally substituted by 1 to 3 substituents selected from
     (i) a $C_{1-6}$ alkoxy group (the $C_{1-6}$ alkoxy group is optionally substituted by 1 to 3 substituents selected from a carboxy group, a $C_{1-6}$ alkoxy-carbonyl group and the like),
     (ii) a hydroxy group,
     (iii) a $C_{1-6}$ alkoxy-carbonyl group,
     (iv) a carboxy group, (v) a carbamoyl group (the carbamoyl group is optionally mono- or di-substituted by substituent(s) selected from a $C_{1-6}$ alkylsulfonyl group, an amino group and the like),
(vi) a $C_{1-6}$ alkylsulfonyl group,
(vii) an aromatic heterocyclic group (preferably, tetrazolyl etc.),
(viii) a non-aromatic heterocyclic group (the non-aromatic heterocyclic group, preferably, is morpholinyl, dihydrooxadiazolyl and the like and optionally substituted by 1 to 3 oxo groups and the like),
(ix) a non-aromatic heterocyclyl-carbonyl group (preferably, morpholinylcarbonyl etc.),
(x) a cyano group,
(xi) a $C_{6-14}$ aryloxy group (the $C_{6-14}$ aryloxy group is optionally substituted by 1 to 3 substituents selected from a carboxy group, a $C_{1-6}$ alkoxy-carbonyl group and the like),
(xii) a $C_{1-6}$ alkylthio group (the $C_{1-6}$ alkylthio group is optionally substituted by 1 to 3 substituents selected from a hydroxy group, a carbamoyl group and the like) and the like,
(2) an amino group optionally mono- or di-substituted by substituent(s) selected from
(i) a $C_{1-6}$ alkyl group,
(ii) a $C_{1-6}$ alkoxy-carbonyl group and the like,
(3) a $C_{1-6}$ alkoxy-carbonyl group,
(4) a carboxy group,
(5) a formyl group, and the like; or
7) a $C_{1-10}$ alkylthio group optionally substituted by 1 to 3 aromatic heterocyclyl-carbonyl groups (the aromatic heterocyclyl-carbonyl group is, preferably, indolylcarbonyl and the like and optionally substituted by 1 to 3 amino group (the amino group is optionally mono- or di-substituted by substituent(s) selected from a $C_{1-6}$ alkyl group, an aromatic heterocyclyl-sulfonyl group (preferably, thienylsulfonyl etc.) and the like)).

Alternatively, $R^1$ and $R^2$ are bonded to each other to preferably form a non-aromatic ring (preferably, cyclohexane, piperidine etc.) optionally substituted by 1 to 3 substituents selected from an oxo group, a hydroxy group and the like.

Examples of the "optionally substituted non-aromatic cyclic hydrocarbon group" for $R^{2a}$ include, from among the "optionally substituted hydrocarbon group" for the aforementioned $R^2$, one wherein the "hydrocarbon group" is a non-aromatic cyclic hydrocarbon group (e.g., $C_{3-10}$ cycloalkyl group, $C_{3-10}$ cycloalkenyl group, $C_{4-10}$ cycloalkadienyl group).

$R^{2a}$ is preferably an optionally substituted heterocyclic group, more preferably heterocyclic group (preferably, aromatic heterocyclic group such as pyridyl, oxadiazolyl, thiadiazolyl, thiazolyl, oxazolyl, triazolyl, tetrazolyl, benzothiazolyl and the like; non-aromatic heterocyclic group such as pyrrolidinyl, piperidinyl, oxazolinyl, thiazolinyl and the like) optionally substituted by 1 to 3 substituents selected from
(1) a $C_{1-6}$ alkyl group optionally substituted by 1 to 3 substituents selected from
(i) a $C_{1-6}$ alkoxy group (the $C_{1-6}$ alkoxy group is optionally substituted by 1 to 3 substituents selected from carboxy group, $C_{1-6}$ alkoxy-carbonyl group and the like),
(ii) a hydroxy group,
(iii) a $C_{1-6}$ alkoxy-carbonyl group,
(iv) a carboxy group,
(v) a carbamoyl group (the carbamoyl group is optionally mono- or di-substituted by substituent(s) selected from a $C_{1-6}$ alkylsulfonyl group, an amino group and the like),
(vi) a $C_{1-6}$ alkylsulfonyl group,
(vii) an aromatic heterocyclic group (preferably, tetrazolyl etc.),
(viii) a non-aromatic heterocyclic group (the non-aromatic heterocyclic group is preferably morpholinyl, dihydrooxadiazolyl and the like, which is optionally substituted by 1 to 3 oxo groups and the like),
(ix) a non-aromatic heterocyclyl-carbonyl group (preferably, morpholinylcarbonyl etc.),
(x) a cyano group,
(xi) a $C_{6-14}$ aryloxy group (the $C_{6-14}$ aryloxy group is optionally substituted by 1 to 3 substituents selected from a carboxy group, a $C_{1-6}$ alkoxy-carbonyl group and the like),
(xii) a $C_{1-6}$ alkylthio group (the $C_{1-6}$ alkylthio group is optionally substituted by 1 to 3 substituents selected from a hydroxy group, a carbamoyl group and the like), and the like
(2) an amino group optionally mono- or di-substituted by substituent(s) selected from
(i) a $C_{1-6}$ alkyl group,
(ii) a $C_{1-6}$ alkoxy-carbonyl group, and the like,
(3) a $C_{1-6}$ alkoxy-carbonyl group,
(4) a carboxy group,
(5) a formyl group and the like.

Alternatively, $R^1$ and $R^{2a}$ are bonded to each other to preferably form a non-aromatic ring (preferably, cyclohexane, piperidine etc.) optionally substituted by 1 to 3 substituents selected from an oxo group, a hydroxy group and the like.

$R^3$ is preferably an optionally substituted hydrocarbon group, an optionally substituted hydroxy group, an optionally substituted amino group or an optionally substituted heterocyclic group, and more preferably an optionally substituted $C_{1-10}$ alkyl group, an optionally substituted $C_{3-10}$ cycloalkyl group, an optionally substituted $C_{6-14}$ aryl group, an optionally substituted $C_{7-13}$ aralkyl group, an optionally substituted amino group, an optionally substituted heterocyclic group or a hydroxy group optionally substituted by a $C_{1-10}$ alkyl group.

Preferable specific examples of $R^3$ include
1) a $C_{1-10}$ alkyl group optionally substituted by 1 to 3 substituents selected from
(1) a halogen atom,
(2) a hydroxy group,
(3) an aromatic heterocyclic group (preferably, thienyl etc.),
(4) an aromatic heterocyclyl-carbonyl group (preferably, thienylcarbonyl etc.), and the like;
2) a $C_{3-10}$ cycloalkyl group optionally substituted by 1 to 3 substituents selected from
(1) a carboxy group,
(2) a $C_{1-6}$ alkoxy-carbonyl group, and the like;
3) a $C_{6-14}$ aryl group optionally substituted by 1 to 3 substituents selected from
(1) a $C_{1-6}$ alkyl group optionally substituted by 1 to 3 halogen atoms,
(2) a $C_{7-13}$ aralkyloxy group optionally substituted by 1 to 3 halogen atoms,
(3) a $C_{1-6}$ alkoxy group,
(4) a carboxy group,
(5) a $C_{1-6}$ alkoxy-carbonyl group,
(6) a $C_{1-6}$ alkylsulfonyl group, and the like;
4) a $C_{7-13}$ aralkyl group;
5) a heterocyclic group (preferably, aromatic heterocyclic group such as thienyl, furyl, pyrazolyl, imidazolyl, thiazolyl, isoxazolyl, pyridyl, imidazothiazolyl and the like; non-aromatic heterocyclic group such as pyrrolidinyl, morpholinyl and the like) optionally substituted by 1 to 3 substituents selected from
(1) a halogen atom,
(2) a carboxy group, (3) a $C_{1-6}$ alkoxy-carbonyl group,
(4) a $C_{1-6}$ alkyl group optionally substituted by 1 to 3 substituents selected from
  (i) a halogen atom,
  (ii) a hydroxy group,
  (iii) a $C_{1-6}$ alkoxy group (the $C_{1-6}$ alkoxy group is optionally substituted by 1 to 3 carboxy groups and the like),
  (iv) a non-aromatic heterocyclic group (the non-aromatic heterocyclic group is preferably piperazinyl, hexahydropyrazinooxazinyl, 1-oxa-3,8-diazaspiro[4.5]decanyl and the like, which is optionally substituted by 1 to 3 substituents selected from an oxo group, a $C_{1-6}$ alkyl-carbonyl group and the like),
  (v) an amino group (the amino group is optionally mono- or di-substituted by $C_{1-6}$ alkyl group(s) (the $C_{1-6}$ alkyl group is optionally substituted by 1 to 3 substituents selected from a non-aromatic heterocyclic group (preferably, morpholinyl etc.), a $C_{1-6}$ alkoxy group, a $C_{1-6}$ alkylsulfonyl group and the like) and the like),
  (vi) a $C_{1-6}$ alkylsulfonyl group (the $C_{1-6}$ alkylsulfonyl group is optionally substituted by 1 to 3 carboxy groups and the like),
  (vii) a $C_{1-6}$ alkylthio group (the $C_{1-6}$ alkylthio group is optionally substituted by 1 to 3 substituents selected from a carboxy group, a $C_{1-6}$ alkoxy-carbonyl group and the like),
  (viii) a phosphono group (the phosphono group is optionally mono- or di-substituted by $C_{1-6}$ alkyl group(s)), and the like,
(5) an aromatic heterocyclic group (preferably, oxazolyl etc.),
(6) a non-aromatic heterocyclyl-carbonyl group (preferably, morpholinylcarbonyl etc.),
(7) a carbamoyl group,
(8) a formyl group,
(9) a $C_{1-6}$ alkyl-carbonyl group, and the like;
6) a hydroxy group;
7) a $C_{1-10}$ alkoxy group; or
8) an amino group optionally mono- or di-substituted by substituent(s) selected from
  (1) a $C_{1-10}$ alkyl group,
  (2) an aromatic heterocyclic group (preferably, thienyl, indolyl etc.) optionally substituted by 1 to 3 non-aromatic heterocyclic groups (preferably, thiazolinyl etc.), and the like; and the like.

$R^3$ is particularly preferably an optionally substituted heterocyclic group, and preferable specific examples thereof include
a heterocyclic group (preferably, aromatic heterocyclic group such as thienyl, furyl, pyrazolyl, imidazolyl, thiazolyl, isoxazolyl, pyridyl, imidazothiazolyl and the like; non-aromatic heterocyclic group such as pyrrolidinyl, morpholinyl and the like) optionally substituted by 1 to 3 substituents selected from
(1) a halogen atom,
(2) a carboxy group,
(3) a $C_{1-6}$ alkoxy-carbonyl group,
(4) a $C_{1-6}$ alkyl group optionally substituted by 1 to 3 substituents selected from
  (i) a halogen atom,
  (ii) a hydroxy group,
  (iii) a $C_{1-6}$ alkoxy group (the $C_{1-6}$ alkoxy group is optionally substituted by 1 to 3 carboxy groups and the like),
  (iv) a non-aromatic heterocyclic group (the non-aromatic heterocyclic group is preferably piperazinyl, hexahydropyrazinooxazinyl, 1-oxa-3,8-diazaspiro[4.5]decanyl and the like, which is optionally substituted by 1 to 3 substituents selected from an oxo group, a $C_{1-6}$ alkyl-carbonyl group and the like),
  (v) an amino group (the amino group is optionally mono- or di-substituted by $C_{1-6}$ alkyl group(s) (the $C_{1-6}$ alkyl group is optionally substituted by 1 to 3 substituents selected from a non-aromatic heterocyclic group (preferably, morpholinyl etc.), a $C_{1-6}$ alkoxy group, a $C_{1-6}$ alkylsulfonyl group and the like) and the like),
  (vi) a $C_{1-6}$ alkylsulfonyl group (the $C_{1-6}$ alkylsulfonyl group is optionally substituted by 1 to 3 carboxy groups and the like),
  (vii) a $C_{1-6}$ alkylthio group (the $C_{1-6}$ alkylthio group is optionally substituted by 1 to 3 substituents selected from a carboxy group, a $C_{1-6}$ alkoxy-carbonyl group and the like),
  (viii) a phosphono group (the phosphono group is optionally mono- or di-substituted by $C_{1-6}$ alkyl group(s)), and the like,
(5) an aromatic heterocyclic group (preferably, oxazolyl etc.),
(6) a non-aromatic heterocyclyl-carbonyl group (preferably, morpholinylcarbonyl etc.),
(7) a carbamoyl group,
(8) a formyl group,
(9) a $C_{1-6}$ alkyl-carbonyl group, and the like, and the like.

Rings A and A' are optionally substituted 6-membered rings.

Examples of the "6-membered ring" of the "optionally substituted 6-membered ring" for ring A or A' include a 6-membered aromatic ring, a 6-membered non-aromatic ring and the like.

Examples of the 6-membered aromatic ring include benzene ring, 6-membered aromatic heterocycle and the like.

Examples of the 6-membered aromatic heterocycle include a ring constituting 6-membered aromatic heterocyclic group exemplified as the "heterocyclic group" of the "optionally substituted heterocyclic group" for $R^2$, $R^{2a}$ or $R^3$. Specifically, pyridine, pyrimidine, pyridazine, pyrazine and the like can be mentioned.

Examples of the 6-membered non-aromatic ring include 6-membered non-aromatic cyclic hydrocarbon, 6-membered non-aromatic heterocycle and the like.

Examples of the 6-membered non-aromatic cyclic hydrocarbon include cyclohexane, cyclohexene, cyclohexadiene and the like.

Examples of the 6-membered non-aromatic heterocycle include a ring constituting the 6-membered non-aromatic heterocyclic group exemplified as the "heterocyclic group" of the "optionally substituted heterocyclic group" for $R^2$, $R^{2a}$ or $R^3$. For example, piperidine, morpholine, thiomorpholine, piperazine, dioxane (e.g., 1,3-dioxane, 1,4-dioxane), dioxene (e.g., 4H-1,3-dioxin, 2,3-dihydro-1,4-dioxin), pyran, tetrahydropyran, thiopyran, tetrahydrothiopyran, 1-oxidotetrahydrothiopyran, 1,1-dioxidotetrahydrothiopyran and the like can be mentioned.

The "6-membered ring" of the aforementioned "optionally substituted 6-membered ring" optionally has 1 to 3 substituents at substitutable position(s). Examples of such substituent include those recited as examples of the substituent that the $C_{3-10}$ cycloalkyl group and the like exemplified as the "hydrocarbon group" of the "optionally substituted hydrocarbon group" for $R^1$, $R^2$ or $R^3$ may have.

Ring A and ring A' are each preferably an optionally substituted benzene ring or an optionally substituted 6-membered aromatic heterocycle (preferably, pyridine ring). More preferred is a benzene ring or a pyridine ring (preferably, benzene ring) optionally substituted by 1 to 3 substituents selected from (1) a halogen atom,
(2) a $C_{1-6}$ alkyl group,
(3) a $C_{1-6}$ alkoxy group optionally substituted by 1 to 3 halogen atoms,
(4) a $C_{1-6}$ alkylthio group,
(5) a $C_{1-6}$ alkylsulfonyl group,
(6) an aromatic heterocyclylthio group (preferably, tetrazolylthio etc.) optionally substituted by 1 to 3 $C_{1-6}$ alkyl groups, and the like.

W is O, $S(O)_m$ (m is 0, 1 or 2), $CR^5R^6$ ($R^5$ and $R^6$ are each independently a hydrogen atom or a $C_{1-6}$ alkyl group) or $NR^7$ ($R^7$ is a hydrogen atom or $R^{3'}$-Y'— ($R^{3'}$ is an optionally substituted hydrocarbon group, an optionally substituted hydroxy group, an optionally substituted mercapto group, an optionally substituted amino group or an optionally substituted heterocyclic group, Y' is a bond, CO, $S(O)_q$ (q is 0, 1 or 2) or $CR^{8'}R^{9'}$ ($R^{8'}$ and $R^{9'}$ are each independently a hydrogen atom or a $C_{1-6}$ alkyl group))).

Wa is O, $S(O)_m$ (m is 0, 1 or 2) or $NR^7$ ($R^7$ is a hydrogen atom or $R^{3'}$—Y'— ($R^{3'}$ is an optionally substituted hydrocarbon group, an optionally substituted hydroxy group, an optionally substituted mercapto group, an optionally substituted amino group or an optionally substituted heterocyclic group, Y' is a bond, CO, $S(O)_q$ (q is 0, 1 or 2) or $CR^{8'}R^{9'}$ ($R^{8'}$ and $R^{9'}$ are each independently a hydrogen atom or a $C_{1-6}$ alkyl group))).

Examples of the "optionally substituted hydrocarbon group", "optionally substituted hydroxy group", "optionally substituted mercapto group", "optionally substituted amino group" and "optionally substituted heterocyclic group" for $R^{3'}$ include those recited as examples of the "optionally substituted hydrocarbon group", "optionally substituted hydroxy group", "optionally substituted mercapto group", "optionally substituted amino group" and "optionally substituted heterocyclic group" for $R^3$.

W is preferably $NR^7$ ($R^7$ is as defined above), O or $CR^5R^6$ ($R^5$ and $R^6$ are each independently a hydrogen atom or a $C_{1-6}$ alkyl group), more preferably, $NR^7$.

Here, $R^{3'}$ is preferably
1) a $C_{1-10}$ alkyl group optionally substituted by 1 to 3 substituents selected from
 (1) a halogen atom,
 (2) a $C_{1-6}$ alkoxy group,
 (3) a hydroxy group,
 (4) a carboxy group,
 (5) a $C_{1-6}$ alkoxy-carbonyl group,
 (6) a non-aromatic heterocyclic group (preferably, morpholinyl etc.),
 (7) a $C_{3-10}$ cycloalkyl group, and the like; or
2) a $C_{6-14}$ aryl group optionally substituted by 1 to 3 substituents selected from
 (1) a $C_{1-6}$ alkyl group optionally substituted by 1 to 3 halogen atoms,
 (2) a $C_{1-6}$ alkylsulfonyl group, and the like; and Y' is preferably a bond or $S(O)_q$ (q is 0, 1 or 2).

$R^7$ is preferably a hydrogen atom or a $C_{1-6}$ alkyl group.

Wa is preferably $NR^7$ ($R^7$ is as defined above) or O, more preferably $NR^7$.

Here, $R^{3'}$ is preferably
1) a $C_{1-10}$ alkyl group optionally substituted by 1 to 3 substituents selected from
 (1) a halogen atom,
 (2) a $C_{1-6}$ alkoxy group,
 (3) a hydroxy group,
 (4) a carboxy group,
 (5) a $C_{1-6}$ alkoxy-carbonyl group,
 (6) a non-aromatic heterocyclic group (preferably, morpholinyl etc.),
 (7) a $C_{3-10}$ cycloalkyl group, and the like; or
2) a $C_{6-14}$ aryl group optionally substituted by 1 to 3 substituents selected from
 (1) a $C_{1-6}$ alkyl group optionally substituted by 1 to 3 halogen atoms,
 (2) a $C_{1-6}$ alkylsulfonyl group, and the like; and Y' is preferably a bond or $S(O)_q$ (q is 0, 1 or 2).

$R^7$ is preferably a hydrogen atom or a $C_{1-6}$ alkyl group.

Y is a bond, CO, $S(O)_p$ (p is 0, 1 or 2) or $CR^8R^9$ ($R^8$ and $R^9$ are each independently a hydrogen atom or a $C_{1-6}$ alkyl group), and Ya is CO, $S(O)_{pa}$ (pa is 0, 1 or 2) or $CR^8R^9$ ($R^8$ and $R^9$ are each independently a hydrogen atom or a $C_{1-6}$ alkyl group).

Y is preferably Ya, i.e., CO, $S(O)_{pa}$ (pa is 0, 1 or 2) or $CR^8R^9$ ($R^8$ and $R^9$ are each independently a hydrogen atom or a $C_{1-6}$ alkyl group), more preferably, CO, $SO_2$ or $CH_2$. Y and Ya are particularly preferably $SO_2$.

Z is a bond, CO, O, $S(O)_n$ (n is 0, 1 or 2) or $NR^{10}$ ($R^{10}$ is a hydrogen atom or a $C_{1-6}$ alkyl group).

Z is preferably CO, a bond or $S(O)_n$ (n is 0, 1 or 2), and more preferably CO or a bond. Of these, a bond is preferable.

As compound (I), the following compounds are preferable.

[Compound (IA)]

A compound wherein
ring A is a benzene ring or a pyridine ring (preferably, benzene ring) each optionally substituted by 1 to 3 substituents selected from (1) a halogen atom,
(2) a $C_{1-6}$ alkyl group,
(3) a $C_{1-6}$ alkoxy group,
(4) a $C_{1-6}$ alkylthio group,
(5) a $C_{1-6}$ alkylsulfonyl group, and the like,
W is $NR^7$ ($R^7$ is a hydrogen atom or a $C_{1-6}$ alkyl group) or O (preferably, $NR^7$)
Y is CO, $SO_2$ or $CR^8R^9$ ($R^8$ and $R^9$ are each independently a hydrogen atom or a $C_{1-6}$ alkyl group) (preferably, CO, $SO_2$ or $CH_2$),
$R^3$ is
1) a $C_{1-6}$ alkyl group;
2) a $C_{6-14}$ aryl group optionally substituted by 1 to 3 substituents selected from
 (1) a $C_{1-6}$ alkyl group,
 (2) a $C_{7-13}$ aralkyloxy group optionally substituted by 1 to 3 halogen atoms, and the like;
3) an aromatic heterocyclic group (preferably, thienyl etc.) optionally substituted by 1 to 3 substituents selected from
 (1) a halogen atom,
 (2) a carboxy group,
 (3) a $C_{1-6}$ alkoxy-carbonyl group, and the like;
4) a hydroxy group; or
5) a $C_{1-6}$ alkoxy group;
Z is CO, a bond or S(O), (n is 0, 1 or 2) (preferably, CO or a bond),
$R^1$ is a hydrogen atom or a $C_{1-10}$ alkyl group,
$R^2$ is
1) a hydrogen atom;
2) a $C_{1-10}$ alkyl group optionally substituted by hydroxy group(s) and the like;
3) a hydroxy group;
4) a $C_{1-6}$ alkoxy group;
5) an amino group optionally mono- or di-substituted by substituent(s) selected from
 (1) a $C_{1-10}$ alkyl group optionally substituted by 1 to 3 substituents selected from
  (i) a halogen atom,
  (ii) a hydroxy group, (iii) a $C_{1-6}$ alkylthio group (the $C_{1-6}$ alkylthio group is optionally substituted by 1 to 3 $C_{6-14}$ aryl groups and the like), and the like, (2) a $C_{1-10}$ alkoxy group, (3) a $C_{6-14}$ aryl group, (4) a $C_{7-13}$ aralkyl group, (5) an aromatic heterocyclic group (preferably, thiazolyl, oxazolyl etc.), (6) an amino group and the like; or 6) a heterocyclic group (preferably, aromatic heterocyclic group such as pyridyl, oxadiazolyl, thiadiazolyl, thiazolyl, oxazolyl and the like; non-aromatic heterocyclic group such as pyrrolidinyl, piperidinyl, oxazolinyl, thiazolinyl and the like) optionally substituted by 1 to 3 substituents selected from (1) a $C_{1-6}$ alkyl group, (2) a $C_{1-6}$ alkoxy-carbonyl group and the like, or $R^1$ and $R^2$ are bonded to each other to form a non-aromatic ring (preferably, cyclohexane, piperidine etc.) optionally substituted by 1 to 3 substituents selected from an oxo group, a hydroxy group and the like.

[Compound (IB)]

A compound wherein ring A is a benzene ring (preferably, benzene ring) or a pyridine ring, each optionally substituted by 1 to 3 substituents selected from (1) a halogen atom, (2) a $C_{1-6}$ alkyl group, (3) a $C_{1-6}$ alkoxy group optionally substituted by 1 to 3 halogen atoms, (4) a $C_{1-6}$ alkylthio group, (5) a $C_{1-6}$ alkylsulfonyl group, (6) an aromatic heterocyclylthio group (preferably, tetrazolylthio etc.) optionally substituted by 1 to 3 $C_{1-6}$ alkyl groups, and the like, W is $NR^7$ ($R^7$ is as defined above) or O (preferably, $NR^7$) (where $R^{3\prime}$ is 1) a $C_{1-10}$ alkyl group optionally substituted by 1 to 3 substituents selected from (1) a halogen atom, (2) a $C_{1-6}$ alkoxy group, (3) a hydroxy group, (4) a carboxy group, (5) a $C_{1-6}$ alkoxy-carbonyl group, (6) a non-aromatic heterocyclic group (preferably, morpholinyl etc.), and the like; or 2) a $C_{6-14}$ aryl group optionally substituted by 1 to 3 substituents selected from (1) a $C_{1-6}$ alkyl group optionally substituted by 1 to 3 halogen atoms, (2) a $C_{1-6}$ alkylsulfonyl group, and the like;

Y' is a bond or $SO_2$),

Y is a bond, CO, $SO_2$ or $CR^8R^9$ ($R^8$ and $R^9$ are each independently a hydrogen atom or a $C_{1-6}$ alkyl group) (preferably, CO, $SO_2$ or $CH_2$), $R^3$ is, 1) a $C_{1-10}$ alkyl group optionally substituted by 1 to 3 substituents selected from (1) a halogen atom, (2) a hydroxy group, (3) an aromatic heterocyclic group (preferably, thienyl etc.), (4) an aromatic heterocyclyl-carbonyl group (preferably, thienylcarbonyl etc.), and the like;

2) a $C_{3-10}$ cycloalkyl group optionally substituted by 1 to 3 substituents selected from (1) a carboxy group, (2) a $C_{1-6}$ alkoxy-carbonyl group, and the like;

3) a $C_{6-14}$ aryl group optionally substituted by 1 to 3 substituents selected from (1) a $C_{1-6}$ alkyl group optionally substituted by 1 to 3 halogen atoms, (2) a $C_{7-13}$ aralkyloxy group optionally substituted by 1 to 3 halogen atoms, (3) a $C_{1-6}$ alkoxy group, (4) a carboxy group, (5) a $C_{1-6}$ alkoxy-carbonyl group, (6) a $C_{1-6}$ alkylsulfonyl group, and the like;

4) a $C_{7-13}$ aralkyl group;

5) a heterocyclic group (preferably, aromatic heterocyclic group such as thienyl, furyl, pyrazolyl, imidazolyl, thiazolyl, isoxazolyl, pyridyl, imidazothiazolyl and the like; non-aromatic heterocyclic group such as pyrrolidinyl, morpholinyl and the like) optionally substituted by 1 to 3 substituents selected from (1) a halogen atom, (2) a carboxy group, (3) a $C_{1-6}$ alkoxy-carbonyl group, (4) a $C_{1-6}$ alkyl group optionally substituted by 1 to 3 substituents selected from (i) a halogen atom, (ii) a hydroxy group, (iii) a $C_{1-6}$ alkoxy group (the $C_{1-6}$ alkoxy group is optionally substituted by 1 to 3 carboxy groups and the like), (iv) a non-aromatic heterocyclic group (the non-aromatic heterocyclic group is, preferably, piperazinyl, hexahydropyrazinooxazinyl, 1-oxa-3,8-diazaspiro[4.5]decanyl and the like, and optionally substituted by 1 to 3 substituents selected from an oxo group, a $C_{1-6}$ alkyl-carbonyl group and the like), (v) an amino group (the amino group is optionally mono- or di-substituted by $C_{1-6}$ alkyl groups (the $C_{1-6}$ alkyl group is optionally substituted by 1 to 3 substituents selected from a non-aromatic heterocyclic group (preferably, morpholinyl etc.), a $C_{1-6}$ alkoxy group, a $C_{1-6}$ alkylsulfonyl group and the like) and the like), (vi) a $C_{1-6}$ alkylsulfonyl group (the $C_{1-6}$ alkylsulfonyl group is optionally substituted by 1 to 3 carboxy groups and the like), (vii) a $C_{1-6}$ alkylthio group (the $C_{1-6}$ alkylthio group is optionally substituted by 1 to 3 substituents selected from a carboxy group, a $C_{1-6}$ alkoxy-carbonyl group and the like), (viii) a phosphono group (the phosphono group is optionally mono- or di-substituted by $C_{1-6}$ alkyl group(s)), and the like, (5) an aromatic heterocyclic group (preferably, oxazolyl etc.), (6) a non-aromatic heterocyclyl-carbonyl group (preferably, morpholinylcarbonyl etc.), (7) a carbamoyl group, and the like;

6) a hydroxy group;

7) a $C_{1-10}$ alkoxy group; or 8) an amino group optionally mono- or di-substituted by substituent(s) selected from (1) a $C_{1-10}$ alkyl group, (2) an aromatic heterocyclic group (preferably, thienyl, indolyl etc.) optionally substituted by 1 to 3 non-aromatic heterocyclic groups (preferably, thiazolinyl etc.), and the like, Z is CO, a bond or $S(O)_n$ (n is 0, 1 or 2) (preferably, CO or a bond), $R^1$ is a hydrogen atom, a halogen atom or a $C_{1-10}$ alkyl group, $R^2$ is 1) a hydrogen atom;

2) a $C_{1-10}$ alkyl group optionally substituted by 1 to 3 substituents selected from (1) a hydroxy group,
(2) a halogen atom,
(3) an aromatic heterocyclyl-carbonylthio group (the aromatic heterocyclyl-carbonylthio group is preferably indolylcarbonylthio and the like and optionally substituted by 1 to 3 amino groups (the amino group is optionally mono- or di-substituted by substituent(s) selected from a $C_{1-6}$ alkyl group, an aromatic heterocyclyl-sulfonyl group (preferably, thienylsulfonyl etc.) and the like) and the like);
3) a hydroxy group;
4) a $C_{1-10}$ alkoxy group;
5) an amino group optionally mono- or di-substituted by substituent(s) selected from
  (1) a $C_{1-10}$ alkyl group optionally substituted by 1 to 3 substituents selected from
    (i) a halogen atom,
    (ii) a hydroxy group,
    (iii) a $C_{1-6}$ alkylthio group (the $C_{1-6}$ alkylthio group is optionally substituted by 1 to 3 $C_{6-14}$ aryl groups and the like),
    (iv) a carbamoyl group (the carbamoyl group is optionally mono- or di-substituted by $C_{1-6}$ alkyl group(s) and the like), and the like,
  (2) a $C_{1-10}$ alkoxy group,
  (3) a $C_{6-14}$ aryl group,
  (4) a $C_{7-13}$ aralkyl group,
  (5) an aromatic heterocyclic group (preferably, thiazolyl, oxazolyl etc.),
  (6) an amino group optionally mono- or di-substituted by substituent(s) selected from
    (i) a $C_{1-6}$ alkyl-carbonyl group (the $C_{1-6}$ alkyl-carbonyl group is optionally substituted by 1 to 3 substituents selected from a $C_{1-6}$ alkoxy group, a $C_{1-6}$ alkoxy-carbonyl group and the like),
    (ii) a $C_{1-6}$ alkoxy-carbonyl-carbonyl group etc., and the like;
6) a heterocyclic group (preferably, aromatic heterocyclic group such as pyridyl, oxadiazolyl, thiadiazolyl, thiazolyl, oxazolyl, triazolyl, tetrazolyl, benzothiazolyl and the like; non-aromatic heterocyclic group such as pyrrolidinyl, piperidinyl, oxazolinyl, thiazolinyl and the like) optionally substituted by 1 to 3 substituents selected from
  (1) a $C_{1-6}$ alkyl group optionally substituted by 1 to 3 substituents selected from
    (i) a $C_{1-6}$ alkoxy group (the $C_{1-6}$ alkoxy group is optionally substituted by 1 to 3 substituents selected from a carboxy group, a $C_{1-6}$ alkoxy-carbonyl group and the like),
    (ii) a hydroxy group,
    (iii) a $C_{1-6}$ alkoxy-carbonyl group,
    (iv) a carboxy group,
    (v) a carbamoyl group (the carbamoyl group is optionally mono- or di-substituted by substituent(s) selected from a $C_{1-6}$ alkylsulfonyl group, an amino group and the like),
    (vi) a $C_{1-6}$ alkylsulfonyl group,
    (vii) an aromatic heterocyclic group (preferably, tetrazolyl etc.),
    (viii) a non-aromatic heterocyclic group (the non-aromatic heterocyclic group is preferably morpholinyl, dihydrooxadiazolyl and the like, which is optionally substituted by 1 to 3 oxo groups and the like),
    (ix) a non-aromatic heterocyclyl-carbonyl group (preferably, morpholinylcarbonyl etc.),
    (x) a cyano group, and the like,
  (2) an amino group optionally mono- or di-substituted by substituent(s) selected from
    (i) a $C_{1-6}$ alkyl group,
    (ii) a $C_{1-6}$ alkoxy-carbonyl group, and the like,
    (3) a $C_{1-6}$ alkoxy-carbonyl group,
    (4) a carboxy group, and the like; or
7) a $C_{1-10}$ alkylthio group optionally substituted by 1 to 3 aromatic heterocyclyl-carbonyl groups (the aromatic heterocyclyl-carbonyl group is, preferably, indolylcarbonyl and the like and optionally substituted by 1 to 3 amino groups (the amino group is optionally mono- or di-substituted by substituent(s) selected from a $C_{1-6}$ alkyl group, an aromatic heterocyclyl-sulfonyl group (preferably, thienylsulfonyl etc.) and the like));
or,
$R^1$ and $R^2$ are bonded to each other to form a non-aromatic ring (preferably, cyclohexane, piperidine etc.) optionally substituted by 1 to 3 substituents selected from an oxo group, a hydroxy group and the like.
[Compound (IC)]
A compound wherein
ring A is a benzene ring or a pyridine ring (preferably, benzene ring), each optionally substituted by 1 to 3 substituents selected from
(1) a halogen atom,
(2) a $C_{1-6}$ alkyl group,
(3) a $C_{1-6}$ alkoxy group optionally substituted by 1 to 3 halogen atoms,
(4) a $C_{1-6}$ alkylthio group,
(5) a $C_{1-6}$ alkylsulfonyl group,
(6) an aromatic heterocyclylthio group (preferably, tetrazolylthio etc.) optionally substituted by 1 to 3 $C_{1-6}$ alkyl groups, and the like,
W is $NR^7$ ($R^7$ is as defined above), O or $CR^5R^6$ ($R^5$ and $R^6$ are each independently a hydrogen atom or a $C_{1-6}$ alkyl group) (preferably, $NR^7$) (here, $R^{3'}$ is
1) a $C_{1-10}$ alkyl group optionally substituted by 1 to 3 substituents selected from
  (1) a halogen atom,
  (2) a $C_{1-6}$ alkoxy group,
  (3) a hydroxy group,
  (4) a carboxy group,
  (5) a $C_{1-6}$ alkoxy-carbonyl group,
  (6) a non-aromatic heterocyclic group (preferably, morpholinyl etc.),
  (7) a $C_{3-10}$ cycloalkyl group, and the like; or
2) $C_{6-14}$ aryl group optionally substituted by 1 to 3 substituents selected from
  (1) a $C_{1-6}$ alkyl group optionally substituted by 1 to 3 halogen atoms,
  (2) a $C_{1-6}$ alkylsulfonyl group, and the like; and
Y' is a bond or $S(O)_q$ (q is 0, 1 or 2)),
Y is a bond, CO, $S(O)_p$ (p is 0, 1 or 2) or $CR^8R^9$ ($R^8$ and $R^9$ are each independently a hydrogen atom or a $C_{1-6}$ alkyl group) (preferably, CO, $SO_2$ or $CH_2$),
$R^1$ is
1) a $C_{1-10}$ alkyl group optionally substituted by 1 to 3 substituents selected from
  (1) a halogen atom,
  (2) a hydroxy group,
  (3) an aromatic heterocyclic group (preferably, thienyl etc.),
  (4) an aromatic heterocyclyl-carbonyl group (preferably, thienylcarbonyl etc.), and the like;
2) a $C_{3-10}$ cycloalkyl group optionally substituted by 1 to 3 substituents selected from
  (1) a carboxy group,
  (2) a $C_{1-6}$ alkoxy-carbonyl group, and the like;
3) a $C_{6-14}$ aryl group optionally substituted by 1 to 3 substituents selected from (1) a $C_{1-6}$ alkyl group optionally substituted by 1 to 3 halogen atoms,
(2) a $C_{7-13}$ aralkyloxy group optionally substituted by 1 to 3 halogen atoms,
(3) a $C_{1-6}$ alkoxy group,
(4) a carboxy group,
(5) a $C_{1-6}$ alkoxy-carbonyl group,
(6) a $C_{1-6}$ alkylsulfonyl group, and the like;
4) a $C_{7-13}$ aralkyl group;
5) a heterocyclic group (preferably, aromatic heterocyclic group such as thienyl, furyl, pyrazolyl, imidazolyl, thiazolyl, isoxazolyl, pyridyl, imidazothiazolyl and the like; non-aromatic heterocyclic group such as pyrrolidinyl, morpholinyl and the like) optionally substituted by 1 to 3 substituents selected from
(1) a halogen atom,
(2) a carboxy group,
(3) a $C_{1-6}$ alkoxy-carbonyl group,
(4) a $C_{1-6}$ alkyl group optionally substituted by 1 to 3 substituents selected from
(i) a halogen atom,
(ii) a hydroxy group,
(iii) a $C_{1-6}$ alkoxy group (the $C_{1-6}$ alkoxy group is optionally substituted by 1 to 3 carboxy groups and the like),
(iv) a non-aromatic heterocyclic group (the non-aromatic heterocyclic group is preferably piperazinyl, hexahydropyrazinooxazinyl, 1-oxa-3,8-diazaspiro[4.5]decanyl and the like, which is optionally substituted by 1 to 3 substituents selected from an oxo group, a $C_{1-6}$ alkyl-carbonyl group and the like),
(v) an amino group (the amino group is optionally mono- or di-substituted by $C_{1-6}$ alkyl group(s) (the $C_{1-6}$ alkyl group is optionally substituted by 1 to 3 substituents selected from a non-aromatic heterocyclic group (preferably, morpholinyl etc.), a $C_{1-6}$ alkoxy group, a $C_{1-6}$ alkylsulfonyl group and the like) and the like),
(vi) a $C_{1-6}$ alkylsulfonyl group (the $C_{1-6}$ alkylsulfonyl group is optionally substituted by 1 to 3 carboxy groups and the like),
(vii) a $C_{1-6}$ alkylthio group (the $C_{1-6}$ alkylthio group is optionally substituted by 1 to 3 substituents selected from a carboxy group, a $C_{1-6}$ alkoxy-carbonyl group and the like),
(viii) a phosphono group (the phosphono group optionally mono- or di-substituted by $C_{1-6}$ alkyl group(s)), and the like,
(5) an aromatic heterocyclic group (preferably, oxazolyl etc.),
(6) a non-aromatic heterocyclyl-carbonyl group (preferably, morpholinylcarbonyl etc.),
(7) a carbamoyl group,
(8) a formyl group,
(9) a $C_{1-6}$ alkyl-carbonyl group, and the like;
6) a hydroxy group;
7) a $C_{1-10}$ alkoxy group; or
8) an amino group optionally mono- or di-substituted by substituent(s) selected from
(1) a $C_{1-10}$ alkyl group,
(2) an aromatic heterocyclic group (preferably, thienyl, indolyl etc.) optionally substituted by 1 to 3 non-aromatic heterocyclic groups (preferably, thiazolinyl etc.), and the like;
Z is CO, a bond or $S(O)_n$ (n is 0, 1 or 2) (preferably, CO or a bond),
$R^1$ is a hydrogen atom, a halogen atom or a $C_{1-10}$ alkyl group, $R^2$ is
1) a hydrogen atom;
2) a $C_{1-10}$ alkyl group optionally substituted by 1 to 3 substituents selected from
(1) a hydroxy group,
(2) a halogen atom,
(3) an aromatic heterocyclyl-carbonylthio group (the aromatic heterocyclyl-carbonylthio group is preferably indolylcarbonylthio and the like, which is optionally substituted by 1 to 3 amino groups (the amino group is optionally mono- or di-substituted by substituent(s) selected from a $C_{1-6}$ alkyl group, an aromatic heterocyclyl-sulfonyl group (preferably, thienylsulfonyl etc.) and the like) and the like);
3) a hydroxy group;
4) a $C_{1-10}$ alkoxy group;
5) an amino group optionally mono- or di-substituted by substituent(s) selected from
(1) a $C_{1-10}$ alkyl group optionally substituted by 1 to 3 substituents selected from
(i) a halogen atom,
(ii) a hydroxy group,
(iii) a $C_{1-6}$ alkylthio group (the $C_{1-6}$ alkylthio group is optionally substituted by 1 to 3 $C_{6-14}$ aryl groups and the like),
(iv) a carbamoyl group (the carbamoyl group is optionally mono- or di-substituted by $C_{1-6}$ alkyl group(s) and the like), and the like,
(2) a $C_{1-10}$ alkoxy group,
(3) a $C_{6-14}$ aryl group,
(4) a $C_{7-13}$ aralkyl group,
(5) an aromatic heterocyclic group (preferably, thiazolyl, oxazolyl etc.),
(6) an amino group optionally mono- or di-substituted by substituent(s) selected from
(i) a $C_{1-6}$ alkyl-carbonyl group (the $C_{1-6}$ alkyl-carbonyl group is optionally substituted by 1 to 3 substituents selected from a $C_{1-6}$ alkoxy group, a $C_{1-6}$ alkoxy-carbonyl group and the like),
(ii) a $C_{1-6}$ alkoxy-carbonyl-carbonyl group, and the like;
6) a heterocyclic group (preferably, aromatic heterocyclic group such as pyridyl, oxadiazolyl, thiadiazolyl, thiazolyl, oxazolyl, triazolyl, tetrazolyl, benzothiazolyl and the like; non-aromatic heterocyclic group such as pyrrolidinyl, piperidinyl, oxazolinyl, thiazolinyl and the like) optionally substituted by 1 to 3 substituents selected from
(1) a $C_{1-6}$ alkyl group optionally substituted by 1 to 3 substituents selected from
(i) a $C_{1-6}$ alkoxy group (the $C_{1-6}$ alkoxy group is optionally substituted by 1 to 3 substituents selected from a carboxy group, a $C_{1-6}$ alkoxy-carbonyl group and the like),
(ii) a hydroxy group,
(iii) a $C_{1-6}$ alkoxy-carbonyl group,
(iv) a carboxy group,
(v) a carbamoyl group (the carbamoyl group is optionally mono- or di-substituted by substituent(s) selected from a $C_{1-6}$ alkylsulfonyl group, an amino group and the like),
(vi) a $C_{1-6}$ alkylsulfonyl group,
(vii) an aromatic heterocyclic group (preferably, tetrazolyl etc.),
(viii) a non-aromatic heterocyclic group (the non-aromatic heterocyclic group is preferably morpholinyl, dihydrooxadiazolyl and the like, which is optionally substituted by 1 to 3 oxo groups and the like),
(ix) a non-aromatic heterocyclyl-carbonyl group (preferably, morpholinylcarbonyl etc.),
(x) a cyano group, (xi) a $C_{6-14}$ aryloxy group (the $C_{6-14}$ aryloxy group is optionally substituted by 1 to 3 substituents selected from a carboxy group, a $C_{1-6}$ alkoxy-carbonyl group and the like), (xii) a $C_{1-6}$ alkylthio group (the $C_{1-6}$ alkylthio group is optionally substituted by 1 to 3 substituents selected from a hydroxy group, a carbamoyl group and the like), and the like, (2) an amino group optionally mono- or di-substituted by substituent(s) selected from (i) a $C_{1-6}$ alkyl group, (ii) a $C_{1-6}$ alkoxy-carbonyl group, and the like, (3) a $C_{1-6}$ alkoxy-carbonyl group, (4) a carboxy group, (5) a formyl group, and the like; or 7) a $C_{1-10}$ alkylthio group optionally substituted by 1 to 3 aromatic heterocyclyl-carbonyl groups (the aromatic heterocyclyl-carbonyl group is preferably indolylcarbonyl and the like, which is optionally substituted by 1 to 3 amino groups (the amino group is optionally mono- or di-substituted by substituent(s) selected from a $C_{1-6}$ alkyl group, an aromatic heterocyclyl-sulfonyl group (preferably, thienylsulfonyl etc.) and the like));

or $R^1$ and $R^2$ are bonded to each other to form a non-aromatic ring (preferably, cyclohexane, piperidine etc.) optionally substituted by 1 to 3 substituents selected from an oxo group, a hydroxy group and the like.

Of compounds (1), compound (II) is a novel compound, and as compound (II), the following compounds are preferable.

[Compound (IIA)]

A compound wherein ring A' is a benzene ring or a pyridine ring (preferably, benzene ring), each optionally substituted by 1 to 3 substituents selected from (1) a halogen atom, (2) a $C_{1-6}$ alkyl group, (3) a $C_{1-6}$ alkoxy group, (4) a $C_{1-6}$ alkylthio group, (5) a $C_{1-6}$ alkylsulfonyl group, and the like, Wa is $NR^7$ ($R^7$ is a hydrogen atom or a $C_{1-6}$ alkyl group) or O (preferably, $NR^7$), Ya is CO, $SO_2$ or $CR^8R^9$ ($R^8$ and $R^9$ are each independently a hydrogen atom or a $C_{1-6}$ alkyl group) (preferably, CO, $SO_2$ or $CH_2$), $R^3$ is 1) a $C_{1-6}$ alkyl group;

2) a $C_{6-14}$ aryl group optionally substituted by 1 to 3 substituents selected from (1) a $C_{1-6}$ alkyl group, (2) a $C_{7-13}$ aralkyloxy group optionally substituted by 1 to 3 halogen atoms, and the like;

3) an aromatic heterocyclic group (preferably, thienyl etc.) optionally substituted by 1 to 3 substituents selected from (1) a halogen atom, (2) a carboxy group, (3) a $C_{1-6}$ alkoxy-carbonyl group, and the like;

4) a hydroxy group; or 5) a $C_{1-6}$ alkoxy group;

$R^1$ is a hydrogen atom or a $C_{1-10}$ alkyl group, $R^{2a}$ is a heterocyclic group (preferably, aromatic heterocyclic group such as pyridyl, oxadiazolyl, thiadiazolyl, thiazolyl, oxazolyl and the like; non-aromatic heterocyclic group such as pyrrolidinyl, piperidinyl, oxazolinyl, thiazolinyl and the like) optionally substituted by 1 to 3 substituents selected from (1) a $C_{1-6}$ alkyl group, (2) a $C_{1-6}$ alkoxy-carbonyl group, and the like, or $R^1$ and $R^{2'}$ are bonded to each other to form a non-aromatic ring (preferably, cyclohexane, piperidine etc.) optionally substituted by 1 to 3 substituents selected from an oxo group, a hydroxy group and the like.

[Compound (IIB)]

A compound wherein ring A' is a benzene ring or a pyridine ring (preferably, benzene ring), each optionally substituted by 1 to 3 substituents selected from (1) a halogen atom, (2) a $C_{1-6}$ alkyl group, (3) a $C_{1-6}$ alkoxy group optionally substituted by 1 to 3 halogen atoms, (4) a $C_{1-6}$ alkylthio group, (5) a $C_{1-6}$ alkylsulfonyl group, (6) an aromatic heterocyclylthio group (preferably, tetrazolylthio etc.) optionally substituted by 1 to 3 $C_{1-6}$ alkyl groups, and the like, Wa is $NR^7$ ($R^7$ is as defined above) or O (preferably, $NR^7$) (where $R^{3'}$ is 1) a $C_{1-10}$ alkyl group optionally substituted by 1 to 3 substituents selected from (1) a halogen atom, (2) a $C_{1-6}$ alkoxy group, (3) a hydroxy group, (4) a carboxy group, (5) a $C_{1-6}$ alkoxy-carbonyl group, (6) a non-aromatic heterocyclic group (preferably, morpholinyl etc.);

or 2) a $C_{6-14}$ aryl group optionally substituted by 1 to 3 substituents selected from (1) a $C_{1-6}$ alkyl group optionally substituted by 1 to 3 halogen atoms, (2) a $C_{1-6}$ alkylsulfonyl group, and the like; and Y' is a bond or $SO_2$), Ya is CO, $SO_2$ or $CR^8R^9$ ($R^8$ and $R^9$ are each independently a hydrogen atom or a $C_{1-6}$ alkyl group) (preferably, CO, $SO_2$ or $CH_2$), $R^3$ is 1) a $C_{1-10}$ alkyl group optionally substituted by 1 to 3 substituents selected from (1) a halogen atom, (2) a hydroxy group, (3) an aromatic heterocyclic group (preferably, thienyl etc.), (4) an aromatic heterocyclyl-carbonyl group (preferably thienylcarbonyl etc.), and the like;

2) a $C_{3-10}$ cycloalkyl group optionally substituted by 1 to 3 substituents selected from (1) a carboxy group, (2) a $C_{1-6}$ alkoxy-carbonyl group, and the like;

3) a $C_{6-14}$ aryl group optionally substituted by 1 to 3 substituents selected from (1) a $C_{1-6}$ alkyl group optionally substituted by 1 to 3 halogen atoms, (2) a $C_{7-13}$ aralkyloxy group optionally substituted by 1 to 3 halogen atoms, (3) a $C_{1-6}$ alkoxy group, (4) a carboxy group, (5) a $C_{1-6}$ alkoxy-carbonyl group, (6) a $C_{1-6}$ alkylsulfonyl group, and the like;

4) a $C_{7-13}$ aralkyl group;

5) a heterocyclic group (preferably, aromatic heterocyclic group such as thienyl, furyl, pyrazolyl, imidazolyl, thiazolyl, isoxazolyl, pyridyl, imidazothiazolyl and the like; non-aromatic heterocyclic group such as pyrrolidinyl, morpholinyl and the like) optionally substituted by 1 to 3 substituents selected from
(1) a halogen atom,
(2) a carboxy group,
(3) a $C_{1-6}$ alkoxy-carbonyl group,
(4) a $C_{1-6}$ alkyl group optionally substituted by 1 to 3 substituents selected from
   (i) a halogen atom,
   (ii) a hydroxy group,
   (iii) a $C_{1-6}$ alkoxy group (the $C_{1-6}$ alkoxy group is optionally substituted by 1 to 3 carboxy groups and the like),
   (iv) a non-aromatic heterocyclic group (the non-aromatic heterocyclic group is preferably piperazinyl, hexahydropyrazinooxazinyl, 1-oxa-3,8-diazaspiro[4.5]decanyl and the like, which is optionally substituted by 1 to 3 substituents selected from an oxo group, a $C_{1-6}$ alkyl-carbonyl group and the like),
   (v) an amino group (the amino group is optionally mono- or di-substituted by $C_{1-6}$ alkyl group(s) (the $C_{1-6}$ alkyl group is optionally substituted by 1 to 3 substituents selected from a non-aromatic heterocyclic group (preferably, morpholinyl etc.), a $C_{1-6}$ alkoxy group, a $C_{1-6}$ alkylsulfonyl group and the like) and the like),
   (vi) a $C_{1-6}$ alkylsulfonyl group (the $C_{1-6}$ alkylsulfonyl group is optionally substituted by 1 to 3 carboxy groups and the like),
   (vii) a $C_{1-6}$ alkylthio group (the $C_{1-6}$ alkylthio group is optionally substituted by 1 to 3 substituents selected from a carboxy group, a $C_{1-6}$ alkoxy-carbonyl group and the like),
   (viii) a phosphono group (the phosphono group is optionally mono- or di-substituted by $C_{1-6}$ alkyl group(s)), and the like,
(5) an aromatic heterocyclic group (preferably, oxazolyl etc.),
(6) a non-aromatic heterocyclyl-carbonyl group (preferably, morpholinylcarbonyl etc.),
(7) a carbamoyl group, and the like;
6) a hydroxy group;
7) a $C_{1-10}$ alkoxy group; or
8) an amino group optionally mono- or di-substituted by substituent(s) selected from
   (1) a $C_{1-10}$ alkyl group,
   (2) a heterocyclic group (preferably, thienyl, indolyl etc.) optionally substituted by 1 to 3 non-aromatic heterocyclic groups (preferably, thiazolinyl etc.), and the like;
$R^1$ is a hydrogen atom, a halogen atom or a $C_{1-10}$ alkyl group,
$R^{2a}$ is a heterocyclic group (preferably, aromatic heterocyclic group such as pyridyl, oxadiazolyl, thiadiazolyl, thiazolyl, oxazolyl, triazolyl, tetrazolyl, benzothiazolyl and the like; non-aromatic heterocyclic group such as pyrrolidinyl, piperidinyl, oxazolinyl, thiazolinyl and the like) optionally substituted by 1 to 3 substituents selected from
(1) a $C_{1-6}$ alkyl group optionally substituted by 1 to 3 substituents selected from
   (i) a $C_{1-6}$ alkoxy group (the $C_{1-6}$ alkoxy group is optionally substituted by 1 to 3 substituents selected from a carboxy group, a $C_{1-6}$ alkoxy-carbonyl group and the like),
   (ii) a hydroxy group,
   (iii) a $C_{1-6}$ alkoxy-carbonyl group,
   (iv) a carboxy group,
   (v) a carbamoyl group (the carbamoyl group is optionally mono- or di-substituted by substituent(s) selected from a $C_{1-6}$ alkylsulfonyl group, an amino group and the like),
   (vi) a $C_{1-6}$ alkylsulfonyl group,
   (vii) an aromatic heterocyclic group (preferably, tetrazolyl etc.),
   (viii) a non-aromatic heterocyclic group (the non-aromatic heterocyclic group is preferably morpholinyl, dihydrooxadiazolyl and the like, which is optionally substituted by 1 to 3 oxo groups and the like),
   (ix) a non-aromatic heterocyclyl-carbonyl group (preferably, morpholinylcarbonyl etc.),
   (x) a cyano group, and the like,
(2) an amino group optionally mono- or di-substituted by substituent(s) selected from
   (i) a $C_{1-6}$ alkyl group,
   (ii) a $C_{1-6}$ alkoxy-carbonyl group, and the like,
(3) a $C_{1-6}$ alkoxy-carbonyl group,
(4) a carboxy group, and the like, or
$R^1$ and $R^{2a}$ are bonded to each other to form a non-aromatic ring (preferably, cyclohexane, piperidine etc.) optionally substituted by 1 to 3 substituents selected from an oxo group, a hydroxy group and the like.

[Compound (IIC)]

A compound wherein
ring A' is a benzene ring or a pyridine ring (preferably, benzene ring), each optionally substituted by 1 to 3 substituents selected from
(1) a halogen atom,
(2) a $C_{1-6}$ alkyl group,
(3) a $C_{1-6}$ alkoxy group optionally substituted by 1 to 3 halogen atoms,
(4) a $C_{1-6}$ alkylthio group,
(5) a $C_{1-6}$ alkylsulfonyl group,
(6) an aromatic heterocyclylthio group (preferably, tetrazolylthio etc.) optionally substituted by 1 to 3 $C_{1-6}$ alkyl groups, and the like,
Wa is $NR^7$ ($R^7$ is as defined above) or O (preferably, $NR^7$) (where $R^{3'}$ is
1) a $C_{1-10}$ alkyl group optionally substituted by 1 to 3 substituents selected from
   (1) a halogen atom,
   (2) a $C_{1-6}$ alkoxy group,
   (3) a hydroxy group,
   (4) a carboxy group,
   (5) a $C_{1-6}$ alkoxy-carbonyl group,
   (6) a non-aromatic heterocyclic group (preferably, morpholinyl etc.),
   (7) a $C_{3-10}$ cycloalkyl group, and the like; or
2) a $C_{6-14}$ aryl group optionally substituted by 1 to 3 substituents selected from
   (1) a $C_{1-6}$ alkyl group optionally substituted by 1 to 3 halogen atoms,
   (2) a $C_{1-6}$ alkylsulfonyl group, and the like; and
Y' is a bond or $S(O)_q$ (q is 0, 1 or 2)),
Ya is CO, $S(O)_{pa}$ (pa is 0, 1 or 2) or $CR^8R^9$ ($R^8$ and $R^9$ are each independently a hydrogen atom or a $C_{1-6}$ alkyl group) (preferably, CO, $SO_2$ or $CH_2$),
$R^3$ is
1) a $C_{1-10}$ alkyl group optionally substituted by 1 to 3 substituents selected from
   (1) a halogen atom,
   (2) a hydroxy group,
   (3) an aromatic heterocyclic group (preferably, thienyl etc.),
   (4) an aromatic heterocyclyl-carbonyl group (preferably, thienylcarbonyl etc.), and the like;

2) a $C_{3-10}$ cycloalkyl group optionally substituted by 1 to 3 substituents selected from
  (1) a carboxy group,
  (2) a $C_{1-6}$ alkoxy-carbonyl group, and the like;
3) a $C_{6-14}$ aryl group optionally substituted by 1 to 3 substituents selected from
  (1) a $C_{1-6}$ alkyl group optionally substituted by 1 to 3 halogen atoms,
  (2) a $C_{7-13}$ aralkyloxy group optionally substituted by 1 to 3 halogen atoms,
  (3) a $C_{1-6}$ alkoxy group,
  (4) a carboxy group,
  (5) a $C_{1-6}$ alkoxy-carbonyl group,
  (6) a $C_{1-6}$ alkylsulfonyl group, and the like;
4) a $C_{7-13}$ aralkyl group;
5) a heterocyclic group (preferably, aromatic heterocyclic group such as thienyl, furyl, pyrazolyl, imidazolyl, thiazolyl, isoxazolyl, pyridyl, imidazothiazolyl and the like; non-aromatic heterocyclic group such as pyrrolidinyl, morpholinyl and the like) optionally substituted by 1 to 3 substituents selected from
  (1) a halogen atom,
  (2) a carboxy group,
  (3) a $C_{1-6}$ alkoxy-carbonyl group,
  (4) a $C_{1-6}$ alkyl group optionally substituted by 1 to 3 substituents selected from
    (i) a halogen atom,
    (ii) a hydroxy group,
    (iii) a $C_{1-6}$ alkoxy group (the $C_{1-6}$ alkoxy group is optionally substituted by 1 to 3 carboxy groups and the like),
    (iv) a non-aromatic heterocyclic group (the non-aromatic heterocyclic group is preferably piperazinyl, hexahydropyrazinooxazinyl, 1-oxa-3,8-diazaspiro[4.5]decanyl and the like, which is optionally substituted by 1 to 3 substituents selected from an oxo group, a $C_{1-6}$ alkyl-carbonyl group and the like),
    (v) an amino group (the amino group is optionally mono- or di-substituted by $C_{1-6}$ alkyl group(s) (the $C_{1-6}$ alkyl group is optionally substituted by 1 to 3 substituents selected from a non-aromatic heterocyclic group (preferably, morpholinyl etc.), a $C_{1-6}$ alkoxy group, a $C_{1-6}$ alkylsulfonyl group and the like) and the like),
    (vi) a $C_{1-6}$ alkylsulfonyl group (the $C_{1-6}$ alkylsulfonyl group is optionally substituted by 1 to 3 carboxy groups and the like),
    (vii) a $C_{1-6}$ alkylthio group (the $C_{1-6}$ alkylthio group is optionally substituted by 1 to 3 substituents selected from a carboxy group, a $C_{1-6}$ alkoxy-carbonyl group and the like),
    (viii) a phosphono group (the phosphono group is optionally mono- or di-substituted by $C_{1-6}$ alkyl group(s)), and the like,
  (5) an aromatic heterocyclic group (preferably, oxazolyl etc.),
  (6) a non-aromatic heterocyclyl-carbonyl group (preferably, morpholinylcarbonyl etc.),
  (7) a carbamoyl group,
  (8) a formyl group,
  (9) a $C_{1-6}$ alkyl-carbonyl group, and the like;
6) a hydroxy group;
7) a $C_{1-10}$ alkoxy group; or
8) an amino group optionally mono- or di-substituted by substituent(s) selected from
  (1) a $C_{1-10}$ alkyl group,
  (2) an aromatic heterocyclic group (preferably, thienyl, indolyl etc.) optionally substituted by 1 to 3 non-aromatic heterocyclic groups (preferably, thiazolinyl etc.), and the like;

$R^1$ is a hydrogen atom, a halogen atom or a $C_{1-10}$ alkyl group, $R^{2a}$ is a heterocyclic group (preferably, aromatic heterocyclic group such as pyridyl, oxadiazolyl, thiadiazolyl, thiazolyl, oxazolyl, triazolyl, tetrazolyl, benzothiazolyl and the like; non-aromatic heterocyclic group such as pyrrolidinyl, piperidinyl, oxazolinyl, thiazolinyl and the like) optionally substituted by 1 to 3 substituents selected from
  (1) a $C_{1-6}$ alkyl group optionally substituted by 1 to 3 substituents selected from
    (i) a $C_{1-6}$ alkoxy group (the $C_{1-6}$ alkoxy group is optionally substituted by 1 to 3 substituents selected from a carboxy group, a $C_{1-6}$ alkoxy-carbonyl group and the like),
    (ii) a hydroxy group,
    (iii) a $C_{1-6}$ alkoxy-carbonyl group,
    (iv) a carboxy group,
    (v) a carbamoyl group (the carbamoyl group is optionally mono- or di-substituted by substituent(s) selected from a $C_{1-6}$ alkylsulfonyl group, an amino group and the like),
    (vi) a $C_{1-6}$ alkylsulfonyl group,
    (vii) an aromatic heterocyclic group (preferably, tetrazolyl etc.),
    (viii) a non-aromatic heterocyclic group (the non-aromatic heterocyclic group is preferably morpholinyl, dihydrooxadiazolyl and the like, which is optionally substituted by 1 to 3 oxo groups and the like),
    (ix) a non-aromatic heterocyclyl-carbonyl group (preferably, morpholinylcarbonyl etc.),
    (x) a cyano group,
    (xi) a $C_{6-14}$ aryloxy group (the $C_{6-14}$ aryloxy group is optionally substituted by 1 to 3 substituents selected from a carboxy group, a $C_{1-6}$ alkoxy-carbonyl group and the like),
    (xii) a $C_{1-6}$ alkylthio group (the $C_{1-6}$ alkylthio group is optionally substituted by 1 to 3 substituents selected from a hydroxy group, a carbamoyl group and the like), and the like,
  (2) an amino group optionally mono- or di-substituted by substituent(s) selected from
    (i) a $C_{1-6}$ alkyl group,
    (ii) a $C_{1-6}$ alkoxy-carbonyl group, and the like,
  (3) a $C_{1-6}$ alkoxy-carbonyl group,
  (4) a carboxy group,
  (5) a formyl group, and the like, or $R^1$ and $R^{2a}$ are bonded to each other to form a non-aromatic ring (preferably, cyclohexane, piperidine etc.) optionally substituted by 1 to 3 substituents selected from an oxo group, a hydroxy group and the like.

[Compound (IID)]
N-[2-(4,5-dihydro-1,3-thiazol-2-yl)-1H-indol-7-yl]thiophene-2-sulfonamide (Example 3);
N-[2-(4,5-dihydro-1,3-thiazol-2-yl)-5-fluoro-1H-indol-7-yl]-N-methylthiophene-2-sulfonamide (Example 165);
N-[2-(4,5-dihydro-1,3-thiazol-2-yl)-5-(trifluoromethoxy)-1H-indol-7-yl]-N-methylthiophene-2-sulfonamide (Example 169);
N-[4-fluoro-2-(1,3-thiazol-2-yl)-1H-indol-7-yl]-N-methylthiophene-2-sulfonamide (Example 182);
N-{4-chloro-2-[5-(hydroxymethyl)-1,3-thiazol-2-yl]-1H-indol-7-yl}-N-methylthiophene-2-sulfonamide (Example 261); and
4-[(2-{7-[ethyl(2-thienylsulfonyl)amino]-1H-indol-2-yl}-1,3-thiazol-5-yl)methoxy]benzoic acid (Example 280).

As salts of compound (I) and compound (II) (hereinafter to be collectively abbreviated as the compound of the present invention), a pharmacologically acceptable salt is preferable. As such salts, for example, a salt with inorganic base, a salt with organic base, a salt with inorganic acid, a salt with organic acid, a salt with basic or acidic amino acid and the like can be mentioned.

Preferable examples of salts with inorganic base include alkali metal salts such as sodium salt, potassium salt and the like; alkaline earth metal salts such as calcium salt, magnesium salt and the like; and aluminum salts; ammonium salts and the like.

As preferable examples of the salts with organic bases, salts with trimethylamine, triethylamine, pyridine, picoline, ethanolamine, diethanolamine, triethanolamine, dicyclohexylamine, N,N-dibenzylethylenediamine and the like can be mentioned.

As preferable examples of the salts with inorganic acids, salts with hydrochloric acid, hydrobromic acid, nitric acid, sulfuric acid, phosphoric acid and the like can be mentioned.

As preferable examples of the salts with organic acids, salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like can be mentioned.

As preferable examples of the salts with basic amino acid, salts with arginine, lysine, ornithine and the like can be mentioned.

As preferable examples of the salts with acidic amino acids, salts with aspartic acid, glutamic acid and the like can be mentioned.

A prodrug of the compound of the present invention means a compound which is converted to the present invention with a reaction due to an enzyme, an gastric acid, etc. under the physiological condition in the living body, that is, a compound which is converted to the compound of the present invention with oxidation, reduction, hydrolysis, etc. according to an enzyme; a compound which is converted to the compound of the present invention by hydrolysis etc. due to gastric acid, etc. A prodrug of the compound of the present invention may be a compound obtained by subjecting an amino group in the compound of the present invention to an acylation, alkylation or phosphorylation (e.g., a compound obtained by subjecting an amino group in the compound of the present invention to an eicosanoylation, alanylation, pentylaminocarbonylation, (5-methyl-2-oxo-1,3-dioxolen-4-yl)methbxycarbonylation, tetrahydrofuranylation, pyrrolidylmethylation, pivaloyloxymethylation or tert-butylation); a compound obtained by subjecting a hydroxy group in the compound of the present invention to an acylation, alkylation, phosphorylation or boration (e.g., a compound obtained by subjecting an hydroxy group in the compound of the present invention to an acetylation, palmitoylation, propanoylation, pivaloylation, succinylation, fumarylation, alanylation or dimethylaminomethylcarbonylation); a compound obtained by subjecting a carboxyl group in the compound of the present invention to an esterification or amidation (e.g., a compound obtained by subjecting a carboxyl group in the compound of the present invention to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like. Any of these compounds can be produced from the compound of the present invention by a method known per se.

A prodrug of the compound of the present invention may also be one which is converted into the present invention under a physiological condition, such as those described in IYAKUHIN NO KAIHATSU (Development of Pharmaceuticals), Vol. 7, Design of Molecules, p. 163-198, Published by HIROKAWA SHOTEN (1990).

The compound of the present invention may be labeled with an isotope (e.g., $^3H$, $^{14}C$, $^{35}S$, $^{125}I$) and the like.

Furthermore, the compound of the present invention may be a non-hydrate or hydrate.

The compound of the present invention or a prodrug thereof (hereinafter sometimes to be abbreviated as the compound of the present invention) shows low toxicity and can be used as an agent for the prophylaxis or treatment of various diseases to be mentioned later for mammals (e.g., humans, mice, rats, rabbits, dogs, cats, bovines, horses, pigs, monkeys) as they are or by admixing with a pharmacologically acceptable carrier and the like to give a pharmaceutical composition.

Here, various organic or inorganic carriers conventionally used as materials for pharmaceutical preparations are used as a pharmacologically acceptable carrier, which are added as excipient, lubricant, binder and disintegrant for solid preparations; or solvent, solubilizing agent, suspending agent, isotonicity agent, buffer and soothing agent for liquid preparations, and the like. Where necessary, an additive for pharmaceutical preparations such as preservative, antioxidant, colorant, sweetening agent and the like can be used.

Preferable examples of the excipient include lactose, sucrose, D-mannitol, D-sorbitol, starch, α-starch, dextrin, crystalline cellulose, low-substituted hydroxypropylcellulose, sodium carboxymethylcellulose, gum acacia, pullulan, light anhydrous silicic acid, synthetic aluminum silicate and magnesium aluminate metasilicate.

Preferred examples of the lubricant include magnesium stearate, calcium stearate, talc and colloidal silica.

Preferable examples of the binder include α-starch, saccharose, gelatin, gum acacia, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, sodium croscarmellose, sodium carboxymethyl starch, light anhydrous silicic acid and low-substituted hydroxypropylcellulose.

Preferable examples of the solvent include water for injection, physiological brine, Ringer's solution, alcohol, propylene glycol, polyethylene glycol, sesame oil, corn oil, olive oil and cottonseed oil.

Preferred examples of the solubilizing agents include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferred examples of the suspending agent include surfactants such as stearyltriethanolamine, sodium lauryl sulfate, lauryl aminopropionate, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates, polyoxyethylene and hydrogenated castor oil.

Preferred examples of the isotonicity agent include sodium chloride, glycerol, D-mannitol, D-sorbitol and glucose.

Preferred examples of the buffer include buffers such as phosphate, acetate, carbonate and citrate.

Preferred examples of the soothing agent include benzyl alcohol.

Preferred examples of the preservative include p-oxybenzoates, chlorobutanol, benzyl alcohol, phenethyl alcohol, dehydroacetate and sorbic acid.

Preferred examples of the antioxidant include sulfite and ascorbate.

Preferable examples of the colorant include aqueous edible tar pigments (e.g., foodcolors such as Food Color Red Nos. 2 and 3, Food Color Yellow Nos. 4 and 5, Food Color Blue Nos. 1 and 2 and the like), water insoluble lake pigments (e.g., aluminum salt of the aforementioned aqueous edible tar pigment) and natural pigments (e.g., beta carotene, chlorophil, red iron oxide).

Preferable examples of the sweetening agent include saccharin sodium, dipotassium glycyrrhizinate, aspartame and stevia.

The dosage form of the aforementioned pharmaceutical composition is, for example, an oral agent such as tablets (inclusive of sublingual tablets and orally disintegrable tablets), capsules (inclusive of soft capsules and microcapsules), granules, powders, troches, syrups, emulsions, suspensions and the like; or a parenteral agent such as injections (e.g., subcutaneous injections, intravenous injections, intramuscular injections, intraperitoneal injections, drip infusions), external agents (e.g., transdermal preparations, ointments), suppositories (e.g., rectal suppositories, vaginal suppositories), pellets, nasal preparations, pulmonary preparations (inhalations), ophthalmic preparations and the like. These may be administered safely via an oral or parenteral route.

These agents may be controlled-release preparations such as rapid-release preparations and sustained-release preparations (e.g., sustained-release microcapsules).

The pharmaceutical composition can be produced according to a method conventionally used in the field of pharmaceutical preparation, such as the method described in Japan Pharmacopoeia and the like. Specific production methods of the preparation are described in detail in the following.

While the content of the compound of the present invention in the pharmaceutical composition varies depending on the dosage form, dose of the compound of the present invention and the like, it is, for example, about 0.1 to 100 wt %.

The compound of the present invention has a superior GK activating action, and can be used as an agent for the prophylaxis or treatment of various diseases for mammals (e.g., human, bovine, horse, dog, cat, monkey, mouse, rat, specifically human). In addition, as the compound of the present invention has a selective GK activating action, it shows low toxicity (e.g., acute toxicity, chronic toxicity, cardiotoxicity, carcinogenic, genetic toxicity), which causes fewer side effects.

The compound of the present invention can be used as an agent for the prophylaxis or treatment of diabetes (e.g., type 1 diabetes, type 2 diabetes, gestational diabetes, obese diabetes); an agent for the prophylaxis or treatment of hyperlipidemia (e.g., hypertriglyceridemia, hypercholesterolemia, hypo-HDL-emia, postprandial hyperlipidemia); an agent for the prophylaxis or treatment of arteriosclerosis; an agent for the prophylaxis or treatment of impaired glucose tolerance (IGT); and an agent for preventing progression of impaired glucose tolerance into diabetes.

For diagnostic criteria of diabetes, Japan Diabetes Society reported new diagnostic criteria in 1999.

According to this report, diabetes is a condition showing any of a fasting blood glucose level (glucose concentration of venous plasma) of not less than 126 mg/dl, a 75 g oral glucose tolerance test (75 g OGTT) 2 h level (glucose concentration of venous plasma) of not less than 200 mg/dl, and a non-fasting blood glucose level (glucose concentration of venous plasma) of not less than 200 mg/dl. A condition not falling under the above-mentioned diabetes and different from "a condition showing a fasting blood glucose level (glucose concentration of venous plasma) of less than 110 mg/dl or a 75 g oral glucose tolerance test (75 g OGTT) 2 h level (glucose concentration of venous plasma) of less than 140 mg/dl" (normal type) is called a "borderline type".

In addition, ADA (American Diabetes Association) and WHO reported new diagnostic criteria of diabetes.

According to these reports, diabetes is a condition showing a fasting blood glucose level (glucose concentration of venous plasma) of not less than 126 mg/dl or a 75 g oral glucose tolerance test 2 h level (glucose concentration of venous plasma) of not less than 200 mg/dl.

According to the reports of ADA and WHO, impaired glucose tolerance is a condition showing a 75 g oral glucose tolerance test 2 h level (glucose concentration of venous plasma) of not less than 140 mg/dl and less than 200 mg/dl. According to the report of ADA, a condition showing a fasting blood glucose level (glucose concentration of venous plasma) of not less than 100 mg/dl and less than 126 mg/dl is called IFG (Impaired Fasting Glucose). According to WHO, among the IFG (Impaired Fasting Glucose), a condition showing a fasting blood glucose level (glucose concentration of venous plasma) of not less than 110 mg/dl and less than 126 mg/dl is called IFG (Impaired Fasting Glycemia).

The compound of the present invention can also be used as an agent for the prophylaxis or treatment of diabetes, borderline type, impaired glucose tolerance, IFG (Impaired Fasting Glucose) and IFG (Impaired Fasting Glycemia), as determined according to the above-mentioned new diagnostic criteria. Moreover, the compound of the present invention can prevent progress of borderline type, impaired glucose tolerance, IFG (Impaired Fasting Glucose) or IFG (Impaired Fasting Glycemia) into diabetes.

The compound of the present invention can also be used as an agent for the prophylaxis or treatment of, for example, diabetic complications [e.g., neuropathy, nephropathy, retinopathy, cataract, macroangiopathy, osteopenia, hyperosmolar diabetic coma, infectious disease (e.g., respiratory infection, urinary tract infection, gastrointestinal infection, dermal soft tissue infections, inferior limb infection), diabetic foot (e.g., gangrene, ulcer), xerostomia, hypacusis, cerebrovascular disorder, peripheral blood circulation disorder, diabetic diarrhea], obesity, osteoporosis, cachexia (e.g., cancerous cachexia, tuberculous cachexia, diabetic cachexia, blood disease cachexia, endocrine disease cachexia, infectious disease cachexia or cachexia due to acquired immunodeficiency syndrome), fatty liver, hypertension, polycystic ovary syndrome, kidney disease (e.g., diabetic nephropathy, glomerular nephritis, glomerulosclerosis, nephrotic syndrome, hypertensive nephrosclerosis, end stage kidney disease, pyelonephritis, hydronephrosis), muscular dystrophy, myocardial infarction, angina pectoris, cerebrovascular accident (e.g., cerebral infarction, cerebral apoplexy), abnormal sugar metabolism, abnormal lipid metabolism, insulin resistance syndrome, Syndrome X, metabolic syndrome (according to the aforementioned report of WHO, state concurrently associated with at least one of type 2 diabetes, impaired glucose tolerance and insulin resistance, and at least two from obesity, abnormal lipid metabolism, hypertension and trace albumin urine), Cushing's syndrome, hyperinsulinemia, hyperinsulinemia-induced sensory disorder, tumor (e.g., leukemia, breast cancer, prostate cancer, skin cancer), irritable bowel syndrome, acute or chronic diarrhea, inflammatory diseases (e.g., chronic rheumatoid arthritis, spondylitis deformans, osteoarthritis, lumbago, gout, postoperative or traumatic inflammation, swelling, neuralgia, pharyngolaryngitis, cystitis, hepatitis (inclusive of non-alcoholic steatohepatitis), pneumonia, pancreatitis, inflammatory bowel disease, ulcerative colitis, stomach mucous membrane injury (including stomach mucous membrane injury caused by aspirin)), visceral fat syndrome, Alzheimer's disease, cerebrovascular dementia, depression and the like.

The compound of the present invention can also be used for improvement of insulin resistance, promotion or increase of insulin secretion, decrease of visceral fat, suppression of accumulation of visceral fat, improvement of sugar metabolism, improvement of lipid metabolism (including suppression of oxidative LDL production, improvement of lipoprotein metabolism, and lowering of blood remnant), improvement of coronary metabolism, prophylaxis or treatment of cardiovascular complication, prophylaxis or treatment of heart failure complication, prophylaxis or treatment of anovulation, prophylaxis or treatment of hirsutism, prophylaxis or treatment of hyperandrogenism, improvement of pancreatic (β cell) function, regeneration of pancreas (β cell), promotion of regeneration of pancreas (β cell) and the like.

The compound of the present invention can also be used for the secondary prevention and suppression of progression of various diseases mentioned above (e.g., cardiovascular event such as myocardial infarction etc.).

The compound of the present invention is particularly useful as an agent for the prophylaxis or treatment of type 2 diabetes, obese diabetes and the like.

While the dose of the compound of the present invention varies depending on the administration subject, administration route, target disease, condition and the like, the compound of the present invention is generally given in a single dose of about 0.01-100 mg/kg body weight, preferably 0.05-30 mg/kg body weight, more preferably 0.1-10 mg/kg body weight, in the case of, for example, oral administration to adult diabetic patients. This dose is desirably given 1 to 3 times a day.

The compound of the present invention can be used in combination with drugs such as a therapeutic agent for diabetes, a therapeutic agent for diabetic complications, a therapeutic agent for hyperlipidemia, an antihypertensive agent, an antiobestic agent, a diuretic, a chemotherapeutic agent, an immunotherapeutic agent, an antithrombotic agent, a therapeutic agent for osteoporosis, a antidementia agent, an erectile dysfunction improver, a therapeutic agent for pollakiuria or urinary incontinence, a therapeutic agent for dysuria and the like (hereinafter to be referred to as a combination drug). In this case, the timing of administration of the compound of the present invention and a combination drug is not limited. These may be simultaneously administered to an administration subject or administered in a staggered manner. Moreover, the compound of the present invention and a combination drug may be administered as two kinds of preparations each containing an active ingredient, or may be administered as a single preparation containing both active ingredients.

The dose of the combination drug can be determined as appropriate based on the dose clinically employed. The proportion of the compound of the present invention and the combination drug can be appropriately determined depending on the administration subject, administration route, target disease, condition, combination and the like. When, for example, the administration subject is human, the combination drug is used in an amount of 0.01-100 parts by weight per 1 part by weight of the compound of the present invention.

Examples of the therapeutic agents for diabetes include insulin preparations (e.g., animal insulin preparations extracted from pancreas of bovine and swine; human insulin preparations genetically synthesized using *Escherichia coli*, yeast; zinc insulin; protamine zinc insulin; fragment or derivative of insulin (e.g., INS-1 etc.), oral insulin preparation and the like), insulin sensitizers (e.g., pioglitazone or a salt thereof (preferably hydrochloride), rosiglitazone or a salt thereof (preferably maleate), Reglixane (JTT-501), Netoglitazone (MCC-555), DRF-2593, Edaglitazone (BM-13.1258), KRP-297, R-119702, Rivoglitazone (CS-011), FK-614, compounds described in WO99/58510 (e.g., (E)-4-[4-(5-methyl-2-phenyl-4-oxazolylmethoxy)benzyloxyimino]-4-phenylbutyric acid), compounds described in WO01/38325, Tesaglitazar (AZ-242), Ragaglitazar (N,N-622), Muraglitazar (BMS-298585), ONO-5816, LM-4156, Metaglidasen (MBX-102), Naveglitazar (LY-519818), MX-6054, LY-510929, Balaglitazone (N,N-2344), T-131 or a salt thereof, THR-0921), PPARγ agonists, PPARγ antagonists, PPARγ/α dual agonists, α-glucosidase inhibitors (e.g., voglibose, acarbose, miglitol, emiglitate etc.), biguanides (e.g., phenformin, metformin, buformin or a salt thereof (e.g., hydrochloride, fumarate, succinate)), insulin secretagogues [sulfonylurea (e.g., tolbutamide, glibenclamide, gliclazide, chlorpropamide, tolazamide, acetohexamide, glyclopyramide, glimepiride, glipizide, glybuzole), repaglinide, senaglinide, nateglinide, mitiglinide or calcium salt hydrate thereof], GPR40 agonists, GLP-1 receptor agonists [e.g., GLP-1, GLP-1MR agent, N,N-2211, AC-2993 (exendin-4), BIM-51077, Aib(8,35)hGLP-1 (7,37)NH$_2$, CJC-1131], amylin agonists (e.g., pramlintide), phosphotyrosine phosphatase inhibitors (e.g., sodium vanadate), dipeptidyl-peptidase IV inhibitors (e.g., NVP-DPP-278, PT-100, P32/98, Vidagliptin (LAF-237), P93/01, TS-021, Sitagliptin (MK-431), Saxagliptin (BMS-477118), Denagliptin (823093), T-6666), P3 agonists (e.g., AJ-9677), gluconeogenesis inhibitors (e.g., glycogen phosphorylase inhibitors, glucose-6-phosphatase inhibitors, glucagon antagonists), SGLT (sodium-glucose cotransporter) inhibitors (e.g., T-1095), 11β-HSD1 inhibitors (e.g., BVT-3498), adiponectin or agonists thereof, IKK inhibitors (e.g., AS-2868), leptin resistance improving drugs, somatostatin receptor agonists (compounds described in WO01/25228, WO03/42204, WO98/44921, WO98/45285 and WO99/22735) and the like.

Examples of the therapeutic agents for diabetic complications include aldose reductase inhibitors (e.g., Tolrestat, Epalrestat, Zenarestat, Zopolrestat, Minalrestat, Fidarestat, CT-112, ranirestst (AS-3201)), neurotrophic factors and increasing drugs thereof (e.g., NGF, NT-3, BDNF, neurotrophin production-secretion promoters described in WO01/14372 (e.g., 4-(4-chlorophenyl)-2-(2-methyl-1-imidazolyl)-5-[3-(2-methylphenoxy)propyl]oxazole)), stimulators (e.g., Y-128), PKC inhibitors (e.g., ruboxistaurin mesylate), AGE inhibitors (e.g., ALT-946, pimagedine, N-phenacylthiazolium bromide (ALT-766), ALT-711, EXO-226, Pyridorin, Pyridoxamine), active oxygen scavengers (e.g., thioctic acid), cerebral vasodilators (e.g., tiapuride, mexiletine), somatostatin receptor agonists (BIM23190), apoptosis signal regulating kinase-1 (ASK-1) inhibitors and the like.

Examples of the therapeutic agents for hyperlipidemia include HMG-CoA reductase inhibitors (e.g., pravastatin, simvastatin, lovastatin, atorvastatin, fluvastatin, pitavastatin, rosuvastatin and salts thereof (e.g., sodium salt, calcium salt)), squalene synthase inhibitors (e.g., compounds described in WO97/10224, such as N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl] acetyl]piperidine-4-acetic acid), fibrate compounds (e.g., bezafibrate, clofibrate, simfibrate, clinofibrate), ACAT inhibitors (e.g., Avasimibe, Eflucimibe), anion exchange resins (e.g., colestyramine), probucol, nicotinic acid drugs (e.g., nicomol, niceritrol), ethyl icosapentate, phytosterols (e.g., soysterol, γ-oryzanol) and the like.

Examples of the antihypertensive agents include angiotensin converting enzyme inhibitors (e.g., captopril, enalapril, delapril), angiotensin II antagonists (e.g., candesartan cilexetil, losartan, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid), calcium antagonists (e.g., manidipine, nifedipine, amlodipine, efonidipine, nicardipine), potassium channel openers (e.g., levcromakalim, L-27152, AL 0671, NIP-121), clonidine and the like.

Examples of the antiobesity agents include antiobesity agents acting on the central nervous system (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compounds described in WO01/82925 and WO01/87834); neuropeptide Y antagonists (e.g., CP-422935); cannabinoid receptor antagonists (e.g., SR-141716, SR-147778); ghrelin antagonists); pancreatic lipase inhibitors (e.g., orlistat, ATL-962), β3 agonists (e.g., AJ-9677), peptide anorexiants (e.g., leptin, CNTF (Ciliary Neurotropic Factor)), cholecystokinin agonists (e.g., lintitript, FPL-15849), feeding deterrents (e.g., P-57) and the like.

Examples of the diuretics include xanthine derivatives (e.g., sodium salicylate and theobromine, calcium salicylate and theobromine), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide), antialdosterone preparations (e.g., spironolactone, triamterene), carbonate dehydratase inhibitors (e.g., acetazolamide), chlorobenzenesulfonamide preparations (e.g., chlortalidone, mefruside, indapamide), azosemide, isosorbide, etacrynic acid, piretanide, bumetanide, furosemide and the like.

Examples of the chemotherapeutic agents include alkylating agents (e.g., cyclophosphamide, ifosfamide), metabolic antagonists (e.g., methotrexate, 5-fluorouracil and derivatives thereof), antitumor antibiotics (e.g., mitomycin, adriamycin), plant-derived antitumor agents (e.g., vincristine, vindesine, Taxol), cisplatin, carboplatin, etoposide and the like. Of these, Furtulon or NeoFurtulon, which are 5-fluorouracil derivatives, and the like are preferable.

Examples of the immunotherapeutic agents include microorganism or bacterial components (e.g., muramyl dipeptide derivatives, Picibanil), polysaccharides having immunity potentiating activity (e.g., lentinan, schizophyllan, krestin), cytokines obtained by genetic engineering techniques (e.g., interferon, interleukin (IL)), colony stimulating factors (e.g., granulocyte colony stimulating factor, erythropoietin) and the like, with preference given to interleukins such as IL-1, IL-2, IL-12 and the like.

Examples of the antithrombotic agents include heparin (e.g., heparin sodium, heparin calcium, dalteparin sodium), warfarins (e.g., warfarin potassium), anti-thrombin drugs (e.g., aragatroban), thrombolytic agents (e.g., urokinase, tisokinase, alteplase, nateplase, monteplase, pamiteplase), platelet aggregation inhibitors (e.g., ticlopidine hydrochloride, cilostazol, ethyl icosapentate, beraprost sodium, sarpogrelate hydrochloride) and the like.

Examples of the therapeutic agents for osteoporosis include alfacalcidol, calcitriol, elcatonin, calcitonin salmon, estriol, ipriflavone, risedronate disodium, pamidronate disodium, alendronate sodium hydrate, incadronate disodium and the like.

Examples of the antidementia agents include tacrine, donepezil, rivastigmine, galanthamine and the like.

Examples of the erectile dysfunction improvers include apomorphine, sildenafil citrate and the like.

Examples of the therapeutic agents for pollakiuria or urinary incontinence include flavoxate hydrochloride, oxybutynin hydrochloride, propiverine hydrochloride and the like.

Examples of the therapeutic agents for dysuria include acetylcholine esterase inhibitors (e.g., distigmine) and the like.

Furthermore, drugs having a cachexia-improving action established in animal models and clinical situations, such as cyclooxygenase inhibitors (e.g., indomethacin), progesterone derivatives (e.g., megestrol acetate), glucosteroids (e.g., dexamethasone), metoclopramide agents, tetrahydrocannabinol agents, fat metabolism improving agents (e.g., eicosapentanoic acid), growth hormones, IGF-1, or antibodies to a cachexia-inducing factor such as TNF-α, LIF, IL-6, oncostatin M and the like, can be used in combination with the compound of the present invention.

The combination drug is preferably insulin preparation, insulin sensitizer, α-glucosidase inhibitor, biguanide, insulin secretagogue (preferably sulfonylurea) and the like.

Two or more kinds of the above-mentioned combination drugs may be used in an appropriate ratio.

When the compound of the present invention is used in combination with a combination drug, the amount thereof can be reduced within a safe range in consideration of counteraction of these agents. Particularly, the dose of an insulin sensitizer, an insulin secretagogue (preferably a sulfonylurea) and a biguanide can be reduced as compared with the normal dose. Therefore, an adverse effect which may be caused by these agents can be prevented safely. In addition, the dose of the therapeutic agent for diabetic complications, therapeutic agent for hyperlipemia and antihypertensive agent can be reduced whereby an adverse effect which may be caused by these agents can be prevented effectively.

Compound (I) can be produced by, for example, the methods shown in the following Reaction Schemes 1 to 9 and 12.

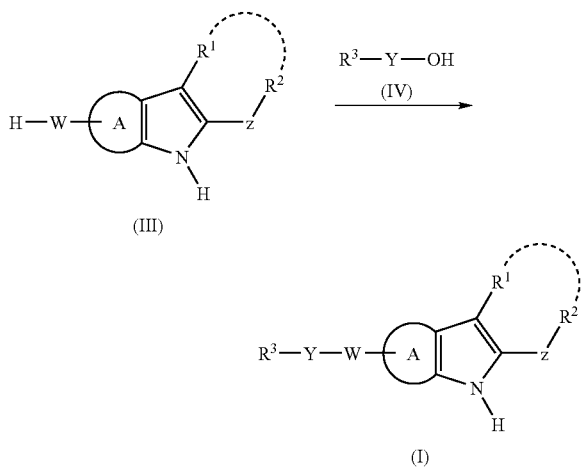

Reaction scheme 1 wherein each symbol is as defined above.

In this method, compound (I) can be produced by reacting compound (III) and compound (IV) (specifically sulfonic acid, sulfamic acid, carboxylic acid, carbonic acid monoester or carbamic acid) or a reactive derivative thereof.

A preferable reactive derivative of compound (IV) is shown in the following.

When compound (IV) is sulfonic acid, a preferable reactive derivative of the sulfonic acid is, for example, a general reactive derivative frequently used such as sulfonyl halide, sulfonic anhydride, N-sulfonyl imidazolide and the like, and particularly preferable example is sulfonyl halide.

When compound (IV) is sulfamic acid, a preferable reactive derivative of the sulfamic acid is, for example, a general reactive derivative frequently used such as sulfamyl halide.

When compound (IV) is carboxylic acid, a preferable reactive derivative of the carboxylic acid is, for example, acid chloride, acid anhydride, activated amide, activated ester and the like. Specifically, acid chloride, mixed acid anhydride, symmetric acid anhydride, activated amide with imidazole and the like, activated ester with N-hydroxy compound such as 1-hydroxy-1H-benzotriazole and the like, and the like can be mentioned. These reactive derivatives can be selected freely according to the kind of carboxylic acid to be used.

When compound (IV) is carbonic acid monoester, a preferable reactive derivative of the carbonic acid monoester is, for example, a general reactive derivative frequently used such as halocarbonate and dicarbonic acid diester.

When compound (IV) is carbamic acid, a preferable reactive derivative of the carbamic acid is, for example, a general reactive derivative frequently used such as carbamoyl halide and isocyanic acid ester.

This reaction may be performed in the presence of a base. Examples of the base include alkali metal hydroxide such as lithium hydroxide, sodium hydroxide, potassium hydroxide and the like; alkaline earth metal hydroxide such as magnesium hydroxide, calcium hydroxide and the like; alkali metal carbonate such as sodium carbonate, potassium carbonate and the like; alkali metal hydrogen carbonate such as sodium hydrogen carbonate, potassium hydrogen carbonate and the like; alkali metal $C_{1-6}$ alkoxide such as sodium methoxide, sodium ethoxide, potassium tert-butoxide and the like; organic base such as trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like; organic lithium such as methyl lithium, n-butyl lithium, sec-butyl lithium, tert-butyl lithium and the like; lithium amide such as lithium diisopropylamide, etc. and the like.

This reaction is preferably performed in a solvent inert to the reaction. Such solvent is not particularly limited as long as the reaction proceeds. For example, alcohols such as methanol, ethanol, propanol, isopropanol, butanol, tert-butanol and the like; ethers such as 1,4-dioxane, tetrahydrofuran, diethyl ether, tert-butyl methyl ether, diisopropyl ether, 1,2-dimethoxyethane and the like; esters such as ethyl formate, ethyl acetate, n-butyl acetate and the like; halogenated hydrocarbons such as dichloromethane, chloroform, carbon tetrachloride, trichloroethylene and the like; hydrocarbons such as n-hexane, benzene, toluene and the like; amides such as formamide, N,N-dimethylformamide, N,N-dimethylacetamide and the like; nitriles such as acetonitrile, propionitrile and the like; sulfoxides such as dimethylsulfoxide and the like; sulfolane; hexamethyl phosphoramide; water and the like can be mentioned. Two or more kinds of these solvents may be mixed at appropriate ratios for use.

In this reaction, when carboxylic acid is used in the form of a free acid or a salt thereof, the reaction is desirably performed in the presence of a conventionally-used condensation agent such as N,N'-dialkylcarbodiimide; diphenylphosphoryl azide; lower alkyl haloformate such as ethyl chloroformate, isopropyl chloroformate and the like; N-hydroxybenzotriazole; a so-called Vilsmeier reagent prepared by a reaction of N,N'-dimethylformamide and thionyl chloride, phosgene, trichloromethyl chloroformate, phosphorus oxychloride and the like, and the like.

The amount of compound (IV) or a reactive derivative thereof to be used is generally 1 to 10 mols, preferably 1 to 3 mols, per 1 mol of compound (III). The amount of the base to be used is generally 1 to 10 mols, preferably 1 to 3 mols, per 1 mol of compound (III).

The reaction temperature is generally from −30° C. to 100° C. The reaction time is generally 0.5 hr to 20 hr.

Compound (IV) or a reactive derivative thereof to be used as a starting material in Reaction Scheme 1 can be produced according to a method known per se.

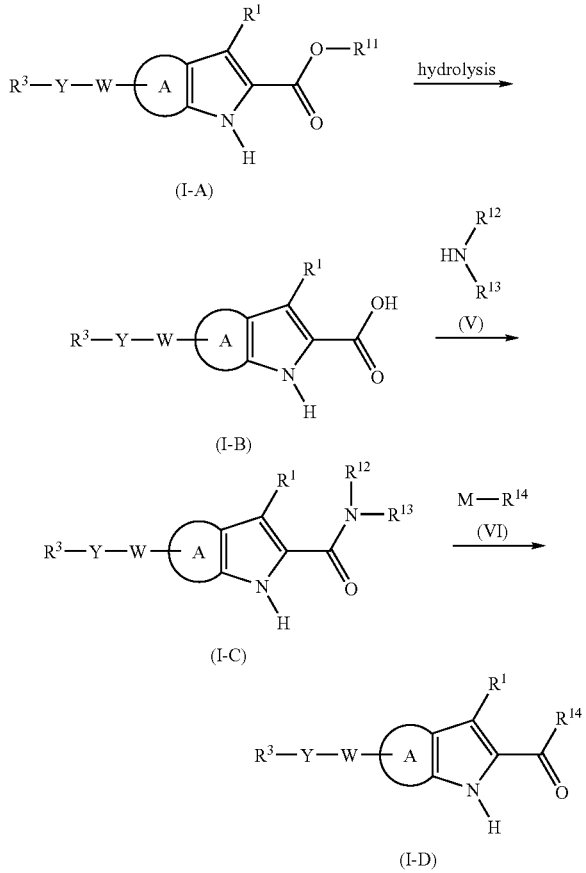

wherein $R^{11}$ is $C_{1-6}$ alkyl group, $R^{12}$ and $R^{13}$ are each independently hydrogen atom or substituent, $R^{14}$ is optionally substituted hydrocarbon group, M is metal (e.g., potassium, sodium, lithium, magnesium, copper, mercury, zinc, thallium, boron, tin and the like, which may form a complex), and other symbols are as defined above.

As the "substituent" for $R^{12}$ or $R^{13}$, those recited as examples of the substituent of the "optionally substituted amino group" for $R^2$ can be mentioned.

As the "optionally substituted hydrocarbon group" for $R^{14}$, those recited as $R^2$ can be mentioned.

Compound (I-B) can be produced by subjecting compound (I-A) to a hydrolysis. The hydrolysis is performed according to a conventional method using an acid or base.

Examples of the acid include mineral acids such as hydrochloric acid, sulfuric acid and the like; Lewis acids such as boron trichloride, boron tribromide and the like; organic acids such as trifluoroacetic acid, p-toluenesulfonic acid, etc. and the like. The Lewis acid can also be used in combination with thiol or sulfide.

Examples of the base include alkali metal hydroxide such as lithium hydroxide, sodium hydroxide, potassium hydroxide, barium hydroxide and the like; alkali metal carbonate such as sodium carbonate, potassium carbonate and the like; alkali metal $C_{1-6}$ alkoxide such as sodium methoxide, sodium ethoxide, potassium tert-butoxide and the like; organic bases such as triethylamine, imidazole, formamidine, etc. and the like.

The amount of these acids and bases to be used is generally about 0.5 to 10 mols, preferably about 0.5 to 6 mols, per 1 mol of compound (I-A).

The hydrolysis is performed without solvent or in a solvent inert to the reaction. Such solvent is not particularly limited as long as the reaction proceeds. For example, alcohols such as methanol, ethanol, propanol and the like; aromatic hydrocarbons such as benzene, toluene and the like; saturated hydrocarbons such as cyclohexane, hexane and the like; organic acids such as formic acid, acetic acid and the like; ethers such as tetrahydrofuran, 1,4-dioxane, 1,2-dimethoxyethane and the like; amides such as N,N-dimethylformamide, N,N-dimethylacetamide and the like; halogenated hydrocarbons such as dichloromethane, chloroform, carbon tetrachloride, 1,2-dichloroethane and the like; nitriles such as acetonitrile, propionitrile and the like; ketones such as acetone, methylethylketone and the like; sulfoxides such as dimethylsulfoxide and the like; water and the like can be mentioned. Two or more kinds of these solvents may be mixed at appropriate ratios for use.

The reaction time is generally from 10 min to 60 hr, preferably from 10 min to 12 hr. The reaction temperature is generally from −10° C. to 200° C., preferably from 0° C. to 120° C.

Compound (I-C) can be produced by reacting compound (I-B) or a reactive derivative in carboxy group thereof or a salt thereof with compound (V).

Examples of the reactive derivative in a carboxy group of compound (I-B) include
1) acid chloride;
2) acid azide;
3) mixed acid anhydride with acid (e.g., substituted phosphoric acid such as dialkylphosphoric acid, phenylphosphoric acid, diphenylphosphoric acid, dibenzylphosphoric acid, halogenated phosphoric acid and the like; dialkylphosphorous acid; sulfurous acid; thiosulfuric acid; sulfuric acid; sulfonic acid such as methanesulfonic acid and the like; aliphatic carboxylic acid such as formic acid, acetic acid, propionic acid, butyric acid, isobutyric acid, pivalic acid, pentanoic acid, isopentanoic acid, trichloroacetic acid and the like; aromatic carboxylic acid such as benzoic acid and the like);
4) symmetric acid anhydride;
5) activated amide with imidazole, 4-substituted imidazole, dimethylpyrazole, triazole or tetrazole;
6) for example, activated ester such as cyanomethyl ester, methoxymethyl ester, dimethyliminomethyl ester, vinyl ester, propargyl ester, p-nitrophenyl ester, trichlorophenyl ester, pentachlorophenyl ester, mesylphenyl ester, phenylazophenyl ester, phenyl thioester, p-nitrophenyl ester, p-cresyl thioester, carboxymethyl thioester, pyranyl ester, pyridyl ester, piperidyl ester, 8-quinolyl thioester and the like;
7) ester with N-hydroxy compound (e.g., N,N-dimethylhydroxyamine, 1-hydroxy-2-(1H)-pyridone, N-hydroxysuccinimide, N-hydroxyphthalimide, 1-hydroxy-1H-benzotriazole); and the like. These reactive derivatives can be freely selected according to the kind of compound (I-B) to be used.

Preferable salts of the reactive derivative of compound (I-B) include basic salts such as alkali metal salt such as sodium salt, potassium salt and the like; alkaline earth metal salt such as calcium salt, magnesium salt and the like; ammonium salt; organic base salt such as trimethylamine salt, triethylamine salt, pyridine salt, picoline salt, dicyclohexylamine salt, N,N-dibenzylethylenediamine salt and the like; and the like.

This reaction is preferably performed in a solvent inert to the reaction. As such solvent, those exemplified for the reaction of compound (III) and compound (IV) shown in Reaction Scheme 1 can be mentioned.

In this reaction, when compound (I-B) is used in the form of a free acid or a salt thereof, the reaction is desirably performed in the presence of a conventionally-used condensation agent, for example, carbodiimide such as N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide and the like; N,N'-carbonylbis(2-methylimidazole); trialkyl phosphite; polyphosphate such as ethyl polyphosphate, isopropyl polyphosphate and the like; phosphorus oxychloride; diphenylphosphoryl azide; thionyl chloride; oxalyl chloride; lower alkyl haloformate such as ethyl chloroformate, isopropyl chloroformate and the like; triphenylphosphine; N-hydroxybenzotriazole; 1-(p-chlorobenzenesulfonyloxy)-6-chloro-1H-benzotriazole; a so-called Vilsmeier reagent prepared by a reaction of N,N'-dimethylformamide and thionyl chloride, phosgene, trichloromethyl chloroformate, phosphorus oxychloride and the like, and the like.

Where desired, this reaction may be performed in the presence of a base. As such base, those exemplified for the reaction of compound (III) and compound (IV) shown in Reaction Scheme 1 can be mentioned.

The amount of compound (V) to be used is generally 1 to 10 mols, preferably 1 to 3 mols, per 1 mol of compound (I-B). The amount of the base to be used is generally 1 to 10 mols, preferably 1 to 3 mols, per 1 mol of compound (I-B).

The reaction temperature is generally from −30° C. to 100° C. The reaction time is generally 0.5 hr to 20 hr.

When a mixed acid anhydride is used as a reactive derivative of compound (I-B), compound (I-B) and chloroformate (e.g., methyl chloroformate, ethyl chloroformate isobutyl chloroformate) may be reacted in the presence of a base (e.g., triethylamine, N-methylmorpholine, N,N-dimethylaniline, sodium hydrogen carbonate, sodium carbonate, potassium carbonate) and then further reacted with compound (V).

This reaction is preferably performed in a solvent inert to the reaction. Such solvent is not particularly limited as long as the reaction proceeds. For example, ethers such as 1,4-dioxane, tetrahydrofuran, diethyl ether, tert-butyl methyl ether, diisopropyl ether, 1,2-dimethoxyethane and the like; esters such as ethyl formate, ethyl acetate, n-butyl acetate and the like; halogenated hydrocarbons such as dichloromethane, chloroform, carbon tetrachloride, trichloroethylene and the like; hydrocarbons such as n-hexane, benzene, toluene and the like; amides such as formamide, N,N-dimethylformamide, N,N-dimethylacetamide and the like; nitriles such as acetonitrile, propionitrile, etc. and the like; sulfoxides such as dimethylsulfoxide and the like; sulfolane; hexamethyl phosphoramide and the like can be mentioned. Two or more kinds of these solvents may be mixed at appropriate ratios for use.

The amount of compound (V) to be used is generally, 1 to 10 mols, preferably 1 to 3 mols, per 1 mol of compound (I-B).

The reaction temperature is generally from −30° C. to 100° C. The reaction time is generally 0.5 hr to 20 hr.

Compound (I-D) can be produced by reacting compound (I-C) with compound (VI).

Preferable examples of compound (VI) include organic lithiums such as methyl lithium, n-butyl lithium, phenyl lithium and the like; Grignard reagents such as methyl magnesium bromide, methyl magnesium chloride, phenyl magnesium bromide and the like.

This reaction is preferably performed in a solvent inert to the reaction. Such solvent is not particularly limited as long as the reaction proceeds. For example, ethers such as 1,4-dioxane, tetrahydrofuran, diethyl ether, tert-butyl methyl ether, diisopropyl ether, 1,2-dimethoxyethane and the like; hydrocarbons such as n-hexane, benzene, toluene, etc. and the like can be mentioned. Two or more kinds of these solvents may be mixed at appropriate ratios for use.

The amount of compound (VI) to be used is generally 1 to 10 mols, preferably 1 to 3 mols, per 1 mol of compound (I-C).

The reaction temperature is generally from −30° C. to 100° C.

The reaction time is generally 0.5 hr to 20 hr.

Compound (I-A) to be used as a starting material in Reaction Scheme 2 can be produced according to the method shown in the aforementioned Reaction Scheme 1. Compounds (V) and (VI) can be produced according to a method known per se.

$C_{6-10}$ arylsulfonyloxy group optionally having 1 to 3 substituents selected from $C_{1-6}$ alkyl group, a $C_{1-6}$ alkoxy group and a nitro group (e.g., phenylsulfonyloxy, m-nitrophenylsulfonyloxy, p-toluenesulfonyloxy); a $C_{1-6}$ alkoxysulfonyloxy group; a $C_{6-10}$ aryloxysulfonyloxy group; a $C_{1-6}$ alkoxy group; a di-$C_{1-6}$ alkylamino group and the like.

Compound (I-F) can be produced by reacting compound (I-C1) in the presence of a base.

As such base, those exemplified for the reaction of compound (III) and compound (IV) shown in Reaction Scheme 1 can be mentioned.

This reaction is preferably performed in a solvent inert to the reaction. As such solvent, those exemplified for the reaction of compound (III) and compound (IV) shown in Reaction Scheme 1 can be mentioned.

The amount of the base to be used is generally 1 to 10 mols, preferably 1 to 3 mols, per 1 mol of compound (I-C1).

The reaction temperature is generally from −30° C. to 100° C. The reaction time is generally 0.5 hr to 20 hr.

Compound (I-C1) to be used as a starting material in Reaction Scheme 3 can be produced according to the method shown in the aforementioned Reaction Scheme 1.

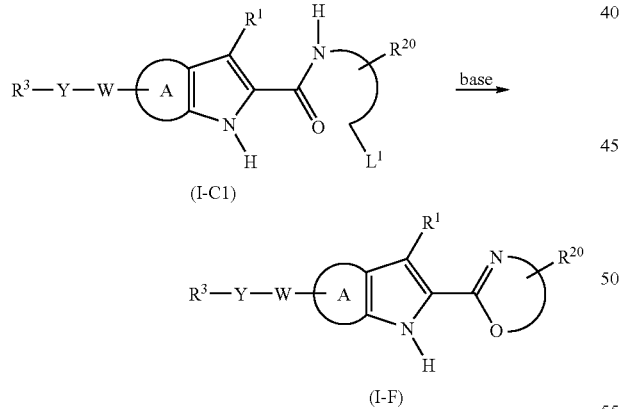

Reaction scheme 3

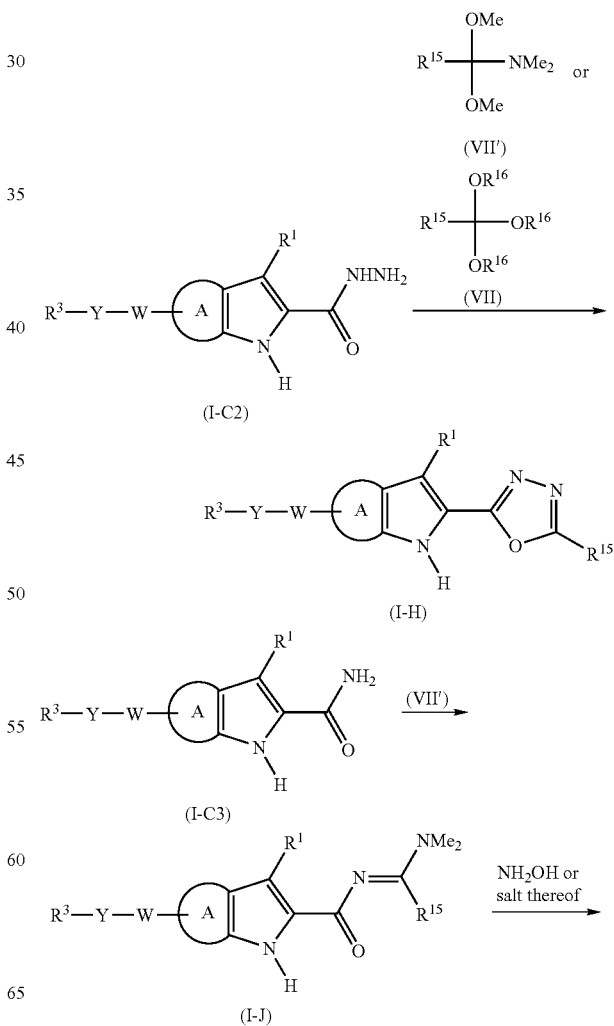

Reaction scheme 4 wherein $R^{20}$ is hydrogen atom or substituent, $L^1$ is leaving group, and other symbols are as defined above.

As the "substituent" for $R^{20}$, those recited as examples of the substituent of the "optionally substituted heterocyclic group" for $R^2$ can be mentioned. $R^{20}$ in the number of 1 to 6 may substitute any position(s). When two or more $R^{20}$ are present, the kind of $R^{20}$ may be different from each other.

Examples of the "leaving group" for $L^1$ include a halogen atom; an optionally halogenated $C_{1-6}$ alkylsulfonyloxy group (e.g., methanesulfonyloxy, ethanesulfonyloxy, trichloromethanesulfonyloxy, trifluoromethanesulfonyloxy); a -continued

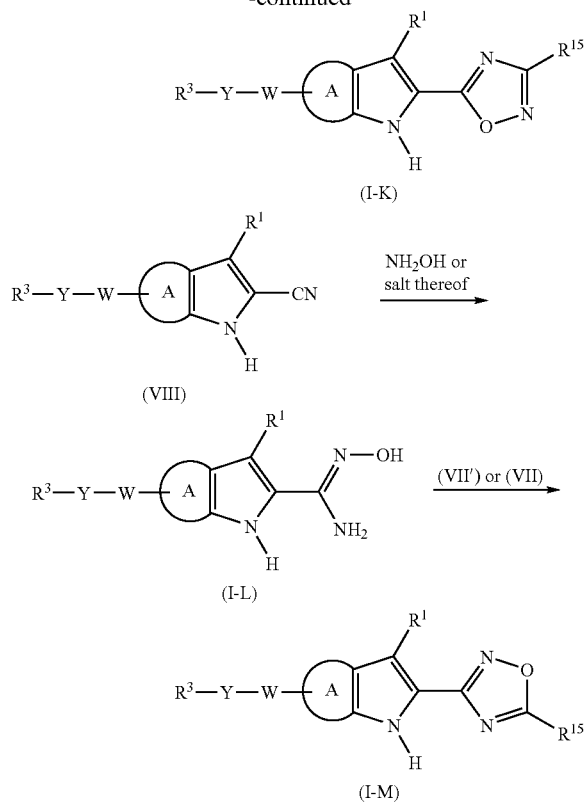

wherein $R^{15}$ is hydrogen atom or substituent, $R^{16}$ is $C_{1-6}$ alkyl group, and other symbols are as defined above.

As the "substituent" for $R^{15}$, those recited as examples of the substituent of the "optionally substituted heterocyclic group" for $R^2$ can be mentioned.

Compound (I-H) can be produced by reacting compound (I-C2) with compound (VII') or compound (VII).

This reaction is performed without solvent or in a solvent inert to the reaction. Such solvent is not particularly limited as long as the reaction proceeds. For example, ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethyl phosphoramide, etc. and the like can be mentioned. Two or more kinds of these solvents may be mixed at appropriate ratios for use.

In this reaction, the reaction can be promoted by generally using an acid catalyst. Examples of the acid catalyst include mineral acid such as hydrochloric acid, sulfuric acid and the like; Lewis acid such as boron trihalide (e.g., boron trichloride, boron trifluoride), titanium tetrahalide (e.g., titanium tetrachloride, titanium tetrabromide), aluminum halide (e.g., aluminum chloride, aluminum bromide) and the like; organic acid such as acetic acid, formic acid, trifluoroacetic acid, etc. and the like.

The amount of compound (VII') or compound (VII) and acid catalyst to be used is generally 1 to 10 mols, preferably 1 to 3 mols, per 1 mol of compound (I-C2), respectively.

While the reaction time varies depending on the kind and amount of compound (I-C2), compound (VII') or compound (VII), and an acid catalyst, it is generally about 1 hr to about 100 hr, preferably about 1 hr to about 50 hr. The reaction temperature is generally about −20° C. to about 120° C., preferably about 0° C. to about 80° C.

Compound (I-K) can be produced in two steps from compound (I-C3) according to a method described in Journal of Organic chemistry (J. Org. Chem.), 1984, vol. 49, page 4800.

In Step 1, compound (I-J) can be produced by reacting compound (I-C3) with compound (VII') without solvent or in a solvent inert to the reaction.

As the solvent to be used for this reaction, those exemplified for the aforementioned reaction of compound (I-C2) with compound (VII') or compound (VII) can be mentioned.

The amount of compound (VII') to be used is generally 1 to 10 mols, preferably 1 to 3 mols, per 1 mol of compound (I-C 3).

The reaction temperature is generally from −30° C. to 100° C. The reaction time is generally 0.5 hr to 20 hr.

In Step 2, compound (I-K) can be produced by reacting compound (I-J) with hydroxylamine or a salt thereof.

This reaction is performed without solvent or in a solvent inert to the reaction. As such solvent, those exemplified for the aforementioned reaction of compound (I-C2) with compound (VII') or compound (VII) can be mentioned.

When desired, this reaction may be performed in the presence of a base. As such base, for example, organic base such as triethylamine, pyridine, 4-dimethylaminopyridine, diisopropylethylamine and the like; inorganic base such as sodium hydroxide, potassium hydroxide, sodium carbonate, potassium carbonate, etc. and the like can be mentioned.

The amount of hydroxylamine or a salt thereof, and the base to be used is each generally 1 to 10 mols, preferably 1 to 3 mols, per 1 mol of compound (I-J).

The reaction temperature is generally from −30° C. to 100° C. The reaction time is generally 0.5 hr to 20 hr.

Compound (I-M) can be produced in two steps from compound (VIII).

In Step 1, compound (I-L) can be produced by reacting compound (VIII) with hydroxylamine or a salt thereof according to the methods described in Journal of Heterocyclic Chemistry (J. Heterocycl. Chem.), 1987, vol. 24, page 863, Bioorganic Medicinal Chemistry Letters (Bioorg. Med. Chem. Lett.), 2003, vol. 13, page 2029 and the like.

When desired, this reaction is performed in the presence of an acid catalyst or a base. Examples of the acid catalyst include mineral acid such as hydrochloric acid, sulfuric acid and the like; organic acid such as acetic acid, formic acid, trifluoroacetic acid and the like. Examples of the base include alkali metal hydroxide such as lithium hydroxide, sodium hydroxide, potassium and the like; alkaline earth metal hydroxide such as magnesium hydroxide, calcium hydroxide and the like; alkali metal carbonate such as sodium carbonate, potassium carbonate and the like; alkali metal hydrogen carbonate such as sodium hydrogen carbonate, potassium hydrogen carbonate and the like; alkali metal $C_{1-6}$ alkoxide such as sodium methoxide, sodium ethoxide, potassium tert-butoxide and the like; organic bases such as trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene, etc. and the like.

This reaction is performed without solvent or in a solvent inert to the reaction. As such solvent, those exemplified for the reaction of compound (III) and compound (IV) shown in Reaction Scheme 1 can be mentioned.

The amount of hydroxylamine or a salt thereof, and acid catalyst or base to be used is generally 1 to 10 mols, preferably 1 to 3 mols, per 1 mol of compound (VIII).

The reaction temperature is generally from −30° C. to 100° C. The reaction time is generally 0.5 hr to 20 hr.

In Step 2, compound (I-M) can be produced by reacting compound (I-L) with compound (VII') or compound (VII).

This reaction is performed without solvent or in a solvent inert to the reaction. As such solvent, those exemplified for the reaction of compound (III) and compound (IV) shown in Reaction Scheme 1 can be mentioned.

The amount of compound (VII') or compound (VII) to be used is generally 1 to 10 mols, preferably 1 to 3 mols, per 1 mol of compound (I-L).

The reaction temperature is generally from −30° C. to 100° C. The reaction time is generally 0.5 hr to 20 hr.

Compounds (I-C2) and (I-C3) to be used as starting materials in Reaction Scheme 4 can be produced, for example, according to the method shown in the aforementioned Reaction Scheme 1. In addition, compounds (VII'), (VII) and (VIII) can be produced according to a method known per se.

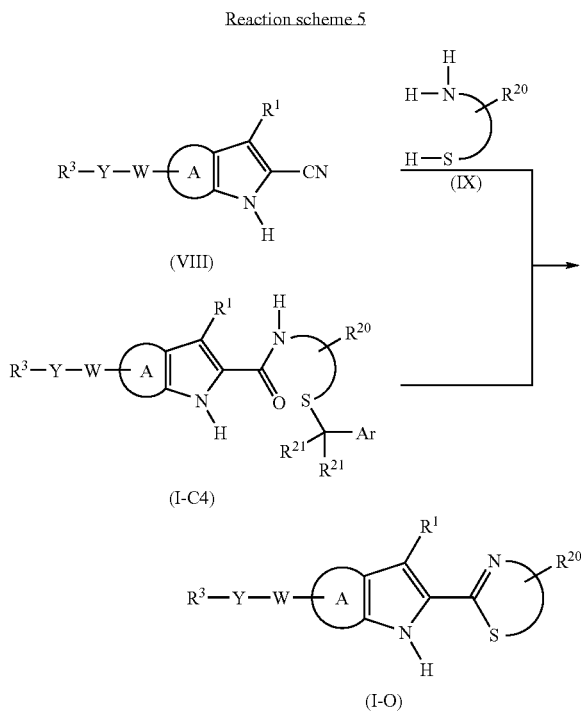

Reaction scheme 5 wherein $R^{21}$ is hydrogen atom or phenyl group, Ar is phenyl group or 4-methoxyphenyl group, and other symbols are as defined above.

Compound (I-O) can be produced by reacting compound (VIII) with compound (IX) according to a method described in European Journal of Medicinal Chemistry (Eur. J. Med. Chem.), 1993, vol. 28, page 29.

This reaction is performed without solvent or in a solvent inert to the reaction. Such solvent is not particularly limited as long as the reaction proceeds. For example, ethers such as 1,4-dioxane, tetrahydrofuran, diethyl ether, tert-butyl methyl ether, diisopropyl ether, 1,2-dimethoxyethane and the like; esters such as ethyl formate, ethyl acetate, n-butyl acetate and the like; halogenated hydrocarbons such as dichloromethane, chloroform, carbon tetrachloride, trichloroethylene and the like; hydrocarbons such as n-hexane, benzene, toluene and the like; nitrites such as acetonitrile, propionitrile, etc. and the like can be mentioned. Two or more kinds of these solvents may be mixed at appropriate ratios for use.

When desired, this reaction may be performed in the presence of an acid catalyst. As the acid catalyst, those exemplified for the reaction of compound (I-C2) with compound (VII') or compound (VII) as shown in Reaction Scheme 4 can be mentioned.

The amount of compound (IX) and acid catalyst to be used is generally 1 to 10 mols, preferably 1 to 3 mols, per 1 mol of compound (VIII), respectively.

The reaction temperature is generally from −30° C. to 100° C. The reaction time is generally 0.5 hr to 20 hr.

Compound (I-O) can also be produced from compound (I-C4) according to the methods described in Angewante Chemie, Intrenational Edition (Angew. Chem., Int. Ed.), 2003, vol. 42, page 83, Tetrahedron (Tetrahedron), 1999, vol. 55, page 10271 and the like.

In this reaction, compound (I-C4) is reacted with triphenylphosphine oxide and trifluoromethanesulfonic anhydride or phosphorus pentachloride.

This reaction is performed without solvent or in a solvent inert to the reaction. Such solvent is not particularly limited as long as the reaction proceeds. For example, ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane, etc. and the like can be mentioned. Two or more kinds of these solvents may be mixed at appropriate ratios for use.

The amount of compound (I-C4), triphenylphosphine oxide, and trifluoromethanesulfonic anhydride or phosphorus pentachloride to be used is generally 1 to 10 mols, preferably 1 to 6 mols, per 1 mol of compound (I-C4).

The reaction temperature is generally from −30° C. to 100° C. The reaction time is generally 0.5 hr to 20 hr.

Compound (I-C4) to be used as a starting material in Reaction Scheme 5 can be produced, for example, according to the method shown in the aforementioned Reaction Scheme 1. In addition, compounds (IX) can be produced according to a method known per se.

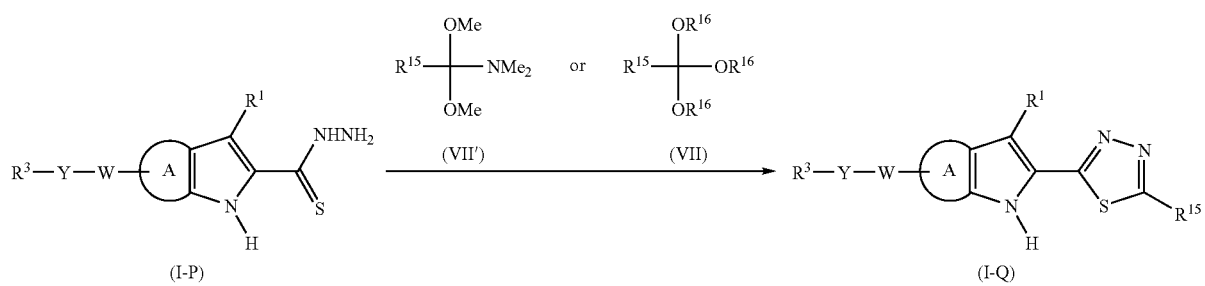

Reaction scheme 6

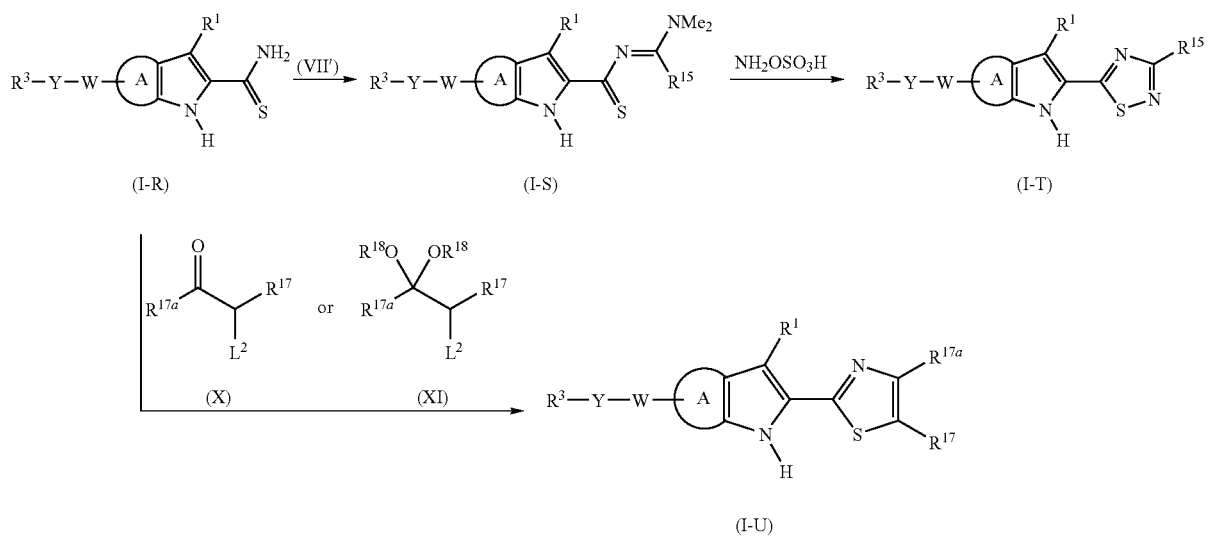

wherein $R^{17a}$ and $R^{17}$ are each independently hydrogen atom or substituent, $R^{18}$ is $C_{1-6}$ alkyl group, $L^2$ is leaving group, and other symbols are as defined above.

As the "substituent" for $R^{17a}$ or $R^{17}$, those recited as examples of the substituent of the "optionally substituted heterocyclic group" for $R^2$ can be mentioned.

As the "leaving group" for $L^2$, those recited as examples of the aforementioned $L^1$ can be mentioned.

Compound (I-Q) can be produced by reacting compound (I-P) with compound (VII') or compound (VII).

This reaction is performed without solvent or in a solvent inert to the reaction. As such solvent, those exemplified for the reaction of compound (I-C2) with compound (VII') or compound (VII) as shown in Reaction Scheme 4 can be mentioned.

In this reaction, the reaction can be generally promoted using an acid catalyst. As the acid catalyst, those exemplified for the reaction of compound (I-C2) with compound (VII') or compound (VII) as shown in Reaction Scheme 4 can be mentioned.

The amount of compound (VII') or compound (VII), and acid catalyst to be used is generally 1 to 10 mols, preferably 1 to 3 mols, per 1 mol of compound (I-P).

The reaction temperature is generally from –30° C. to 100° C. The reaction time is generally 0.5 hr to 20 hr.

Compound (I-T) can be produced in two steps from compound (I-R) according to the method described in Journal Organic Chemistry (J. Org. Chem.), 1984, vol. 49, page 4800.

In Step 1, compound (I-S) can be produced by reacting compound (I-R) with compound (VII') without solvent or in a solvent inert to the reaction.

As the solvent to be used for this reaction, those exemplified for the reaction of compound (I-C2) with compound (VII') or compound (VII) as shown in Reaction Scheme 4 can be mentioned.

The amount of compound (VII') to be used is generally 1 to 10 mols, preferably 1 to 3 mols, per 1 mol of compound (I-R).

The reaction temperature is generally from –30° C. to 100° C. The reaction time is generally 0.5 hr to 20 hr.

In Step 2, compound (I-T) can be produced by reacting compound (I-S) with hydroxylamine-O-sulfonic acid.

When desired, this reaction is performed in the presence of a base. As the base, those exemplified for the reaction of compound (VIII) with hydroxylamine or a salt thereof shown in Reaction Scheme 4 can be mentioned.

This reaction is performed without solvent or in a solvent inert to the reaction. As such solvent, those exemplified for the reaction of compound (I-C2) with compound (VII') or compound (VII) as shown in Reaction Scheme 4 can be mentioned.

The amount of hydroxylamine-O-sulfonic acid and base to be used is generally 1 to 10 mols, preferably 1 to 3 mols, per 1 mol of compound (I-S).

The reaction temperature is generally from –30° C. to 100° C. The reaction time is generally 0.5 hr to 20 hr.

Compound (I-U) can be produced by reacting compound (I-R) with compound (X) or compound (XI).

When desired, this reaction is performed in the presence of a base. Examples of the base include organic base such as triethylamine, pyridine, 4-dimethylaminopyridine, diisopropylethylamine and the like; inorganic base such as sodium hydroxide, potassium hydroxide, sodium carbonate, potassium carbonate, etc. and the like.

This reaction is performed without solvent or in a solvent inert to the reaction. As such solvent, those exemplified for the reaction of compound (I-C2) with compound (VII') or compound (VII) as shown in Reaction Scheme 4 can be mentioned.

The amount of compound (X) or compound (XI), and base to be used is generally 1 to 10 mols, preferably 1 to 3 mols, per 1 mol of compound (I-R).

The reaction temperature is generally from –30° C. to 100° C. The reaction time is generally 0.5 hr to 20 hr.

Compounds (I-P) and (I-R) to be used as starting materials in Reaction Scheme 6 can be produced, for example, according to the method shown in the aforementioned Reaction Scheme 1. In addition, compounds (X) and (XI) can be produced according to a method known per se.

Compound (I-Q) can also be produced by the method shown in the following Reaction Scheme 6A.

Reaction scheme 6A

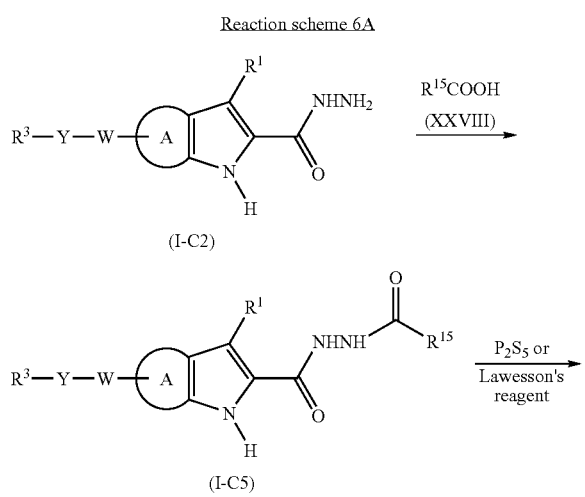

(I-C2)

(I-C5)

-continued

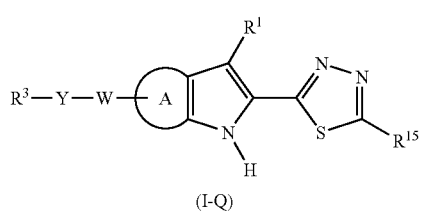

(I-Q)

wherein each symbol is as defined above.

Compound (I-C5.) can be produced by reacting compound (I-C 2) with compound (XXVIII) or a reactive derivative thereof.

As the reactive derivative of compound (XXVIII), those exemplified as the reactive derivative of compound (I-B) in carboxy group can be mentioned.

This reaction is performed in the same manner as in the reaction of compound (I-B) or a reactive derivative thereof in carboxy group or a salt thereof with compound (V) as shown in Reaction Scheme 2.

Compound (I-Q) can be produced by reacting compound (I-C 5) with diphosphorus pentasulfide or Lawesson's reagent.

This reaction is performed in the same manner as in the reaction of compound (I-C3) with diphosphorus pentasulfide or Lawesson's reagent as shown in the following Reaction Scheme 7.

Compound (XXVIII) to be used as a starting material in Reaction Scheme 6A can be produced according to a method known per se.

Reaction scheme 7

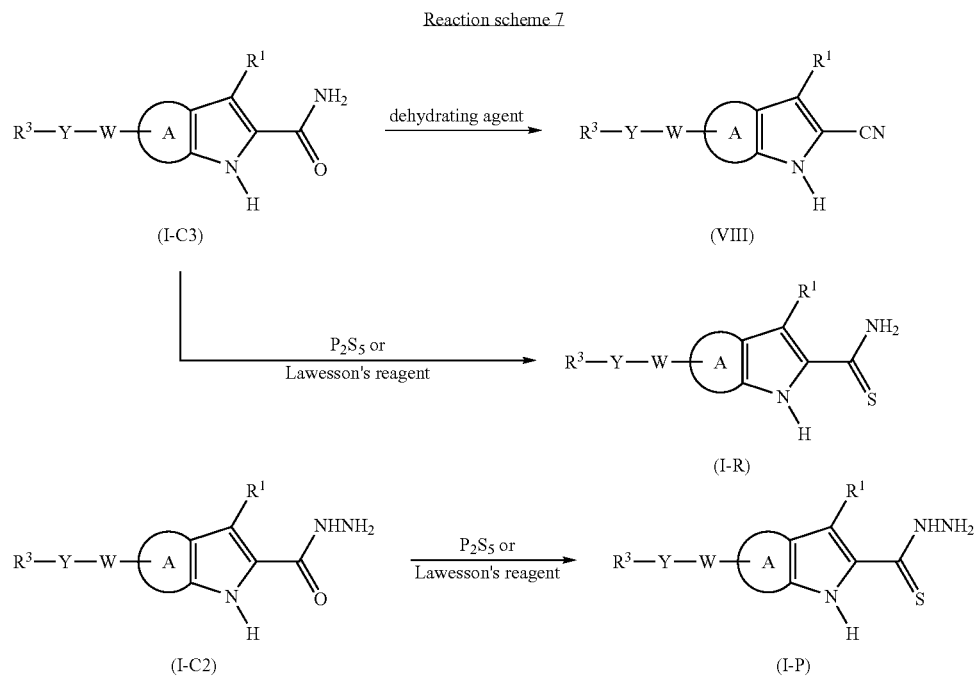

wherein each symbol is as defined above.

Compound (VIII) can be produced by reacting compound (I-C 3) with a dehydrating agent.

Examples of the dehydrating agent include acetic anhydride, trifluoroacetic anhydride, phosphorus pentaoxide, phosphorus pentachloride, phosphorus oxychloride, thionyl chloride, 1,3-dicyclohexyl carbodiimide and the like.

When desired, this reaction is performed in the presence of a base. Examples of the base include organic base such as triethylamine, pyridine, 4-dimethylaminopyridine, diisopropylethylamine and the like; inorganic base such as sodium carbonate, potassium carbonate, etc. and the like.

This reaction is performed without solvent or in a solvent inert to the reaction. As such solvent, those exemplified for the reaction of compound (I-C2) with compound (VII') or compound (VII) as shown in Reaction Scheme 4 can be mentioned.

The amount of the dehydrating agent and base to be used is generally 1 to 10 mols, preferably 1 to 3 mols, per 1 mol of compound (I-C3).

The reaction temperature is generally from −30° C. to 100° C. The reaction time is generally 0.5 hr to 20 hr.

Compound (I-R) can be produced by reacting compound (I-C 3) with diphosphorus pentasulfide or Lawesson's reagent.

This reaction is performed without solvent or in a solvent inert to the reaction. Such solvent is not particularly limited as long as the reaction proceeds. For example, ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane, etc. and the like can be mentioned. Two or more kinds of these solvents may be mixed at appropriate ratios for use.

The amount of diphosphorus pentasulfide or Lawesson's reagent to be used is generally 1 to 10 mols, preferably 1 to 3 mols, per 1 mol of compound (I-C3).

The reaction temperature is generally from −30° C. to 100° C. The reaction time is generally 0.5 hr to 20 hr.

Compound (I-P) can be produced by reacting compound (I-C 2) with diphosphorus pentasulfide or Lawesson's reagent. This reaction is performed in the same manner as in the aforementioned reaction of compound (I-C3) with diphosphorus pentasulfide or Lawesson's reagent.

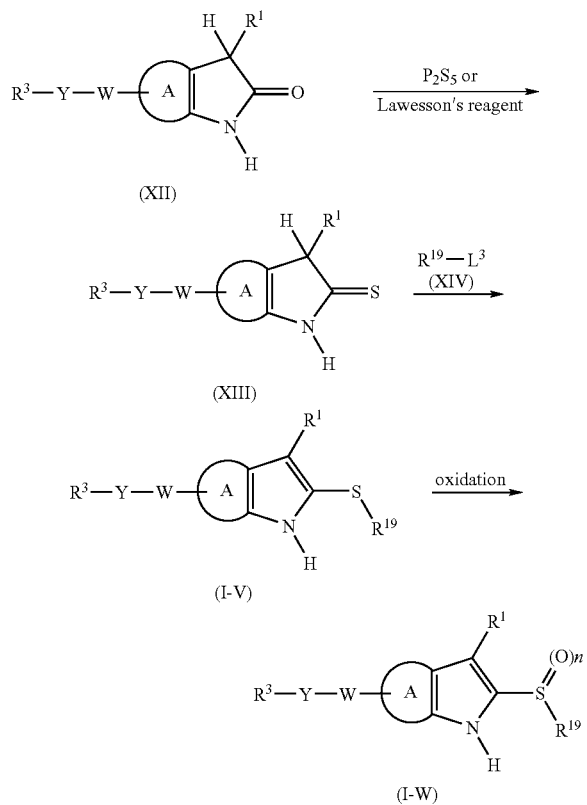

optionally substituted $C_{6-14}$ aryl group or optionally substituted aromatic heterocyclic group, $L^3$ is leaving group, n is 1 or 2, and other symbols are as defined above.

As each group for $R^{19}$, those recited as examples of the substituent of the "optionally substituted mercapto group" for $R^2$ can be mentioned.

As the "leaving group" for $L^3$, those recited as examples of the aforementioned $L^1$ can be mentioned.

Compound (XIII) can be produced by reacting compound (XII) with diphosphorus pentasulfide or Lawesson's reagent.

This reaction is performed in the same manner as in the reaction of compound (I-C3) with diphosphorus pentasulfide or Lawesson's reagent as shown in Reaction Scheme 7.

Compound (I-V) can be produced by reacting compound (XIII) with compound (XIV) in the presence of a base.

Examples of the base include alkali metal hydride such as sodium hydride, potassium hydride and the like; alkali metal hydroxide such as lithium hydroxide, sodium hydroxide, potassium hydroxide and the like; alkaline earth metal hydroxide such as magnesium hydroxide, calcium hydroxide and the like; alkali metal carbonate such as sodium carbonate, potassium carbonate and the like; alkali metal hydrogen carbonate such as sodium hydrogen carbonate, potassium hydrogen carbonate and the like; alkali metal $C_{1-6}$ alkoxide such as sodium methoxide, sodium ethoxide, sodium tert-butoxide and the like; organic bases such as trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene, etc. and the like.

The amount of compound (XIV) and base to be used is generally 1 to 10 mols, preferably 1 to 3 mols, per 1 mol of compound (XIII).

The reaction temperature is generally from −30° C. to 100° C. The reaction time is generally 0.5 hr to 20 hr.

Compound (I-W) can be produced by subjecting compound (I-V) to an oxidization reaction.

The oxidization reaction is performed, for example, using an oxidant. Examples of the oxidant include peracids such as hydrogen peroxide, acetic peracid, m-chloroperbenzoic acid and the like; sodium metaperiodate, hydroperoxide, ozone, selenium dioxide, potassium permanganate, chromic acid, iodine, bromine, N-bromosuccinimide, iodosylbenzene, sodium hypochlorite, tert-butyl hypochlorite, potassium peroxosulfate, ruthenium oxide and the like.

The amount of oxidant to be used is generally 1 to 10 mols, preferably 1 to 3 mols, per 1 mol of compound (I-V).

The reaction temperature is generally from −30° C. to 100° C. The reaction time is generally 0.5 hr to 20 hr.

Compound (XII) to be used as a starting material in Reaction Scheme 8 can be produced according to a method known per se.

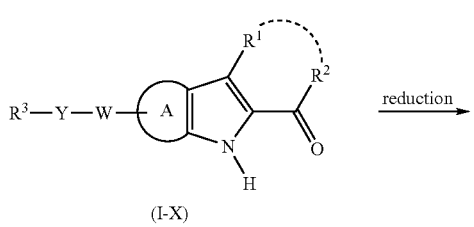

wherein $R^{19}$ is hydrogen atom, optionally substituted $C_{1-10}$ alkyl group, optionally substituted $C_{2-10}$ alkenyl group, -continued

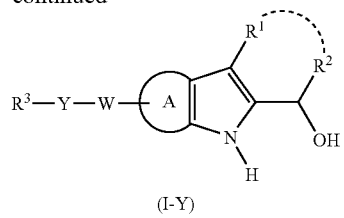

(I-Y)

wherein each symbol is as defined above.

Compound (I-Y) can be produced by subjecting compound (I-X) to a reduction reaction.

The reduction reaction is performed, for example, using a reducing agent. Examples of the reducing agent include metal hydride such as aluminum hydride, diisobutylaluminum hydride, tributyltin hydride and the like; metal hydride complex compound such as lithium aluminum hydride, sodium borohydride and the like; borane complex such as borane tetrahydrofuran complex, borane dimethylsulfide complex and the like; alkyl boranes such as thexyl borane, disiamyl borane and the like; diborane; metals such as zinc, aluminum, tin, iron and the like; alkali metal such as sodium, lithium, etc./liquid ammonia (Birch reduction) and the like.

The amount of the reducing agent to be used is appropriately determined according to the kind of the reducing agent. For example, the amount of metal hydride or metal hydride complex compound to be used is generally about 0.25 to about 10 mols, preferably about 0.5 to about 5 mols, per 1 mol of compound (I-X), the amount of borane complex, alkyl boranes or diborane to be used is generally about 1 to about 10 mols, preferably about 1 to about 5 mols, per 1 mol of compound (I-X), and the amount of metals (including alkali metal to be used for Birch reduction) to be used is generally about 1 to about 20 equivalents, preferably about 1 to about 5 equivalents, per 1 equivalent of compound (I-X).

The reduction reaction is preferably performed in a solvent inert to the reaction. Such solvent is not particularly limited as long as the reaction proceeds. For example, alcohols such as methanol, ethanol, 1-propanol, 2-propanol, tert-butyl alcohol and the like; ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethyl phosphoramide and the like; organic acids such as formic acid, acetic acid, propionic acid, trifluoroacetic acid, methanesulfonic acid, etc. and the like can be mentioned. Two or more kinds of these solvents may be mixed at appropriate ratios for use.

While the reaction time varies depending on the kind and amount of the reducing agent to be used, it is generally about 1 hr to about 100 hr, preferably about 1 hr to about 50 hr. The reaction temperature is generally about $-20°$ C. to about $120°$ C., preferably about $0°$ C. to about $80°$ C.

Compound (I-X) to be used as a starting material in Reaction Scheme 9 can be produced, for example, according to the method shown in the aforementioned Reaction Scheme 1.

Compound (III) to be used as a starting material in the aforementioned Reaction Scheme 1 can be produced, for example, according to the methods shown in the following Reaction Scheme 10 and Reaction Scheme 11, or a method analogous thereto.

Reaction scheme 10

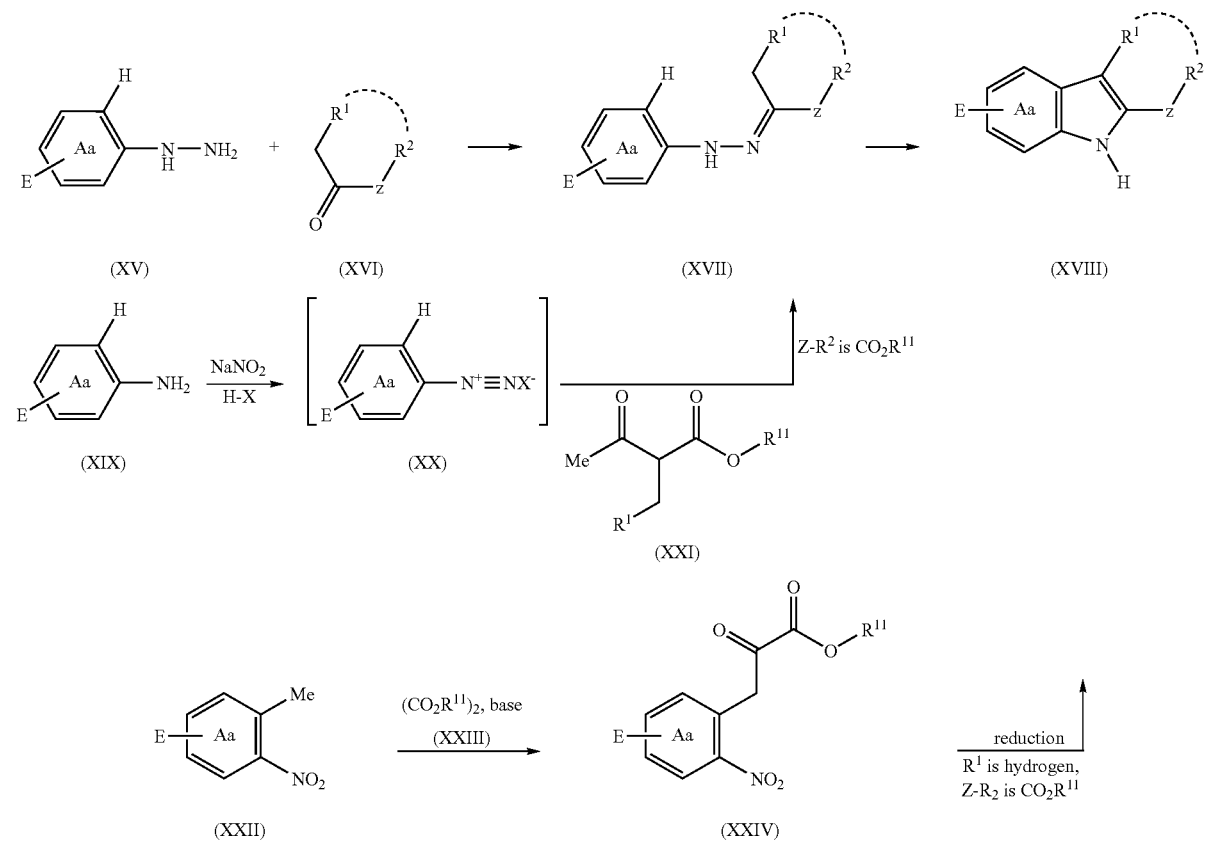

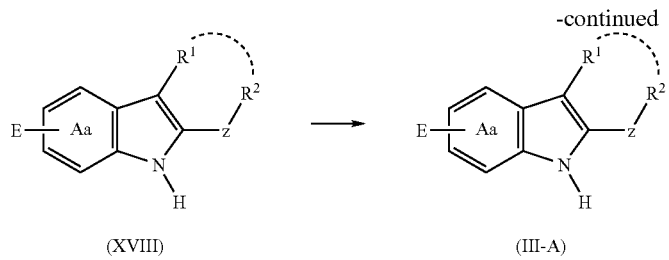

(XVIII)     (III-A)

wherein Aa is optionally substituted benzene ring, E is nitro group, optionally protected amino group, optionally protected hydroxy group or optionally protected mercapto group, H—X is mineral acid such as hydrochloric acid, sulfuric acid and the like; or organic acid such as acetic acid, formic acid, trifluoroacetic acid and the like, E' is amino group, hydroxy group or mercapto group, and each symbol is as defined above.

As the "optionally substituted benzene ring" for Aa, those wherein the 6-membered ring in the "optionally substituted 6-membered ring" for A is a benzene ring can be mentioned.

With regard to the "optionally protected amino group" for E, as the amino-protecting group, for example, a formyl group; and $C_{1-6}$ alkyl-carbonyl group, phenylcarbonyl group, $C_{1-6}$ alkoxy-carbonyl group, allyloxycarbonyl group, phenyloxycarbonyl group, fluorenylmethyloxycarbonyl group, $C_{7-10}$ aralkyl-carbonyl group (e.g., benzylcarbonyl), $C_{7-10}$ aralkyloxy-carbonyl group (e.g., benzyloxycarbonyl), $C_{7-20}$ aralkyl group (e.g., benzyl, trityl), phthaloyl group, dithiasuccinoyl group, N,N-dimethylaminomethylene group and the like, each of which optionally has substituent(s), can be mentioned. Here, examples of the substituent include phenyl group, halogen atom, $C_{1-6}$ alkyl-carbonyl group, $C_{1-6}$ alkoxy group optionally substituted by halogen atom(s), nitro group and the like, where the number of the substituents is 1 to 3.

With regard to the "optionally protected hydroxy group" for E, as the hydroxy-protecting group, for example, $C_{1-6}$ alkyl group, $C_{7-20}$ aralkyl group (e.g., benzyl, trityl), formyl group, $C_{1-6}$ alkyl-carbonyl group, benzoyl group, $C_{7-10}$ aralkyl-carbonyl group (e.g., benzylcarbonyl), 2-tetrahydropyranyl group, tetrahydrofuranyl group, trialkylsilyl group (e.g., trimethylsilyl, tert-butyldimethylsilyl, diisopropylethylsilyl) and the like, each of which optionally has substituent(s), can be mentioned. Here, examples of the substituent include halogen atom, $C_{1-6}$ alkyl group, phenyl group, $C_{7-10}$ aralkyl group (e.g., benzyl etc.), $C_{1-6}$ alkoxy group, nitro group and the like, where the number of the substituents is 1 to 4.

With regard to the "optionally protected mercapto group" for E, as the mercapto-protecting group, for example, $C_{1-6}$ alkyl group, $C_{7-20}$ aralkyl group (e.g., benzyl, trityl) and the like, each of which optionally has substituent(s), can be mentioned. Here, examples of the substituent include halogen atom, $C_{1-6}$ alkyl group, phenyl group, $C_{7-10}$ aralkyl group (e.g., benzyl), $C_{1-6}$ alkoxy group, $C_{1-6}$ alkyl-carbonyl group, nitro group and the like, where the number of the substituents is 1 to 4.

Compound (XVII) can be produced by reacting compound (XV) with compound (XVI).

This reaction is performed in the same manner as in the reaction of compound (I-C2) with compound (VII') or compound (VII) as shown in Reaction Scheme 4.

Compound (XVII) can also be produced by subjecting compound (XIX) to Japp-Klingemann reaction [Organic Reactions (Org. Reactions), 1959, vol. 10, page 143; Journal of Chemical Society (J. Chem. Soc.), 1927, page 1].

In this reaction, compound (XX) produced using compound (XIX), acid(H—X) and sodium nitrite by a method known per se is reacted with compound (XXI) in the presence of a base.

Examples of the base include alkali metal hydroxide such as lithium hydroxide, sodium hydroxide, potassium hydroxide and the like; alkaline earth metal hydroxide such as magnesium hydroxide, calcium hydroxide and the like; alkali metal carbonate such as sodium carbonate, potassium carbonate and the like; alkali metal hydrogen carbonate such as sodium hydrogen carbonate, potassium hydrogen carbonate and the like; organic bases such as trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene, etc. and the like.

This reaction is preferably performed in a solvent inert to the reaction. Such solvent is not particularly limited as long as the reaction proceeds. For example, alcohols such as methanol, ethanol, propanol, isopropanol, butanol, tert-butanol and the like; ethers such as 1,4-dioxane, tetrahydrofuran, diethyl ether, tert-butyl methyl ether, diisopropyl ether, 1,2-dimethoxyethane and the like; halogenated hydrocarbons such as dichloromethane, chloroform, carbon tetrachloride, trichloroethylene and the like; hydrocarbons such as n-hexane, benzene, toluene and the like; amides such as formamide, N,N-dimethylformamide, N,N-dimethylacetamide and the like; nitrites such as acetonitrile, propionitrile, etc. and the like; water and the like can be mentioned. Two or more kinds of these solvents may be mixed at appropriate ratios for use.

The amount of compound (XXI) to be used is generally 1 to 10 mols, preferably 1 to 3 mols, per 1 mol of compound (XX). The amount of the base to be used is generally 1 to 10 mols, preferably 1 to 3 mols, per 1 mol of compound (XX).

The reaction time is generally about 1 hr to about 100 hr, preferably about 1 hr to about 50 hr. The reaction temperature is generally about −20° C. to about 120° C., preferably about 0° C. to about 80° C.

Compound (XVIII) can be produced by subjecting compound (XVII) to the Fischer's method [Berichte, 1883, vol. 16, page 2241]. In this reaction, compound (XVII) is reacted with an acid catalyst with heating.

Examples of the acid catalyst include zinc chloride (without solvent or in a solvent such as naphthaline, ethanol and the like), hydrogen chloride/ethanol, sulfuric acid/ethanol, concentrated sulfuric acid, hydrogen chloride/acetic acid, acetic acid, boron trifluoride, polyphosphoric acid and the like.

The amount of the acid catalyst to be used is generally 1 to 10 mols, preferably 1 to 3 mols, per 1 mol of compound (XVII).

While the reaction time varies depending on the kind and amount of the acid catalyst to be used, it is generally about 1 hr to about 100 hr, preferably about 1 hr to about 50 hr. The reaction temperature is generally about 0° C. to about 200° C., preferably about 80° C. to about 190° C.

Compound (XVIII) can also be produced in two steps by subjecting compound (XXII) to the Reissert's method [Berichte, 1897, vol. 30, p. 1030].

In Step 1, compound (XXIV) can be produced by reacting compound (XXII) with compound (XXIII) in the presence of a base. In Step 2, compound (XVIII) can be produced by subjecting compound (XXIV) to a reduction reaction.

As the base to be used in Step 1, for example, alkali metal $C_{1-6}$ alkoxide such as sodium methoxide, sodium ethoxide, potassium ethoxide, potassium tert-butoxide and the like, and the like can be mentioned.

The amount of compound (XXIII) and the base to be used is generally 1 to 10 mols, preferably 1 to 3 mols, per 1 mol of compound (XXII).

The reaction temperature is generally from −30° C. to 100° C. The reaction time is generally 0.5 hr to 20 hr.

The reduction reaction in Step 2 is performed, for example, using a reducing agent. Examples of the reducing agent include metals such as iron, zinc, tin and the like; sulfide such as sodium dithionite, etc. and the like. The amount of the reducing agent to be used is appropriately determined according to the kind of the reducing agent. For example, the amount of the metals to be used is generally about 1 to about 20 equivalents, preferably about 1 to about 5 equivalents, per 1 equivalent of compound (XXIV). The amount of the sulfide to be used is generally about 1 to about 20 equivalents, preferably about 1 to about 5 equivalents, per 1 equivalent of compound (XXIV).

The reduction reaction can also be performed by hydrogenation. In this case, for example, a catalyst such as palladium carbon, palladium black, platinum dioxide, Raney-nickel, Raney cobalt, iron(III) chloride and the like is used. The amount of the catalyst to be used is generally about 5 to 1000 wt %, preferably about 10 to 300 wt %, relative to compound (XXIV). The hydrogenation can also be performed using various hydrogen sources instead of hydrogen gas. Examples of such hydrogen source include formic acid, ammonium formate, triethylammonium formate, sodium phosphinate, hydrazine and the like. The amount of the hydrogen source to be used is generally about 1 to 100 mols, preferably about 1 to 5 mols, per 1 mol of compound (XXIV).

The reduction reaction is preferably performed in a solvent inert to the reaction. As such solvent, those recited as examples for the reduction reaction of compound (I-X) in Reaction Scheme 9 can be mentioned.

While the reaction time varies depending on the kind and amount of the reducing agent or the activity and amount of the catalyst to be used, it is generally about 1 hr to about 100 hr, preferably about 1 hr to about 50 hr. The reaction temperature is generally about −20° C. to about 120° C., preferably about 0° C. to about 80° C.

In compound (XVIII), when E is a protected amino group, protected hydroxy group or protected mercapto group, when desired, a general deprotection method such as acid treatment, alkali treatment, hydrogenation and the like is performed, whereby compound (III-A) can be produced.

In compound (XVIII), when E is a nitro group, compound (III-A) wherein E' is an amino group can be produced by reaction with a reducing agent.

As the reducing agent, for example, metals such as iron, zinc, tin and the like; and sulfide such as sodium dithionite and the like can be mentioned. The amount of the reducing agent to be used is appropriately determined according to the kind of the reducing agent. For example, the amount of metals to be used is generally about 1 to about 20 equivalents, preferably about 1 to about 5 equivalents, per 1 equivalent of compound (XVIII). The amount of the sulfide to be used is generally about 1 to about 20 equivalents, preferably about 1 to about 5 equivalents, per 1 equivalent of compound (XVIII).

The reduction reaction can also be performed by hydrogenation. In this case, for example, a catalyst such as palladium carbon, palladium black, platinum dioxide, Raney-nickel, Raney cobalt, iron(III) chloride and the like is used. The amount of the catalyst to be used is generally about 5 to 1000 wt %, preferably about 10 to 300 wt %, relative to 1 mol of compound (XVIII). The hydrogenation can also be performed using various hydrogen sources instead of hydrogen gas. Examples of such hydrogen source include formic acid, ammonium formate, triethylammonium formate, sodium phosphinate, hydrazine and the like. The amount of the hydrogen source to be used is generally about 1 to 100 mols, preferably about 1 to 5 mols, per 1 mol of compound (XVIII).

This reaction is preferably performed in a solvent inert to the reaction. Such solvent is not particularly limited as long as the reaction proceeds. For example, alcohols such as methanol, ethanol, propanol, isopropanol, butanol, tert-butanol and the like; ethers such as 1,4-dioxane, tetrahydrofuran, diethyl ether, tert-butyl methyl ether, diisopropyl ether, 1,2-dimethoxyethane and the like; esters such as ethyl formate, ethyl acetate, n-butyl acetate and the like; hydrocarbons such as n-hexane, benzene, toluene and the like; amides such as formamide, N,N-dimethylformamide, N,N-dimethylacetamide and the like; organic acids such as formic acid, acetic acid, propionic acid, trifluoroacetic acid, methanesulfonic acid and the like; water and the like can be mentioned. Two or more kinds of these solvents may be mixed at appropriate ratios for use.

While the reaction time varies depending on the kind and amount of the reducing agent or the activity and amount of the catalyst to be used, it is generally about 1 hr to about 100 hr, preferably about 1 hr to about 50 hr. The reaction temperature is generally about −20° C. to about 120° C., preferably about 0° C. to about 80° C.

Compounds (XV), (XVI), (XIX), (XXI), (XXII) and (XXIII) to be used as starting materials in Reaction Scheme 10 can be produced, for example, according to a method known per se.

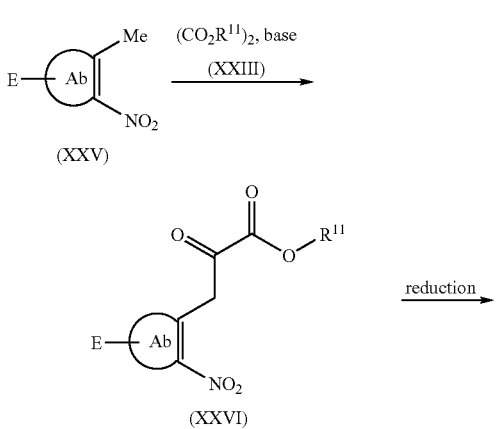

Reaction scheme 11

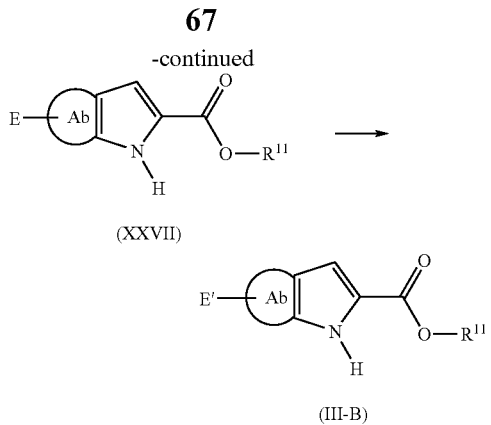

(XXVII)

(III-B)

wherein ring Ab is an optionally substituted 6-membered aromatic ring, and other symbols are as defined above.

As the "optionally substituted 6-membered aromatic ring" for ring Ab, the "optionally substituted 6-membered ring" for ring A, wherein the 6-membered ring is a 6-membered aromatic ring, can be mentioned.

Compound (XXVII) can be produced in two steps from compound (XXV) according to the Reissert's method [Berichte, 1897, vol. 30, page 1030].

In Step 1, compound (XXVI) is produced by reacting compound (XXV) with compound (XXIII) in the presence of a base. In Step 2, compound (XXVII) is produced by subjecting compound (XXVI) to a reduction reaction.

Step 1 is performed in the same manner as in the reaction of compound (XXII) with compound (XXIII) as shown in Reaction Scheme 10. Step 2 is performed in the same manner as in the reduction reaction of compound (XXIV) as shown in Reaction Scheme 10.

In compound (XXVII), when E is a protected amino group, protected hydroxy group or protected mercapto group, when desired, a general deprotection method such as acid treatment, alkali treatment, hydrogenation and the like is performed, whereby compound (III-B) can be produced.

Compound (XXV) to be used as a starting material in Reaction Scheme 11 can be produced according to a method known per se.

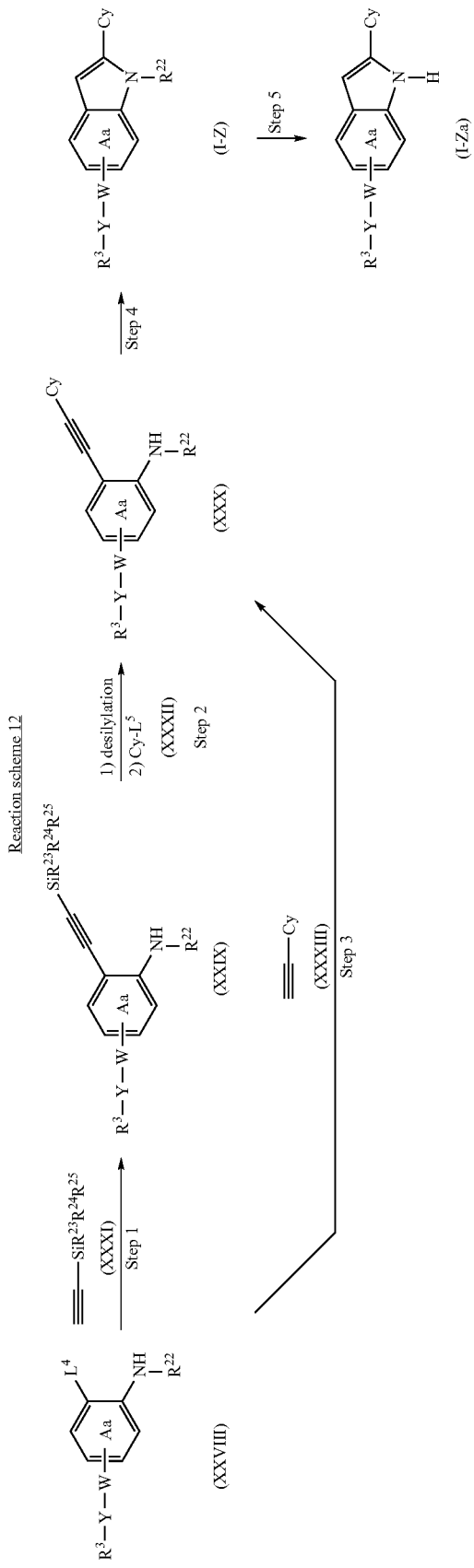

wherein $R^{22}$ is hydrogen atom or amino-protecting group, $R^{23}$, $R^{24}$ and $R^{25}$ are each independently $C_{1-6}$ alkyl group, Cy is optionally substituted cyclic group, $L^4$ and $L^5$ are each independently leaving group, and other symbols are as defined above.

As the "amino-protecting group" for $R^{22}$, for example, formyl group; $C_{1-6}$ alkyl-carbonyl group, phenylcarbonyl group, $C_{1-6}$ alkoxy-carbonyl group, allyloxycarbonyl (Alloc) group, phenyloxycarbonyl group, fluorenylmethyloxycarbonyl (Fmoc) group, $C_{7-10}$ aralkyl-carbonyl group, $C_{7-10}$ aralkyl-oxycarbonyl group, $C_{7-20}$ aralkyl group (e.g., benzyl, trityl), $C_{1-6}$ alkylsulfonyl group (e.g., methanesulfonyl, trifluoromethanesulfonyl), arylsulfonyl group (e.g., benzenesulfonyl, p-toluenesulfonyl) and the like, each of which optionally has substituent(s), can be mentioned. As the substituent, for example, phenyl group, halogen atom, $C_{1-6}$ alkyl-carbonyl group, $C_{1-6}$ alkoxy group optionally substituted by halogen atom(s), nitro group and the like can be mentioned, where the number of the substituents is 1 to 3.

As the "optionally substituted cyclic group" for Cy, "optionally substituted non-aromatic cyclic hydrocarbon group" and "optionally substituted heterocyclic group" recited as examples of the aforementioned $R^{2a}$; and "optionally substituted aromatic hydrocarbon group" can be mentioned. Here, as the "optionally substituted aromatic hydrocarbon group", an "optionally substituted hydrocarbon group" recited as examples of the aforementioned $R^2$, wherein the "hydrocarbon group" is $C_{6-14}$ aryl group, can be mentioned.

As the "leaving group" for $L^4$ or $L^5$, those recited as examples of the aforementioned $L^1$ can be used.

Reaction Scheme 12 may be performed, for example, according to the method described in Tetrahedron, 2003, vol. 59, page 1571.

[Step 1]

Compound (XXIX) can be produced by reacting compound (XXVIII) with compound (XXXI).

This reaction is performed in the presence, for example, of a base and copper(I) iodide. As the base, those recited as examples for the reaction of compound (VIII) with hydroxylamine or a salt thereof as shown in Reaction Scheme 4 can be mentioned.

In this reaction, the reaction can be generally promoted using a metal catalyst. As the metal catalyst, a metal complex having various ligands is used and, for example, palladium compound [e.g.: tetrakis(triphenylphosphine)palladium(0), bis(triphenylphosphine)palladium(II) chloride, tris(dibenzylideneacetone)dipalladium(0), palladium(II) acetate and the like], nickel compound [e.g.: tetrakis(triphenylphosphine)nickel(0), bis(triethylphosphine)nickel(II) chloride, bis(triphenylphosphine)nickel(II) chloride and the like], rhodium compound [e.g.: tris(triphenylphosphine)rhodium (III) chloride and the like], cobalt compound, platinum compound and the like are used. Of these, palladium compound is preferable.

The amount of copper(I) iodide and metal catalyst to be used is about 0.000001 to 5 mols, preferably about 0.0001 to 1 mol, per 1 mol of compound (XXVIII), respectively. In this reaction, when a metal catalyst unstable to oxygen is used, the reaction is preferably carried out in an inert gas (for example, argon gas or nitrogen gas) stream.

This reaction is performed without solvent or in a solvent inert to the reaction. As such solvent, those exemplified for the reaction of compound (I-C2) with compound (VII') or compound (VII) as shown in Reaction Scheme 4 can be mentioned.

The amount of compound (XXXI) and the base to be used is generally 1 to 10 mols, preferably 1 to 3 mols, per 1 mol of compound (XXVIII), respectively.

The reaction temperature is generally from –30° C. to 100° C. The reaction time is generally 0.5 hr to 20 hr.

Compound (XXVIII) can be produced according to a method known per se.

[Step 2]

Compound (XXX) can be produced by subjecting compound (XXIX) to a desilylation reaction, and then reacting with compound (XXXII).

For the desilylation reaction, fluoride [e.g., hydrogen fluoride, potassium fluoride, boron trifluoride-ether complex, tetrabutylammonium fluoride and the like], or a base is used.

As the base, those recited as examples for the reaction of compound (VIII) with hydroxylamine or a salt thereof as shown in Reaction Scheme 4 can be mentioned.

This reaction is performed without solvent or in a solvent inert to the reaction. As such solvent, those exemplified for the reaction of compound (I-C2) with compound (VII') or compound (VII) as shown in Reaction Scheme 4 can be mentioned.

The amount of fluoride or the base to be used is generally 1 to 10 mols, preferably 1 to 3 mols, per 1 mol of compound (XXIX), respectively.

The reaction temperature is generally from –30° C. to 100° C. The reaction time is generally 0.5 hr to 20 hr.

The reaction with compound (XXXII) after desilylation reaction is performed in the same manner as in the aforementioned Step 1.

Compound (XXXII) can be produced according to a method known per se.

[Step 3]

Compound (XXX) can also be produced by reacting compound (XXVIII) with compound (XXXIII). This reaction is performed in the same manner as in the aforementioned Step 1.

Compound (XXXIII) can be produced according to a method known per se.

[Step 4]

Compound (I-Z) can be produced by reacting compound (XXX) with a base.

As the base, those exemplified for the reaction of compound (VIII) with hydroxylamine or a salt thereof shown in Reaction Scheme 4 can be mentioned.

In this reaction, the reaction can be generally promoted using a metal catalyst. As the metal catalyst, a metal complex having various ligands is used and, for example, palladium compound [e.g.: tetrakis(triphenylphosphine)palladium(0), bis(triphenylphosphine)palladium(II) chloride, tris(dibenzylideneacetone)dipalladium(0), palladium(II) acetate and the like], copper compound [e.g.: copper(I) cyanide, copper (I) chloride, copper(I) bromide, copper(I) iodide, copper(I) acetate, copper(I) trifluoroacetate, copper(I) methanesulfonate, copper(I) trifluoromethanesulfonate, (1,10-phenenthroline)bis(triphenylphosphine)copper(I) nitrate, copper (II) oxide, copper(II) fluoride, copper(II) chloride, copper(II) bromide, copper(II) iodide, copper(II) acetate, copper(II) trifluoroacetate, copper(II) methanesulfonate, copper (II) trifluoromethanesulfonate, copper (II) nitrate, copper(II) formate, copper(II) sulfate and the like] and the like are used.

The amount of metal catalyst to be used is about 0.000001 to 5 mols, preferably about 0.0001 to 1 mol, per 1 mol of compound (XXX). In this reaction, when a metal catalyst unstable to oxygen is used, the reaction is preferably carried out in an inert gas (for example, argon gas or nitrogen gas) stream.

This reaction is performed without solvent or in a solvent inert to the reaction. As such solvent, those exemplified for the reaction of compound (I-C2) with compound (VII') or compound (VII) as shown in the aforementioned Reaction Scheme 4 can be mentioned.

The amount of the base to be used is generally 1 to 10 mols, preferably 1 to 3 mols, per 1 mol of compound (XXX).

The reaction temperature is generally from −30° C. to 100° C. The reaction time is generally 0.5 hr to 20 hr.

[Step 5]

Compound (I-Za) can be produced by subjecting compound (I-Z), wherein $R^{22}$ is an amino-protecting group, to deprotection of amino group.

The deprotection of amino group can be performed by a method known per se or a method analogous thereto, for example, a method using acid, base, reduction, hydrazine, phenylhydrazine, sodium N-methyl-dithiocarbamate, tetrabutylammonium fluoride, palladium(II) acetate and the like.

Depending on the reaction conditions of the aforementioned Step 4, compound (I-Z) wherein $R^{22}$ is a hydrogen atom may be obtained using compound (XXX) wherein $R^{22}$ is an amino-protecting group. In this case, the present Step 5 can be omitted.

In each of the above-mentioned production methods, when the starting material compound or the compound of the present invention has an amino group, carboxy group, hydroxy group or mercapto group, a protecting group conventionally used in peptide chemistry may be introduced into these groups, where the protecting group can be removed by a conventional deprotection method during any step of each reaction scheme.

Compound (I) can also be produced by subjecting the object compound obtained by each of the above-mentioned production methods to a substituent conversion reaction known per se.

For example, when compound (I-U) wherein at least one of $R^{17a}$ and $R^{17}$ is a substituent having a $C_{1-6}$ alkoxy-carbonyl group or a $C_{1-6}$ alkoxy-carbonyl group [hereinafter to be abbreviated as compound (I-U1)] is obtained by the method shown in Reaction Scheme 6, "compound (I-U1) wherein the aforementioned $C_{1-6}$ alkoxy-carbonyl group is converted to a carboxy group [hereinafter to be abbreviated as compound (I-U2)]", "compound (I-U1) wherein the aforementioned $C_{1-6}$ alkoxy-carbonyl group is converted to a carbamoyl group" and "compound (I-U1) wherein the aforementioned $C_{1-6}$ alkoxy-carbonyl group is converted to a $C_{1-6}$ alkyl-carbonyl group" can be produced by subjecting compound (I-U1) to each reaction described in Reaction Scheme 2.

In addition, by subjecting compound (I-U1) or compound (I-U2) to a reduction reaction, "compound (I-U1) wherein the aforementioned $C_{1-6}$ alkoxy-carbonyl group is converted to a hydroxymethyl group [hereinafter to be abbreviated as compound (I-U3)]" can be produced. Here, the reduction reaction is performed in the same manner as in the reduction reaction of, for example, compound (I-X) in Reaction Scheme 9.

Moreover, after introduction of a leaving group recited as example of the aforementioned $L^1$ into compound (I-U3), followed by a nucleophilic substitution reaction known per se, "a compound wherein the aforementioned $C_{1-6}$ alkoxy-carbonyl group is converted to a $C_{1-6}$ alkoxy-methyl group, $C_{1-6}$ alkylthio-methyl group, $C_{1-6}$ alkylsulfonyl-methyl group, (mono- or di-$C_{1-6}$ alkyl)amino-methyl group and the like" can be produced.

Even when compound (I) wherein $R^3$ is a substituent having a $C_{1-6}$ alkoxy-carbonyl group is obtained by the method shown in Reaction Scheme 1, "a compound wherein the aforementioned $C_{1-6}$ alkoxy-carbonyl group is converted to a carboxy group, carbamoyl group, $C_{1-6}$ alkyl-carbonyl group, hydroxymethyl group, $C_{1-6}$ alkoxy-methyl group, $C_{1-6}$ alkylthio-methyl group, (mono- or di-$C_{1-6}$ alkyl)amino-methyl group and the like" can be produced in the same manner as in the above-mentioned compound (I-U1).

The "compound (I-Za) wherein $R^3$—Y—W is replaced by a $C_{1-6}$ alkoxy-carbonyl group, $C_{7-10}$ aralkyl-oxycarbonyl group or formyl group [hereinafter to be abbreviated as compound (I-Za1)]" can be produced from the "compound (XXVIII) wherein $R^3$—Y—W is replaced by a $C_{1-6}$ alkoxy-carbonyl group, $C_{7-10}$ aralkyl-oxycarbonyl group or formyl group [hereinafter to be abbreviated as compound (XXVIIIa)]" by the method shown in the aforementioned Reaction Scheme 12.

Moreover, in the same manner as in the above-mentioned compound (I-U1), a compound wherein $C_{1-6}$ alkoxy-carbonyl group, $C_{7-10}$ aralkyl-oxycarbonyl group or formyl group that compound (1-Za1) has is converted to a carboxy group, carbamoyl group, $C_{1-6}$ alkyl-carbonyl group, hydroxymethyl group, $C_{1-6}$ alkoxy-methyl group, $C_{1-6}$ alkylthio-methyl group, (mono- or di-$C_{1-6}$ alkyl)amino-methyl group and the like can be produced from compound (I-Za1).

Furthermore, by reacting compound (I-Za1) with an alkylating agent (e.g., Grignard reagent, alkylmetal reagent) according to a method known per se, "compound (I-Za) wherein $R^3$—Y—W is replaced by ketone, secondary alcohol or tertiary alcohol derived from the aforementioned alkylating agent [hereinafter to be abbreviated as compound (I-Za2)]" can be produced.

Moreover, of compounds (I-Za2), in a "compound (I-Za) wherein $R^3$—Y—W is replaced by secondary alcohol or tertiary alcohol derived from the aforementioned alkylating agent", the hydroxyl group of the secondary alcohol or tertiary alcohol is converted to a leaving group recited as example of the aforementioned $L^1$ by a method known per se, followed by a nucleophilic substitution reaction known per se, whereby a compound wherein the hydroxyl group is converted to a $C_{1-6}$ alkylthio group, $C_{7-10}$ aralkylthio group, Cy-thio group, $C_{1-6}$ alkoxy group, $C_{7-10}$ aralkyloxy group, Cy-oxy group, (mono- or di-$C_{1-6}$ alkyl)amino group, (mono- or di-$C_{7-10}$ aralkyl)amino group, (mono- or di-Cy)amino group and the like (Cy is as defined above) can be produced. Here, the $C_{1-6}$ alkylthio group, $C_{7-10}$ aralkylthio group and Cy-thio group can be converted to a $C_{1-6}$ alkylsulfinyl group, $C_{7-10}$ aralkylsulfinyl group, Cy-sulfinyl group, $C_{1-6}$ alkylsulfonyl group, $C_{7-10}$ aralkylsulfonyl group or Cy-sulfonyl group by an oxidization reaction known per se.

The compound of the present invention obtained by each of the above-mentioned production methods can be isolated and purified by a known means such as concentration, concentration under reduced pressure, solvent extraction, crystallization, recrystallization, phase transfer, chromatography and the like. In addition, each starting material compound used for each of the above-mentioned production methods can be isolated and purified by a known means similar to the aforementioned means. On the other hand, these starting material compounds may be directly used in the form of a reaction mixture without isolation, as a starting material for the next step.

For production of the compound of the present invention, when the starting material compound can form a salt, the compound may be used as a salt. As such salt, for example, those recited as examples of the salt of the compound of the present invention can be mentioned.

When the compound of the present invention contains an optical isomer, steric isomer, positional isomer or rotamer, they are encompassed in the compound of the present invention and can be each obtained as single products by a synthetic means or separation means known per se. For example, when the compound of the present invention contains an optical isomer, an optical isomer resolved from the compound is also encompassed in the compound of the present invention.

The compound of the present invention may be a crystal.

A crystal of the compound of the present invention (hereinafter sometimes to be abbreviated as the crystal of the present invention) can be produced by crystallizing the compound of the present invention by applying a crystallization method known per se.

In the present specification, the melting point means a value measured, for example, using a trace melting point measurement device (YANACO, type MP-500D or Buchi, B-545) or DSC (differential scanning calorimetry analysis) apparatus (SEIKO, EXSTAR6000) and the like.

In general, the melting point may vary depending on the measurement device, measurement condition and the like. In the present specification, the crystal may have a melting point different from that described in the present specification, as long as the variation is within the general range of error.

The crystal of the present invention is superior in the physicochemical properties (e.g., melting point, solubility, stability) and biological properties (e.g., in vivo kinetics (absorbability, distribution, metabolism, excretion), efficacy expression) and is extremely useful as a pharmaceutical agent.

EXAMPLES

The present invention is explained in detail in the following by referring to the following Reference Examples, Examples, Experimental Examples and Formulation Examples, which are not to be construed as limitative. In addition, the present invention may be modified without departing from the scope of invention.

The term "room temperature" in the following Reference Examples and Examples indicates the range of generally from about 10° C. to about 35° C. As for "%", the yield is in mol/mol %, the solvent used for chromatography is in % by volume and other "%" is in % by weight. OH proton, NH proton etc. on proton NMR spectrum that could not be confirmed due to broad peak are not included in the data.

The other symbols used herein mean the following:
s: singlet
d: doublet
t: triplet
q: quartet
m: multiplet
br: broad
J: coupling constant
Hz: Hertz
CDCl$_3$: deuterated chloroform
DMSO-d$_6$: dimethyl sulfoxide-d$_6$
$^1$H-NMR: proton nuclear magnetic resonance
TFA: trifluoroacetic acid In the following Reference Examples and Examples, mass spectrum (MS) and nuclear magnetic resonance spectrum (NMR) were measured under the following conditions.
MS measurement tools: Waters Corporation ZMD, Waters Corporation ZQ2000 or Micromass Ltd., platform II
Ionization method: Electron Spray Ionization (ESI) or Atmospheric Pressure Chemical Ionization (APCI). Unless specifically indicated, ESI was used.
NMR measurement tools: Varian Inc. Varian Gemini 200 (200 MHz), Varian Gemini 300 (300 MHz), Bruker BioSpin Corp. AVANCE 300.

In the following Reference Examples and Examples, purification by preparative HPLC was performed under the following conditions.
Preparative HPLC tools: Gilson, Inc., high through-put purification system
column: YMC Combiprep ODS-A S-5 Wu, 20×50 mm
solvent: SOLUTION A; 0.1% trifluoroacetic acid-containing water,
SOLUTION B; 0.1% trifluoroacetic acid containing-acetonitrile
gradient cycle: 0.00 min (SOLUTION A/SOLUTION B=90/10), 1.20 min (SOLUTION A/SOLUTION B=90/10), 4.75 min (SOLUTION A/SOLUTION B=0/100), 7.30 min (SOLUTION A/SOLUTION B=0/100), 7.40 min (SOLUTION A/SOLUTION B=90/10), 7.50 min (SOLUTION A/SOLUTION B=90/10).
flow rate: 25 ml/min, detection: UV 220 nm Reference Example 1A Construction of Glucokinase (GK) Expression Vector Plasmid DNA to be used for the expression of a protein (GST-hLGK1) containing GST (Glutathione S-transferase) added to the amino terminal of human liver type GK in *Escherichia coli* was prepared as shown below.

First, PCR was performed using human liver cDNA (Clontech Laboratories, Inc. Marathon Ready cDNA) as a template and two kinds of synthetic DNAs (5'-CAGCTCTCCATC-CAAGCAGCCGTTGCT-3' and 5'-GGCGGCCTGGGTC-CTGACAAG-3'). The obtained DNA fragment was cloned using a TOPO TA Cloning Kit (Invitrogen Corporation). PCR was performed using the obtained plasmid DNA as a template, and a synthetic DNA (5'-GGATCCATGCCCAGAC-CAAGATCCCAACTCCCACAACCCAACTC-CCAGGTAGAGCAGATCCTGG CAGAG-3') with a BamHI site added to immediately before the initiation codon and a synthetic DNA (5'-GAATTCCTGGCCCAGCATA-CAGGC-3') with an EcoRI site added to immediately after the stop codon. The obtained DNA fragment was subcloned to pGEX6P-2 (Amersham Biosciences K.K.) cleaved with BamHI and EcoRI to give a plasmid (pGEX6P-2/hLGK1) for expression of human liver GK.

Reference Example 2A

Expression and Purification of GST-hLGK1

BL21 strain (Stratagene) transformed with pGEX6P-2/hLGK1 obtained in Reference Example 1A was cultured with shaking at 37° C. for 14 hr in a 200 ml Erlenmeyer flask containing 50 ml of 100 µg/ml ampicillin-containing LB medium. The culture medium (25 ml) was diluted with 225 ml of 100 µg/ml ampicillin-containing LB medium, and further cultured with shaking at 37° C. for 1 hr in a 1 L Erlenmeyer flask. After culture, the Erlenmeyer flask was cooled on ice, 125 µL of 100 mM isopropyl-thio-β-D-galactopyranoside (IPTG) was added (final concentration 50 µM), and cultured at 17° C. for 20 hr. The culture medium was centrifuged, and the obtained fungus was disrupted by ultrasonication. The object protein (GST-hLGK1) was purified from the supernatant using Glutathione Sepharose 4B (Amersham Biosciences K.K.).

Reference Example 1

N-(2-Cyano-1H-indol-7-yl)thiophene-2-sulfonamide

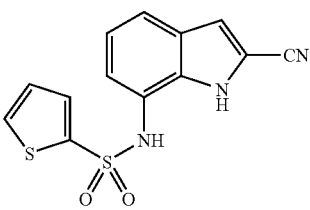 [SMILES: N#Cc1cc2cccc(NS(=O)(=O)c3cccs3)c2[nH]1]

To a mixture of 7-[(2-thienylsulfonyl)amino]-1H-indole-2-carboxamide (4.65 g) and pyridine (20 mL) was slowly added trifluoroacetic anhydride (4.50 mL) at 0° C., and the mixture was stirred for 1 hr. The reaction mixture was concentrated, 10% aqueous citric acid solution was added, and the resulting crystals were filtrated, washed with water and dried. The obtained crystals were subjected to silica gel column chromatography, and eluted with tetrahydrofuran-hexane (2:3, volume ratio). The eluate was treated with activated carbon and concentrated to give the title compound (4.04 g, yield 92%) as pale-yellow crystals. The crystals were recrystallized from ethyl acetate-hexane. melting point 283-284° C.

Reference Example 2

1-(Pyridin-2-yl)ethanone (2-nitrophenyl)hydrazone

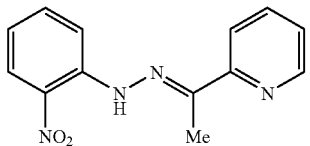 [SMILES: C/C(=N\Nc1ccccc1[N+](=O)[O-])c1ccccn1]

A mixture of (2-nitrophenyl)hydrazine (2.00 g), 1-(pyridin-2-yl)ethanone (1.67 g), sulfuric acid (0.73 mL) and ethanol (50 mL) was heated under reflux for 1 hr. Water was added to the reaction mixture, and the obtained crystals were filtrated, washed with water and dried to give the title compound (2.84 g, 85%) as brown crystals. melting point 145-146° C.

Reference Example 3

7-Nitro-2-(pyridin-2-yl)-1H-indole

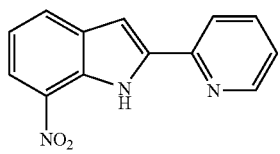

A mixture of 1-(pyridin-2-yl)ethanone (2-nitrophenyl)hydrazone (1.60 g) and polyphosphoric acid (40.0 g) was stirred at 100° C. overnight. The reaction mixture was poured into ice water (100 mL), neutralized with 50% aqueous sodium hydroxide solution, and extracted with ethyl acetate. The ethyl acetate layer was washed with saturated brine, dried (MgSO$_4$) and concentrated. The residue was subjected to silica gel column chromatography and the title compound (0.47 g, yield 32%) was obtained as yellow crystals from a fraction eluted with tetrahydrofuran-hexane (1:2, volume ratio). melting point 162-163° C.

Reference Example 4

2-(Pyridin-2-yl)-1H-indole-7-amine

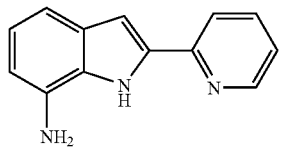

A mixture of 7-nitro-2-(pyridin-2-yl)-1H-indole (0.47 g), 10% palladium-carbon (50% water, 0.05 g), ethanol (4 mL) and tetrahydrofuran (10 mL) was stirred at room temperature overnight under a hydrogen atmosphere. Palladium-carbon was filtered off, and the filtrate was concentrated. The residue was subjected to silica gel column chromatography and the title compound (0.35 g, yield 85%) was obtained as pale-yellow crystals from a fraction eluted with ethyl acetate-hexane (1:1, volume ratio). melting point 165-166° C.

Reference Example 5

8-Amino-2,3,4,9-tetrahydro-1H-carbazole-1-one

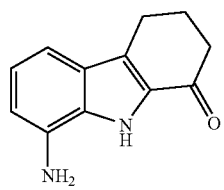 [SMILES: Nc1cccc2c3c([nH]c12)C(=O)CCC3]

A mixture of 8-nitro-2,3,4,9-tetrahydro-1H-carbazol-1-one (1.50 g), 10% palladium-carbon (0.20 g), ethanol (5 mL) and tetrahydrofuran (10 mL) was stirred at room temperature overnight under a hydrogen atmosphere. Palladium-carbon was filtered off, and the filtrate was concentrated to give the title compound (1.20 g, yield 92%) as yellow crystals. melting point 233-234° C.

Reference Example 6

Hexane-3,4-dione (2-nitrophenyl)hydrazone

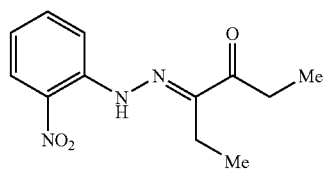 [SMILES: CCC(=O)/C(CC)=N/Nc1ccccc1[N+](=O)[O-]]

A mixture of 2-nitrophenylhydrazine (2.00 g), hexane-3,4-dione (1.80 g), sulfuric acid (2 drops) and ethanol (20 mL) was heated under reflux for 1 hr. The reaction mixture was poured into water, and the resulting crystals were collected by filtration, washed with water and dried to give the title compound (3.13 g, 96%) as brown crystals. melting point 96-97° C.

Reference Example 7

1-(3-Methyl-7-nitro-1H-indol-2-yl)propan-1-one

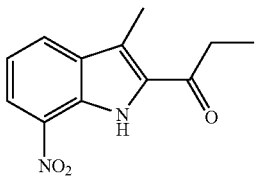 [SMILES: CCC(=O)c1[nH]c2c([N+](=O)[O-])cccc2c1C]

A mixture of hexane-3,4-dione (2-nitrophenyl)hydrazone (3.13 g) and polyphosphoric acid (50 g) was stirred at 80° C. overnight. The reaction mixture was poured into ice water, neutralized with 50% aqueous sodium hydroxide solution, and extracted with ethyl acetate. The ethyl acetate layer was washed with saturated brine, dried (MgSO$_4$) and concentrated. The residue was subjected to silica gel column chromatography and the title compound (0.29 g, yield 10%) was obtained as yellow crystals from a fraction eluted with ethyl acetate-hexane (1:2, volume ratio). melting point>164° C. (decomposition).

Reference Example 8

1-(7-Amino-3-methyl-1H-indol-2-yl)propan-1-one

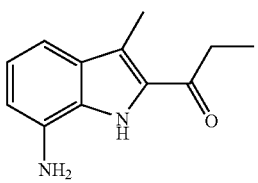

A mixture of 1-(3-methyl-7-nitro-1H-indol-2-yl)propan-1-one (0.29 g), 10% palladium-carbon (50% containing water, 0.03 g), ethanol (4 mL) and tetrahydrofuran (4 mL) was stirred at room temperature overnight under a hydrogen atmosphere. Palladium-carbon was filtered off, and the filtrate was concentrated. The residue was subjected to silica gel column chromatography and the title compound (0.17 g, yield 70%) was obtained as yellow crystals from a fraction eluted with tetrahydrofuran-hexane (1:1, volume ratio). melting point>194° C. (decomposition).

Reference Example 9

N-(2-Oxo-2,3-dihydro-1H-indol-7-yl)thiophene-2-sulfonamide

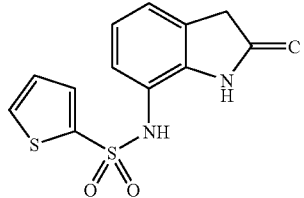 [SMILES: C=C1Cc2cccc(NS(=O)(=O)c3cccs3)c2N1]

To a mixture of 7-amino-2-oxo-2,3-dihydro-1H-indole (1.53 g) and pyridine (20 mL) was added thiophene-2-sulfonyl chloride (2.26 g) at 0° C., and the mixture was stirred at room temperature for 2 hr. The reaction mixture was concentrated, 10% aqueous citric acid solution was added, and the resulting crystals were filtered, washed with water and dried. The obtained crystals were subjected to silica gel column chromatography, and eluted with ethyl acetate. The eluate was treated with activated carbon and concentrated to give the title compound (2.93 g, yield 97%) as colorless crystals. The crystals were recrystallized from tetrahydrofuran-hexane. melting point>230° C. (decomposition)

Reference Example 10

7-[(2-Thienylsulfonyl)amino]-1H-indole-2-carbothioamide

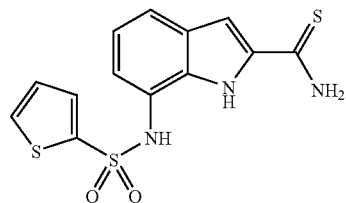 [SMILES: NC(=S)c1cc2cccc(NS(=O)(=O)c3cccs3)c2[nH]1]

A mixture of 7-[(2-thienylsulfonyl)amino]-1H-indole-2-carboxamide (0.66 g), Lawesson's reagent (0.88 g) and tetrahydrofuran (20 mL) was stirred at 40° C. overnight. The reaction mixture was concentrated, the obtained residue was subjected to silica gel column chromatography, and the title compound (0.61 g, yield 86%) was obtained as yellow crystals from a fraction eluted with tetrahydrofuran-hexane (3:2, volume ratio). melting point 249-250° C. (decomposition).

Reference Example 11

Ethyl 1-(methoxymethyl)-7-nitro-1H-indole-2-carboxylate

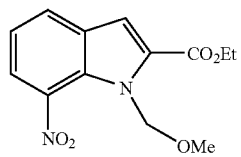 [SMILES: CCOC(=O)c1cc2cccc([N+](=O)[O-])c2n1COC]

To a suspension of sodium hydride (60% in oil, 0.51 g) in N,N-dimethylformamide (15 mL) was slowly added ethyl 7-nitro-1H-indole-2-carboxylate (2.50 g) at 0° C., and the mixture was stirred for 30 min. To the reaction mixture was added chloromethyl methyl ether (1.00 mL) at 0° C. over 20 min, and the mixture was stirred at room temperature for 1 hr. Water was added to the reaction mixture, and the mixture was extracted with ethyl acetate. The ethyl acetate layer was washed with saturated brine, dried (MgSO$_4$) and concentrated. The obtained residue was subjected to silica gel column chromatography and the title compound (2.29 g, yield 77%) was obtained as pale-yellow crystals from a fraction eluted with ethyl acetate-hexane (1:3, volume ratio). melting point 62-63° C.

Reference Example 12

Ethyl 7-amino-1-(methoxymethyl)-1H-indole-2-carboxylate

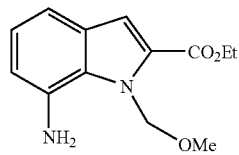 [SMILES: CCOC(=O)c1cc2cccc(N)c2n1COC]

A mixture of ethyl 1-(methoxymethyl)-7-nitro-1H-indole-2-carboxylate (2.35 g), 10% palladium-carbon (0.24 g), ethanol (4 ml) and tetrahydrofuran (10 ml) was stirred at room temperature overnight under a hydrogen atmosphere. Palladium-carbon was filtered off, and the filtrate was concentrated. The residue was subjected to silica gel column chromatography and the title compound (1.92 g, yield 91%) was obtained as a yellow oil from a fraction eluted with ethyl acetate-hexane (1:3, volume ratio).

$^1$H-NMR (CDCl$_3$) δ:1.41 (3H, t, J=7.2 Hz), 3.44 (3H, s), 4.36 (2H, q, J=7.2 Hz), 4.53 (2H, brs), 6.16 (2H, s), 6.61 (1H, dd, J=7.7, 0.9 Hz), 6.97 (1H, t, J=7.7 Hz), 7.10 (1H, dd, J=7.7, 0.9 Hz), 7.28 (1H, s).

Reference Example 13

Ethyl 1-(methoxymethyl)-7-[(2-thienylsulfonyl)amino]-1H-indole-2-carboxylate

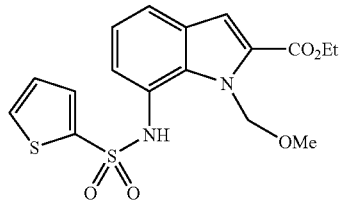 [SMILES: CCOC(=O)c1cc2cccc(NS(=O)(=O)c3cccs3)c2n1COC]

To a mixture of ethyl 7-amino-1-(methoxymethyl)-1H-indole-2-carboxylate (0.70 g) and pyridine (8 mL) was added thiophene-2-sulfonyl chloride (0.57 g) at 0° C., and the mixture was stirred at room temperature for 2 hr. The reaction mixture was concentrated, 10% aqueous citric acid solution was added, and the mixture was extracted with ethyl acetate. The ethyl acetate layer was washed with saturated brine, dried (MgSO$_4$) and concentrated. The obtained residue was subjected to silica gel column chromatography and the title compound (1.03 g, yield 93%) was obtained as a yellow oil from a fraction eluted with ethyl acetate-hexane (1:2, volume ratio).

$^1$H-NMR (CDCl$_3$) δ:1.40 (3H, t, J=7.2 Hz), 3.45 (3H, s), 4.35 (2H, q, J=7.2 Hz), 5.70 (2H, s), 7.00 (1H, dd, J=5.1, 3.7 Hz), 7.19 (1H, t, J=7.8 Hz), 7.32 (1H, s), 7.46-7.64 (4H, m), 8.87 (1H, brs).

Reference Example 14

Ethyl 1-(methoxymethyl)-7-[methyl(2-thienylsulfonyl)amino]-1H-indole-2-carboxylate

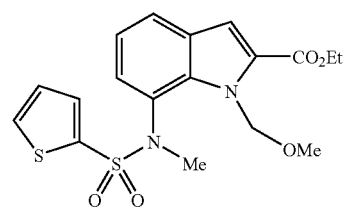 [SMILES: CCOC(=O)c1cc2cccc(N(C)S(=O)(=O)c3cccs3)c2n1COC]

A mixture of ethyl 1-(methoxymethyl)-7-[(2-thienylsulfonyl)amino]-1H-indole-2-carboxylate (1.03 g), methyl iodide (0.24 mL), potassium carbonate (0.36 g) and N,N-dimethylformamide (10 mL) was stirred at room temperature overnight. Water was added to the reaction mixture, and the obtained crystals were filtrated, washed with water and dried to give the title compound (1.06 g, yield 99%) as colorless crystals. melting point 143-145° C.

Reference Example 15

Ethyl 1-(methoxymethyl)-7-[(methoxymethyl)(2-thienylsulfonyl)amino]-1H-indole-2-carboxylate

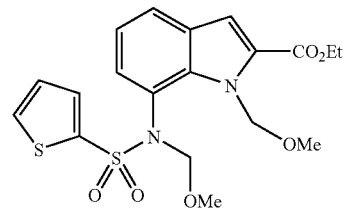 [SMILES: CCOC(=O)c1cc2cccc(N(COC)S(=O)(=O)c3cccs3)c2n1COC]

To a suspension of sodium hydride (60% in oil, 1.15 g) in N,N-dimethylformamide (30 mL) was slowly added ethyl 7-[(2-thienylsulfonyl)amino]-1H-indole-2-carboxylate (4.00 g) at 0° C., and the mixture was stirred for 15 min. To the reaction mixture was added chloromethyl methyl ether (2.20 mL) at 0° C. over 20 min, and the mixture was stirred at room temperature overnight. Water was added to the reaction mixture, and the mixture was extracted with ethyl acetate. The ethyl acetate layer was washed with saturated brine, dried (MgSO$_4$) and concentrated. The obtained residue was subjected to silica gel column chromatography and the title compound (4.07 g, yield 81%) was obtained as a colorless oil from a fraction eluted with ethyl acetate-hexane (1:2, volume ratio).

$^1$H-NMR (CDCl$_3$) δ:1.41 (3H, t, J=7.2 Hz), 3.27 (3H, s), 3.33 (3H, s), 4.38 (2H, q, J=7.2 Hz), 4.70 (1H, d, J=10.2 Hz), 5.51 (1H, d, J=10.2 Hz), 6.23 (1H, d, J=10.2 Hz), 6.36 (1H, d, J=10.2 Hz), 6.89-7.10 (3H, m), 7.39 (1H, s), 7.60-7.70 (2H, m).

Reference Example 16

1-(Methoxymethyl)-7-[(methoxymethyl) (2-thienyl-sulfonyl)amino]-1H-indole-2-carboxylic acid

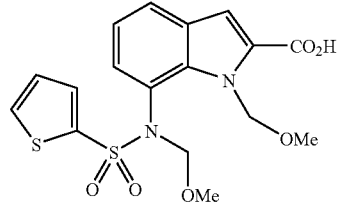 [SMILES: COCN(c1cccc2cc(C(=O)O)n(COC)c12)S(=O)(=O)c1cccs1]

A mixture of ethyl 1-(methoxymethyl)-7-[(methoxymethyl)(2-thienylsulfonyl)amino]-1H-indole-2-carboxylate (4.43 g), 8N aqueous sodium hydroxide solution (2.5 mL), tetrahydrofuran (10 mL) and ethanol (10 mL) was stirred at 60° C. for 1 hr. The reaction mixture was concentrated, and water was added to the residue. The mixture was acidified with 10% aqueous citric acid solution, and the resulting crystals were filtrated, washed with water, and dried to give the title compound (3.86 g, yield 93%) as colorless crystals. melting point 183-184° C.

Reference Example 17

1-(Methoxymethyl)-7-[(methoxymethyl) (2-thienyl-sulfonyl)amino]-1H-indole-2-carboxamide

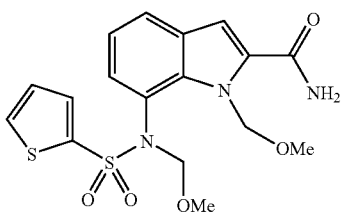 [SMILES: COCN(c1cccc2cc(C(N)=O)n(COC)c12)S(=O)(=O)c1cccs1]

To a mixture of 1-(methoxymethyl)-7-[(methoxymethyl) (2-thienylsulfonyl)amino]-1H-indole-2-carboxylic acid (3.83 g), 1H-1,2,3-benzotriazol-1-ol (1.51 g) and N,N-dimethylformamide (30 mL) was added N-[3-(dimethylamino)propyl]-N'-ethylcarbodiimide hydrochloride (2.15 g) at room temperature, and the mixture was stirred for 20 min and 28% aqueous ammonia (3.4 mL) was added. The reaction mixture was stirred at room temperature for 3 hr, and water was added. The mixture was acidified with 10% aqueous citric acid solution, and the resulting crystals were filtrated, washed with water, and dried to give the title compound (3.67 g, yield 96%) as colorless crystals. melting point 203-204° C.

Reference Example 18

N-[(1E)-(Dimethylamino)methylene]-1-(methoxymethyl)-7-[(methoxymethyl)(2-thienylsulfonyl)amino] 1H-indole-2-carboxamide

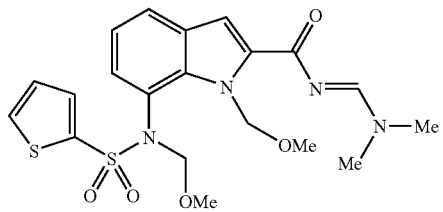 [SMILES: COCN(c1cccc2cc(C(=O)/N=C/N(C)C)n(COC)c12)S(=O)(=O)c1cccs1]

A mixture of 1-(methoxymethyl)-7-[(methoxymethyl)(2-thienylsulfonyl)amino]-1H-indole-2-carboxamide (1.00 g) and N,N-dimethylformamide dimethyl acetal (10 mL) was stirred at 50° C. overnight. To the reaction mixture was added diisopropyl ether, and the resulting crystals were filtrated and dried to give the title compound (1.06 g, yield 93%) as colorless crystals. melting point 146-147° C.

Reference Example 19

N-(Methoxymethyl)-N-[1-(methoxymethyl)-2-(1H-1,2,4-triazol-3-yl)-1H-indol-7-yl]thiophene-2-sulfonamide

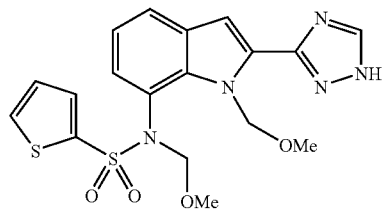 [SMILES: COCN(c1cccc2cc(-c3nc[nH]n3)n(COC)c12)S(=O)(=O)c1cccs1]

A mixture of N-[(1E)-(dimethylamino)methylene]-1-(methoxymethyl)-7-[(methoxymethyl)(2-thienylsulfonyl)amino]-1H-indole-2-carboxamide (1.06 g), hydrazine monohydrate (0.22 mL) and acetic acid (10 mL) was stirred at 80° C. for 1 hr. Water was added to the reaction mixture, and the obtained crystals were filtrated, washed with water and dried to give the title compound (0.99 g, quantitative) as colorless crystals. melting point 97-99° C.

Reference Example 20

N-(Methoxymethyl)-N-[1-(methoxymethyl)-2-(1-methyl-1H-1,2,4-triazol-5-yl)-1H-indol-7-yl]thiophene-2-sulfonamide

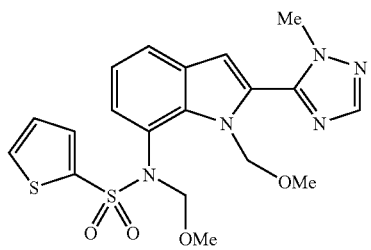 [SMILES: COCN(c1cccc2cc(-c3ncnn3C)n(COC)c12)S(=O)(=O)c1cccs1]

A mixture of N-(methoxymethyl)-N-[1-(methoxymethyl)-2-(1H-1,2,4-triazol-3-yl)-1H-indol-7-yl]thiophene-2-sulfonamide (0.70 g), methyl iodide (0.20 mL), potassium carbonate (0.25 g) and N,N-dimethylformamide (8 mL) was stirred at room temperature overnight. Water was added to the reaction mixture, and the mixture was extracted with ethyl acetate. The ethyl acetate layer was washed with saturated brine, dried (MgSO$_4$) and concentrated. The obtained residue was subjected to silica gel column chromatography and the title compound (0.14 g, yield 19%) was obtained as colorless crystals from a fraction eluted with ethyl acetate-hexane (1:4-1:0, volume ratio). melting point 110-111° C.

Reference Example 21

N-(Methoxymethyl)-N-[1-(methoxymethyl)-2-(1-methyl-1H-1,2,4-triazol-3-yl)-1H-indol-7-yl]thiophene-2-sulfonamide

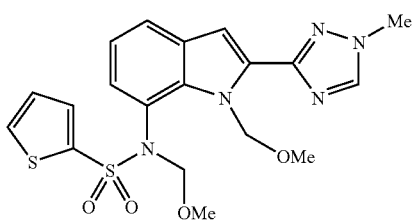 [SMILES: COCN(c1cccc2cc(-c3ncn(C)n3)n(COC)c12)S(=O)(=O)c1cccs1]

The title compound (0.42 g, yield 59%) was obtained as colorless crystals by silica gel column chromatography from the fraction after elution of the compound of Reference Example 20. melting point 157-158° C.

Reference Example 22

7-Nitro-1H-indole-2-carboxamide

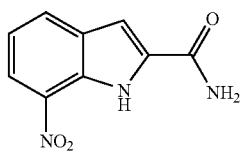

To a mixture of 7-nitro-1H-indole-2-carboxylic acid (4.40 g), 1H-1,2,3-benzotriazol-1-ol (3.45 g) and N,N-dimethylformamide (80 mL) was added N-[3-(dimethylamino)propyl]-N'-ethylcarbodiimide hydrochloride (4.90 g) at room temperature, and the mixture was stirred for 20 min and 28% aqueous ammonia (7.8 mL) was added. The reaction mixture was stirred at room temperature for 1 hr, and water was added. The resulting crystals were filtered, washed with water, and dried to give the title compound (3.21 g, yield 73%) as yellow crystals. melting point 297-298° C. (decomposition).

Reference Example 23

7-Nitro-1H-indole-2-carbothioamide

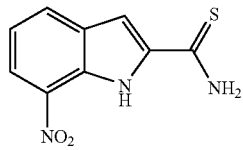 [SMILES: NC(=S)c1cc2cccc([N+](=O)[O-])c2[nH]1]

A mixture of 7-nitro-1H-indole-2-carboxamide (2.50 g), Lawesson's reagent (5.42 g) and tetrahydrofuran (50 mL) was stirred at 50° C. overnight. The reaction mixture was concentrated, and the resulting crystals were filtrated, washed with toluene, and dried to give the title compound (2.08 g, yield 77%) as yellow crystals. melting point>237° C. (decomposition).

Reference Example 24

7-Nitro-2-(1,2,4-thiadiazol-5-yl)-1H-indole

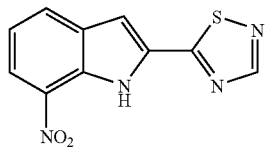

A mixture of 7-nitro-1H-indole-2-carbothioamide (1.00 g) and N,N-dimethylformamide dimethyl acetal (10 mL) was stirred at 60° C. for 4 hr. To the reaction mixture was added diisopropyl ether, and the resulting crystals were filtrated and dried.
A mixture of the obtained crystals, pyridine (0.91 mL), hydroxylamine-O-sulfonic acid (0.56 g), ethanol (10 mL) and tetrahydrofuran (10 mL) was stirred at 50° C. overnight. The reaction mixture was concentrated, and water was added to the residue. The resulting crystals were filtrated, washed with water and dried. The obtained crystals were subjected to silica gel column chromatography and the title compound (0.41 g, yield 38%) was obtained as yellow crystals from a fraction eluted with tetrahydrofuran-hexane (1:1, volume ratio). melting point 186-187° C.

Reference Example 25

2-(1,2,4-Thiadiazol-5-yl)-1H-indole-7-amine

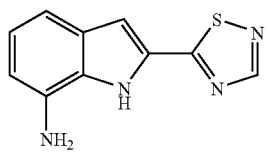 [SMILES: O=[N+]([O-])c1cccc2cc(-c3ncns3)[nH]c12]

A mixture of 7-nitro-2-(1,2,4-thiadiazol-5-yl)-1H-indole (0.41 g), iron(III) chloride hexahydrate (33 mg), activated carbon (0.33 g), tetrahydrofuran (12 mL) and methanol (6 mL) was heated under reflux for 20 min. To the reaction mixture was added hydrazine monohydrate (0.50 g) over 10 min while heating under reflux. The reaction mixture was heated under reflux for 2 hr, filtrated, and the filtrate was concentrated. The resulting crystals were washed with water, and dried to give the title compound (0.35 g, yield 94%) as colorless crystals. melting point>223° C. (decomposition).

Reference Example 26

7-Nitro-2-(1,3-thiazol-2-yl)-1H-indole

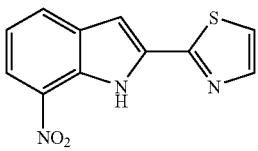

A mixture of 7-nitro-1H-indole-2-carbothioamide (2.06 g), 2-bromo-1,1-diethoxyethane (3.67 g), ethanol (10 mL) and N,N-dimethylacetamide (10 mL) was stirred at 100° C. for 4 hr. To the reaction mixture was added water, and the resulting crystals were filtrated, washed with water and hexane, and dried to give the title compound (2.21 g, yield 97%) as yellow crystals. melting point 130-131° C.

Reference Example 27

2-(1,3-Thiazol-2-yl)-1H-indole-7-amine

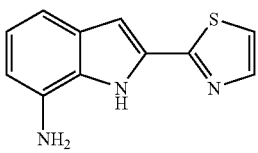

A mixture of 7-nitro-2-(1,3-thiazol-2-yl)-1H-indole (2.21 g), iron(III) chloride hexahydrate (0.12 g), activated carbon (1.20 g), tetrahydrofuran (10 mL) and methanol (10 mL) was heated under reflux for 20 min. To the reaction mixture was added hydrazine monohydrate (2.70 g) over 15 min while heating under reflux. The reaction mixture was heated under reflux for 2 hr, filtrated, and the filtrate was concentrated. The residue was dissolved in ethyl acetate, washed with saturated brine, dried (MgSO$_4$), and concentrated. The obtained residue was subjected to silica gel column chromatography and the title compound (1.76 g, yield 90%) was obtained as yellow crystals from a fraction eluted with ethyl acetate-hexane (1:2, volume ratio). melting point 173-174° C.

Reference Example 28

1-(Methoxymethyl)-7-nitro-2-(1,3-thiazol-2-yl)-1H-indole

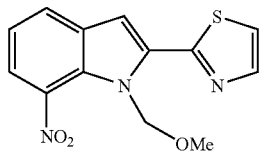 [SMILES: COCn1c(-c2nccs2)cc2cccc([N+](=O)[O-])c21]

To a suspension of sodium hydride (60% in oil, 0.47 g) in N,N-dimethylformamide (15 mL) was slowly added 7-nitro-2-(1,3-thiazol-2-yl)-1H-indole (2.21 g) at 0° C., and the mixture was stirred for 20 min. To the reaction mixture was added a solution of chloromethyl methyl ether (0.81 mL) in tetrahydrofuran (2 mL) at 0° C. over 20 min, and the mixture was stirred at room temperature overnight. Water was added to the reaction mixture, and the mixture was extracted with ethyl acetate. The ethyl acetate layer was washed with saturated brine, dried (MgSO$_4$) and concentrated. The obtained residue was subjected to silica gel column chromatography and the title compound (2.14 g, yield 82%) was obtained as a yellow oil from a fraction eluted with ethyl acetate-hexane (1:2, volume ratio).

$^1$H-NMR (CDCl$_3$) δ:2.91 (3H, s), 6.13 (2H, s), 7.14 (1H, s), 7.26 (1H, t, J=7.9 Hz), 7.44 (1H, d, J=3.2 Hz), 7.84 (1H, dd, J=8.0, 1.2 Hz), 7.90 (1H, d, J=8.0, 1.2 Hz), 7.96 (1H, d, J=3.2 Hz).

Reference Example 29

1-(Methoxymethyl)-2-(1,3-thiazol-2-yl)-1H-indole-7-amine

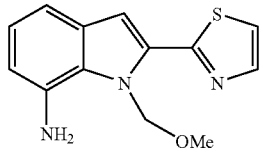 [SMILES: COCn1c(-c2nccs2)cc2cccc(N)c21]

A mixture of 1-(methoxymethyl)-7-nitro-2-(1,3-thiazol-2-yl)-1H-indole (2.14 g), iron(III) chloride hexahydrate (0.12 g), activated carbon (1.20 g), tetrahydrofuran (10 mL) and methanol (10 mL) was heated under reflux for 20 min. To the reaction mixture was added hydrazine monohydrate (2.20 g) over 15 min while heating under reflux. The reaction mixture was heated under reflux for 2 hr, filtrated, and the filtrate was concentrated. The residue was dissolved in ethyl acetate, washed with saturated brine, dried (MgSO$_4$), and concentrated. The obtained residue was subjected to silica gel column chromatography and the title compound (1.87 g, yield 97%) was obtained as a yellow oil from a fraction eluted with ethyl acetate-hexane (1:2, volume ratio).

$^1$H-NMR (CDCl$_3$) δ:3.42 (3H, s), 4.51 (2H, brs), 6.30 (2H, s), 6.58 (1H, dd, J=7.8, 1.2 Hz), 6.95 (1H, s), 6.97 (1H, t, J=7.8 Hz), 7.07 (1H, dd, J=7.8, 1.2 Hz), 7.32 (1H, d, J=3.2 Hz), 7.86 (1H, d, J=3.2 Hz).

Reference Example 30

N-[1-(Methoxymethyl)-2-(1,3-thiazol-2-yl)-1H-indol-7-yl]thiophene-2-sulfonamide

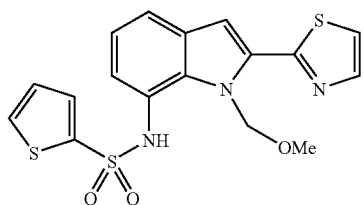 [SMILES: COCn1c(-c2nccs2)cc2cccc(NS(=O)(=O)c3cccs3)c21]

To a mixture of 1-(methoxymethyl)-2-(1,3-thiazol-2-yl)-1H-indole-7-amine (1.87 g) and pyridine (10 mL) was added thiophene-2-sulfonyl chloride (1.57 g) at 0° C., and the mixture was stirred at room temperature for 2 hr. The reaction mixture was concentrated, 10% aqueous citric acid solution was added, and the mixture was extracted with ethyl acetate. The ethyl acetate layer was washed with saturated brine, dried (MgSO$_4$) and concentrated. The obtained residue was subjected to silica gel column chromatography and the title compound (2.69 g, yield 92%) was obtained as yellow crystals from a fraction eluted with ethyl acetate-hexane (1:2, volume ratio). melting point 95-97° C.

Reference Example 31

Ethyl N-[1-(Methoxymethyl)-2-(1,3-thiazol-2-yl)-1H-indol-7-yl]-N-(2-thienylsulfonyl)aminoacetate

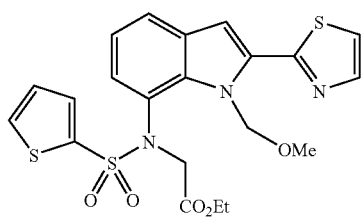 [SMILES: CCOC(=O)CN(c1cccc2cc(-c3nccs3)n(COC)c12)S(=O)(=O)c1cccs1]

A mixture of N-[1-(methoxymethyl)-2-(1,3-thiazol-2-yl)-1H-indol-7-yl]thiophene-2-sulfonamide (0.68 g), ethyl bromoacetate (0.23 mL), potassium carbonate (0.35 g) and N,N-dimethylformamide (6 mL) was stirred at room temperature for 4 hr. Water was added to the reaction mixture, and the mixture was extracted with ethyl acetate. The ethyl acetate layer was washed with saturated brine, dried (MgSO$_4$) and concentrated. The obtained residue was subjected to silica gel column chromatography and the title compound (0.82 g, quantitative) was obtained as pale-yellow crystals from a fraction eluted with ethyl acetate-hexane (2:3, volume ratio). melting point 124-125° C.

Reference Example 32

3-Chloro-1-(methoxymethyl)-7-nitro-2-(1,3-thiazol-2-yl)-1H-indole

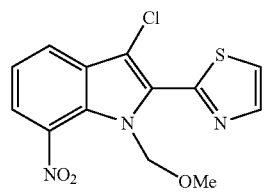 [SMILES: COCn1c(-c2nccs2)c(Cl)c2cccc([N+](=O)[O-])c21]

A mixture of 7-nitro-2-(1,3-thiazol-2-yl)-1H-indole (0.30 g), sulfuryl chloride (0.11 mL) and chloroform (10 mL) was heated under reflux for 4 hr. The reaction mixture was concentrated, and water was added. The resulting crystals were collected by filtration, washed with water, and dried to give crude crystals (0.35 g).

To a suspension of sodium hydride (60% in oil, 0.12 g) in N,N-dimethylformamide (15 mL) were slowly added the above-mentioned crude crystals at 0° C., and the mixture was stirred for 15 min. To the reaction mixture was added chloromethyl methyl ether (0.21 mL) at 0° C. over 10 min, and the mixture was stirred at room temperature overnight. Water was added to the reaction mixture, and the mixture was extracted with ethyl acetate. The ethyl acetate layer was washed with saturated brine, dried (MgSO$_4$) and concentrated. The obtained residue was subjected to silica gel column chromatography and the title compound (0.30 g, yield 72%) was obtained as yellow crystals from a fraction eluted with ethyl acetate-hexane (1:3, volume ratio). melting point 106-107° C.

Reference Example 33

3-Chloro-1-(methoxymethyl)-2-(1,3-thiazol-2-yl)-1H-indole-7-amine

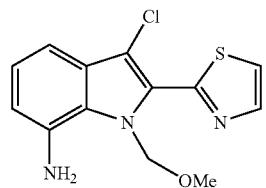 [SMILES: COCn1c(-c2nccs2)c(Cl)c2cccc(N)c21]

A mixture of 3-chloro-1-(methoxymethyl)-7-nitro-2-(1,3-thiazol-2-yl)-1H-indole (0.30 g), iron(III) chloride hexahydrate (15 mg), activated carbon (0.15 g), tetrahydrofuran (6 mL) and methanol (6 mL) was heated under reflux for 20 min. To the reaction mixture was added hydrazine monohydrate (0.27 g) while heating under reflux. The reaction mixture was heated under reflux for 2 hr, filtrated, and the filtrate was concentrated. The residue was dissolved in ethyl acetate, washed with saturated brine, dried (MgSO$_4$) and concentrated to give the title compound (0.25 g, yield 91%) as a yellow oil.

$^1$H-NMR (CDCl$_3$) δ:3.42 (3H, s), 4.56 (2H, brs), 6.23 (2H, s), 6.64 (1H, dd, J=7.0, 1.4 Hz), 6.97-7.17 (2H, m), 7.52 (1H, d, J=3.2 Hz), 7.97 (1H, d, J=3.2 Hz).

Reference Example 34

N-[3-Chloro-1-(methoxymethyl)-2-(1,3-thiazol-2-yl)-1H-indol-7-yl]thiophene-2-sulfonamide

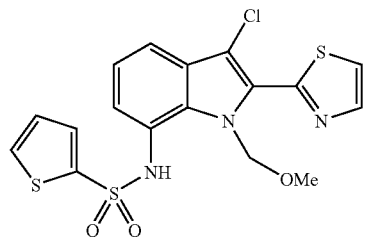 [SMILES: COCn1c(-c2nccs2)c(Cl)c2cccc(NS(=O)(=O)c3cccs3)c21]

To a mixture of 3-chloro-1-(methoxymethyl)-2-(1,3-thiazol-2-yl)-1H-indole-7-amine (0.25 g) and pyridine (8 mL) was added thiophene-2-sulfonyl chloride (0.19 g) at 0° C., and the mixture was stirred at room temperature overnight. The reaction mixture was concentrated, 10% aqueous citric acid solution was added, and the mixture was extracted with ethyl acetate. The ethyl acetate layer was washed with saturated brine, dried (MgSO$_4$) and concentrated. The obtained residue was subjected to silica gel column chromatography and the title compound (0.36 g, yield 96%) was obtained as yellow crystals from a fraction eluted with ethyl acetate-hexane (1:2, volume ratio). melting point 128-129° C.

Reference Example 35

Ethyl 2-[1-(methoxymethyl)-7-nitro-1H-indol-2-yl]-1,3-thiazole-5-carboxylate

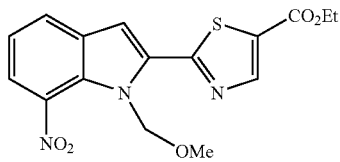 [SMILES: CCOC(=O)c1cnc(-c2cc3cccc([N+](=O)[O-])c3n2COC)s1]

A mixture of 7-nitro-1H-indole-2-carbothioamide (3.00 g), potassium 2-chloro-3-oxopropanoate (5.12 g), acetic acid (10 mL) and N,N-dimethylacetamide (30 mL) was stirred at 100° C. for 6 hr. To the reaction mixture was added water, the mixture was concentrated, and water was added to the residue. The mixture was acidified with 10% aqueous citric acid solution, and the resulting crystals were filtrated, washed with water, and dried to give colorless crude crystals (3.19 g) as colorless crystals.

To a suspension of sodium hydride (60% in oil, 0.60 g) in N,N-dimethylformamide (30 mL) was slowly added the above-mentioned colorless crude crystals (3.19 g) at 0° C., and the mixture was stirred for 15 min. To the reaction mixture was added chloromethyl methyl ether (1.10 mL) in tetrahydrofuran (2 mL) at 0° C. over 30 min, and the mixture was stirred at room temperature for 1 hr. Water was added to the reaction mixture, and the mixture was extracted with ethyl acetate. The ethyl acetate layer was washed with saturated brine, dried (MgSO$_4$) and concentrated. The obtained residue was subjected to silica gel column chromatography and the title compound (2.88 g, yield 59%) was obtained as yellow crystals from a fraction eluted with ethyl acetate-hexane (1:4, volume ratio). melting point 92-93° C.

Reference Example 36

Ethyl 2-[7-amino-1-(methoxymethyl)-1H-indol-2-yl]-1,3-thiazole-5-carboxylate

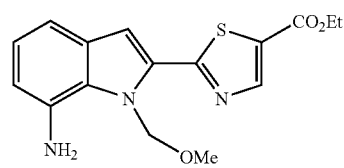

A mixture of ethyl 2-[1-(methoxymethyl)-7-nitro-1H-indol-2-yl]-1,3-thiazole-5-carboxylate (2.44 g), iron(III) chloride hexahydrate (92 mg), activated carbon (1.0 g), tetrahydrofuran (10 mL) and ethanol (5 mL) was heated under reflux for 20 min. To the reaction mixture was added hydrazine monohydrate (2.05 g) over 15 min while heating under reflux. The reaction mixture was heated under reflux for 5 hr, filtrated, and the filtrate was concentrated. The residue was dissolved in ethyl acetate, washed with saturated brine, dried (MgSO$_4$), and concentrated. Isopropyl ether was added to the obtained residue. The resulting crystals were collected by filtration, washed with isopropyl ether, and dried to give the title compound (2.18 g, yield 97%) as yellow crystals. melting point 188-190° C.

Reference Example 37

Ethyl 2-{1-(methoxymethyl)-7-[(2-thienylsulfonyl)amino]-1H-indol-2-yl}-1,3-thiazole-5-carboxylate

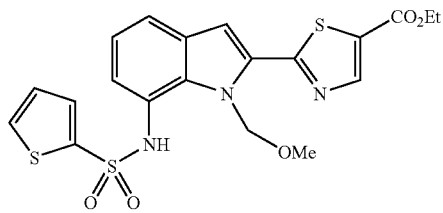 [SMILES: CCOC(=O)c1cnc(-c2cc3cccc(NS(=O)(=O)c4cccs4)c3n2COC)s1]

To a mixture of ethyl 2-[7-amino-1-(methoxymethyl)-1H-indol-2-yl]-1,3-thiazole-5-carboxylate (2.18 g) and pyridine (25 mL) was added thiophene-2-sulfonyl chloride (1.50 g) at 0° C., and the mixture was stirred at room temperature overnight. The reaction mixture was concentrated, 10% aqueous citric acid solution was added, and the mixture was extracted with ethyl acetate. The ethyl acetate layer was washed with saturated brine, dried (MgSO₄) and concentrated. The obtained residue was subjected to silica gel column chromatography and the title compound (2.19 g, yield 70%) was obtained as yellow crystals from a fraction eluted with ethyl acetate-hexane (1:3, volume ratio). melting point 133-134° C.

Reference Example 38

Ethyl 2-{1-(methoxymethyl)-7-[methyl(2-thienylsulfonyl)amino]-1H-indol-2-yl}-1,3-thiazole-5-carboxylate

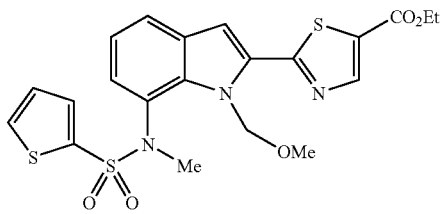 [SMILES: CCOC(=O)c1cnc(-c2cc3cccc(N(C)S(=O)(=O)c4cccs4)c3n2COC)s1]

A mixture of ethyl 2-{1-(methoxymethyl)-7-[(2-thienylsulfonyl)amino]-1H-indol-2-yl}-1,3-thiazole-5-carboxylate (2.19 g), methyl iodide (0.57 mL), potassium carbonate (0.95 g) and N,N-dimethylformamide (20 mL) was stirred at room temperature overnight. Water was added to the reaction mixture, and the obtained crystals were filtrated, washed with water and dried to give the title compound (2.18 g, yield 97%) as pale-yellow crystals. melting point 142-143° C.

Reference Example 39

N-{2-[5-(Hydroxymethyl)-1,3-thiazol-2-yl]-1-(methoxymethyl)-1H-indol-7-yl}-N-methylthiophene-2-sulfonamide

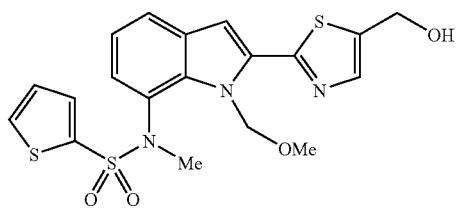 [SMILES: COCn1c(-c2ncc(CO)s2)cc2cccc(N(C)S(=O)(=O)c3cccs3)c21]

To a mixture of ethyl 2-{1-(methoxymethyl)-7-[methyl(2-thienylsulfonyl)amino]-1H-indol-2-yl}-1,3-thiazole-5-carboxylate (2.13 g) and tetrahydrofuran (30 mL) was added lithium aluminum hydride (0.21 g) at 0° C., and the mixture was stirred at 0° C. for 30 min. To the reaction mixture was added ethanol (5 mL) and then saturated aqueous ammonium chloride solution (4 mL). The resulting inorganic salt was filtered off, and the filtrate was concentrated. The obtained crystals were subjected to silica gel column chromatography and eluted with ethyl acetate to give the title compound (1.95 g, quantitative) as pale-yellow crystals. melting point 156-157° C.

Reference Example 40

7-[Methyl(2-thienylsulfonyl)amino]-1H-indole-2-carbothioamide

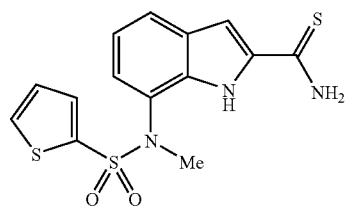 [SMILES: CN(c1cccc2cc(C(N)=S)[nH]c12)S(=O)(=O)c1cccs1]

A mixture of 7-[methyl(2-thienylsulfonyl)amino]-1H-indole-2-carboxamide (11.47 g), Lawesson's reagent (15.2 g) and tetrahydrofuran (150 mL) was stirred at 50° C. for 4 hr. The reaction mixture was concentrated, and the resulting crystals were filtrated, washed with toluene, and dried to give the title compound (11.16 g, yield 93%) as yellow crystals. melting point 239-240° C.

Reference Example 41

2-(4,5-Dimethyl-1,3-thiazol-2-yl)-7-nitro-1H-indole

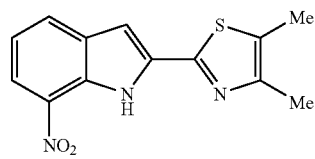 [SMILES: Cc1nc(-c2cc3cccc([N+](=O)[O-])c3[nH]2)sc1C]

A mixture of 7-nitro-1H-indole-2-carbothioamide (0.50 g) obtained in Reference Example 23, 3-bromo-2-butanone (0.48 mL), N,N-dimethylacetamide (10 mL) and ethanol (50 mL) was stirred at 100° C. for 2 days. The reaction mixture was concentrated, diluted with ethyl acetate, washed twice with water, dried over anhydrous magnesium sulfate, and concentrated under reduced pressure. The obtained crystals were washed with diethyl ether-hexane to give the title compound (538 mg, yield 87%) as pale-yellow crystals. MS:274 (MH⁺).

Reference Example 42

2-(4,5-Dimethyl-1,3-thiazol-2-yl)-1H-indole-2-amine

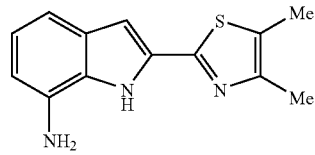

A mixture of 2-(4,5-dimethyl-1,3-thiazol-2-yl)-7-nitro-1H-indole (0.40 g), iron powder (0.41 g), acetic acid (10 mL) and ethanol (20 mL) was vigorously stirred at 100° C. for 90 min. The reaction solution was diluted with ethyl acetate, washed with water, aqueous sodium hydrogencarbonate solution and saturated brine, dried over anhydrous magnesium sulfate, and concentrated under reduced pressure. The obtained residue was subjected to silica gel column chromatography (ethyl acetate) to give the title compound (209 mg, yield 59%) as pale-yellow crystals. melting point 250-251° C.

Ethyl 7-nitro-1H-indole-2-carboxylate derivative used in the following Reference Examples was synthesized according to the method described in a literature [Synthesis, 1996, pp. 377-382].

Reference Example 43

Ethyl 5-fluoro-1-(methoxymethyl)-7-[(2-thienylsulfonyl)amino]-1H-indole-2-carboxylate

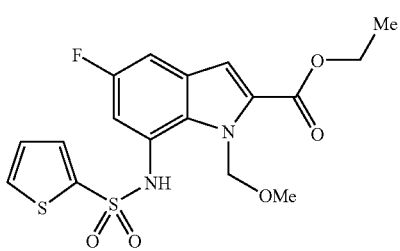 [SMILES: CCOC(=O)c1cc2cc(F)cc(NS(=O)(=O)c3cccs3)c2n1COC]

and ethyl 5-fluoro-7-[(2-thienylsulfonyl)amino]-1H-indole-2-carboxylate

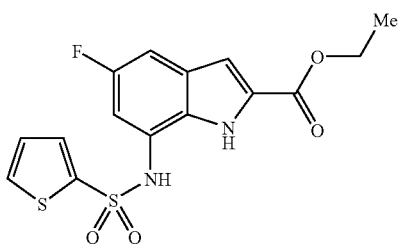 [SMILES: CCOC(=O)c1cc2cc(F)cc(NS(=O)(=O)c3cccs3)c2[nH]1]

To a solution (10 mL) of ethyl 5-fluoro-7-nitro-1H-indole-2-carboxylate (0.68 g) in N,N-dimethylacetamide was added 60% sodium hydride (0.12 g) under ice-cooling, and the mixture was stirred at the same temperature for 30 min. Then, chloromethyl methyl ether (0.23 mL) was added to the solution, and the mixture was stirred for 5 hr under ice-cooling. The reaction solution was diluted with ethyl acetate, washed with aqueous citric acid solution, water and saturated brine, dried over anhydrous magnesium sulfate, and concentrated under reduced pressure. The obtained residue was subjected to silica gel column chromatography (ethyl acetate:hexane=1:9-1:4) to give yellow crystals (400 mg).

Then, the obtained yellow crystals and 10% palladium-carbon (50% containing water, 0.13 g) were added to a mixed solvent of tetrahydrofuran (20 mL) and ethanol (10 mL), and the mixture was stirred at room temperature under a hydrogen atmosphere for 5 hr. The catalyst was filtered off, and the filtrate was concentrated under reduced pressure.

The obtained crystals were dissolved in pyridine (10 mL), and under ice-cooling, thiophene-2-sulfonyl chloride (0.47 g) was added, and the mixture was stirred at room temperature for 17 hr. The reaction solution was concentrated under reduced pressure, and the residue was diluted with ethyl acetate, washed with aqueous citric acid solution and brine, dried over anhydrous magnesium sulfate, and concentrated under reduced pressure. The obtained residue was subjected to silica gel column chromatography (ethyl acetate:hexane=1:9-2:8) to give ethyl 5-fluoro-1-(methoxymethyl)-7-[(2-thienylsulfonyl)amino]-1H-indole-2-carboxylate (450 mg, yield 40%) as a pale-yellow oil.

$^1$H-NMR (CDCl$_3$) δ:1.39 (3H, t, J=7.2 Hz), 3.49 (3H, s), 4.35 (2H, q, J=7.2 Hz), 5.71 (2H, s), 7.02 (1H, dd, J=3.6, 5.2 Hz), 7.13 (1H, dd, J=2.4, 7.8 Hz), 7.26 (1H, s), 7.43 (1H, dd, J=2.4, 10.6 Hz), 7.52 (1H, dd, J=1.4, 5.2 Hz), 7.60 (1H, dd, J=1.4, 3.6 Hz), 9.16 (1H, brs).

In addition, ethyl 5-fluoro-7-[(2-thienylsulfonyl)amino]-1H-indole-2-carboxylate (272 mg, 27%) was obtained as pale-yellow needle crystals. melting point 174-175° C.

Reference Example 44

Ethyl 5-fluoro-1-(methoxymethyl)-7-[methyl(2-thienylsulfonyl)amino]-1H-indole-2-carboxylate

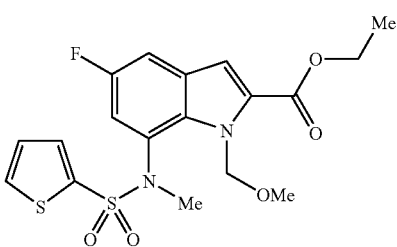 [SMILES: CCOC(=O)c1cc2cc(F)cc(N(C)S(=O)(=O)c3cccs3)c2n1COC]

A mixture of ethyl 5-fluoro-1-(methoxymethyl)-7-[(2-thienylsulfonyl)amino]-1H-indole-2-carboxylate (0.45 g), 60% sodium hydride (52 mg) and N,N-dimethylformamide (10 mL) was stirred at 4° C. for 30 min. Methyl iodide (0.095 mL) was added to the solution, and the mixture was stirred at room temperature for 2 days. The reaction solution was diluted with ethyl acetate, washed with aqueous citric acid solution and saturated brine, dried over anhydrous magnesium sulfate, and concentrated under reduced pressure. The obtained residue was subjected to silica gel column chromatography (ethyl acetate:hexane=1:9-2:8) to give the title compound (0.20 g, yield 43%) as colorless prism crystals.

$^1$H-NMR (CDCl$_3$) δ:1.41 (3H, t, J=7.0 Hz), 3.29 (3H, s), 3.34 (3H, s), 4.39 (2H, q, J=7.0 Hz), 6.29 (1H, d, J=10.0 Hz), 6.33 (1H, dd, J=2.2, 9.8 Hz), 6.42 (1H, d, J=10.0 Hz), 7.20 (1H, dd, J=3.6, 5.0 Hz), 7.28-7.38 (2H, m), 7.50 (1H, dd, J=1.4, 3.6 Hz), 7.72 (1H, dd, J=1.4, 5.0 Hz).

Reference Example 45

Ethyl 1-(methoxymethyl)-7-nitro-5-(trifluoromethoxy)-1H-indole-2-carboxylate

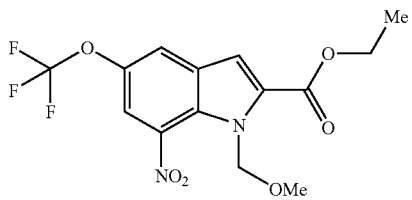 [SMILES: CCOC(=O)c1cc2cc(OC(F)(F)F)cc([N+](=O)[O-])c2n1COC]

A mixture of ethyl 7-nitro-5-(trifluoromethoxy)-1H-indole-2-carboxylate (1.19 g), 60% sodium hydride (0.18 g) and N,N-dimethylformamide (20 mL) was stirred at 4° C. for 20 min. A solution (5 mL) of chloromethyl methyl ether (0.33 mL) in tetrahydrofuran was added dropwise. After stirring at 4° C. for 3 hr, the reaction solution was diluted with ethyl acetate, washed with aqueous citric acid solution, water and saturated brine, dried over anhydrous magnesium sulfate, and concentrated under reduced pressure. The obtained residue was subjected to silica gel column chromatography (ethyl acetate:hexane=5:95-20:80) to give the title compound (1.0 g, yield 74%) as pale-yellow prism crystals.

$^1$H-NMR (CDCl$_3$) δ:1.44 (3H, t, J=7.0 Hz), 2.97 (3H, s), 4.43 (2H, q, J=7.0 Hz), 6.03 (2H, s), 7.47 (1H, s), 7.75-7.85 (2H, m).

Reference Example 46

Ethyl 1-(methoxymethyl)-7-[(2-thienylsulfonyl)amino]-5-(trifluoromethoxy)-1H-indole-2-carboxylate

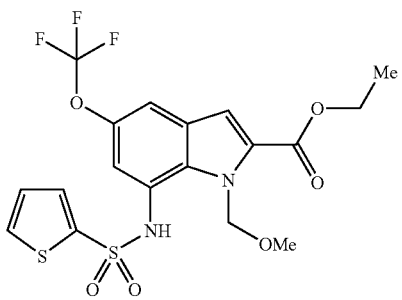 [SMILES: CCOC(=O)c1cc2cc(OC(F)(F)F)cc(NS(=O)(=O)c3cccs3)c2n1COC]

Ethyl 1-(methoxymethyl)-7-nitro-5-(trifluoromethoxy)-1H-indole-2-carboxylate (1.0 g) and 10% palladium-carbon (50% containing water, 0.25 g) were added to a mixed solvent of tetrahydrofuran (20 mL) and ethanol (10 mL), and the mixture was stirred at room temperature under a hydrogen atmosphere for 6 hr. The catalyst was filtered off, and the filtrate was concentrated under reduced pressure.

The obtained residue was dissolved in pyridine (15 mL), and under ice-cooling, thiophene-2-sulfonyl chloride (0.60 g) was added, and the mixture was stirred at room temperature for 15 hr. The reaction solution was concentrated under reduced pressure, and the residue was diluted with ethyl acetate, washed with aqueous citric acid solution and brine, dried over anhydrous magnesium sulfate, and concentrated under reduced pressure. The obtained residue was subjected to silica gel column chromatography (ethyl acetate:hexane=5:95-20:80) to give the title compound (1.07 g, yield 81%) as a pale-yellow oil.

$^1$H-NMR (CDCl$_3$) δ:1.40 (3H, t, J=7.4 Hz), 3.50 (3H, s), 4.36 (2H, q, J=7.4 Hz), 5.77 (2H, s), 7.02 (1H, dd, J=3.8, 5.0 Hz), 7.30 (1H, s), 7.32-7.36 (1H, m), 7.50-7.57 (2H, m), 7.59 (1H, dd, J=1.6, 3.8 Hz), 9.13 (1H, brs).

Reference Example 47

Ethyl 1-(methoxymethyl)-7-[methyl(2-thienylsulfonyl)amino]-5-(trifluoromethoxy)-1H-indole-2-carboxylate

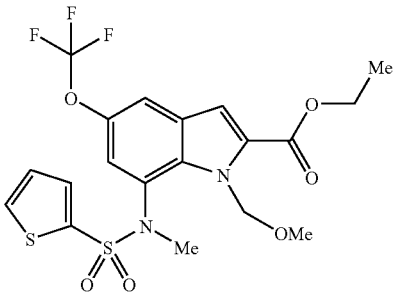 [SMILES: CCOC(=O)c1cc2cc(OC(F)(F)F)cc(N(C)S(=O)(=O)c3cccs3)c2n1COC]

A mixture of ethyl 1-(methoxymethyl)-7-[(2-thienylsulfonyl)amino]-5-(trifluoromethoxy)-1H-indole-2-carboxylate (1.07 g), 60% sodium hydride (0.10 g) and N,N-dimethylformamide (14 mL) was stirred at room temperature for 40 min. A solution of methyl iodide (0.20 mL) in tetrahydrofuran (3 mL) was added dropwise, and the mixture was stirred at room temperature for 18 hr. The reaction solution was diluted with ethyl acetate, washed with aqueous citric acid solution, water and saturated brine, dried over anhydrous magnesium sulfate, and concentrated under reduced pressure. The obtained residue was subjected to silica gel column chromatography (ethyl acetate:hexane=5:95-15:85) to give the title compound (0.75 g, yield 68%) as pale-yellow needle crystals.

$^1$H-NMR (CDCl$_3$) δ:1.42 (3H, t, J=7.2 Hz), 3.30 (3H, s), 3.35 (3H, s), 4.32-4.50 (2H, m), 6.32 (1H, d, J=10.2 Hz), 6.40-6.48 (2H, m), 7.19 (1H, dd, J=3.6, 7.8 Hz), 7.38 (1H, s), 7.46 (1H, dd, J=1.6, 3.6 Hz), 7.54-7.56 (1H, m), 7.72 (1H, dd; J=1.6, 4.8 Hz).

Reference Example 48

Methyl 7-amino-1H-pyrrolo[2,3-c]pyridine-2-carboxylate

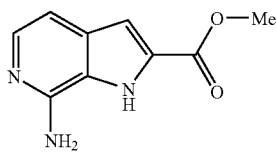

A mixture of methyl 7-(benzylamino)-1H-pyrrolo[2,3-c]pyridine-2-carboxylate (3.2 g), ammonium formate (7.2 g), 10% palladium-carbon (50% containing water, 3.2 g) and methanol (120 mL) was heated under reflux for 4 hr. Ammonium formate (6.0 g) was further added to the reaction solution, and the mixture was heated under reflux for 16 hr. The insoluble material was filtered off by passing the reaction solution through celite without cooling. The filtrate was concentrated and the obtained crystals were washed with metha-

Reference Example 49

Ethyl 1-(methoxymethyl)-4-methyl-7-nitro-1H-indole-2-carboxylate

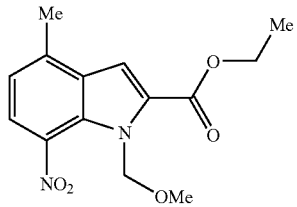 [SMILES: CCOC(=O)c1cc2c(C)ccc([N+](=O)[O-])c2n1COC]

A mixture of ethyl 4-methyl-7-nitro-1H-indole-2-carboxylate (7.0 g), 60% sodium hydride (1.35 g) and N,N-dimethylformamide (40 mL) was stirred at room temperature for 30 min. The solution was ice-cooled, and a solution (15 mL) of chloromethyl methyl ether (2.6 mL) in tetrahydrofuran was added dropwise. The mixture was stirred at 4° C. for 4 hr, and the reaction solution was diluted with ethyl acetate, washed with aqueous citric acid solution, water and saturated brine, dried over anhydrous magnesium sulfate, and concentrated under reduced pressure. The obtained residue was subjected to silica gel column chromatography (ethyl acetate:hexane=5:95-1:5) to give the title compound (5.6 g, yield 68%) as pale-yellow needle crystals.

$^1$H-NMR (CDCl$_3$) δ:1.44 (3H, t, J=7.2 Hz), 2.65 (3H, s), 2.92 (3H, s), 4.42 (2H, q, J=7.2. Hz), 6.04 (2H, s), 7.05 (1H, dd, J=0.8, 8.0 Hz), 7.49 (1H, s), 7.82 (1H, d, J=8.0 Hz).

Reference Example 50

Ethyl 1-(methoxymethyl)-4-methyl-7-[(2-thienylsulfonyl)amino]-1H-indole-2-carboxylate

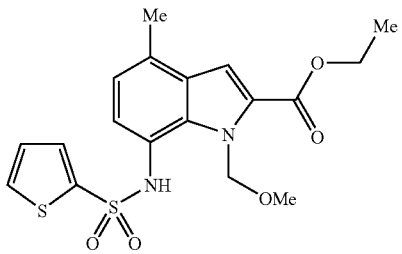 [SMILES: CCOC(=O)c1cc2c(C)ccc(NS(=O)(=O)c3cccs3)c2n1COC]

Ethyl 1-(methoxymethyl)-4-methyl-7-nitro-1H-indole-2-carboxylate (5.6 g) and 10% palladium-carbon (50% containing water, 1.25 g) were added to a mixed solvent of tetrahydrofuran (70 mL) and ethanol (70 mL), and the mixture was stirred at room temperature under a hydrogen atmosphere for 5 hr. The catalyst was filtered off, and the filtrate was concentrated under reduced pressure.

The obtained residue was dissolved in pyridine (50 mL), and under ice-cooling, thiophene-2-sulfonyl chloride (4.0 g) was added, and the mixture was stirred at room temperature for 18 hr. The reaction solution was concentrated under reduced pressure, and the residue was diluted with ethyl acetate, washed with aqueous citric acid solution and brine, dried over anhydrous magnesium sulfate, and concentrated under reduced pressure. The obtained residue was subjected to silica gel column chromatography (ethyl acetate:hexane=1:9-1:3) to give the title compound (8.4 g, yield 100%) as a pale-yellow oil.

$^1$H-NMR (CDCl$_3$) δ:1.41 (3H, t, J=7.0 Hz), 2.52 (3H, s), 3.41 (3H, s), 4.35 (2H, q, J=7.0 Hz), 5.69 (2H, s), 6.92-7.02 (2H, m), 7.34 (1H, s), 7.44-7.52 (3H, m), 8.65 (1H, brs).

Reference Example 51

Ethyl 1-(methoxymethyl)-4-methyl-7-[methyl(2-thienylsulfonyl)amino]-1H-indole-2-carboxylate

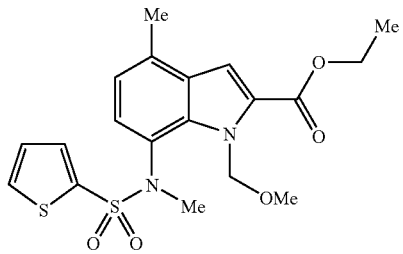 [SMILES: CCOC(=O)c1cc2c(C)ccc(N(C)S(=O)(=O)c3cccs3)c2n1COC]

A mixture of ethyl 1-(methoxymethyl)-4-methyl-7-[(2-thienylsulfonyl)amino]-1H-indole-2-carboxylate (7.8 g), methyl iodide (1.7 mL), potassium carbonate (2.9 g) and N,N-dimethylformamide (14 mL) was stirred at room temperature for 18 hr. The reaction solution was concentrated under reduced pressure. The obtained residue was diluted with ethyl acetate, washed with aqueous citric acid solution, water and saturated brine, dried over anhydrous magnesium sulfate, and concentrated under reduced pressure. The obtained colorless crystals were washed with diethyl ether-hexane to give the title compound (6.85 g, yield 85%) as colorless needle crystals.

$^1$H-NMR (CDCl$_3$) δ:1.42 (3H, t, J=7.0 Hz), 2.54 (3H, s), 3.29 (3H, s), 3.35 (3H, s), 4.40 (2H, q, J=7.0 Hz), 6.33 (1H, d, J=9.8 Hz), 6.43 (1H, d, J=9.8 Hz), 6.45 (1H, d, J=7.8 Hz), 6.78 (1H, dd, J=0.8, 7.8 Hz), 7.16 (1H, dd, J=4.0, 5.0 Hz), 7.40 (1H, s), 7.47 (1H, dd, J=1.4, 4.0 Hz), 7.67 (1H, dd, J=1.4, 5.0 Hz).

Reference Example 52

Ethyl 4-fluoro-1-(methoxymethyl)-7-nitro-1H-indole-2-carboxylate

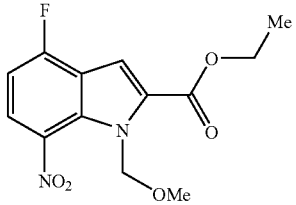 [SMILES: CCOC(=O)c1cc2c(F)ccc([N+](=O)[O-])c2n1COC]

A mixture of ethyl 4-fluoro-7-nitro-1H-indole-2-carboxylate (0.48 g), 60% sodium hydride (0.12 g) and N,N-dimethylformamide (20 mL) was stirred at 4° C. for 30 min. A solution (5 mL) of chloromethyl methyl ether (0.25 mL) in tetrahydrofuran was added dropwise under ice-cooling. After stirring at room temperature for 18 hr, the reaction solution was diluted with ethyl acetate, washed with aqueous citric acid solution, water and saturated brine, dried over anhydrous magnesium sulfate, and concentrated under reduced pressure.

The obtained residue was subjected to silica gel column chromatography (ethyl acetate:hexane=1:5) to give the title compound (0.46 g, yield 81%) as pale-brown needle crystals.

$^1$H-NMR (CDCl$_3$) δ:1.44 (3H, t, J=7.2 Hz), 2.95 (3H, m), 4.43 (2H, q, J=7.2 Hz), 6.05 (2H, s), 6.92 (1H, t, J=8.4 Hz), 7.54 (1H, s), 7.92 (1H, dd, J=4.5, 8.4 Hz).

Reference Example 53

Ethyl 4-fluoro-1-(methoxymethyl)-7-[(2-thienylsulfonyl)amino]-1H-indole-2-carboxylate

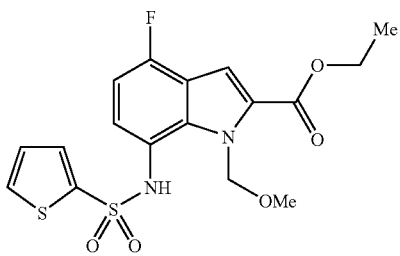 [SMILES: CCOC(=O)c1cc2c(F)ccc(NS(=O)(=O)c3cccs3)c2n1COC]

Ethyl 4-fluoro-1-(methoxymethyl)-7-nitro-1H-indole-2-carboxylate (0.46 g) and 10% palladium-carbon (50% containing water, 0.20 g) were added to a mixed solvent of tetrahydrofuran (15 mL) and ethanol (15 mL), and the mixture was stirred at room temperature under a hydrogen atmosphere for 3 hr. The catalyst was filtered off, and the filtrate was concentrated under reduced pressure.

The obtained residue was dissolved in pyridine (15 mL), and under ice-cooling, thiophene-2-sulfonyl chloride (0.35 g) was added, and the mixture was stirred at room temperature for 18 hr. The reaction solution was concentrated under reduced pressure, and the residue was diluted with ethyl acetate, washed with aqueous citric acid solution and brine, dried over anhydrous magnesium sulfate, and concentrated under reduced pressure. The obtained residue was subjected to silica gel column chromatography (ethyl acetate:hexane=10:90-25:75) to give the title compound (455 mg, yield 71%) as a pale-yellow oil.

$^1$H-NMR (CDCl$_3$) δ:1.40 (3H, t, J=7.2 Hz), 3.41 (3H, s), 4.36 (2H, q, J=7.2 Hz), 5.70 (2H, s), 6.85 (1H, t, J=8.7 Hz), 7.02 (1H, dd, J=4.2, 4.5 Hz), 7.40 (1H, s), 7.43-7.54 (3H, m), 8.51 (1H, brs).

Reference Example 54

Ethyl 4-fluoro-1-(methoxymethyl)-7-[methyl(2-thienylsulfonyl)amino]-1H-indole-2-carboxylate

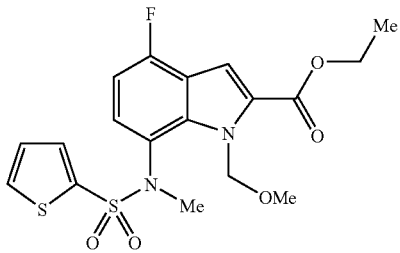 [SMILES: CCOC(=O)c1cc2c(F)ccc(N(C)S(=O)(=O)c3cccs3)c2n1COC]

A mixture of ethyl 4-fluoro-1-(methoxymethyl)-7-[(2-thienylsulfonyl)amino]-1H-indole-2-carboxylate (455 mg), methyl iodide (0.103 mL), potassium carbonate (183 mg) and N,N-dimethylformamide (10 mL) was stirred at room temperature for 18 hr. The reaction solution was diluted with ethyl acetate, washed with aqueous citric acid solution, water and saturated brine, dried over anhydrous magnesium sulfate, and concentrated under reduced pressure to give the title compound (0.45 g, yield 96%) as pale-pink crystals.

$^1$H-NMR (CDCl$_3$) δ:1.42 (3H, t, J=7.2 Hz), 3.31 (3H, s), 3.34 (3H, s), 4.39 (2H, dq, J=1.5, 7.2 Hz), 6.31 (1H, d, J=10.2 Hz), 6.42 (1H, d, J=10.2 Hz), 6.46 (1H, dd, J=1.5, 7.4 Hz), 6.65 (1H, t, J=7.4 Hz), 7.17 (1H, dd, J=3.6, 5.4 Hz), 7.44 (1H, s), 7.46 (1H, dd, J=1.5, 3.6 Hz), 7.68 (1H, dd, J=1.5, 5.4 Hz).

Reference Example 55

4-Fluoro-1-(methoxymethyl)-7-[methyl(2-thienylsulfonyl)amino]-1H-indole-2-carboxylic acid

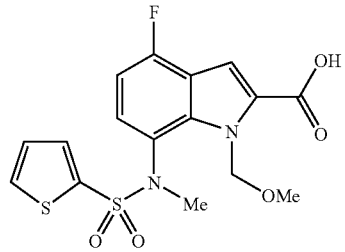 [SMILES: COCn1c(C(=O)O)cc2c(F)ccc(N(C)S(=O)(=O)c3cccs3)c21]

To a mixed solution of ethyl 4-fluoro-1-(methoxymethyl)-7-[methyl(2-thienylsulfonyl)amino]-1H-indole-2-carboxylate (0.45 g) in tetrahydrofuran (10 mL)-methanol (10 mL) was added aqueous solution (5 mL) of 85% potassium hydroxide (0.25 g), and the mixture was stirred at room temperature for 18 hr. The reaction solution was acidified with aqueous citric acid solution, extracted with ethyl acetate, washed with water and saturated brine, dried over anhydrous magnesium sulfate, and concentrated under reduced pressure to give the title compound (0.41 g, yield 98%) as pale-yellow crystals.

$^1$H-NMR (CDCl$_3$) δ:3.33 (3H, s), 3.35 (3H, s), 6.35 (1H, d, J=10.5 Hz), 6.41 (1H, d, J=10.5 Hz), 6.51 (1H, dd, J=4.5, 8.4 Hz), 6.68 (1H, t, J=8.4 Hz), 7.18 (1H, dd, J=3.6, 4.8 Hz), 7.47 (1H, dd, J=1.5, 3.6 Hz), 7.62 (1H, s), 7.70 (1H, dd, J=1.5, 4.8 Hz).

Reference Example 56

4-Fluoro-1-(methoxymethyl)-7-[methyl (2-thienylsulfonyl)amino]-1H-indole-2-carboxamide

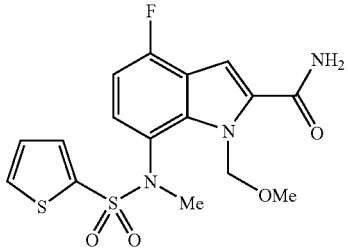 [SMILES: COCn1c(C(N)=S)cc2c(F)ccc(N(C)S(=O)(=O)c3cccs3)c21]

To a mixture of 4-fluoro-1-(methoxymethyl)-7-[methyl(2-thienylsulfonyl)amino]-1H-indole-2-carboxylic acid (0.41 g), 1H-1,2,3-benzotriazol-1-ol-ammonia complex (0.21 g) and N,N-dimethylformamide (15 ml) was added N-[3-(dimethylamino)propyl]-N'-ethylcarbodiimide hydrochloride (0.26 g) at 4° C., and the mixture was stirred at room temperature for 2 days. The reaction solution was diluted with ethyl acetate, washed with water, aqueous sodium hydrogencarbonate solution and saturated brine, dried over anhydrous magnesium sulfate, and concentrated under reduced pressure to give the title compound (0.41 g, yield 100%) as pale-yellow needle crystals.

$^1$H-NMR (CDCl$_3$) δ:3.33 (3H, s), 3.37 (3H, s), 6.20 (1H, d, J=10.2 Hz), 6.29 (1H, d, J=10.2 Hz), 6.46 (1H, dd, J=4.5, 8.4 Hz), 6.60 (1H, t, J=8.4 Hz), 7.11 (1H, s), 7.17 (1H, dd, J=3.6, 5.4 Hz), 7.47 (1H, dd, J=1.2, 3.6 Hz), 7.69 (1H, dd, J=1.2, 5.4 Hz).

Reference Example 57

4-Fluoro-1-(methoxymethyl)-7-[methyl(2-thienylsulfonyl)amino]-1H-indole-2-carbothioamide

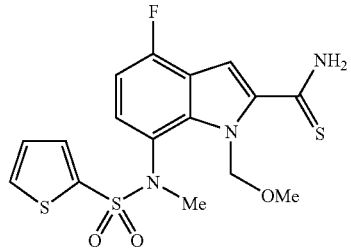

A mixture of 4-fluoro-1-(methoxymethyl)-7-[methyl(2-thienylsulfonyl)amino]-1H-indole-2-carboxamide (0.41 g), Lawesson's reagent (0.50 g) and tetrahydrofuran (40 mL) was stirred at 60° C. for 3 hr. The reaction solution was concentrated under reduced pressure, and the obtained residue was subjected to silica gel column chromatography (ethyl acetate:hexane=2:8-4:6) to give the title compound (0.25 g, yield 59%) as pale-yellow crystals.

$^1$H-NMR (CDCl$_3$) δ:3.32 (3H, s), 3.49 (3H, s), 5.80 (1H, d, J=10.5 Hz), 6.28 (1H, d, J=10.5 Hz), 6.44 (1H, dd, J=4.8, 8.4 Hz), 6.65 (1H, t, J=8.4 Hz), 7.19 (1H, dd, J=3.9, 4.8 Hz), 7.41 (1H, s), 7.49 (1H, dd, J=1.2, 3.9 Hz), 7.72 (1H, dd, J=1.2, 4.8 Hz), 7.77 (1H, brs), 8.35 (1H, brs).

Reference Example 58

N-[4-Fluoro-1-(methoxymethyl)-2-(1,3-thiazol-2-yl)-1H-indol-7-yl]-N-methylthiophene-2-sulfonamide

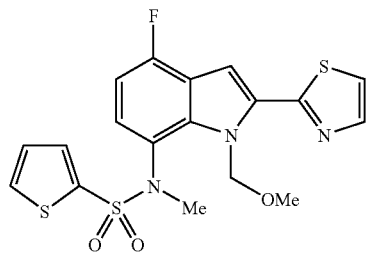 [SMILES: COCn1c(-c2nccs2)cc2c(F)ccc(N(C)S(=O)(=O)c3cccs3)c21]

A mixed solution of 4-fluoro-1-(methoxymethyl)-7-[methyl(2-thienylsulfonyl)amino]-1H-indole-2-carbothioamide (0.25 g), 1-bromo-2,2-diethoxyethane (0.24 mL) and N,N-dimethylacetamide (10 ml) was stirred at 90° C. for 7 hr. The reaction solution was diluted with ethyl acetate, washed with water and saturated brine, dried over anhydrous magnesium sulfate, and concentrated under reduced pressure. The obtained residue was subjected to silica gel column chromatography (ethyl acetate:hexane=15:85-30:70) to give the title compound (165 mg, yield 62%) as colorless needle crystals.

$^1$H-NMR (CDCl$_3$) δ:3.28 (3H, s), 3.36 (3H, s), 6.36 (1H, d, J=10.2 Hz), 6.41 (1H, dd, J=4.8, 8.4 Hz), 6.54 (1H, d, J=10.2 Hz), 6.66 (1H, t, J=8.4 Hz), 7.11 (1H, s), 7.18 (1H, dd, J=3.6, 4.8 Hz), 7.40 (1H, d, J=3.3 Hz), 7.49 (1H, dd, J=1.2, 3.6 Hz), 7.69 (1H, dd, J=11.2, 4.8 Hz), 7.94 (1H, d, J=3.3 Hz).

Reference Example 59

4-Methyl-7-[methyl(2-thienylsulfonyl)amino]-1H-indole-2-carbothioamide

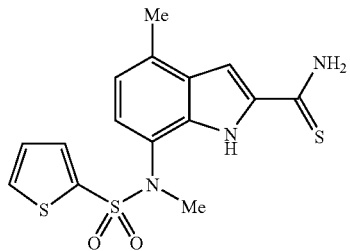 [SMILES: Cc1ccc(N(C)S(=O)(=O)c2cccs2)c2[nH]c(C(N)=S)cc12]

A mixture of 4-methyl-7-[methyl(2-thienylsulfonyl)amino]-1H-indole-2-carboxamide (1.78 g), Lawesson's reagent (2.26 g) and tetrahydrofuran (120 mL) was stirred at 60° C. for 2 hr. The reaction solution was concentrated under reduced pressure, and the obtained oil was crystallized from dichloromethane-toluene to give the title compound (1.56 g, yield 84%) as pale-yellow crystals. MS:366 (MH$^+$).

Reference Example 60

7-Nitro-N-[2-(tritylthio)ethyl]-1H-indole-2-carboxamide

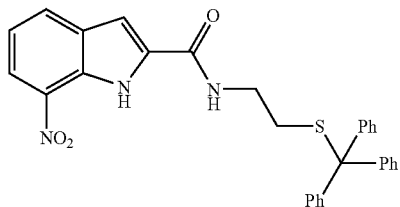 [SMILES: O=C(NCCSC(c1ccccc1)(c1ccccc1)c1ccccc1)c1cc2cccc([N+](=O)[O-])c2[nH]1]

A solution of 7-nitro-1H-indole-2-carboxylic acid (4.4 g), 1H-1,2,3-benzotriazol-1-ol (3.8 g), N-[3-(dimethylamino)propyl]-N'-ethylcarbodiimide hydrochloride (4.8 g), 2-(tritylthio)ethylamine hydrochloride (7.4 g) and triethylamine (3.5 mL) in N,N-dimethylformamide (50 mL) was stirred at room temperature for 4 hr. Water was added to the reaction mixture, and the mixture was extracted with ethyl acetate. The ethyl acetate layer was washed with saturated brine, dried (MgSO$_4$) and concentrated. The obtained residue was crystallized from diethyl ether-hexane to give the title compound (10.1 g, yield 95%) as yellow crystals.

$^1$H-NMR (DMSO-$d_6$) δ:2.37 (2H, t, J=6.6 Hz), 3.38 (2H, t, J=6.6 Hz), 7.19-7.34 (17H, m), 8.17-8.22 (2H, m), 9.08 (1H, brs), 11.29 (1H, brs).

Reference Example 61

2-(4,5-Dihydro-1,3-thiazol-2-yl)-7-nitro-1H-indole

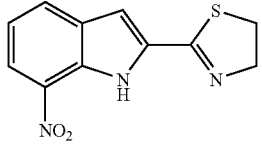 [SMILES: O=[N+]([O-])c1cccc2cc(C3=NCCS3)[nH]c12]

To a solution of triphenylphosphine oxide (16.7 g) in dichloromethane (30 mL) was slowly added trifluoromethanesulfonic anhydride (5.0 mL) at 0° C., and the mixture was stirred for 10 min and 7-nitro-N-[2-(tritylthio)ethyl]-1H-indole-2-carboxamide (10.1 g) was added. The reaction mixture was stirred at room temperature for 8 hr and concentrated. Saturated aqueous sodium hydrogen carbonate was added, and the mixture was extracted with ethyl acetate. The ethyl acetate layer was washed with saturated brine, dried (MgSO$_4$) and concentrated. The residue was subjected to silica gel column chromatography (ethyl acetate:hexane=1:3) to give the title compound (4.0 g, yield 81%) as yellow crystals.

$^1$H-NMR (DMSO-$d_6$) δ:3.52 (2H, t, J=8.4 Hz), 4.31 (2H, t, J=8.4 Hz), 7.19 (1H, s), 7.31 (1H, t, J=8.1 Hz), 8.13-8.25 (2H, m), 10.95 (1H, brs).

Reference Example 62

2-(4,5-Dihydro-1,3-thiazol-2-yl)-1H-indole-7-amine

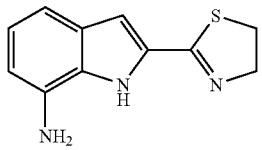 [SMILES: Nc1cccc2cc(C3=NCCS3)[nH]c12]

To a mixture of 2-(4,5-dihydro-1,3-thiazol-2-yl)-7-nitro-1H-indole (4.0 g), iron powder (4.0 g), calcium chloride (770 mg), ethanol (45 mL) and water (5 mL) was added 1N hydrochloric acid (0.2 mL), and the mixture was stirred at 80° C. for 2 hr. After cooling the reaction mixture to room temperature, and the insoluble material was filtered off. Saturated aqueous sodium hydrogen carbonate was added to the filtrate, and the mixture was extracted with ethyl acetate. The ethyl acetate layer was washed with saturated brine, dried (MgSO$_4$) and concentrated. The residue was subjected to silica gel column chromatography (ethyl acetate) to give the title compound (1.9 g, yield 56%) as pale-yellow crystals.

$^1$H-NMR (DMSO-$d_6$) δ:3.46 (2H, t, J=8.1 Hz), 4.40 (2H, t, J=8.1 Hz), 5.34 (2H, s), 6.37 (1H, dd, J=6.9 Hz, 1.2 Hz), 6.73-6.83 (3H, m), 11.32 (1H, brs).

M+1=218.

Reference Example 63

Ethyl 1-(methoxymethyl)-7-{methyl[(4-nitrophenyl)sulfonyl]amino}-1H-indole-2-carboxylate

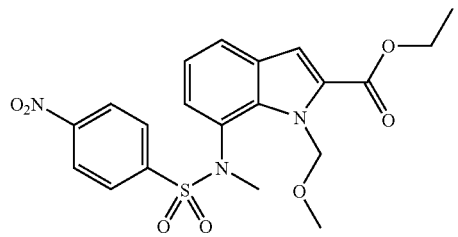 [SMILES: CCOC(=O)c1cc2cccc(N(C)S(=O)(=O)c3ccc([N+](=O)[O-])cc3)c2n1COC]

To a solution of ethyl 7-amino-1-(methoxymethyl)-1H-indole-2-carboxylate (1.12 g) in pyridine (10 mL) was added 4-nitrobenzenesulfonyl chloride (1.1 g) under ice-cooling, and the mixture was stirred at room temperature for 12 hr. The reaction mixture was concentrated, water was added, and the mixture was extracted with ethyl acetate. The ethyl acetate layer was washed with saturated brine, dried (MgSO$_4$) and concentrated. The obtained residue was crystallized from diethyl ether-hexane to give yellow crystals (1.45 g, yield 74%). The obtained yellow crystals were dissolved in N,N-dimethylformamide (10 mL), sodium hydride (60% in oil, 200 mg) was added under ice-cooling, and the mixture was stirred for 30 min. To the reaction mixture was added methyl iodide (100 μL), and the mixture was stirred at room temperature for 1 hr. Water was added to the reaction solution, and the mixture was extracted with ethyl acetate. The ethyl acetate layer was washed with saturated brine, dried (MgSO$_4$) and concentrated. The obtained residue was subjected to silica gel column chromatography (ethyl acetate:hexane=1:3) to give yellow crystals (1.42 g, yield 95%).

$^1$H-NMR (CDCl$_3$) δ:1.41 (3H, t, J=7.2 Hz), 3.28 (3H, s), 3.54 (3H, s), 4.39 (2H, q, J=7.2 Hz), 4.53 (2H, brs), 6.28 (1H, d, J=10.2 Hz), 6.36 (1H, d, J=10.2 Hz), 6.71 (1H, dd, J=0.6 Hz, 4.2 Hz), 6.97 (1H, t, J=7.8 Hz), 7.40 (1H, s), 7.46-7.54 (2H, m), 7.61-7.74 (3H, m).

Reference Example 64

Ethyl 7-(methylamino)-1H-indole-2-carboxylate

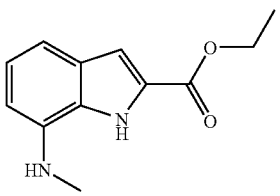 [SMILES: CCOC(=O)c1cc2cccc(NC)c2[nH]1]

To a solution of ethyl 1-(methoxymethyl)-7-{methyl[(4-nitrophenyl)sulfonyl]amino}-1H-indole-2-carboxylate (1.42 g) in ethanol (10 mL) was added 6N hydrochloric acid (10 mL), and the mixture was stirred at 70° C. for 12 hr. The reaction mixture was concentrated, water was added, and the mixture was extracted with ethyl acetate. The ethyl acetate layer was washed with saturated brine, dried (MgSO$_4$) and concentrated. The obtained residue was dissolved in N,N-dimethylformamide (8 mL), lithium hydroxide (520 mg) and mercaptoacetic acid (430 µL) were added, and the mixture was stirred at room temperature for 12 hr. To the reaction mixture was added methyl iodide (100 µL), and the mixture was stirred at room temperature for 1 hr. Saturated aqueous sodium hydrogencarbonate solution was added to the reaction solution, and the mixture was extracted with ethyl acetate. The ethyl acetate layer was washed with saturated brine, dried (MgSO$_4$) and concentrated. The obtained residue was subjected to silica gel column chromatography (ethyl acetate:hexane=1:1) to give a yellow amorphous (182 mg, yield 26%). M+1=219.

Reference Example 65

2-(4,5-Dihydro-1,3-thiazol-2-yl)-N-methyl-1H-indole-7-amine

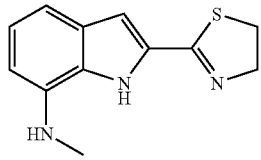 [SMILES: CNc1cccc2cc(C3=NCCS3)[nH]c12]

2-(4,5-Dihydro-1,3-thiazol-2-yl)-1H-indole-7-amine (1.08 g), aqueous formaldehyde solution (37%, 372 µL) and benzotriazole (595 mg) were dissolved in ethanol (15 mL) and tetrahydrofuran (15 mL), and the mixture was stirred at room temperature for 2 days. Water was added to the reaction solution, and the mixture was extracted with ethyl acetate. The ethyl acetate layer was washed with saturated brine, dried (MgSO$_4$) and concentrated. The obtained residue was subjected to silica gel column chromatography (ethyl acetate: hexane=1:1) to give a yellow oil (360 mg, yield 31%). M+1=232.

Reference Example 66

N-Methyl-2-(1,3-thiazol-2-yl)-1H-indole-7-amine hydrochloride

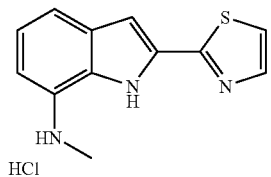 [SMILES: CNc1cccc2cc(-c3nccs3)[nH]c12 ; Cl]

Under ice-cooling, formic acid (6.0 mL) was added dropwise to acetic anhydride (12.5 mL). After dropwise addition, the reaction mixture was stirred at 60° C. for 2 hr. Tetrahydrofuran (10 mL) was added to the reaction mixture, and a solution of 2-(1,3-thiazol-2-yl)-1H-indole-7-amine (10 g) in tetrahydrofuran (10 mL) was added dropwise under ice-cooling. The reaction mixture was stirred for 30 min and concentrated. Tetrahydrofuran (10 mL) was added to the obtained residue, and borane-tetrahydrofuran complex (1.0 M tetrahydrofuran solution, 30 mL) was added. The reaction mixture was stirred with heating under reflux for 1 hr. The reaction mixture was cooled to room temperature, and methanol (5 mL) was added. The reaction mixture was stirred with heating under reflux for 1 hr, concentrated, and the obtained residue was subjected to silica gel column chromatography (ethyl acetate:hexane=1:1). To the obtained yellow oil was added 4N hydrogen chloride-ethyl acetate solution (30 mL). The obtained yellow crystals were collected by filtration, and washed with diethyl ether and hexane to give the title compound (10 g, yield 70%) as yellow crystals. melting point 89° C.

Reference Example 67

N-Methyl-4-[(1-methyl-1H-tetrazol-5-yl)thio]-2-(1,3-thiazol-2-yl)-1H-indole-7-amine

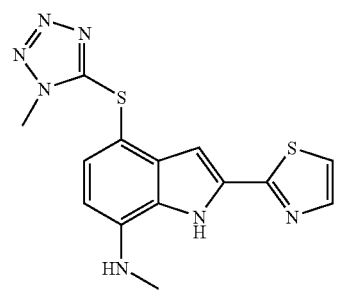 [SMILES: CNc1ccc(Sc2nnnn2C)c2cc(-c3nccs3)[nH]c12]

Chlorine gas was blown into a solution of 1-methyl-1H-tetrazole-5-thiol (10 g) in 2N hydrochloric acid (150 mL) under ice-cooling for 30 min. The precipitated crystals were collected by filtration, washed with water, and dried to give colorless crystals (2.9 g). The colorless crystals (400 mg) were added to a solution of N-methyl-2-(1,3-thiazol-2-yl)-1H-indole-7-amine hydrochloride (530 mg) in pyridine (5 mL). The reaction mixture was stirred at room temperature for 1 hr and concentrated. The obtained residue was subjected to silica gel column chromatography (ethyl acetate:hexane=1:3) to give the title compound (341 mg, yield 45%) as pale-yellow crystals. melting point 211° C.

Reference Example 68

Methyl 3-{[[1-(methoxymethyl)-2-(1,3-thiazol-2-yl)-1H-indol-7-yl](methyl)amino]sulfonyl}thiophene-2-carboxylate

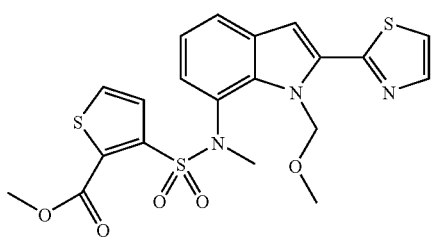 [SMILES: COCn1c(-c2nccs2)cc2cccc(N(C)S(=O)(=O)c3ccsc3C(=O)OC)c21]

The title compound (2.6 g, yield 72%) was obtained as a yellow oil from methyl 3-({methyl[2-(1,3-thiazol-2-yl)-1H-indol-7-yl]amino}sulfonyl)thiophene-2-carboxylate (3.3 g) in the same manner as in Reference Example 11.

$^1$H-NMR (CDCl$_3$) δ:3.27 (3H, s), 3.56 (3H, s), 3.84 (3H, s), 6.38 (2H, d, J=10.2 Hz), 6.80 (2H, d, J=10.2 Hz), 6.60 (1H, dd, J=0.9 Hz, 7.5 Hz), 6.94-9.99 (2H, m), 7.05 (1H, s), 7.12 (1H, d, J=5.1 Hz), 7.37-7.42 (2H, m), 7.57 (1H, dd, J=1.8 Hz, 8.7 Hz), 7.92 (1H, d, J=3.3 Hz).

Reference Example 69

2-(Hydroxymethyl)-N-[1-(methoxymethyl)-2-(1,3-thiazol-2-yl)-1H-indol-7-yl]-N-methylthiophene-3-sulfonamide

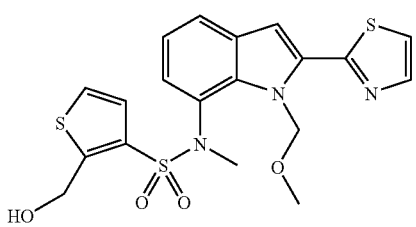 [SMILES: COCn1c(-c2nccs2)cc2cccc(N(C)S(=O)(=O)c3ccsc3CO)c21]

The title compound (1.1 g, yield 44%) was obtained as a yellow oil from methyl 3-{[[1-(methoxymethyl)-2-(1,3-thiazol-2-yl)-1H-indol-7-yl](methyl)amino]sulfonyl}thiophene-2-carboxylate (2.6 g) in the same manner as in Reference Example 39.

$^1$H-NMR (CDCl$_3$) δ:3.24 (3H, s), 3.40 (3H, s), 4.23-4.40 (2H, m), 6.38 (2H, d, J=10.2 Hz), 6.80 (2H, d, J=10.2 Hz), 6.46 (1H, dd, J=1.2 Hz, 7.5 Hz), 6.52 (2H, d, J=10.2 Hz), 7.00 (1H, t, J=7.8 Hz), 7.06 (1H, s), 7.33-7.39 (3H, m), 7.62 (1H, dd, J=1.2 Hz, 7.8 Hz), 7.94 (1H, d, J=3.3 Hz).

Reference Example 70

Ethyl 7-amino-4-chloro-1-(methoxymethyl)-1H-indole-2-carboxylate

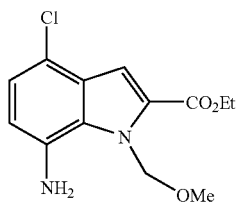

A mixture of ethyl 7-amino-1-(methoxymethyl)-1H-indole-2-carboxylate (3.18 g), N-chlorosuccinimide (1.74 g) and N,N-dimethylformamide (20 mL) was stirred at room temperature overnight. Water was added to the reaction mixture, and the mixture was extracted with ethyl acetate. The ethyl acetate layer was washed with saturated brine, dried (MgSO$_4$) and concentrated. The residue was subjected to silica gel column chromatography and the title compound (0.91 g, yield 25%) was obtained as a yellow oil from a fraction eluted with ethyl acetate-hexane (1:4, volume ratio).

$^1$H-NMR (CDCl$_3$) δ:1.42 (3H, t, J=7.2 Hz), 3.44 (3H, s), 4.37 (2H, q, J=7.2 Hz), 4.51 (2H, brs), 6.16 (2H, s), 6.50 (1H, d, J=8.1 Hz), 6.94 (1H, d, J=8.1 Hz), 7.36 (1H, s).

Reference Example 71

Ethyl 4-chloro-1-(methoxymethyl)-7-[(2-thienylsulfonyl)amino]-1H-indole-2-carboxylate

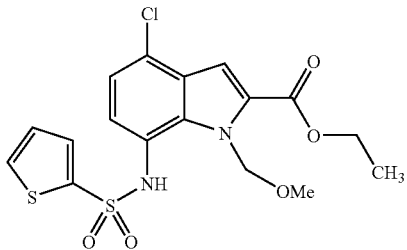 [SMILES: CCOC(=O)c1cc2c(Cl)ccc(NS(=O)(=O)c3cccs3)c2n1COC]

To a mixture of ethyl 7-amino-4-chloro-1-(methoxymethyl)-1H-indole-2-carboxylate (0.91 g) and pyridine (10 mL) was added thiophene-2-sulfonyl chloride (0.50 g) at 0° C., and the mixture was stirred at room temperature overnight. The reaction mixture was concentrated, 10% aqueous citric acid solution was added, and the mixture was extracted with ethyl acetate. The ethyl acetate layer was washed with saturated brine, dried (MgSO$_4$) and concentrated. The obtained residue was subjected to silica gel column chromatography and the title compound (1.14 g, yield 83%) was obtained as a yellow oil from a fraction eluted with ethyl acetate-hexane (1:2, volume ratio).

$^1$H-NMR (CDCl$_3$) δ:1.41 (3H, t, J=7.1 Hz), 3.44 (3H, s), 4.36 (2H, q, J=7.1 Hz), 5.69 (2H, s), 6.99-7.03 (1H, m), 7.18 (1H, t, J=8.4 Hz), 7.40 (1H, s), 7.48-7.54 (3H, m), 8.77 (1H, brs).

Reference Example 72

Ethyl 4-chloro-1-(methoxymethyl)-7-[methyl(2-thienylsulfonyl)amino]-1H-indole-2-carboxylate

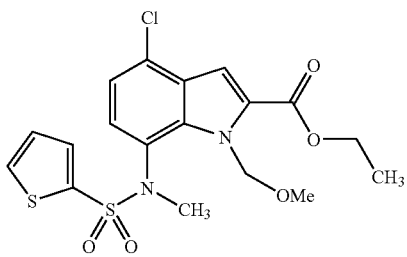 [SMILES: CCOC(=O)c1cc2c(Cl)ccc(N(C)S(=O)(=O)c3cccs3)c2n1COC]

A mixture of ethyl 4-chloro-1-(methoxymethyl)-7-[(2-thienylsulfonyl)amino]-1H-indole-2-carboxylate (1.14 g), methyl iodide (0.33 mL), potassium carbonate (0.37 g) and N,N-dimethylformamide (10 mL) was stirred at room temperature overnight. To the reaction mixture was added water, and the resulting crystals were filtrated, washed with water, and dried to give the title compound (1.10 g, yield 93%) as colorless crystals. melting point 137-138° C.

Reference Example 73

4-Chloro-7-[methyl(2-thienylsulfonyl)amino]-1H-indole-2-carbothioamide

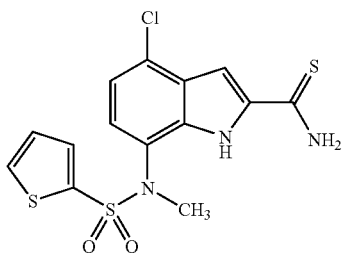 [SMILES: CN(c1ccc(Cl)c2cc(C(N)=S)[nH]c12)S(=O)(=O)c1cccs1]

A mixture of 4-chloro-7-[methyl(2-thienylsulfonyl)amino]-1H-indole-2-carboxamide (0.54 g), Lawesson's reagent (0.59 g) and tetrahydrofuran (20 mL) was stirred at 60° C. for 3 hr. The reaction mixture was concentrated, toluene was added, and the resulting crystals were filtrated, washed with toluene, and dried to give the title compound (0.51 g, yield 87%) as yellow crystals. melting point>248° C. (decomposition).

Reference Example 74

Ethyl 7-amino-6-chloro-1H-indole-2-carboxylate

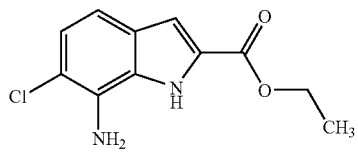 [SMILES: CCOC(=O)c1cc2ccc(Cl)c(N)c2[nH]1]

A mixture of ethyl 7-amino-1H-indole-2-carboxylate (2.30 g), N-chlorosuccinimide (1.40 g) and N,N-dimethylformamide (10 mL) was stirred at room temperature overnight. To the reaction mixture was added water, and the resulting crystals were filtrated, washed with water and dried. The obtained crystals were subjected to silica gel column chromatography and the title compound (1.59 g, yield 63%) was obtained as pale-yellow crystals from a fraction eluted with ethyl acetate-hexane (2:3, volume ratio). melting point 217-218° C. (decomposition).

Reference Example 75

6-Chloro-7-[(2-thienylsulfonyl)amino]-1H-indole-2-carbothioamide

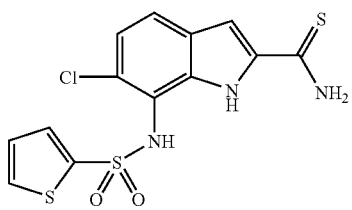

A mixture of 6-chloro-7-[(2-thienylsulfonyl)amino]-1H-indole-2-carboxamide (0.80 g), Lawesson's reagent (0.90 g) and tetrahydrofuran (15 mL) was stirred at 60° C. for 3 hr. The reaction mixture was concentrated, toluene was added, and the resulting crystals were filtrated, washed with toluene, and dried to give the title compound (0.75 g, yield 91%) as yellow crystals. melting point 228-230° C. (decomposition).

Reference Example 76

6-Chloro-7-[methyl(2-thienylsulfonyl)amino]-1H-indole-2-carbothioamide

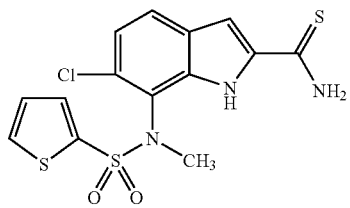 [SMILES: CN(c1c(Cl)ccc2cc(C(N)=S)[nH]c12)S(=O)(=O)c1cccs1]

A mixture of 6-chloro-7-[methyl(2-thienylsulfonyl)amino]-1H-indole-2-carboxamide (0.70 g), Lawesson's reagent (0.77 g) and tetrahydrofuran (20 mL) was stirred at 60° C. for 2 hr. The reaction mixture was concentrated, toluene was added, and the resulting crystals were filtrated, washed with toluene, and dried to give the title compound (0.60 g, yield 84%) as yellow crystals. melting point 200-201° C.

Reference Example 77

Benzyl 2-amino-3-iodobenzoate

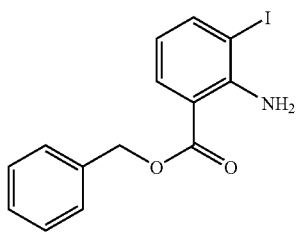 [SMILES: Nc1c(I)cccc1C(=O)OCc1ccccc1]

To a solution of 2-amino-3-iodobenzoic acid (5.00 g), benzyl alcohol (2.17 mL) and triphenylphosphine (7.97 g) in tetrahydrofuran (76 mL) was added a 40% toluene solution (13.2 g) of diethyl azodicarboxylate, and the mixture was stirred at room temperature for 0.5 hr. Water was added to the reaction mixture, and the mixture was extracted with ethyl acetate. The extract was washed successively with water and saturated brine, dried over anhydrous magnesium sulfate, and concentrated under reduced pressure. The residue was purified by silica gel column chromatography (ethyl acetate:hexane=0:100-15:85) to give the title compound (5.56 g, yield 83%) as an orange oil. MS m/z 354 (M+H$^+$).

Reference Example 78

Benzyl 2-amino-3-ethynylbenzoate

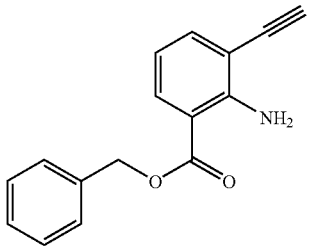 [SMILES: C#Cc1cccc(C(=O)OCc2ccccc2)c1N]

A solution of benzyl 2-amino-3-iodobenzoate (5.56 g), trimethylsilylacetylene (3.26 mL), bis(triphenylphosphine)palladium(II) dichloride (0.350 g) and copper iodide (0.299 g) in triethylamine (75 mL) was stirred under a nitrogen atmosphere at room temperature for 1.5 hr. The reaction mixture was diluted with diisopropyl ether, washed successively with water and saturated brine, dried over anhydrous magnesium sulfate, and concentrated under reduced pressure. The residue was dissolved in tetrahydrofuran (75 mL), 1.0 M tetrabutylammonium fluoride (25 mL) was added under ice-cooling, and the mixture was stirred at 0° C. for 1.5 hr. A saturated aqueous ammonium chloride solution was added to the reaction mixture, and the mixture was extracted with ethyl acetate. The extract was washed successively with water and saturated brine, dried over anhydrous magnesium sulfate, and concentrated under reduced pressure. The residue was purified by silica gel column chromatography (ethyl acetate:hexane=0:100-15:85) to give the title compound (3.06 g, yield 77%) as colorless crystals. melting point 42-43° C.

Reference Example 79

Benzyl 2-amino-3-(1,3-thiazol-2-ylethynyl)benzoate

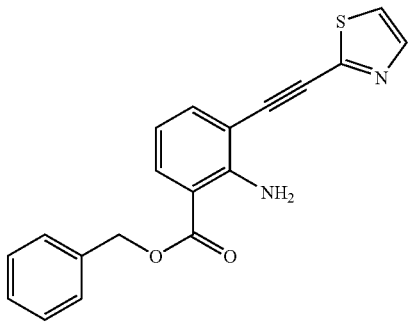 [SMILES: Nc1c(C#Cc2nccs2)cccc1C(=O)OCc1ccccc1]

A solution of benzyl 2-amino-3-ethynylbenzoate (3.06 g), 2-bromothiazole (1.65 mL), bis(triphenylphosphine)palladium(II) dichloride (0.704 g) and copper iodide (0.232 g) in triethylamine (60 mL) was stirred under a nitrogen atmosphere at 60° C. for 1.5 hr with heating. The reaction mixture was diluted with ethyl acetate and filtered through celite. The filtrate was concentrated under reduced pressure. The residue was purified by silica gel column chromatography (ethyl acetate:hexane=10:90-50:50) to give the title compound (3.32 g, yield 82%) as a yellow oil.

MS m/z 335 (M+H$^+$).

Reference Example 80

Benzyl 3-(1,3-thiazol-2-ylethynyl)-2-[(trifluoroacetyl)amino]benzoate

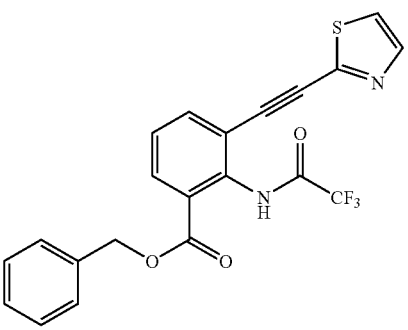 [SMILES: O=C(OCc1ccccc1)c1cccc(C#Cc2nccs2)c1NC(=O)C(F)(F)F]

To a solution of benzyl 2-amino-3-(1,3-thiazol-2-ylethynyl)benzoate (4.95 g) in tetrahydrofuran (50 mL) was added trifluoroacetic anhydride (2.26 mL), and the mixture was stirred at room temperature for 0.5 hr. Saturated aqueous sodium hydrogencarbonate solution was added to the reaction mixture, and the mixture was extracted with ethyl acetate. The extract was washed successively with water and saturated brine, dried over anhydrous magnesium sulfate, and concentrated under reduced pressure. The residue was purified by silica gel column chromatography (ethyl acetate:hexane=10:90-70:30) to give the title compound (5.80 g, yield 91%) as pale-yellow crystals.

MS m/z 431 (M+H$^+$).

Reference Example 81

Benzyl 2-(1,3-thiazol-2-yl)-1H-indole-7-carboxylate

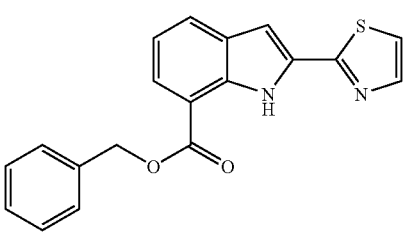 [SMILES: O=C(OCc1ccccc1)c1cccc2cc(-c3nccs3)[nH]c12]

A solution (50 mL) of benzyl 3-(1,3-thiazol-2-ylethynyl)-2-[(trifluoroacetyl)amino]benzoate (2.21 g), copper iodide (0.146 mg), trans-cyclohexane-1,2-diamine (0.177 g) and tripotassium phosphate (3.27 g) in anhydrous 1,4-dioxane was stirred with heating under reflux for 2 hr. A saturated aqueous ammonium chloride solution was added to the reaction mixture, and the mixture was extracted with ethyl acetate. The extract was washed successively with water and saturated brine, dried over anhydrous magnesium sulfate, and concentrated under reduced pressure. The residue was purified by silica gel column chromatography (ethyl acetate:hexane=10:90-50:50) to give the title compound (1.20 g, yield 70%) as a pale-yellow oil.

MS m/z 335 (M+H$^+$).

Reference Example 82

[2-(1,3-Thiazol-2-yl)-1H-indol-7-yl]methanol

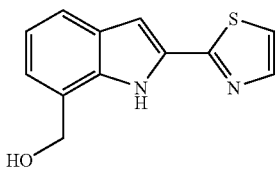 [SMILES: OCc1cccc2cc(-c3nccs3)[nH]c12]

To a solution of benzyl 2-(1,3-thiazol-2-yl)-1H-indol-7-carboxylate (1.39 g) in tetrahydrofuran (30 mL) was added lithium aluminum hydride (0.200 g), and the mixture was stirred at room temperature for 1 hr. Lithium aluminum hydride (0.600 g) was added to the reaction solution, and the mixture was stirred at room temperature for 4 hr. Sodium sulfate-decahydrate (7.80 g) was added to the reaction mixture, and the mixture was stirred for 30 min and diluted with ethyl acetate. The obtained suspension was filtered through celite, washed with ethyl acetate, and the filtrate was concentrated. The residue was purified by silica gel column chromatography (ethyl acetate:hexane=15:85-70:30) to give the title compound (0.564 g, yield 59%) as colorless crystals.

MS m/z 231 (M+H$^+$).

Reference Example 83

2-(1,3-Thiazol-2-yl)-1H-indole-7-carbaldehyde

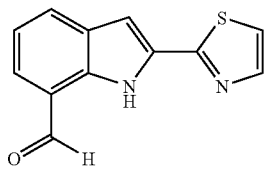 [SMILES: O=Cc1cccc2cc(-c3nccs3)[nH]c12]

To a solution of [2-(1,3-thiazol-2-yl)-1H-indol-7-yl]methanol (0.610 g) in dichloromethane (50 mL) was added Dess-Martin oxidant (1.50 g), and the mixture was stirred at room temperature for 0.5 hr. the reaction mixture was added saturated aqueous sodium hydrogencarbonate solution and 1N aqueous sodium thiosulfate solution, and extracted with ethyl acetate. The extract was washed successively with water and saturated brine, dried over anhydrous magnesium sulfate, and concentrated under reduced pressure. The residue was purified by silica gel column chromatography (ethyl acetate:hexane=5:95-50:50) to give the title compound (0.450 g, yield 74%) as pale-yellow crystals.

MS m/z 229 (M+H$^+$).

Reference Example 84

1-[2-(1,3-thiazol-2-yl)-1H-indol-7-yl]ethanol

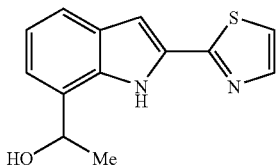 [SMILES: CC(O)c1cccc2cc(-c3nccs3)[nH]c12]

To a solution of 2-(1,3-thiazol-2-yl)-1H-indole-7-carbaldehyde (0.446 g) in anhydrous tetrahydrofuran (10 mL) was added 1.0 M methylmagnesium bromide (4 mL) under ice-cooling, and the mixture was stirred at 0° C. for 1 hr. Under ice-cooling, 1.0 M methylmagnesium bromide (4 mL) was added to the reaction mixture, and the mixture was stirred at room temperature for 1 hr. The reaction mixture was ice-cooled, 1.0 M methylmagnesium bromide (2 mL) was added, and the mixture was stirred at room temperature for 1 hr. A saturated aqueous ammonium chloride solution was added to the reaction mixture, and the mixture was extracted with ethyl acetate. The extract was washed successively with water and saturated brine, dried over anhydrous magnesium sulfate, and concentrated under reduced pressure. The residue was purified by preparative HPLC to give the title compound (0.090 g, yield 19%) as colorless crystals.

MS m/z 245 (M+H$^+$).

Reference Example 85

7-[(Cyclopropylmethyl)(2-thienylsulfonyl)amino]-1-(methoxymethyl)-1H-indole-2-carboxamide

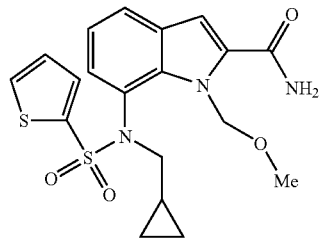 [SMILES: COCn1c(C(N)=O)cc2cccc(N(CC3CC3)S(=O)(=O)c3cccs3)c21]

A mixture of 1-(methoxymethyl)-7-[(2-thienylsulfonyl)amino]-1H-indole-2-carboxamide (1.0 g), (bromomethyl)cyclopropane (456 mg), potassium carbonate (1.13 g) and N,N-dimethylformamide (5 mL) was stirred at 85° C. for 20 hr. The reaction mixture was diluted with ethyl acetate and saturated brine. The organic layer was washed with aqueous sodium bicarbonate and saturated brine, dried over magnesium sulfate and filtrated. The filtrate was concentrated, subjected to NH silica gel column chromatography, and eluted with an ethyl acetate-hexane mixture (2:1) to give the title compound (820 mg, yield 72%) as an amorphous form.

$^1$H-NMR (CDCl$_3$) δ: −0.16--−0.05 (1H, m), 0.08-0.186 (1H, m), 0.37-0.47 (1H, m), 0.86-1.08 (1H, m), 3.43 (1H, dd, J=13.5, 7.3 Hz), 3.45 (3H, s), 3.79 (1H, dd, J=13.5, 7.3 Hz), 6.20 (2H, s), 6.68 (1H, d, J=7.7 Hz), 7.01 (1H, t, J=7.7 Hz), 7.08-7.18 (2H, m), 7.44-7.51 (1H, m), 7.59-7.72 (2H, m).

Reference Example 86

7-[(Cyclopropylmethyl)(2-thienylsulfonyl)amino]-1H-indole-2-carboxamide

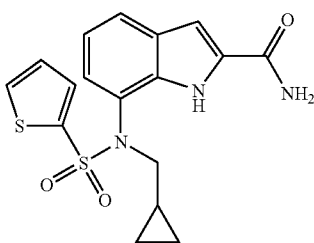 [SMILES: NC(=O)c1cc2cccc(N(CC3CC3)S(=O)(=O)c3cccs3)c2[nH]1]

A mixture of 7-[(cyclopropylmethyl)(2-thienylsulfonyl)amino]-1-(methoxymethyl)-1H-indole-2-carboxamide (390 mg), oxalic acid dihydrate (351 mg), methanol (15 mL) and water (15 mL) was stirred at 70° C. for 1 hr, and further at 90° C. for 14 hr. The reaction mixture was allowed to cool to room temperature. The resulting crystals were collected by filtration, washed successively with water, a diethyl ether-hexane mixture and hexane, and dried to give the title compound (286 mg, yield 81%) as crystals. melting point 229-231° C.

Reference Example 87

7-[(Cyclopropylmethyl) (2-thienylsulfonyl)amino]-1H-indole-2-carbothioamide

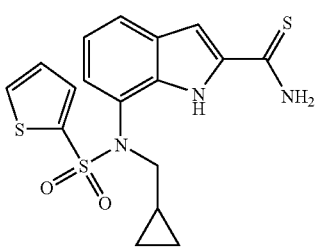

7-[(Cyclopropylmethyl)(2-thienylsulfonyl)amino]-1H-indole-2-carboxamide (264 mg), Lawesson's reagent (339 mg) and tetrahydrofuran (5 mL) were stirred at 60° C. for 2 hr. The reaction mixture was concentrated under reduced pressure, subjected to silica gel column chromatography, and eluted with an ethyl acetate-hexane (1:1) mixed solvent to give the title compound (243 mg, yield 88%) as an amorphous solid.

MS m/z 392 (M+H⁺).

Reference Example 88

7-[Isopropyl(2-thienylsulfonyl)amino]-1H-indole-2-carboxamide

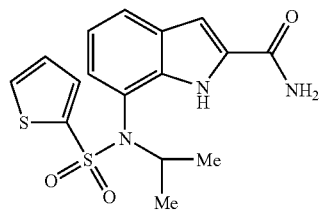

A mixture of 1-(methoxymethyl)-7-[(2-thienylsulfonyl)amino]-1H-indole-2-carboxamide (1.0 g), 2-iodopropane (574 mg), potassium carbonate (1.13 g) and N,N-dimethylacetamide (5 mL) was stirred at room temperature for 1 week. The reaction mixture was diluted with ethyl acetate and saturated brine. The organic layer was washed with aqueous sodium bicarbonate and saturated brine, dried over magnesium sulfate and filtrated. The filtrate was concentrated, subjected to NH silica gel column chromatography, and eluted with an ethyl acetate.hexane (2:1) mixture to give a solid. A mixture of this solid, oxalic acid dihydride (605 mg), methanol (15 mL) and water (15 mL) was stirred at 100° C. for 3.5 days. The reaction mixture was cooled to room temperature, and the obtained solid was collected by filtration, washed with water, a hexane. diisopropyl ether mixture and hexane in this order. The obtained solid was subjected to NH silica gel column chromatography, and eluted with an ethyl acetate. hexane mixture (2:1) to give the title compound (340 mg, yield 34%) as an amorphous solid.

¹H-NMR (CDCl₃) δ:1.04-1.21 (6H, m), 4.79-4.96 (1H, m), 6.79-6.94 (2H, m), 7.01-7.11 (2H, m), 7.47-7.55 (1H, m), 7.59 (1H, dd, J=5.1, 1.3 Hz), 7.66 (1H, d, J=7.9 Hz), 9.98 (1H, s).

Reference Example 89

7-[Isopropyl(2-thienylsulfonyl)amino]-1H-indole-2-carbothioamide

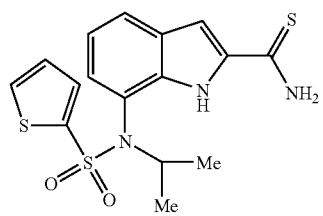 [SMILES: CC(C)N(c1cccc2cc(C(N)=S)[nH]c12)S(=O)(=O)c1cccs1]

A mixture of 7-[isopropyl(2-thienylsulfonyl)amino]-1H-indole-2-carboxamide (320 mg), Lawesson's reagent (213 mg) and tetrahydrofuran (5 mL) was stirred at 70° C. for 1 hr. The reaction mixture was concentrated under reduced pressure, and the residue was crystallized from a methylene chlo-

Reference Example 90

7-[Ethyl(2-thienylsulfonyl)amino]-1H-indole-2-carbothioamide

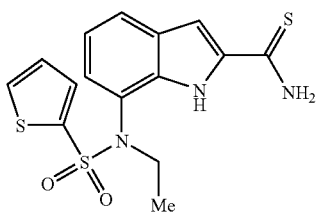 [SMILES: CCN(c1cccc2cc(C(N)=S)[nH]c12)S(=O)(=O)c1cccs1]

A mixture of 1-(methoxymethyl)-7-[(2-thienylsulfonyl)amino]-1H-indole-2-carboxamide (6.0 g), ethyl iodide (1.6 mL), potassium carbonate (6.78 g) and N,N-dimethylformamide (30 mL) was stirred at room temperature for 20 hr. The reaction mixture was diluted with ethyl acetate and saturated brine. The organic layer was washed with aqueous sodium bicarbonate and saturated brine, dried over magnesium sulfate and filtrated. The filtrate was concentrated, subjected to NH silica gel column chromatography, and eluted with an ethyl acetate-hexane (1:1) mixture to give a solid. A mixture of this solid, oxalic acid dihydrate (5.84 g), methanol (50 mL) and water (50 mL) was stirred at 95° C. for 7 hr. The reaction mixture was concentrated, diluted with an ethyl acetate-tetrahydrofuran mixture and washed with water. The aqueous layer was extracted with an ethyl acetate-tetrahydrofuran mixture. The organic layer was dried over magnesium sulfate and filtrated. The filtrate was concentrated, and the obtained solid was washed with water. This solid, Lawesson's reagent (3.76 g) and tetrahydrofuran (50 mL) were stirred at 65° C. for 2.5 hr. The reaction mixture was concentrated, and the residue was crystallized from a methylene chloride.toluene mixture to give the title compound (3.5 g, yield 62%) as crystals. melting point 163° C.

Reference Example 91

7-[(2-Ethoxyethyl) (2-thienylsulfonyl)amino]-1H-indole-2-carboxamide

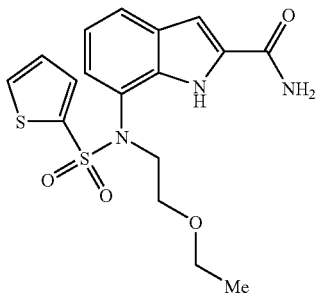

A mixture of 1-(methoxymethyl)-7-[(2-thienylsulfonyl)amino]-1H-indole-2-carboxamide (6.25 g), 1-bromo-2-ethoxyethane (3.41 g), potassium carbonate (7.09 g) and N,N-dimethylformamide (30 mL) was stirred at 75° C. for 6 hr. The reaction mixture was diluted with ethyl acetate and saturated brine. The organic layer was washed with aqueous sodium bicarbonate and saturated brine, dried over magnesium sulfate and filtrated. The filtrate was concentrated, subjected to NH silica gel column chromatography, and eluted with an ethyl acetate.hexane (2:1) mixture to give a solid. A mixture of this solid (5.50 g), oxalic acid dihydrate (4.77 g), methanol (50 mL) and water (50 mL) was stirred at 90° C. for 14 hr. The reaction mixture was cooled to room temperature and diluted with water. The crystallized solid was washed with water to give the title compound (4.70 g, yield 95%) as crystals. melting point 135° C.

Reference Example 92

7-[(2-Ethoxyethyl) (2-thienylsulfonyl)amino]-1H-indole-2-carbothioamide

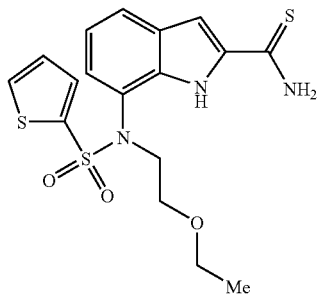 [SMILES: CCOCCN(c1cccc2cc(C(N)=S)[nH]c12)S(=O)(=O)c1cccs1]

A mixture of 7-[(2-ethoxyethyl)(2-thienylsulfonyl)amino]-1H-indole-2-carboxamide (4.70 g), Lawesson's reagent (3.06 g) and tetrahydrofuran (30 mL) was stirred at 70° C. for 3 hr. The reaction mixture was concentrated, and toluene was added to the residue. The obtained solid was washed with toluene to give the title compound (2.99 g, yield 58%) as crystals. melting point 182° C.

Reference Example 93

N-{2-[5-(Chloromethyl)-1,3-thiazol-2-yl]-1H-indol-7-yl}-N-methylthiophene-2-sulfonamide

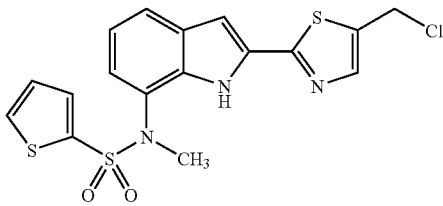 [SMILES: CN(c1cccc2cc(-c3ncc(CCl)s3)[nH]c12)S(=O)(=O)c1cccs1]

A mixture of N-{2-[5-(hydroxymethyl)-1,3-thiazol-2-yl]-1H-indol-7-yl}-N-methylthiophene-2-sulfonamide (0.10 g), thionyl chloride (0.03 mL), N,N-dimethylformamide (1 drop) and tetrahydrofuran (6 mL) was stirred at room temperature overnight. Water was added to the reaction mixture, and the mixture was extracted with ethyl acetate. The ethyl acetate layer was washed with saturated brine, aqueous sodium bicarbonate, and saturated brine in this order, dried (MgSO$_4$) and concentrated to give the title compound (0.08 g, yield 76%) as yellow crystals. melting point 204-205° C.

Reference Example 94

N-{2-[5-(Chloromethyl)-1,3-thiazol-2-yl]-1H-indol-7-yl}-N-isopropylthiophene-2-sulfonamide

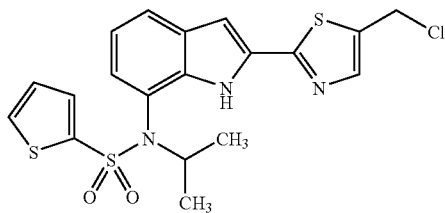 [SMILES: CC(C)N(c1cccc2cc(-c3ncc(CCl)s3)[nH]c12)S(=O)(=O)c1cccs1]

A mixture of N-{2-[5-(hydroxymethyl)-1,3-thiazol-2-yl]-1H-indol-7-yl}-N-isopropylthiophene-2-sulfonamide (2.12 g), thionyl chloride (0.70 mL), N,N-dimethylformamide (2 drops) and tetrahydrofuran (30 mL) was stirred at room temperature overnight. Water was added to the reaction mixture, and the mixture was extracted with ethyl acetate. The ethyl acetate layer was washed successively with saturated brine, aqueous sodium bicarbonate and saturated brine, dried (MgSO$_4$), and concentrated. The residue was crystallized from diethyl ether. The crystals were collected by filtration, washed with diethyl ether, and dried to give the title compound (2.00 g, yield 90%) as yellow crystals. melting point 184-185° C.

Reference Example 95

N-{2-[5-(Chloromethyl)-1,3-thiazol-2-yl]-1H-indol-7-yl}-N-ethylthiophene-2-sulfonamide

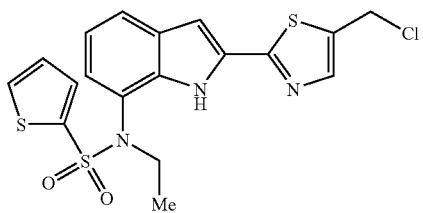 [SMILES: CCN(c1cccc2cc(-c3ncc(CCl)s3)[nH]c12)S(=O)(=O)c1cccs1]

To a mixture of N-ethyl-N-{2-[5-(hydroxymethyl)-1,3-thiazol-2-yl]-1H-indol-7-yl}thiophene-2-sulfonamide (3.43 g), N,N-dimethylformamide (0.05 mL) and tetrahydrofuran (50 mL) was added thionyl chloride (1.56 g), and the mixture was stirred at room temperature overnight. The reaction mixture was diluted with ethyl acetate and saturated brine and washed with saturated brine. The organic layer was dried over magnesium sulfate and filtrated. The filtrate was concentrated, and the obtained solid was washed with ether-hexane (1:1) to give the title compound (3.27 g, yield 91%) as a pale-yellow solid.

$^1$H-NMR (CDCl$_3$) δ:1.12 (3H, t, J=7.1 Hz), 3.77 (2H, q, J=7.1 Hz), 4.85 (2H, d, J=0.8 Hz), 6.57 (1H, dd, J=7.6, 0.9 Hz), 6.96-7.03 (2H, m), 7.09 (1H, dd, J=4.9, 3.8 Hz), 7.39 (1H, dd, J=3.8, 1.3 Hz), 7.56-7.64 (2H, m), 7.74 (1H, s), 9.48 (1H, s).

Reference Example 96

N-{2-[5-(Chloromethyl)-1,3-thiazol-2-yl]-1H-indol-7-yl}-N-(cyclopropylmethyl)thiophene-2-sulfonamide

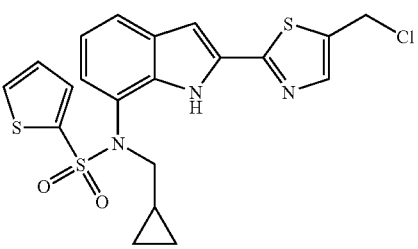 [SMILES: O=S(=O)(c1cccs1)N(CC1CC1)c1cccc2cc(-c3ncc(CCl)s3)[nH]c12]

To a mixture of N-(cyclopropylmethyl)-N-{2-[5-(hydroxymethyl)-1,3-thiazol-2-yl]-1H-indol-7-yl}thiophene-2-sulfonamide (2.15 g), N,N-dimethylformamide (0.03 mL) and tetrahydrofuran (30 mL) was added thionyl chloride (918 mg), and the mixture was stirred at room temperature for 1 hr. The reaction mixture was diluted with ethyl acetate and saturated brine, and washed with saturated brine. The organic layer was dried over magnesium sulfate and filtrated. The filtrate was concentrated, and the residue was subjected to silica gel column chromatography, and eluted with ethyl acetate. The obtained solid was washed with ether-hexane (1:1) to give the title compound (2.05 g, yield 97%) as a pale-yellow solid. melting point 135° C.

Reference Example 97

N-{2-[5-(Chloromethyl)-1,3-thiazol-2-yl]-1H-indol-7-yl}-N-(2-ethoxyethyl)thiophene-2-sulfonamide

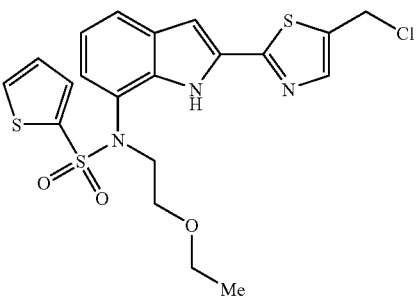 [SMILES: CCOCCN(c1cccc2cc(-c3ncc(CCl)s3)[nH]c12)S(=O)(=O)c1cccs1]

To a mixture of N-(2-ethoxyethyl)-N-{2-[5-(hydroxymethyl)-1,3-thiazol-2-yl]-1H-indol-7-yl}thiophene-2-sulfonamide (1.00 g), N,N-dimethylformamide (1 drop) and tetrahydrofuran (15 mL) was added thionyl chloride (409 mg), and the mixture was stirred at room temperature overnight. The reaction mixture was diluted with ethyl acetate and saturated brine, and washed with saturated brine. The organic layer was dried over magnesium sulfate and filtrated. The filtrate was concentrated, and the obtained solid was washed with ether-hexane (1:1) to give the title compound (970 mg, yield 93%) as a pale-yellow solid.

$^1$H-NMR (CDCl$_3$) δ:1.14 (3H, t, J=7.0 Hz), 3.38-3.55 (4H, m), 3.91 (2H, s), 4.85 (2H, s), 6.69 (1H, d, J=7.5 Hz), 6.95-7.03 (2H, m), 7.05-7.10 (1H, m), 7.42-7.46 (1H, m), 7.57-7.62 (2H, m), 7.73 (1H, s), 9.75 (1H, s).

Example 1

7-[(2-Thienylsulfonyl)amino]-1H-indole-2-carboxylic acid

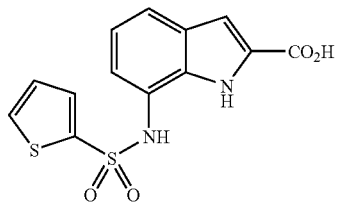 [SMILES: O=C(O)c1cc2cccc(NS(=O)(=O)c3cccs3)c2[nH]1]

A mixture of ethyl 7-[(2-thienylsulfonyl)amino]-1H-indole-2-carboxylate (7.81 g), 8N aqueous sodium hydroxide solution (11.0 mL), tetrahydrofuran (20 mL) and ethanol (30 mL) was stirred at 50° C. overnight. The reaction mixture was concentrated, and water was added to the residue. The mixture was acidified with 10% aqueous citric acid solution, and the resulting crystals were filtrated, washed with water, and dried to give the title compound (7.00 g, yield 97%) as colorless crystals. melting point>268° C. (decomposition).

Example 2

7-[(2-Thienylsulfonyl)amino]-1H-indole-2-carboxamide

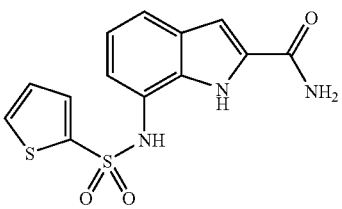 [SMILES: NC(=O)c1cc2cccc(NS(=O)(=O)c3cccs3)c2[nH]1]

To a mixture of 7-[(2-thienylsulfonyl)amino]-1H-indole-2-carboxylic acid (1.50 g), 1H-1,2,3-benzotriazol-1-ol (0.75 g) and N,N-dimethylformamide (15 mL) was added N-[3-(dimethylamino)propyl]-N'-ethylcarbodiimide hydrochloride (1.10 g) at room temperature. The mixture was stirred for 10 min, and 28% aqueous ammonia (1.70 mL) was added. The reaction mixture was stirred at room temperature for 3 hr, and water was added. The mixture was acidified with 10% aqueous citric acid solution, and the resulting crystals were filtrated, washed with water, and dried to give the title compound (1.46 g, yield 98%) as yellow crystals. melting point>300° C. (decomposition).

Example 3

N-[2-(4,5-Dihydro-1,3-thiazol-2-yl)-1H-indol-7-yl]thiophene-2-sulfonamide

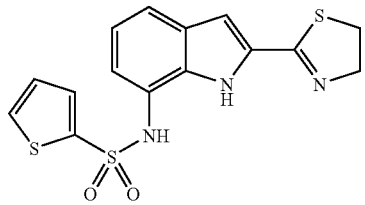

A mixture of N-(2-cyano-1H-indol-7-yl)thiophene-2-sulfonamide (0.54 g), 2-aminoethanethiol (0.14 g) and ethanol (20 mL) was stirred at 60° C. overnight. Water was added to the reaction mixture, and the obtained crystals were filtrated, washed with water and dried. The obtained crystals were subjected to silica gel column chromatography, and eluted with ethyl acetate. The eluate was treated with activated carbon and concentrated to give the title compound (0.19 g, yield 29%) as colorless crystals. The crystals were recrystallized from ethyl acetate-hexane. melting point 189-190° C.

$^1$H-NMR (DMSO-d$_6$) δ:3.48 (2H, t, J=8.3 Hz), 4.40 (2H, t, J=8.3 Hz), 6.84 (1H, d, J=1.8 Hz), 6.97-7.60 (2H, m), 7.28 (1H, d, J=7.8 Hz), 7.37 (1H, d, J=7.8 Hz), 7.55 (1H, dt, J=3.9, 1.2 Hz), 7.83 (1H, dt, J=4.8, 1.2 Hz), 10.22 (1H, brs), 11.39 (1H, brs).

Example 4

N-(2-Bromoethyl)-7-[(2-thienylsulfonyl)amino]-1H-indole-2-carboxamide

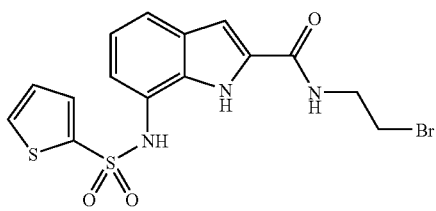 [SMILES: O=C(NCCBr)c1cc2cccc(NS(=O)(=O)c3cccs3)c2[nH]1]

To a mixture of 7-[(2-thienylsulfonyl)amino]-1H-indole-2-carboxylic acid (0.70 g), (2-bromoethyl)amine hydrobromide (0.49 g), 1H-1,2,3-benzotriazol-1-ol (0.32 g), triethylamine (0.34 mL) and N,N-dimethylformamide (20 mL) was added N-[3-(dimethylamino)propyl]-N'-ethylcarbodiimide hydrochloride (0.46 g) at 0° C., and the mixture was stirred at room temperature overnight. Water was added to the reaction mixture, and the obtained crystals were filtrated, washed with

Example 5

N-[2-(4,5-Dihydro-1,3-oxazol-2-yl)-1H-indol-7-yl]thiophene-2-sulfonamide

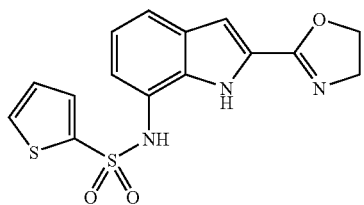 [SMILES: O=S(=O)(Nc1cccc2cc(C3=NCCO3)[nH]c12)c1cccs1]

To a solution of N-(2-bromoethyl)-7-[(2-thienylsulfonyl)amino]-1H-indole-2-carboxamide (0.35 g) in tetrahydrofuran (6 mL) was slowly added sodium hydride (60% in oil, 0.04 g) at 0° C., and the mixture was stirred at room temperature overnight. To the reaction mixture was added 10% aqueous citric acid solution, and the mixture was extracted with ethyl acetate. The ethyl acetate layer was washed with saturated brine, dried (MgSO$_4$) and concentrated. The obtained residue was subjected to silica gel column chromatography and the title compound (0.20 g, yield 71%) was obtained as colorless crystals from a fraction eluted with ethyl acetate. The crystals were recrystallized from ethyl acetate-hexane. melting point>260° C. (decomposition).

$^1$H-NMR (DMSO-d$_6$) δ:3.99 (2H, t, J=9.3 Hz), 4.43 (2H, t, J=9.3 Hz), 6.89 (1H, d, J=2.2 Hz), 6.94-7.10 (2H, m), 7.28 (1H, d, J=7.8 Hz), 7.37 (1H, d, J=7.8 Hz), 7.55 (1H, dd, J=3.7, 1.5 Hz), 7.83 (1H, dd, J=4.7, 1.5 Hz), 10.20 (1H, brs), 11.36 (1H, brs).

Example 6

Methyl 7-(benzylamino)-1H-pyrrolo[2,3-c]pyridine-2-carboxylate

To a suspension of potassium ethoxide (2.94 g) in diethyl ether (50 mL) was slowly added dropwise diethyl oxalate (4.82 mL) under ice-cooling. The suspension was stirred under ice-cooling for 10 min, and a solution (100 mL) of tert-butyl benzyl(4-methyl-3-nitropyridin-2-yl)carbamate (10 g) in diethyl ether was added. Under ice-cooling, the mixture was stirred for 4 hr, the precipitate was collected by filtration, and washed with diisopropyl ether to give a red solid. The red solid was dissolved in methanol (250 mL), 10% palladium-carbon (50% containing water, 1.2 g) was added, and the mixture was stirred at room temperature under a hydrogen atmosphere for 6 hr. The catalyst was filtered off, and the filtrate was concentrated under reduced pressure. The obtained residue was diluted with ethyl acetate, washed with water and saturated brine, dried over anhydrous magnesium sulfate, and concentrated under reduced pressure. The obtained residue was subjected to silica gel column chromatography (ethyl acetate:hexane=5:95-25:75) to give pale-yellow prism crystals (5.8 g). The obtained crystals were dissolved in methanol (50 mL), 6N-hydrochloric acid (25 mL) was added, and the mixture was stirred at 60° C. for 4 hr. The reaction mixture was concentrated under reduced pressure. The obtained residue was diluted with ethyl acetate, washed with aqueous sodium hydrogencarbonate solution and saturated brine, dried over anhydrous magnesium sulfate, and concentrated under reduced pressure. The obtained crystals were washed with ethyl acetate-hexane to give the title compound (3.25 g, yield 40%) as pale-yellow prism crystals. melting point 154-155° C.

Example 7

N-[2-(1,3-Thiazol-2-yl)-1H-indol-7-yl]thiophene-2-sulfonamide

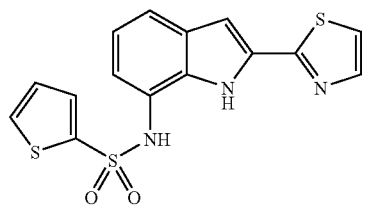 [SMILES: O=S(=O)(Nc1cccc2cc(-c3nccs3)[nH]c12)c1cccs1]

A mixture of 7-[(2-thienylsulfonyl)amino]-1H-indole-2-carbothioamide (0.61 g), 1-bromo-2,2-diethoxyethane (0.32 mL) and ethanol (10 mL) was heated under reflux overnight. Water was added to the reaction mixture, and the obtained crystals were filtered, washed with water and dried. The obtained crystals were subjected to silica gel column chromatography and the title compound (0.06 g, yield 9%) was obtained as colorless crystals from a fraction eluted with ethyl acetate-hexane (1:1, volume ratio). The crystals were recrystallized from ethyl acetate-hexane. melting point 164-165° C.

$^1$H-NMR (DMSO-d$_6$) δ:6.67 (1H, dd, J=7.7, 0.7 Hz), 6.90-7.20 (3H, m), 7.04 (1H, brs), 7.32 (1H, d, J=3.2 Hz), 7.40 (1H, dd, J=3.7, 1.5 Hz), 7.49-7.56 (2H, m), 7.82 (1H, d, J=3.2 Hz), 9.94 (1H, brs).

Example 8

N-[2-(Pyridin-2-yl)-1H-indol-7-yl]thiophene-2-sulfonamide

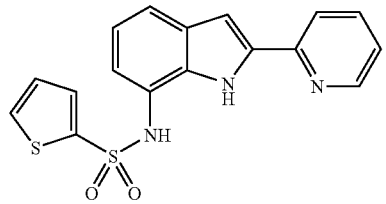 [SMILES: O=S(=O)(Nc1cccc2cc(-c3ccccn3)[nH]c12)c1cccs1]

To a mixture of 2-(pyridin-2-yl)-1H-indole-7-amine (0.35 g) and pyridine (6 mL) was added thiophene-2-sulfonyl chloride (0.38 g) at 0° C., and the mixture was stirred at room temperature for 2 hr. The reaction mixture was concentrated, 10% aqueous citric acid solution was added, and the mixture was extracted with ethyl acetate. The ethyl acetate layer was washed with saturated brine, dried (MgSO$_4$) and concentrated. The residue was subjected to silica gel column chromatography and the title compound (0.50 g, yield 82%) was obtained as pale-yellow crystals from a fraction eluted with ethyl acetate-hexane (1:3, volume ratio). The crystals were recrystallized from ethyl acetate-hexane. melting point 161-162° C.

$^1$H-NMR (DMSO-d$_6$) δ:6.63 (1H, d, J=7.8 Hz), 6.84-6.98 (3H, m), 7.00 (1H, d, J=1.8 Hz), 7.13-7.23 (1H, m), 7.40 (1H, dd, J=3.6, 1.4 Hz), 7.48-7.58 (2H, m), 7.65-7.82 (2H, m), 8.58-8.64 (1H, m), 10.16 (1H, brs).

Example 9

N-[2-(Hydrazinocarbonyl)-1H-indol-7-yl]thiophene-2-sulfonamide

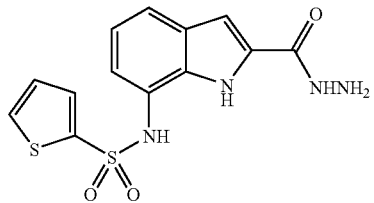 [SMILES: NNC(=O)c1cc2cccc(NS(=O)(=O)c3cccs3)c2[nH]1]

To a mixture of 7-[(2-thienylsulfonyl)amino]-1H-indole-2-carboxylic acid (0.60 g), 1H-1,2,3-benzotriazol-1-ol (0.28 g) and N,N-dimethylformamide (6 mL) was added N-[3-(dimethylamino)propyl]-N'-ethylcarbodiimide hydrochloride (0.40 g) at room temperature. The mixture was stirred for 10 min and hydrazine monohydrate (0.28 mL) was added. The reaction mixture was stirred at room temperature overnight, and water was added. The resulting crystals were filtrated, washed with water, and dried to give the title compound (0.28 g, yield 44%) as colorless crystals. melting point>276° C. (decomposition).

Example 10

N-[2-(1,3,4-Oxadiazol-2-yl)-1H-indol-7-yl]thiophene-2-sulfonamide

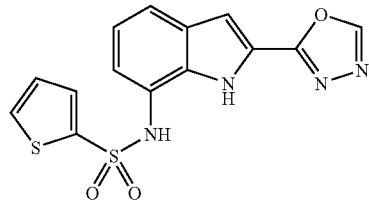 [SMILES: O=S(=O)(Nc1cccc2cc(-c3nnco3)[nH]c12)c1cccs1]

A mixture of N-[2-(hydrazinocarbonyl)-1H-indol-7-yl]thiophene-2-sulfonamide (0.28 g) and trimethyl orthoformate (0.13 g) was stirred at 100° C. overnight. The reaction mixture was concentrated, and the residue was subjected to silica gel column chromatography and the title compound (0.11 g, yield 39%) was obtained as colorless crystals from a fraction eluted with tetrahydrofuran-hexane (1:1, volume ratio). The crystals were recrystallized from ethyl acetate-hexane. melting point 271-272° C. (decomposition).

$^1$H-NMR (DMSO-d$_6$) δ:7.02-7.13 (2H, m), 7.20-7.34 (2H, m), 7.46 (1H, d, J=8.0 Hz), 7.58 (1H, dd, J=3.9, 1.2 Hz), 7.84 (1H, dd, J=4.8, 1.2 Hz), 9.38 (1H, s), 10.16 (1H, brs), 11.85 (1H, brs).

Example 11

N-(1-Oxo-2,3,4,9-tetrahydro-1H-carbazol-8-yl)thiophene-2-sulfonamide

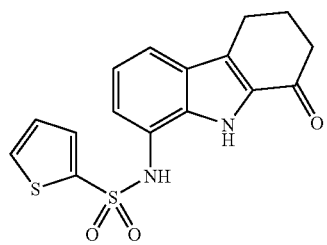 [SMILES: O=C1CCCc2c1[nH]c1c(NS(=O)(=O)c3cccs3)cccc21]

To a mixture of 8-amino-2,3,4,9-tetrahydro-1H-carbazol-1-one (1.20 g) and pyridine (20 mL) was added thiophene-2-sulfonyl chloride (1.30 g) at 0° C., and the mixture was stirred at room temperature for 2 hr. The reaction mixture was concentrated, 10% aqueous citric acid solution was added, and the resulting crystals were filtrated, washed with water and dried. The obtained crystals were subjected to silica gel column chromatography and the title compound (1.94 g, yield 86%) was obtained as colorless crystals from a fraction eluted with tetrahydrofuran. The crystals were recrystallized from tetrahydrofuran-hexane. melting point>280° C. (decomposition).

$^1$H-NMR (DMSO-d$_6$) δ:2.03-2.21 (2H, m), 2.54 (2H, t, J=5.6 Hz), 2.90 (2H, t, J=5.6 Hz), 7.00-7.10 (2H, m), 7.35 (1H, d, J=7.2 Hz), 7.44 (1H, d, J=8.0 Hz), 7.56 (1H, dd, J=3.8, 1.3 Hz), 7.84 (1H, dd, J=5.1, 1.3 Hz), 10.04 (1H, brs), 11.16 (1H, brs).

Example 12

N-(1-Hydroxy-2,3,4,9-tetrahydro-1H-carbazol-8-yl)thiophene-2-sulfonamide

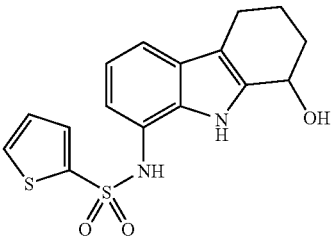 [SMILES: O=S(=O)(Nc1cccc2c3c([nH]c12)C(O)CCC3)c1cccs1]

To a mixture of N-(1-oxo-2,3,4,9-tetrahydro-1H-carbazol-8-yl)thiophene-2-sulfonamide (0.50 g), tetrahydrofuran (20 mL) and methanol (2 mL) was added sodium borohydride (0.11 g) at 0° C., and the mixture was stirred at room temperature for 3 hr. The reaction mixture was concentrated, 10% aqueous citric acid solution was added, and the resulting crystals were filtrated, washed with water, and dried to give the title compound (0.43 g, yield 86%) as colorless crystals. The crystals were recrystallized from ethyl acetate-hexane. melting point>175° C. (decomposition).

$^1$H-NMR (DMSO-d$_6$) δ:1.60-2.10 (4H, m), 2.45-2.63 (2H, m), 4.66-4.82 (1H, m), 5.24 (1H, d, J=5.8 Hz), 6.80-6.98 (2H, m), 7.08 (1H, dd, J=4.9, 3.9 Hz), 7.16 (1H, d, J=7.0 Hz), 7.52 (1H, dd, J=3.9, 1.2 Hz), 7.86 (1H, dd, J=4.9, 1.2 Hz), 10.00 (1H, brs), 10.40 (1H, brs).

Example 13

Methyl 3-{[(1-oxo-2,3,4,9-tetrahydro-1H-carbazol-8-yl)amino]sulfonyl}thiophene-2-carboxylate

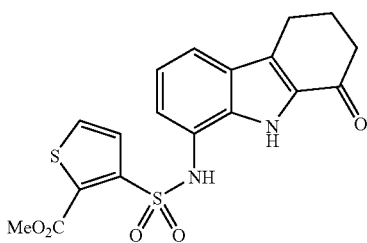 [SMILES: COC(=O)c1sccc1S(=O)(=O)Nc1cccc2c3c([nH]c12)C(=O)CCC3]

To a mixture of 8-amino-2,3,4,9-tetrahydro-1H-carbazol-1-one (0.30 g) and pyridine (8 mL) was added methyl 3-(chlorosulfonyl)thiophene-2-carboxylate (0.43 g) at 0° C., and the mixture was stirred at room temperature for 2 hr. The reaction mixture was concentrated, 10% aqueous citric acid solution was added, and the resulting crystals were filtrated, washed with water and dried. The obtained crystals were subjected to silica gel column chromatography and the title compound (0.47 g, yield 80%) was obtained as pale-yellow crystals from a fraction eluted with tetrahydrofuran-hexane (1:1, volume ratio). The crystals were recrystallized from ethyl acetate-hexane. melting point 239-240° C. (decomposition).

$^1$H-NMR (DMSO-d$_6$) δ:2.06-2.24 (2H, m), 2.57 (2H, t, J=6.1 Hz), 2.90 (2H, t, J=6.0 Hz), 3.83 (3H, s), 6.93 (1H, t, J=7.8 Hz), 7.09 (1H, d, J=7.8 Hz), 7.36 (1H, d, J=7.8 Hz), 7.55 (1H, d, J=5.0 Hz), 7.95 (1H, d, J=5.0 Hz), 10.04 (1H, brs), 11.35 (1H, brs).

Example 14

2-Methyl-N-(1-oxo-2,3,4,9-tetrahydro-1H-carbazol-8-yl)benzenesulfonamide

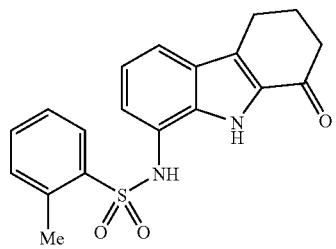 [SMILES: Cc1ccccc1S(=O)(=O)Nc1cccc2c3c([nH]c12)C(=O)CCC3]

To a mixture of 8-amino-2,3,4,9-tetrahydro-1H-carbazol-1-one (0.30 g) and pyridine (8 mL) was added 2-methylbenzenesulfonyl chloride (0.26 mL) at 0° C., and the mixture was stirred at room temperature for 2 hr. The reaction mixture was concentrated, 10% aqueous citric acid solution was added, and the resulting crystals were filtrated, washed with water and dried. The obtained crystals were subjected to silica gel column chromatography and the title compound (0.38 g, yield 73%) was obtained as colorless crystals from a fraction eluted with tetrahydrofuran-hexane (1:1, volume ratio). The crystals were recrystallized from ethyl acetate-hexane. melting point 255-256° C. (decomposition).

$^1$H-NMR (DMSO-d$_6$) δ:2.03-2.23 (2H, m), 2.27 and 2.59 (3H, 2s, 3:7), 2.50-2.65 (2H, m), 2.80-2.96 (2H, m), 6.86-7.14 (2H, m), 7.25-7.56 (4H, m), 7.68 and 7.96 (1H, 2d, J=8.3 Hz, 3:7), 9.89 and 10.10 (1H, 2brs, 3:7), 11.17 and 11.32 (1H, 2brs, 3:7).

Example 15

N-(1-Oxo-2,3,4,9-tetrahydro-1H-carbazol-8-yl)propane-2-sulfonamide

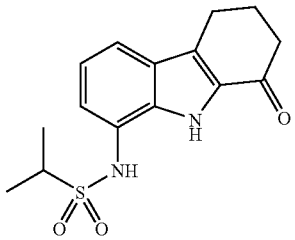 [SMILES: CC(C)S(=O)(=O)Nc1cccc2c3c([nH]c12)C(=O)CCC3]

To a mixture of 8-amino-2,3,4,9-tetrahydro-1H-carbazol-1-one (0.35 g) and pyridine (8 mL) was added propane-2-sulfonyl chloride (0.24 mL) at 0° C., and the mixture was stirred at room temperature for 2 hr. The reaction mixture was concentrated, 10% aqueous citric acid solution was added, and the resulting crystals were filtrated, washed with water and dried. The obtained crystals were subjected to silica gel column chromatography and the title compound (1.94 g, yield 19%) was obtained as colorless crystals from a fraction eluted with tetrahydrofuran-hexane (1:1, volume ratio). The crystals were recrystallized from ethyl acetate. melting point 267-268° C.

$^1$H-NMR (DMSO-d$_6$) δ:1.21 (6H, d, J=6.8 Hz), 2.10-2.25 (2H, m), 2.58 (2H, t, J=6.4 Hz), 2.94 (2H, t, J=5.8 Hz), 3.30 (1H, septet, J=6.8 Hz), 7.07 (1H, t, J=7.8 Hz), 7.35-7.50 (2H, m), 9.40 (1H, brs), 11.31 (1H, brs).

Example 16

Ethyl 2-{7-[(2-thienylsulfonyl)amino]-1H-indol-2-yl}-4,5-dihydro-1,3-thiazole-4-carboxylate

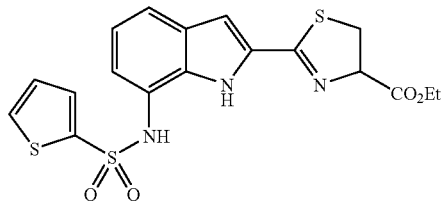 [SMILES: CCOC(=O)C1CSC(c2cc3cccc(NS(=O)(=O)c4cccs4)c3[nH]2)=N1]

A mixture of N-(2-cyano-1H-indol-7-yl)thiophene-2-sulfonamide (0.30 g), cysteine ethyl ester hydrochloride (0.22 g) and ethanol (10 mL) was heated under reflux overnight. Water was added to the reaction mixture, and the mixture was extracted with ethyl acetate. The ethyl acetate layer was washed with saturated brine, dried (MgSO$_4$) and concentrated. The obtained residue was subjected to silica gel column chromatography and the title compound (0.11 g, yield 25%) was obtained as pale-yellow crystals from a fraction eluted with ethyl acetate-hexane (1:1, volume ratio). The crystals were recrystallized from ethyl acetate-hexane. melting point 156-157° C.

$^1$H-NMR (DMSO-d$_6$) δ:1.33 (3H, t, J=7.2 Hz), 3.61-3.82 (2H, m), 4.29 (2H, qd, J=7.2, 1.1 Hz), 5.27 (1H, t, J=9.2 Hz), 6.78 (1H, dd, J=7.6, 1.0 Hz), 6.84 (1H, dd, J=5.1, 3.7 Hz), 6.90-7.01 (3H, m), 7.30 (1H, dd, J=3.7, 1.3 Hz), 7.44 (1H, dd, J=5.1, 1.3 Hz), 7.51 (1H, d, J=7.6 Hz), 9.94 (1H, brs).

Example 17

N-[2-(1,2,4-Oxadiazol-3-yl)-1H-indol-7-yl]thiophene-2-sulfonamide

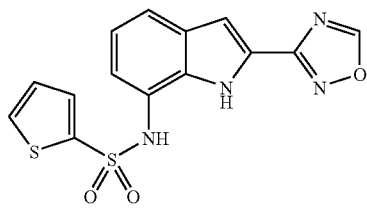 [SMILES: O=S(=O)(Nc1cccc2cc(-c3ncon3)[nH]c12)c1cccs1]

A mixture of N-(2-cyano-1H-indol-7-yl)thiophene-2-sulfonamide (0.50 g), hydroxyamine hydrochloride (0.17 g), triethylamine (0.83 mL), tetrahydrofuran (2 mL) and methanol (2 mL) was stirred at room temperature overnight. Water was added to the reaction mixture, and the obtained crystals were filtered, washed with water and dried. A mixture of the obtained crystals and methyl orthoformate (10 mL) was heated under reflux for 4 hr. The reaction mixture was concentrated, and the residue was subjected to silica gel column chromatography. The title compound (0.18 g, yield 33%) was obtained as pale-yellow crystals from a fraction eluted with ethyl acetate-hexane (2:1, volume ratio). The crystals were recrystallized from ethyl acetate-hexane. melting point>185° C. (decomposition).

$^1$H-NMR (DMSO-d$_6$) δ:7.01-7.09 (2H, m), 7.19 (1H, d, J=2.1 Hz), 7.28 (1H, d, J=7.8 Hz), 7.44 (1H, d, J=7.8 Hz), 7.57 (1H, dt, J=3.6, 1.2 Hz), 7.81-7.86 (1H, m), 9.75 (1H, s), 10.21 (1H, brs), 11.65 (1H, brs).

Example 18

N-(3-Methyl-2-propionyl-1H-indol-7-yl)thiophene-2-sulfonamide

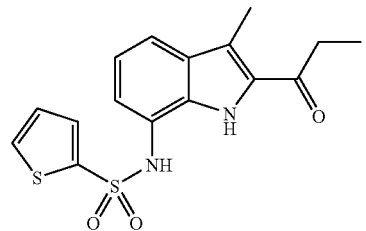 [SMILES: CCC(=O)c1[nH]c2c(NS(=O)(=O)c3cccs3)cccc2c1C]

To a mixture of 1-(7-amino-3-methyl-1H-indol-2-yl)propan-1-one (0.17 g) and pyridine (6 mL) was added thiophene-2-sulfonyl chloride (0.18 g) at 0° C., and the mixture was stirred at room temperature for 2 hr. The reaction mixture was concentrated, 10% aqueous citric acid solution was added, and the resulting crystals were filtered, washed with water and dried. The obtained crystals were subjected to silica gel column chromatography, and eluted with ethyl acetate. The eluate was treated with activated carbon and concentrated to give the title compound (0.19 g, yield 65%) as colorless crystals. The crystals were recrystallized from ethyl acetate-hexane. melting point >185° C. (decomposition).

$^1$H-NMR (DMSO-d$_6$) δ:1.36 (3H, t, J=7.2 Hz), 2.66 (3H, s), 3.10 (2H, q, J=7.2 Hz), 6.86 (1H, dd, J=5.0, 3.8 Hz), 7.09 (1H, dd, J=8.2, 7.6 Hz), 7.27-7.35 (2H, m), 7.44 (1H, dd, J=5.0, 1.5 Hz), 7.57 (1H, d, J=8.2 Hz), 8.40 (1H, brs), 10.27 (1H, brs).

Example 19

N-(2-hydroxy-1,1-dimethylethyl)-7-[(2-thienylsulfonyl)amino]-1H-indole-2-carboxamide

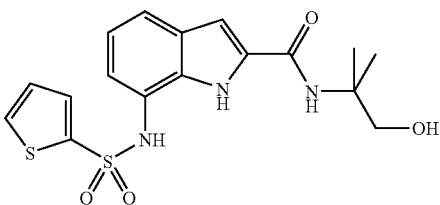 [SMILES: CC(C)(CO)NC(=O)c1cc2cccc(NS(=O)(=O)c3cccs3)c2[nH]1]

To a mixture of 7-[(2-thienylsulfonyl)amino]-1H-indole-2-carboxylic acid (1.00 g), 2-amino-2-methylpropan-1-ol (0.55 g), 1H-1,2,3-benzotriazol-1-ol (0.50 g) and N,N-dimethylformamide (15 mL) was added N-[3-(dimethylamino)propyl]-N'-ethylcarbodiimide hydrochloride (0.71 g) at 0° C., and the mixture was stirred at 60° C. overnight. Water was added to the reaction mixture and the mixture was acidified with 10% aqueous citric acid solution. The resulting crystals were filtered, washed with water, and dried to give the title compound (0.89 g, yield 74%) as colorless crystals. melting point>217° C. (decomposition).

$^1$H-NMR (DMSO-d$_6$) δ:1.33 (6H, s), 3.53 (2H, d, J=6.0 Hz), 4.92 (1H, t, J=6.0 Hz), 6.97 (1H, dd, J=8.1, 7.5 Hz), 7.05 (1H, dd, J=5.1, 3.6 Hz), 7.16-7.22 (2H, m), 7.36 (1H, d, J=8.1 Hz), 7.54 (1H, dd, J=3.6, 1.4 Hz), 7.63 (1H, brs), 7.84 (1H, dd, J=5.1, 1.4), 10.25 (1H, brs), 11.21 (1H, brs).

Example 20

N-(2-Hydroxy-2-methylpropyl)-7-[(2-thienylsulfonyl)amino]-1H-indole-2-carboxamide

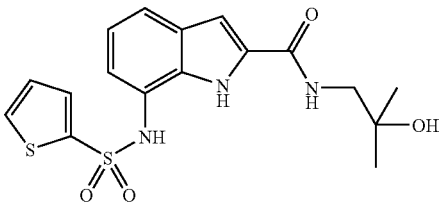 [SMILES: CC(C)(O)CNC(=O)c1cc2cccc(NS(=O)(=O)c3cccs3)c2[nH]1]

To a mixture of 7-[(2-thienylsulfonyl)amino]-1H-indole-2-carboxylic acid (1.00 g), 1-amino-2-methylpropan-2-ol (0.55 g), 1H-1,2,3-benzotriazol-1-ol (0.50 g) and N,N-dimethylformamide (15 mL) was added N-[3-(dimethylamino)propyl]-N'-ethylcarbodiimide hydrochloride (0.71 g) at 0° C., and the mixture was stirred at 60° C. overnight. Water was added to the reaction mixture and the mixture was acidified with 10% aqueous citric acid solution. The resulting crystals were filtrated, washed with water, and dried to give the title compound (0.77 g, yield 65%) as colorless crystals. melting point>234° C. (decomposition).

1H-NMR (DMSO-$d_6$) δ:1.11 (6H, s), 3.26 (2H, d, J=6.0 Hz), 4.56 (1H, s), 6.94-7.08 (2H, m), 7.16-7.24 (2H, m), 7.37 (1H, d, J=7.5 Hz), 7.54 (1H, d, J=3.9 Hz), 7.83 (1H, d, J=5.1 Hz), 8.36 (1H, t, J=6.0 Hz), 10.24 (1H, brs), 11.27 (1H, brs).

Example 21

N-[2-(Methylthio)-1H-indol-7-yl]thiophene-2-sulfonamide

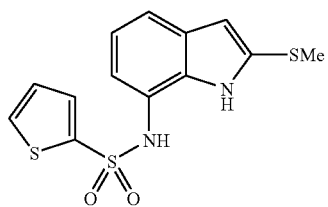 [SMILES: CSc1cc2cccc(NS(=O)(=O)c3cccs3)c2[nH]1]

A mixture of N-(2-oxo-2,3-dihydro-1H-indol-7-yl)thiophene-2-sulfonamide (1.00 g), Lawesson's reagent (1.50 g) and tetrahydrofuran (40 mL) was stirred at room temperature for 2 days. The reaction mixture was concentrated, and the obtained residue was subjected to silica gel column chromatography. Yellow crystals (0.97 g) were obtained from a fraction eluted with tetrahydrofuran-hexane (1:1, volume ratio). To a mixture of the obtained yellow crystals, 8N aqueous sodium hydroxide solution (0.80 mL), methanol (4 mL) and water (10 mL) was added dimethylsulfate (0.43 g), and the mixture was stirred at room temperature for 1 hr. The reaction mixture was concentrated, and water was added to the residue. The mixture was acidified with 10% aqueous citric acid solution, and extracted with ethyl acetate. The ethyl acetate layer was washed with saturated brine, dried ($MgSO_4$) and concentrated. The residue was subjected to silica gel column chromatography and the title compound (0.35 g, yield 32%) was obtained as colorless crystals from a fraction eluted with ethyl acetate-hexane (1:2, volume ratio). melting point 102-103° C.

$^1$H-NMR ($CDCl_3$) δ:2.54 (3H, s), 6.46 (1H, dd, J=7.7, 0.9 Hz), 6.51 (1H, d, J=2.2 Hz), 6.66 (1H, brs), 6.88 (1H, t, J=7.7 Hz), 6.99 (1H, dd, J=4.9, 3.9 Hz), 7.35-7.44 (2H, m), 7.56 (1H, dd, J=4.9, 1.4 Hz), 9.02 (1H, brs).

Example 22

N-[2-(Methylsulfonyl)-1H-indol-7-yl]thiophene-2-sulfonamide

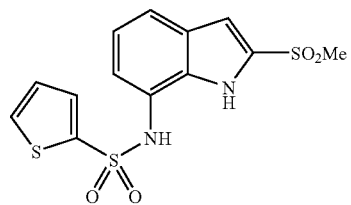 [SMILES: CS(=O)(=O)c1cc2cccc(NS(=O)(=O)c3cccs3)c2[nH]1]

To a solution of N-[2-(methylthio)-1H-indol-7-yl]thiophene-2-sulfonamide (0.35 g) in ethyl acetate (10 mL) was added m-chloroperbenzoic acid (0.60 g) at 0° C., and the mixture was stirred at room temperature overnight. To the reaction mixture was added saturated aqueous sodium hydrogen carbonate, and the mixture was extracted with ethyl acetate. The ethyl acetate layer was washed with aqueous sodium hydrogen sulfite solution and saturated brine, dried ($MgSO_4$) and concentrated. The resulting crystals were dissolved in tetrahydrofuran, treated with activated carbon, and concentrated to give the title compound (0.20 g, yield 51%) as colorless crystals. The crystals were recrystallized from ethyl acetate-hexane. melting point 266-267° C. (decomposition).

$^1$H-NMR (DMSO-$d_6$) δ:3.33 (3H, s), 7.02-7.18 (4H, m), 7.47-7.58 (2H, m), 7.86-7.91 (1H, m), 10.11 (1H, brs), 11.93 (1H, brs).

Example 23

Ethyl 3-methyl-7-[(2-thienylsulfonyl)amino]-1H-indole-2-carboxylate

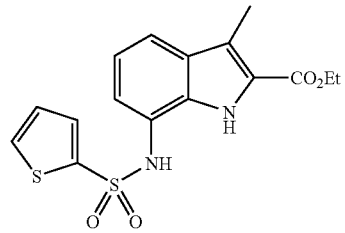 [SMILES: CCOC(=O)c1[nH]c2c(NS(=O)(=O)c3cccs3)cccc2c1C]

To a mixture of ethyl 7-amino-3-methyl-1H-indole-2-carboxylate (0.95 g) and pyridine (10 mL) was added thiophene-2-sulfonyl chloride (0.95 g) at 0° C., and the mixture was stirred at room temperature for 2 hr. The reaction mixture was concentrated, 10% aqueous citric acid solution was added, and the resulting crystals were filtrated, washed with water and dried. The obtained crystals were subjected to silica gel column chromatography, and eluted with ethyl acetate. The eluate was treated with activated carbon and concentrated to give the title compound (1.13 g, yield 70%) as colorless crystals. The crystals were recrystallized from ethyl acetate-hexane. melting point 198-199° C.

Example 24

3-Methyl-7-[(2-thienylsulfonyl)amino]-1H-indole-2-carboxylic acid

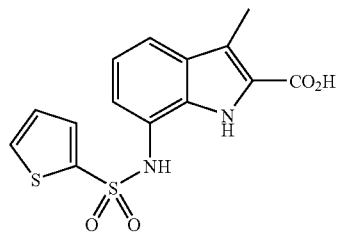 [SMILES: Cc1c(C(=O)O)[nH]c2c(NS(=O)(=O)c3cccs3)cccc12]

A mixture of ethyl 3-methyl-7-[(2-thienylsulfonyl)amino]-1H-indole-2-carboxylate (1.33 g), 8N aqueous sodium hydroxide solution (2.0 mL), tetrahydrofuran (5 mL) and ethanol (10 mL) was stirred at 60° C. for 3 hr. The reaction mixture was concentrated, and water was added to the residue. The mixture was acidified with 10% aqueous citric acid solution, and the resulting crystals were filtrated, washed with water, and dried to give the title compound (1.15 g, yield 94%) as colorless crystals. melting point>263° C. (decomposition).

Example 25

3-Methyl-7-[(2-thienylsulfonyl)amino]-N-[2-(tritylthio)ethyl]-1H-indole-2-carboxamide

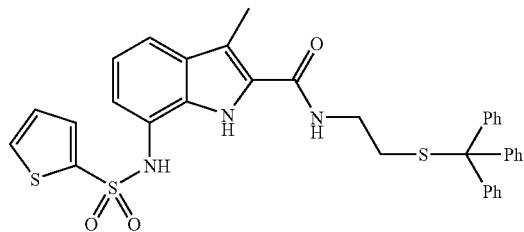 [SMILES: Cc1c(C(=O)NCCSC(c2ccccc2)(c2ccccc2)c2ccccc2)[nH]c2c(NS(=O)(=O)c3cccs3)cccc12]

To a mixture of 3-methyl-7-[(2-thienylsulfonyl)amino]-1H-indole-2-carboxylic acid (0.70 g), 2-(tritylthio)ethylamine hydrochloride (0.82 g), 1H-1,2,3-benzotriazol-1-ol (0.34 g), triethylamine (0.35 mL) and N,N-dimethylformamide (15 mL) was added N-[3-(dimethylamino)propyl]-N'-ethylcarbodiimide hydrochloride (0.48 g) at 0° C., and the mixture was stirred at room temperature overnight. Water was added to the reaction mixture, and the obtained crystals were filtrated, washed with water and dried. The obtained crystals were subjected to silica gel column chromatography and the title compound (1.36 g, quantitative) was obtained as colorless crystals from a fraction eluted with ethyl acetate. melting point>214° C. (decomposition).

Example 26

N-[2-(4,5-Dihydro-1,3-thiazol-2-yl)-3-methyl-1H-indol-7-yl]thiophene-2-sulfonamide

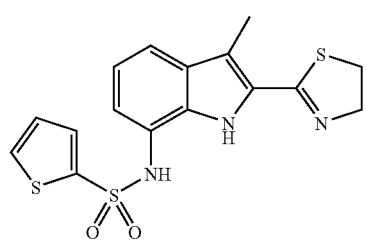 [SMILES: Cc1c(C2=NCCS2)[nH]c2c(NS(=O)(=O)c3cccs3)cccc12]

To a solution of triphenylphosphine oxide (3.56 g) in dichloromethane (30 mL) was slowly added trifluoromethanesulfonic anhydride (1.10 mL) at 0° C. The mixture was stirred for 10 min, and 3-methyl-7-[(2-thienylsulfonyl)amino]-N-[2-(tritylthio)ethyl]-1H-indole-2-carboxamide (1.36 g) was added. The reaction mixture was stirred at room temperature for 3 hr and concentrated. Saturated aqueous sodium hydrogen carbonate was added, and the mixture was extracted with ethyl acetate. The ethyl acetate layer was washed with saturated brine, dried (MgSO$_4$) and concentrated. The residue was subjected to silica gel column chromatography and the title compound (0.33 g, yield 41%) was obtained as colorless crystals from a fraction eluted with ethyl acetate-hexane (1:20→1:1, volume ratio). melting point 163-164° C.

$^1$H-NMR (DMSO-d$_6$) δ:2.46 (3H, s), 3.47 (2H, t, J=8.3 Hz), 4.34 (2H, t, J=8.3 Hz), 6.96-7.07 (2H, m), 7.25-7.41 (2H, m), 7.51-7.57 (1H, m), 7.80-7.86 (1H, m), 10.31 (1H, brs), 10.96 (1H, brs).

Example 27

Ethyl 7-{[(5-chloro-2-thienyl)sulfonyl]amino}-1H-indole-2-carboxylate

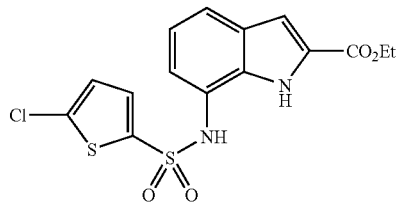 [SMILES: CCOC(=O)c1cc2cccc(NS(=O)(=O)c3ccc(Cl)s3)c2[nH]1]

To a mixture of ethyl 7-amino-1H-indole-2-carboxylate (0.70 g) and pyridine (10 mL) was added 5-chlorothiophene-2-sulfonyl chloride (0.89 g) at 0° C., and the mixture was stirred at room temperature for 2 hr. The reaction mixture was concentrated, 10% aqueous citric acid solution was added, and the resulting crystals were filtrated, washed with water and dried. The obtained crystals were subjected to silica gel column chromatography, and eluted with ethyl acetate. The eluate was treated with activated carbon and concentrated to give the title compound (1.09 g, yield 83%) as colorless crystals. The crystals were recrystallized from ethyl acetate-hexane. melting point 180-181° C.

Example 28

7-{[(5-Chloro-2-thienyl)sulfonyl]amino}-1H-indole-2-carboxylic acid

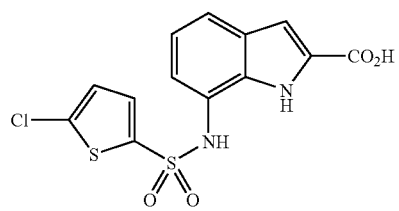 [SMILES: O=C(O)c1cc2cccc(NS(=O)(=O)c3ccc(Cl)s3)c2[nH]1]

A mixture of ethyl 7-{[(5-chloro-2-thienyl)sulfonyl]amino}-1H-indole-2-carboxylate (1.03 g), 8N aqueous sodium hydroxide solution (1.3 mL), tetrahydrofuran (5 mL) and ethanol (15 mL) was stirred at 60° C. for 2 hr. The reaction mixture was concentrated, and water was added to the residue. The mixture was acidified with 10% aqueous citric acid solution, and the resulting crystals were filtrated, washed with water, and dried to give the title compound (0.92 g, yield 90%) as colorless crystals. melting point>277° C. (decomposition).

Example 29

7-{[(5-Chloro-2-thienyl)sulfonyl]amino}-N-[2-(tritylthio)ethyl]-1H-indole-2-carboxamide

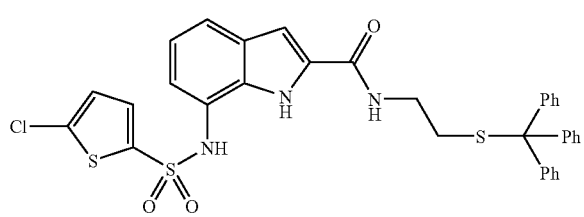 [SMILES: O=C(NCCSC(c1ccccc1)(c1ccccc1)c1ccccc1)c1cc2cccc(NS(=O)(=O)c3ccc(Cl)s3)c2[nH]1]

To a mixture of 7-{[(5-chloro-2-thienyl)sulfonyl]amino}-1H-indole-2-carboxylic acid (0.84 g), 2-(tritylthio)ethylamine hydrochloride (0.85 g), 1H-1,2,3-benzotriazol-1-ol (0.35 g), triethylamine (0.36 mL) and N,N-dimethylformamide (20 mL) was added N-[3-(dimethylamino)propyl]-N'-ethylcarbodiimide hydrochloride (0.50 g) at 0° C., and the mixture was stirred at room temperature overnight. Water was added to the reaction mixture, and the obtained crystals were filtrated, washed with water and dried. The obtained crystals were subjected to silica gel column chromatography and the title compound (1.41 g, yield 97%) was obtained as colorless crystals from a fraction eluted with ethyl acetate. melting point>197° C. (decomposition).

Example 30

5-Chloro-N-[2-(4,5-dihydro-1,3-thiazol-2-yl)-1H-indol-7-yl]thiophene-2-sulfonamide

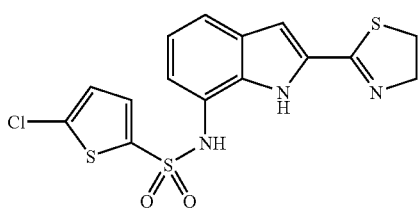 [SMILES: O=S(=O)(Nc1cccc2cc(C3=NCCS3)[nH]c12)c1ccc(Cl)s1]

To a solution of triphenylphosphine oxide (3.57 g) in dichloromethane (20 mL) was slowly added trifluoromethanesulfonic anhydride (1.10 mL) at 0° C. The mixture was stirred for 10 min, and 7-{[(5-chloro-2-thienyl)sulfonyl]amino}-N-[2-(tritylthio)ethyl]-1H-indole-2-carboxamide (1.41 g) was added. The reaction mixture was stirred at room temperature for 3 hr and concentrated. Saturated aqueous sodium hydrogen carbonate was added, and the mixture was extracted with ethyl acetate. The ethyl acetate layer was washed with saturated brine, dried (MgSO$_4$) and concentrated. The residue was subjected to silica gel column chromatography and the title compound (0.32 g, yield 37%) was obtained as colorless crystals from a fraction eluted with ethyl acetate-hexane (1:20→1:1, volume ratio). melting point>210° C. (decomposition).
$^1$H-NMR (DMSO-d$_6$) δ:3.47 (2H, t, J=8.2 Hz), 4.41 (2H, t, J=8.2 Hz), 6.87 (1H, d, J=2.0 Hz), 7.03 (1H, t, J=7.8 Hz), 7.13 (1H, t, J=4.2 Hz), 7.27 (1H, d, J=7.8 Hz), 7.39-7.46 (2H, m), 10.33 (1H, brs), 11.37 (1H, brs).

Example 31

N-[2-(Benzylthio)-2-methylpropyl]-7-[(2-thienylsulfonyl)amino]-1H-indole-2-carboxamide

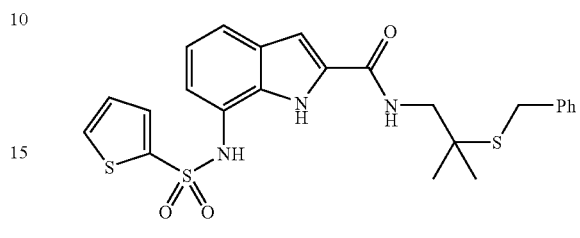

To a mixture of 7-[(2-thienylsulfonyl)amino]-1H-indole-2-carboxylic acid (0.70 g), 2-(benzylthio)-2-methylpropylamine (0.47 g), 1H-1,2,3-benzotriazol-1-ol (0.35 g) and N,N-dimethylformamide (15 mL) was added N-[3-(dimethylamino)propyl]-N'-ethylcarbodiimide hydrochloride (0.50 g) at 0° C., and the mixture was stirred at room temperature overnight. Water was added to the reaction mixture, and the mixture was extracted with ethyl acetate. The ethyl acetate layer was washed with saturated brine, dried (MgSO$_4$) and concentrated. The residue was subjected to silica gel column chromatography and the title compound (0.86 g, yield 77%) was obtained as yellow crystals from a fraction eluted with ethyl acetate-hexane (1:9-42:3, volume ratio). melting point 170-171° C.

Example 32

N-[2-(5,5-Dimethyl-4,5-dihydro-1,3-thiazol-2-yl)-1H-indol-7-yl]thiophene-2-sulfonamide

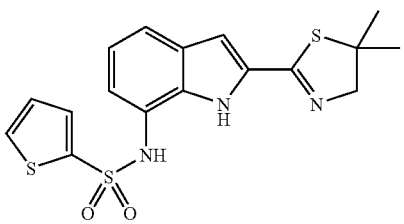 [SMILES: CC1(C)CN=C(c2cc3cccc(NS(=O)(=O)c4cccs4)c3[nH]2)S1]

To a solution of triphenylphosphine oxide (2.74 g) in dichloromethane (25 mL) was slowly added trifluoromethanesulfonic anhydride (0.83 mL) at 0° C. The mixture was stirred for 10 min, and N-[2-(benzylthio)-2-methylpropyl]-7-[(2-thienylsulfonyl)amino]-1H-indole-2-carboxamide (0.82 g) was added. The reaction mixture was stirred at room temperature overnight and concentrated. Saturated aqueous sodium hydrogen carbonate was added, and the mixture was extracted with ethyl acetate. The ethyl acetate layer was washed with saturated brine, dried (MgSO$_4$) and concentrated. The residue was subjected to silica gel column chromatography and the title compound (0.05 g, yield 8%) was obtained as colorless crystals from a fraction eluted with ethyl acetate-hexane (1:3, volume ratio). melting point 176-177° C.
$^1$H-NMR (CDCl$_3$) δ:1.59 (6H, s), 4.04 (2H, s), 6.68 (1H, dd, J=7.5, 0.9 Hz), 6.82-6.98 (3H, m), 7.10 (1H, brs), 7.36 (1H, dd, J=3.7, 1.5 Hz), 7.48-7.56 (2H, m), 9.78 (1H, brs).

Example 33

Ethyl 7-[(tert-butoxycarbonyl)amino]-1H-indole-2-carboxylate

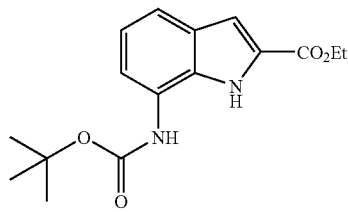

A mixture of ethyl 7-amino-1H-indole-2-carboxylate (3.00 g), di-tert-butyl dicarbonate (3.50 g), triethylamine (3.00 mL) and tetrahydrofuran (60 mL) was stirred at room temperature overnight. The reaction mixture was concentrated, and the obtained residue was subjected to silica gel column chromatography and the title compound (2.67 g, yield 60%) was obtained as colorless crystals from a fraction eluted with ethyl acetate-hexane (1:4, volume ratio). melting point 132-133° C.

Example 34

7-[(tert-Butoxycarbonyl)amino]-1H-indole-2-carboxylic acid

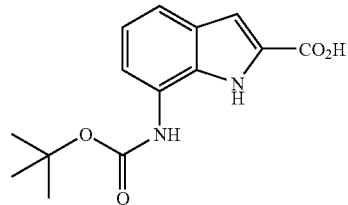 [SMILES: CC(C)(C)OC(=O)Nc1cccc2cc(C(=O)O)[nH]c12]

A mixture of ethyl 7-[(tert-butoxycarbonyl)amino]-1H-indole-2-carboxylate (2.65 g), 1N aqueous sodium hydroxide solution (22.0 mL), tetrahydrofuran (20 mL) and ethanol (30 mL) was stirred at 50° C. for 3 hr. The reaction mixture was concentrated, and water was added to the residue. The mixture was acidified with 10% aqueous citric acid solution, and the resulting crystals were filtrated, washed with water, and dried to give the title compound (2.27 g, yield 94%) as colorless crystals. melting point>246° C. (decomposition).

Example 35

N-[2-(Hydroxymethyl)-1H-indol-7-yl]thiophene-2-sulfonamide

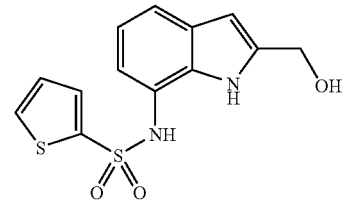 [SMILES: O=S(=O)(Nc1cccc2cc(CO)[nH]c12)c1cccs1]

To a mixture of ethyl 7-[(2-thienylsulfonyl)amino]-1H-indole-2-carboxylate (0.76 g) and tetrahydrofuran (15 mL) was added lithium aluminum hydride (0.15 g) at 0° C., and the mixture was stirred at room temperature for 1 hr. To the reaction mixture was added ethanol (5 mL), and saturated aqueous ammonium chloride solution (0.5 mL) was added. The resulting inorganic salt was removed by filtration, and the filtrate was concentrated. The residue was subjected to silica gel column chromatography, and the title compound (0.55 g, yield 82%) was obtained as colorless crystals from a fraction eluted with ethyl acetate-hexane (1:2, volume ratio). melting point>173° C. (decomposition).

Example 36

N-(2-Formyl-1H-indol-7-yl)thiophene-2-sulfonamide

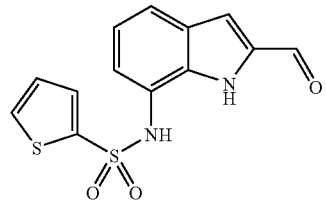 [SMILES: O=Cc1cc2cccc(NS(=O)(=O)c3cccs3)c2[nH]1]

A mixture of N-[2-(hydroxymethyl)-1H-indol-7-yl]thiophene-2-sulfonamide (1.30 g), activated manganese dioxide (8.0 g) and tetrahydrofuran (30 mL) was stirred at room temperature for 5 hr. The reaction mixture was filtered, and the filtrate was concentrated. The residue was subjected to silica gel column chromatography, and the title compound (0.12 g, yield 9%) was obtained as yellow crystals from a fraction eluted with tetrahydrofuran-hexane (2:1, volume ratio). melting point>226° C. (decomposition).

Example 37

7-(Benzyloxy)-N-[2-(tritylthio)ethyl]-1H-indole-2-carboxamide

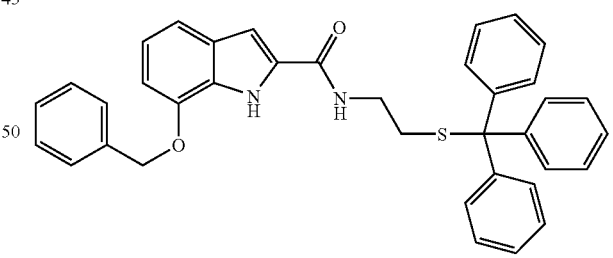

To a mixture of 7-(benzyloxy)-1H-indole-2-carboxylic acid (0.80 g), 2-(tritylthio)ethylamine hydrochloride (1.07 g), 1H-1,2,3-benzotriazol-1-ol (0.49 g), triethylamine (0.50 mL) and N,N-dimethylformamide (15 mL) was added N-[3-(dimethylamino)propyl]-N'-ethylcarbodiimide hydrochloride (0.69 g) at 0° C., and the mixture was stirred at room temperature overnight. Water was added to the reaction mixture, and the mixture was extracted with ethyl acetate. The ethyl acetate layer was washed with saturated brine, dried (MgSO$_4$) and concentrated. The residue was subjected to silica gel column chromatography and the title compound (1.60 g, yield 94%) was obtained as colorless crystals from a fraction eluted with ethyl acetate-hexane (2:3, volume ratio). melting point 156-157° C.

Example 38

7-(Benzyloxy)-2-(4,5-dihydro-1,3-thiazol-2-yl)-1H-indole

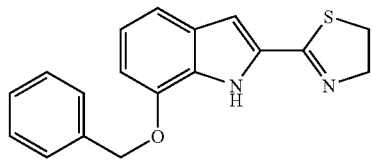 [SMILES: c1ccc(COc2cccc3cc(C4=NCCS4)[nH]c23)cc1]

To a solution of triphenylphosphine oxide (4.70 g) in dichloromethane (20 mL) was slowly added trifluoromethanesulfonic anhydride (1.42 mL) at 0° C. The mixture was stirred for 10 min, and 7-(benzyloxy)-N-[2-(tritylthio)ethyl]-1H-indole-2-carboxamide (1.60 g) was added. The reaction mixture was stirred at room temperature for 3 hr and concentrated. Saturated aqueous sodium hydrogen carbonate was added, and the mixture was extracted with ethyl acetate. The ethyl acetate layer was washed with saturated brine, dried (MgSO$_4$) and concentrated. The residue was subjected to silica gel column chromatography and the title compound (0.23 g, yield 27%) was obtained as colorless crystals from a fraction eluted with ethyl acetate-hexane (1:20→1:2, volume ratio). The crystals were recrystallized from ethyl acetate-hexane. melting point 129-130° C.

$^1$H-NMR (DMSO-d$_6$) δ:3.45 (2H, t, J=8.2 Hz), 4.41 (2H, t, J=8.2 Hz), 5.26 (2H, s), 6.80-7.00 (3H, m), 7.15-7.45 (4H, m), 7.60-7.69 (2H, m), 11.79 (1H, brs).

Ethyl 7-nitro-1H-indole-2-carboxylate derivative used in the following Examples was synthesized according to the method described in a literature [Synthesis, 1996, pp. 377-382].

Example 39

Ethyl 7-{[(4-methylphenyl)sulfonyl]amino}-1H-indole-2-carboxylate

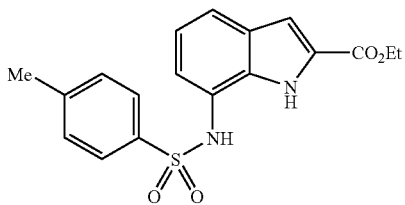 [SMILES: CCOC(=O)c1cc2cccc(NS(=O)(=O)c3ccc(C)cc3)c2[nH]1]

To a mixture of ethyl 7-amino-1H-indole-2-carboxylate (0.30 g) and pyridine (8 mL) was added 4-methylphenylsulfonyl chloride (0.34 g) at 4° C., and the mixture was stirred at room temperature for 18 hr. The reaction mixture was concentrated, diluted with ethyl acetate, washed with aqueous citric acid solution, water and saturated brine, dried over anhydrous magnesium sulfate, and concentrated under reduced pressure. The obtained crystals were recrystallized from ethyl acetate-hexane to give the title compound (465 mg, yield 88%) as pale-yellow prism crystals. MS:359 (MH$^+$).

Example 40

7-{[(4-Methylphenyl)sulfonyl]amino}-1H-indole-2-carboxylic acid

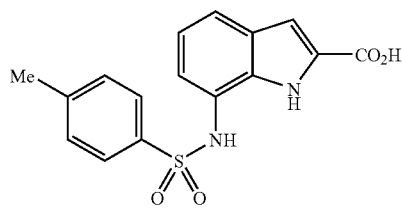 [SMILES: Cc1ccc(S(=O)(=O)Nc2cccc3cc(C(=O)O)[nH]c23)cc1]

To a mixed solution of ethyl 7-{[(4-methylphenyl)sulfonyl]amino}-1H-indole-2-carboxylate (356 mg) in tetrahydrofuran (6 mL)-methanol (6 mL) was added aqueous solution (3 mL) of 85% potassium hydroxide (450 mg), and the mixture was stirred at room temperature for 18 hr. Aqueous citric acid solution was added to the reaction mixture, and the mixture was extracted with ethyl acetate, washed with saturated brine, dried over anhydrous magnesium sulfate, and concentrated under reduced pressure. The obtained crystals were washed with ethyl acetate-hexane to give the title compound (312 mg, yield 95%) as pale-yellow crystals. melting point 268-269° C.

Example 41

7-{[(4-Methylphenyl)sulfonyl]amino}-1H-indole-2-carboxamide

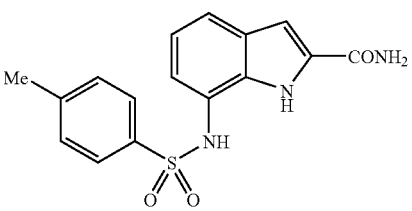 [SMILES: Cc1ccc(S(=O)(=O)Nc2cccc3cc(C(N)=O)[nH]c23)cc1]

To a mixture of 7-{[(4-methylphenyl)sulfonyl]amino}-1H-indole-2-carboxylic acid (105 mg), 1H-1,2,3-benzotriazol-1-ol-ammonia complex (58 mg) and N,N-dimethylformamide (5 mL) was added N-[3-(dimethylamino)propyl]-N'-ethylcarbodiimide hydrochloride (80 mg) at 4° C., and the mixture was stirred at room temperature for 5 hr. The reaction mixture was diluted with ethyl acetate, washed with aqueous sodium hydrogencarbonate solution, water and saturated brine, dried over anhydrous magnesium sulfate, and concentrated under reduced pressure. The obtained crystals were

Example 42

N-[2-(Piperidin-1-ylcarbonyl)-1H-indol-7-yl]
thiophene-2-carboxamide

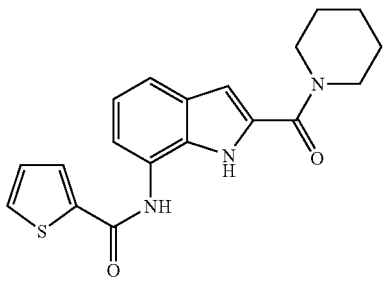 [SMILES: O=C(Nc1cccc2cc(C(=O)N3CCCCC3)[nH]c12)c1cccs1]

To a mixture of 7-[(2-thienylcarbonyl)amino]-1H-indole-2-carboxylic acid (100 mg), piperidine (42 μL), 1H-1,2,3-benzotriazol-1-ol (75 mg) and N,N-dimethylformamide (4 mL) was added N-[3-(dimethylamino)propyl]-N'-ethylcarbodiimide hydrochloride (94 mg) at 4° C., and the mixture was stirred at room temperature for 2 days. The reaction mixture was diluted with ethyl acetate, washed with aqueous sodium hydrogencarbonate solution, water and saturated brine, dried over anhydrous magnesium sulfate, and concentrated under reduced pressure. The obtained residue was subjected to silica gel column chromatography (ethyl acetate:hexane=1:9-6:4) and the obtained oil was recrystallized from diethyl ether to give the title compound (115 mg, yield 93%) as colorless prism crystals. melting point 131-132° C.

Example 43

7-{[(4-Methylphenyl)sulfonyl]amino}-N-phenyl-1H-indole-2-carboxamide

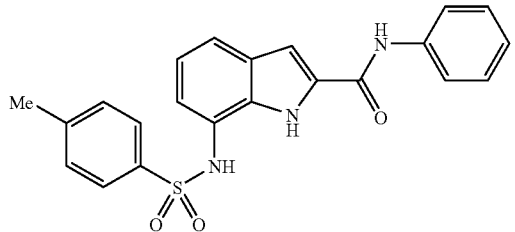 [SMILES: Cc1ccc(S(=O)(=O)Nc2cccc3cc(C(=O)Nc4ccccc4)[nH]c23)cc1]

A mixture of 7-{[(4-methylphenyl)sulfonyl]amino}-1H-indole-2-carboxylic acid (110 mg), aniline (38 μL), ethyldiisopropylamine (0.29 mL), O-(7-azabenzotriazol-1-yl)-N,N,N',N'-tetramethyluronium hexafluorophosphate (180 mg) and N,N-dimethylformamide (4 mL) was stirred at 60° C. for 7 hr. The reaction mixture was diluted with ethyl acetate, washed with aqueous sodium hydrogencarbonate solution, water and saturated brine, dried over anhydrous magnesium sulfate, and concentrated under reduced pressure. The obtained residue was subjected to silica gel column chromatography (ethyl acetate:hexane=1:1), and the obtained crystals were washed with ethyl acetate-hexane to give the title compound (75 mg, yield 55%) as colorless crystals. melting point 247-248° C.

Example 44

N-[2-(Pyrrolidin-1-ylcarbonyl)-1H-indol-7-yl]
thiophene-2-sulfonamide

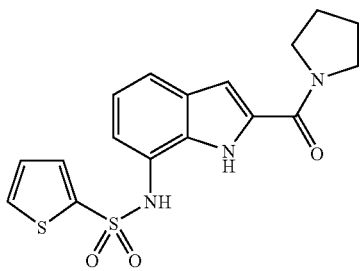 [SMILES: O=C(c1cc2cccc(NS(=O)(=O)c3cccs3)c2[nH]1)N1CCCC1]

To a mixture of 7-[(2-thienylsulfonyl)amino]-1H-indole-2-carboxylic acid (200 mg), pyrrolidine (65 μL), 1H-1,2,3-benzotriazol-1-ol (150 mg) and N,N-dimethylformamide (8 mL) was added N-[3-(dimethylamino)propyl]-N'-ethylcarbodiimide hydrochloride (190 mg) at 4° C., and the mixture was stirred at room temperature for 18 hr. The reaction mixture was diluted with ethyl acetate, washed with aqueous citric acid solution, aqueous sodium hydrogencarbonate solution and saturated brine, dried over anhydrous magnesium sulfate, and concentrated under reduced pressure. The obtained crystals were washed with ethyl acetate-hexane to give the title compound (210 mg, yield 90%) as pale-yellow needle crystals. melting point 248-249° C.

Example 45

N-(1,3-Thiazol-2-yl)-7-[(2-thienylsulfonyl)amino]-1H-indole-2-carboxamide

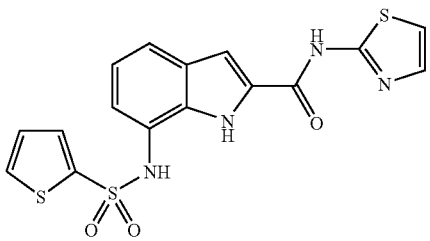 [SMILES: O=C(Nc1nccs1)c1cc2cccc(NS(=O)(=O)c3cccs3)c2[nH]1]

A mixture of 7-[(2-thienylsulfonyl)amino]-1H-indole-2-carboxylic acid (200 mg), 2-aminothiazole (75 mg), ethyldiisopropylamine (0.16 mL), O-(7-azabenzotriazol-1-yl)-N,N,N',N'-tetramethyluronium hexafluorophosphate (354 mg) and N,N-dimethylformamide (8 mL) was stirred at 60° C. for 18 hr. The reaction mixture was diluted with ethyl acetate, washed with aqueous citric acid solution, aqueous sodium hydrogencarbonate solution and saturated brine, dried over anhydrous magnesium sulfate, and concentrated under reduced pressure. The obtained residue was subjected to silica gel column chromatography (ethyl acetate), and the obtained crystals were washed with ethyl acetate-hexane to

Example 46

N-Methoxy-N-methyl-7-[(2-thienylsulfonyl)amino]-1H-indole-2-carboxamide

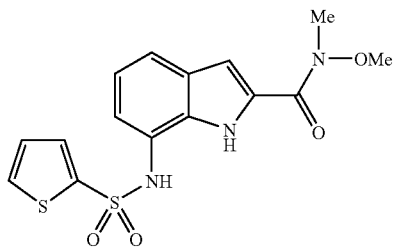 [SMILES: CON(C)C(=O)c1cc2cccc(NS(=O)(=O)c3cccs3)c2[nH]1]

To a mixture of 7-[(2-thienylsulfonyl)amino]-1H-indole-2-carboxylic acid (420 mg), N,O-dimethylhydroxylamine hydrochloride (150 mg), triethylamine (0.24 mL), 1H-1,2,3-benzotriazol-1-ol (300 mg) and N,N-dimethylformamide (10 mL) was added N-[3-(dimethylamino)propyl]-N'-ethylcarbodiimide hydrochloride (380 mg) at 4° C., and the mixture was stirred at room temperature for 18 hr. The reaction mixture was diluted with ethyl acetate, washed with aqueous citric acid solution, aqueous sodium hydrogencarbonate solution and saturated brine, dried over anhydrous magnesium sulfate, and concentrated under reduced pressure. The obtained residue was subjected to silica gel column chromatography (ethyl acetate:hexane=5:95-1:1), and the obtained crystals were recrystallized from ethyl acetate-diethyl ether to give the title compound (395 mg, yield 83%) as pale-yellow needle crystals. melting point 180-181° C.

Example 47

N,N-Dibenzyl-7-[(2-thienylsulfonyl)amino]-1H-indole-2-carboxamide

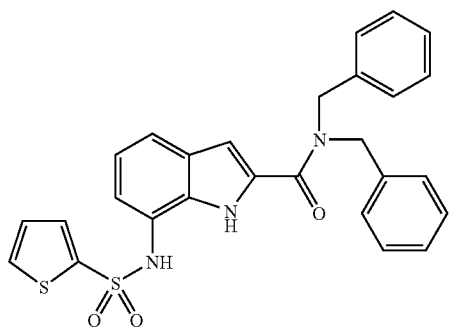 [SMILES: O=C(c1cc2cccc(NS(=O)(=O)c3cccs3)c2[nH]1)N(Cc1ccccc1)Cc1ccccc1]

To a mixture of 7-[(2-thienylsulfonyl)amino]-1H-indole-2-carboxylic acid (44 mg), dibenzylamine (32 mg), 1H-1,2,3-benzotriazol-1-ol (31 mg) and N,N-dimethylformamide (8 mL) was added N-[3-(dimethylamino)propyl]-N'-ethylcarbodiimide hydrochloride (39 mg) at 4° C., and the mixture was stirred at room temperature for 18 hr. The reaction mixture was diluted with ethyl acetate, washed with aqueous citric acid solution, aqueous sodium hydrogencarbonate solution and saturated brine, dried over anhydrous magnesium sulfate, and concentrated under reduced pressure. The obtained crystals were washed with diethyl ether to give the title compound (53 mg, yield 78%) as pale-brown crystals. melting point 198-199° C.

Example 48

N-(2-Acetyl-1H-indol-7-yl)thiophene-2-sulfonamide

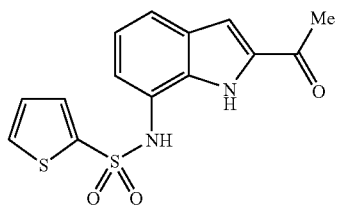 [SMILES: CC(=O)c1cc2cccc(NS(=O)(=O)c3cccs3)c2[nH]1]

A solution of N-methoxy-N-methyl-7-[(2-thienylsulfonyl)amino]-1H-indole-2-carboxamide (160 mg) in anhydrous tetrahydrofuran (10 mL) was cooled to −70° C. under nitrogen atmosphere. A solution (1.8 mL) of 1.2M-methyllithium in diethyl ether was added dropwise. The temperature of the solution was gradually raised from −70° C. to 0° C., and the mixture was stirred for 4 hr. The reaction mixture was poured into aqueous citric acid solution, and the mixture was extracted with ethyl acetate, washed with saturated brine, dried over anhydrous magnesium sulfate, and concentrated under reduced pressure. The obtained residue was subjected to silica gel column chromatography (ethyl acetate:hexane=1:10-3:7), and the obtained crystals were washed with ethyl acetate-hexane to give the title compound (22 mg, yield 16%) as colorless crystals. melting point 241-243° C.

Example 49

Ethyl 7-[(methylsulfonyl)amino]-1H-indole-2-carboxylate

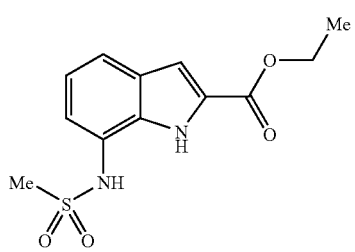 [SMILES: CCOC(=O)c1cc2cccc(NS(C)(=O)=O)c2[nH]1]

To a mixture of ethyl 7-amino-1H-indole-2-carboxylate (0.28 g) and pyridine (8 mL) was added methylsulfonyl chloride (0.13 mL) at 4° C., and the mixture was stirred at room temperature for 2 days. The reaction mixture was concentrated, diluted with ethyl acetate, washed with aqueous citric acid solution, water and saturated brine, dried over anhydrous magnesium sulfate, and concentrated under reduced pressure. The obtained crystals were washed with ethyl acetate-hexane to give the title compound (240 mg, yield 62%) as pale-yellow crystals. melting point 157-158° C.

Example 50

Ethyl 7-({[2-(methoxycarbonyl)-3-thienyl]sulfonyl}amino)-1H-indole-2-carboxylate

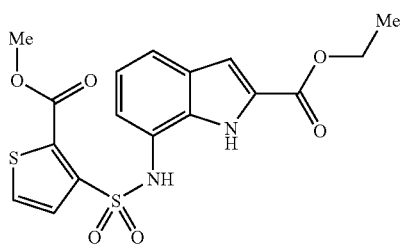 [SMILES: CCOC(=O)c1cc2cccc(NS(=O)(=O)c3ccsc3C(=O)OC)c2[nH]1]

To a mixture of ethyl 7-amino-1H-indole-2-carboxylate (0.30 g) and pyridine (5 mL) was added 2-methoxycarbonyl-3-thiophenesulfonyl chloride (0.42 g) at 4° C., and the mixture was stirred at room temperature for 2 days. The reaction mixture was concentrated, diluted with ethyl acetate, washed with aqueous citric acid solution, water and saturated brine, dried over anhydrous magnesium sulfate, and concentrated under reduced pressure. The obtained residue was subjected to silica gel column chromatography (ethyl acetate:hexane=1:4-ethyl acetate.), and the obtained crystals were washed with ethyl acetate-hexane to give the title compound (550 mg, yield 92%) as pale-yellow crystals. melting point 173-174° C.

Example 51

7-{[(2-Carboxy-3-thienyl)sulfonyl]amino}-1H-indole-2-carboxylic acid

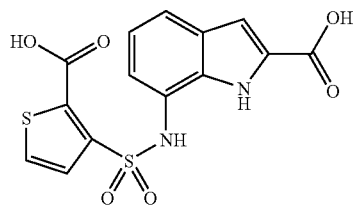 [SMILES: O=C(O)c1cc2cccc(NS(=O)(=O)c3ccsc3C(=O)O)c2[nH]1]

To a mixed solution of ethyl 7-({[2-(methoxycarbonyl)-3-thienyl]sulfonyl}amino)-1H-indole-2-carboxylate (0.35 g) in tetrahydrofuran (10 mL)-methanol (10 mL) was added aqueous solution (5 mL) of 85% potassium hydroxide (350 mg), and the mixture was stirred at room temperature for 18 hr. Aqueous citric acid solution was added to the reaction mixture, and the mixture was extracted with ethyl acetate, washed with saturated brine, dried over anhydrous magnesium sulfate, and concentrated under reduced pressure. The obtained crystals were washed with ethyl acetate-hexane to give the title compound (193 mg, yield 62%) as pale-yellow crystals. melting point 272-275° C. (decomposition).

Example 52

N-(6-Methyl-1-oxo-2,3,4,9-tetrahydro-1H-β-carbolin-8-yl)thiophene-2-sulfonamide

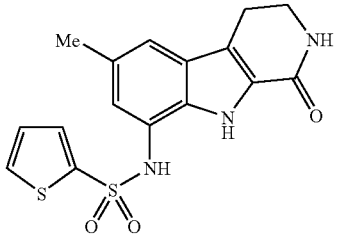 [SMILES: Cc1cc(NS(=O)(=O)c2cccs2)c2[nH]c3c(c2c1)CCNC3=O]

A mixture of 6-methyl-8-nitro-2,3,4,9-tetrahydro-1H-β-carbolin-1-one (75 mg) and 10% palladium-carbon (50% containing water, 40 mg) in tetrahydrofuran (15 mL)-methanol (15 mL) was stirred at room temperature for 4 hr under a hydrogen atmosphere. The catalyst was filtered off, and the filtrate was concentrated under reduced pressure. The obtained residue was dissolved in pyridine (6 mL). 2-Thiophenesulfonyl chloride (70 mg) was added, and the mixture was stirred at room temperature for 18 hr. The reaction mixture was diluted with ethyl acetate, washed with water, and the solvent was concentrated under reduced pressure. The obtained crystals were recrystallized from tetrahydrofuran-ethyl acetate to give the title compound (79 mg, yield 72%) as pale-yellow crystals. melting point>300° C. (decomposition).

Example 53

Ethyl 4,5-dimethyl-7-[(2-thienylsulfonyl)amino]-1H-indole-2-carboxylate

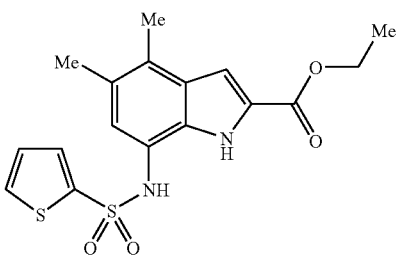 [SMILES: CCOC(=O)c1cc2c(C)c(C)cc(NS(=O)(=O)c3cccs3)c2[nH]1]

A mixture of ethyl 4,5-dimethyl-7-nitro-1H-indole-2-carboxylate (0.94 g), 10% palladium-carbon (50% containing water, 0.40 g), tetrahydrofuran (40 mL) and ethanol (40 mL) was stirred at room temperature for 3 hr under a hydrogen atmosphere. The catalyst was filtered off, and the filtrate was concentrated under reduced pressure. The obtained residue was dissolved in pyridine (12 mL). 2-Thiophenesulfonyl chloride (0.85 g) was added, and the mixture was stirred at room temperature for 15 hr. The reaction mixture was concentrated under reduced pressure, and the residue was diluted with ethyl acetate, washed with aqueous citric acid solution and brine, dried over anhydrous magnesium sulfate, and concentrated under reduced pressure. The obtained residue was

Example 54

4,5-Dimethyl-7-[(2-thienylsulfonyl)amino]-1H-indole-2-carboxylic acid

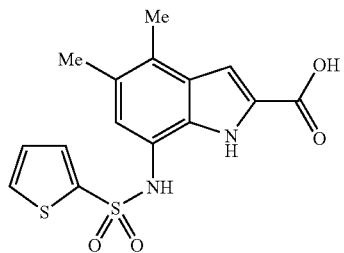 [SMILES: Cc1cc(NS(=O)(=O)c2cccs2)c2[nH]c(C(=O)O)cc2c1C]

To a mixed solution of ethyl 4,5-dimethyl-7-[(2-thienylsulfonyl)amino]-1H-indole-2-carboxylate (1.69 g) in tetrahydrofuran (30 mL)-methanol (20 mL) was added aqueous solution (10 mL) of 85% potassium hydroxide (0.90 g), and the mixture was stirred at room temperature for 15 hr. Aqueous citric acid solution was added to the reaction mixture, and the mixture was extracted with ethyl acetate, washed with saturated brine, dried over anhydrous magnesium sulfate, and concentrated under reduced pressure. The obtained crystals were washed with ethyl acetate-hexane to give the title compound (1.47 g, yield 94%) as colorless crystals. melting point>285° C. (decomposition).

Example 55

4,5-Dimethyl-7-[(2-thienylsulfonyl)amino]-N-[2-(tritylthio)ethyl]-1H-indole-2-carboxamide

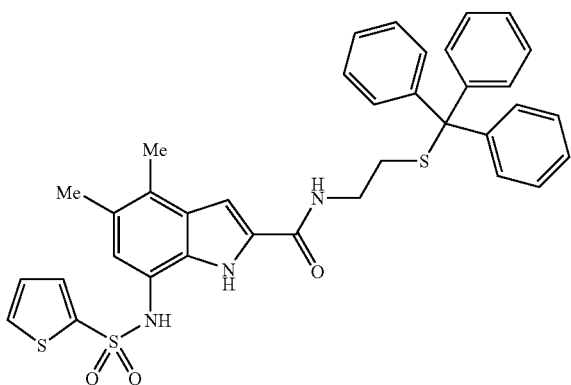 [SMILES: Cc1cc(NS(=O)(=O)c2cccs2)c2[nH]c(C(=O)NCCSC(c3ccccc3)(c3ccccc3)c3ccccc3)cc2c1C]

To a mixture of 2-(tritylthio)ethylamine hydrochloride (0.62 g), triethylamine (0.23 mL) and N,N-dimethylformamide (20 mL) were added 4,5-dimethyl-7-[(2-thienylsulfonyl)amino]-1H-indole-2-carboxylic acid (0.47 g), 1H-1,2,3-benzotriazol-1-ol (0.29 g) and N-[3-(dimethylamino)propyl]-N'-ethylcarbodiimide hydrochloride (0.36 g) under ice-cooling, and the mixture was stirred at room temperature for 2 days. The reaction mixture was diluted with ethyl acetate, washed with aqueous citric acid solution, aqueous sodium hydrogencarbonate solution and saturated brine, dried over anhydrous magnesium sulfate, and concentrated under reduced pressure. The obtained oil was crystallized from ethyl acetate-hexane to give the title compound (0.84 g, yield 96%) as pale-yellow crystals. melting point 238-239° C.

Example 56

N-[2-(4,5-Dihydro-1,3-thiazol-2-yl)-4,5-dimethyl-1H-indol-7-yl]thiophene-2-sulfonamide

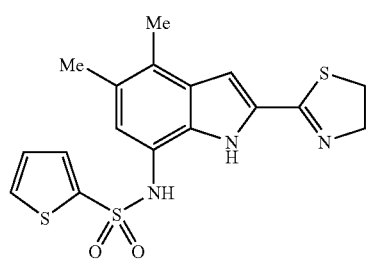 [SMILES: Cc1cc(NS(=O)(=O)c2cccs2)c2[nH]c(C3=NCCS3)cc2c1C]

A mixture of triphenylphosphine oxide (1.1 g), trifluoromethanesulfonic anhydride (0.31 mL) and dichloromethane (20 mL) was stirred for 10 min under ice-cooling. 4,5-Dimethyl-7-[(2-thienylsulfonyl)amino]-N-[2-(tritylthio)ethyl]-1H-indole-2-carboxamide (0.40 g) was added, and the mixture was stirred for 3 hr under ice-cooling. The reaction mixture was poured into aqueous sodium hydrogencarbonate solution and extracted with dichloromethane. The aqueous layer was extracted with dichloromethane, and the combined dichloromethane layer was dried over anhydrous magnesium sulfate, and concentrated under reduced pressure. The obtained residue was subjected to silica gel column chromatography (ethyl acetate:hexane=3:7-5:5), and the obtained crystals were recrystallized from ethyl acetate-hexane to give the title compound (201 mg, yield 84%) as colorless prism crystals. melting point 201-202° C.

Example 57

Ethyl 4-methyl-7-[(2-thienylsulfonyl)amino]-1H-indole-2-carboxylate

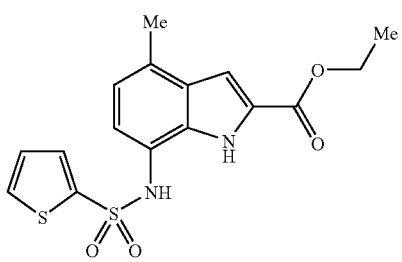 [SMILES: CCOC(=O)c1cc2c(C)ccc(NS(=O)(=O)c3cccs3)c2[nH]1]

To a mixed solution of ethyl 7-amino-4-methyl-1H-indole-2-carboxylate (0.71 g) and pyridine (20 mL) was added 2-thiophenesulfonyl chloride (0.78 g) under ice-cooling, and the mixture was stirred at room temperature for 2 days. The reaction mixture was concentrated under reduced pressure, and the residue was diluted with ethyl acetate, washed with aqueous citric acid solution, aqueous sodium hydrogencarbonate solution and brine, dried over anhydrous magnesium sulfate, and concentrated under reduced pressure. The obtained residue was subjected to silica gel column chromatography (ethyl acetate:hexane=5:95-20:80), and the obtained crystals were recrystallized from ethyl acetate-hexane to give the title compound (957 mg, yield 81%) as colorless needle crystals. melting point 180-181° C.

Example 58

4-Methyl-7-[(2-thienylsulfonyl)amino]-1H-indole-2-carboxylic acid

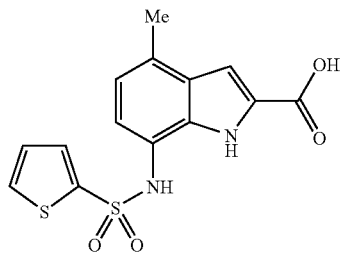 [SMILES: Cc1ccc(NS(=O)(=O)c2cccs2)c2[nH]c(C(=O)O)cc12]

To a mixed solution of ethyl-4-methyl-7-[(2-thienylsulfonyl)amino]-1H-indole-2-carboxylate (0.88 g) in tetrahydrofuran (20 mL)-methanol (10 mL) was added aqueous solution (5 mL) of 85% potassium hydroxide (0.56 g), and the mixture was stirred at room temperature for 15 hr. Aqueous citric acid solution was added to the reaction mixture, and the mixture was extracted with ethyl acetate, washed with saturated brine, dried over anhydrous magnesium sulfate, and concentrated under reduced pressure. The obtained crystals were washed with ethyl acetate-hexane to give the title compound (777 mg, yield 96%) as colorless crystals. melting point>280° C. (decomposition).

Example 59

4-Methyl-7-[(2-thienylsulfonyl)amino]-N-[2-(tritylthio)ethyl]-1H-indole-2-carboxamide

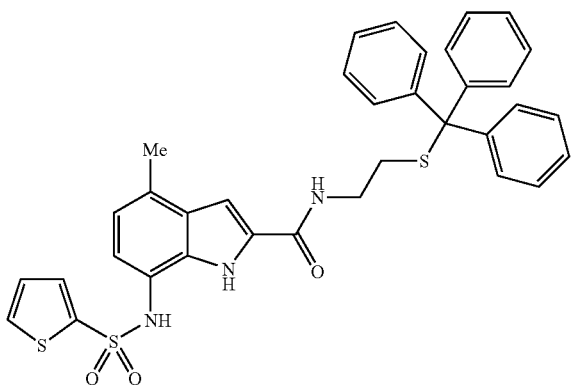 [SMILES: Cc1ccc(NS(=O)(=O)c2cccs2)c2[nH]c(C(=O)NCCSC(c3ccccc3)(c3ccccc3)c3ccccc3)cc12]

To a mixture of 2-(tritylthio)ethylamine hydrochloride (0.93 g), triethylamine (0.37 mL) and N,N-dimethylformamide (15 mL) were added 4-methyl-7-[(2-thienylsulfonyl)amino]-1H-indole-2-carboxylic acid (0.73 g), 1H-1,2,3-benzotriazol-1-ol (0.47 g) and N-[3-(dimethylamino)propyl]-N'-ethylcarbodiimide hydrochloride (0.59 g) under ice-cooling, and the mixture was stirred at room temperature for 15 hr. The reaction mixture was diluted with ethyl acetate, washed with aqueous citric acid solution, aqueous sodium hydrogencarbonate solution and saturated brine, dried over anhydrous magnesium sulfate, and concentrated under reduced pressure. The obtained crystals were washed with ethyl acetate-hexane to give the title compound (1.31 g, yield 95%) as pale-yellow crystals. melting point 241-242° C.

Example 60

N-[2-(4,5-Dihydro-1,3-thiazol-2-yl)-4-methyl-1H-indol-7-yl]thiophene-2-sulfonamide

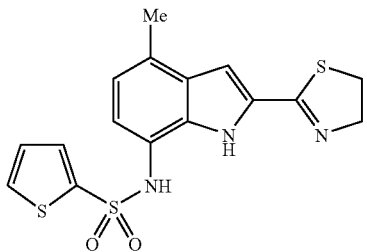 [SMILES: Cc1ccc(NS(=O)(=O)c2cccs2)c2[nH]c(C3=NCCS3)cc12]

A mixture of triphenylphosphine oxide (2.1 g), trifluoromethanesulfonic anhydride (0.63 mL) and dichloromethane (35 mL) was stirred for 30 min under ice-cooling. 4-Methyl-7-[(2-thienylsulfonyl)amino]-N-[2-(tritylthio)ethyl]-1H-indole-2-carboxamide (0.80 g) was added, and the mixture was stirred for 90 min under ice-cooling. The reaction mixture was poured into aqueous sodium hydrogencarbonate solution and extracted with dichloromethane. The aqueous layer was extracted with dichloromethane, and the combined dichloromethane layer was dried over anhydrous magnesium sulfate, and concentrated under reduced pressure. The obtained residue was subjected to silica gel column chromatography (ethyl acetate:hexane=3:7-5:5), and the obtained crystals were recrystallized from ethyl acetate-hexane to give the title compound (431 mg, yield 91%) as colorless prism crystals. melting point 198-199° C.

Example 61

Ethyl 5-methyl-7-[(2-thienylsulfonyl)amino]-1H-indole-2-carboxylate

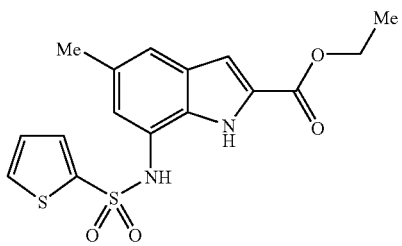 [SMILES: CCOC(=O)c1cc2cc(C)cc(NS(=O)(=O)c3cccs3)c2[nH]1]

To a mixed solution of ethyl 7-amino-5-methyl-1H-indole-2-carboxylate (0.60 g) and pyridine (10 mL) was added 2-thiophenesulfonyl chloride (0.66 g) under ice-cooling, and the mixture was stirred at room temperature for 15 hr. The reaction mixture was concentrated under reduced pressure, and the residue was diluted with ethyl acetate, washed with aqueous citric acid solution, aqueous sodium hydrogencarbonate solution and brine, dried over anhydrous magnesium sulfate, and concentrated under reduced pressure. The obtained residue was subjected to silica gel column chromatography (ethyl acetate:hexane=3:7-5:5), and the obtained crystals were recrystallized from ethyl acetate-hexane to give the title compound (910 mg, yield 91%) as colorless needle crystals. melting point 168-169° C.

Example 62

5-Methyl-7-[(2-thienylsulfonyl)amino]-1H-indole-2-carboxylic acid

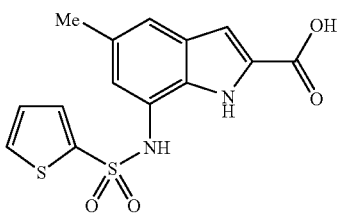 [SMILES: Cc1cc(NS(=O)(=O)c2cccs2)c2[nH]c(C(=O)O)cc2c1]

To a mixed solution of ethyl 5-methyl-7-[(2-thienylsulfonyl)amino]-1H-indole-2-carboxylate (0.80 g) in tetrahydrofuran (15 mL)-methanol (15 mL) was added aqueous solution (5 mL) of 85% potassium hydroxide (0.65 g), and the mixture was stirred at room temperature for 15 hr. Aqueous citric acid solution was added to the reaction mixture, and the mixture was extracted with ethyl acetate, washed with saturated brine, dried over anhydrous magnesium sulfate, and concentrated under reduced pressure. The obtained crystals were washed with ethyl acetate-hexane to give the title compound (735 mg, yield 99%) as pale-yellow crystals. melting point>280° C. (decomposition).

Example 63

5-Methyl-7-[(2-thienylsulfonyl)amino]-N-[2-(tritylthio)ethyl]-1H-indole-2-carboxamide

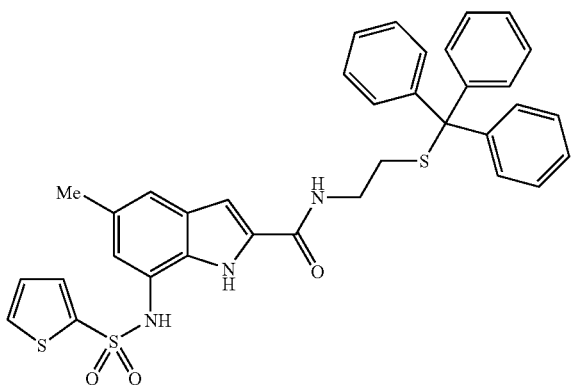 [SMILES: Cc1cc(NS(=O)(=O)c2cccs2)c2[nH]c(C(=O)NCCSC(c3ccccc3)(c3ccccc3)c3ccccc3)cc2c1]

To a mixture of 2-(tritylthio)ethylamine hydrochloride (0.77 g), triethylamine (0.31 mL) and N,N-dimethylformamide (20 mL) were added 5-methyl-7-[(2-thienylsulfonyl)amino]-1H-indole-2-carboxylic acid (0.60 g), 1H-1,2,3-benzotriazol-1-ol (0.36 g) and N-[3-(dimethylamino)propyl]-N'-ethylcarbodiimide hydrochloride (0.45 g) under ice-cooling, and the mixture was stirred at room temperature for 15 hr. The reaction mixture was diluted with ethyl acetate, washed with aqueous citric acid solution, aqueous sodium hydrogencarbonate solution and saturated brine, dried over anhydrous magnesium sulfate, and concentrated under reduced pressure. The obtained oil was crystallized from ethyl acetate-hexane to give the title compound (1.07 g, yield 95%) as pale-yellow crystals. melting point 214-215° C.

Example 64

N-[2-(4,5-Dihydro-1,3-thiazol-2-yl)-5-methyl-1H-indol-7-yl]thiophene-2-sulfonamide

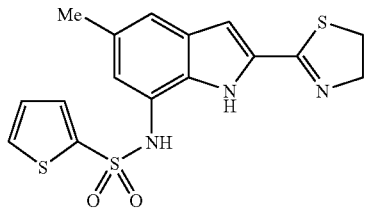 [SMILES: Cc1cc(NS(=O)(=O)c2cccs2)c2[nH]c(C3=NCCS3)cc2c1]

A mixture of triphenylphosphine oxide (2.6 g), trifluoromethanesulfonic anhydride (0.80 mL) and dichloromethane (25 mL) was stirred for 15 min under ice-cooling. 5-Methyl-7-[(2-thienylsulfonyl)amino]-N-[2-(tritylthio)ethyl]-1H-indole-2-carboxamide (1.0 g) was added, and the mixture was stirred for 2 hr under ice-cooling. The reaction mixture was poured into aqueous sodium hydrogencarbonate solution and extracted with dichloromethane. The aqueous layer was extracted with dichloromethane, and the combined dichloromethane layer was dried over anhydrous magnesium sulfate, and concentrated under reduced pressure. The obtained residue was subjected to silica gel column chromatography (ethyl acetate:hexane=3:7-5:5), and the obtained crystals were recrystallized from ethyl acetate-hexane to give the title compound (528 mg, yield 89%) as colorless prism crystals. melting point 202-203° C.

Example 65

Ethyl 4-(propylthio)-7-[(2-thienylsulfonyl)amino]-1H-indole-2-carboxylate

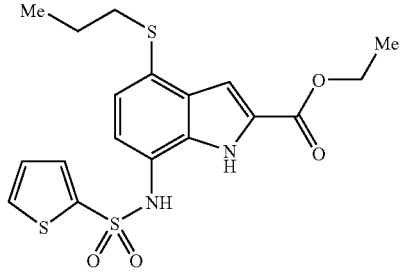 [SMILES: CCCSc1ccc(NS(=O)(=O)c2cccs2)c2[nH]c(C(=O)OCC)cc12]

To a mixed solution of ethyl 7-amino-4-(propylthio)-1H-indole-2-carboxylate (0.90 g) and pyridine (10 mL) was added 2-thiophenesulfonyl chloride (0.72 g) under ice-cooling, and the mixture was stirred at room temperature for 16 hr. The reaction mixture was concentrated under reduced pressure, and the residue was diluted with ethyl acetate, washed with aqueous citric acid solution, aqueous sodium hydrogencarbonate solution and brine, dried over anhydrous magnesium sulfate, and concentrated under reduced pressure. The obtained residue was subjected to silica gel column chromatography (ethyl acetate:hexane=1:9-1:3), and the obtained crystals were recrystallized from ethyl acetate-hexane to give the title compound (0.64 g, yield 47%) as colorless needle crystals. melting point 150-151° C.

Example 66

Ethyl 4-(propylsulfonyl)-7-[(2-thienylsulfonyl)amino]-1H-indole-2-carboxylate

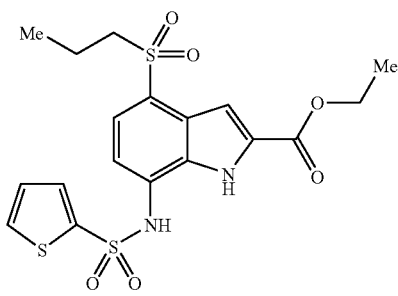 [SMILES: CCCS(=O)(=O)c1ccc(NS(=O)(=O)c2cccs2)c2[nH]c(C(=O)OCC)cc12]

To a solution of ethyl 4-(propylthio)-7-[(2-thienylsulfonyl)amino]-1H-indole-2-carboxylate (0.88 g) in ethyl acetate (30 mL) was added 70% m-chloroperbenzoic acid (0.91 g) under ice-cooling, and the mixture was stirred for 3 hr while the temperature was raising from under ice-cooling to room temperature. The reaction mixture was diluted with ethyl acetate, washed with aqueous sodium thiosulfate solution, aqueous sodium hydrogencarbonate solution and saturated brine, dried over anhydrous magnesium sulfate, and concentrated under reduced pressure. The obtained oil was crystallized from ethyl acetate-hexane to give the title compound (618 mg, yield 89%) as pale-yellow prism crystals. melting point 201-202° C.

Example 67

4-(Propylsulfonyl)-7-[(2-thienylsulfonyl)amino]-1H-indole-2-carboxylic acid

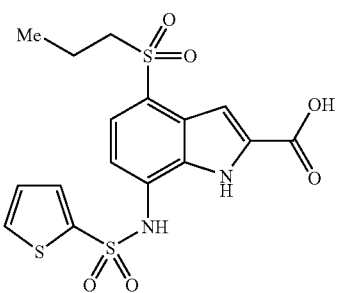 [SMILES: CCCS(=O)(=O)c1ccc(NS(=O)(=O)c2cccs2)c2[nH]c(C(=O)O)cc12]

To a mixed solution of ethyl 4-(propylsulfonyl)-7-[(2-thienylsulfonyl)amino]-1H-indole-2-carboxylate (0.56 g) in tetrahydrofuran (15 mL)-methanol (15 mL) was added aqueous solution (5 mL) of 85% potassium hydroxide (0.35 g), and the mixture was stirred at room temperature for 15 hr. Aqueous citric acid solution was added to the reaction mixture, and the mixture was extracted with ethyl acetate, washed with saturated brine, dried over anhydrous magnesium sulfate, and concentrated under reduced pressure. The obtained oil was crystallized from ethyl acetate-hexane to give the title compound (486 mg, yield 93%) as pale-yellow prism crystals. melting point 247-248° C.

Example 68

4-(Propylsulfonyl)-7-[(2-thienylsulfonyl)amino]-N-[2-(tritylthio)ethyl]-1H-indole-2-carboxamide

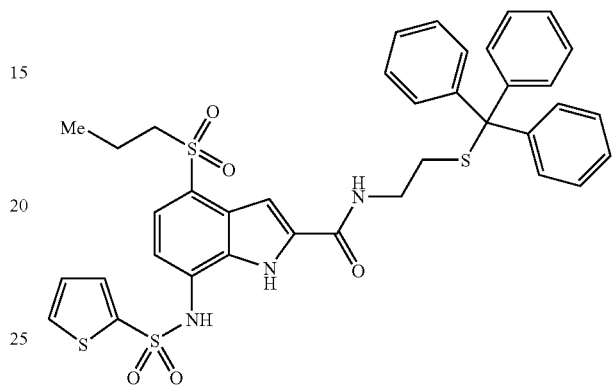

To a mixture of 2-(tritylthio)ethylamine hydrochloride (0.42 g), triethylamine (0.17 mL) and N,N-dimethylformamide (15 mL) were added 4-(propylsulfonyl)-7-[(2-thienylsulfonyl)amino]-1H-indole-2-carboxylic acid (0.42 g), 1H-1,2,3-benzotriazol-1-ol (0.20 g) and N-[3-(dimethylamino)propyl]-N'-ethylcarbodiimide hydrochloride (0.25 g) under ice-cooling, and the mixture was stirred at room temperature for 18 hr. The reaction mixture was diluted with ethyl acetate, washed with aqueous citric acid solution, aqueous sodium hydrogencarbonate solution and saturated brine, dried over anhydrous magnesium sulfate, and concentrated under reduced pressure. The obtained oil was crystallized from ethyl acetate-hexane to give the title compound (690 mg, yield 97%) as pale-yellow prism crystals. melting point 200-201° C.

Example 69

N-[2-(4,5-Dihydro-1,3-thiazol-2-yl)-4-(propylsulfonyl)-1H-indol-7-yl]thiophene-2-sulfonamide

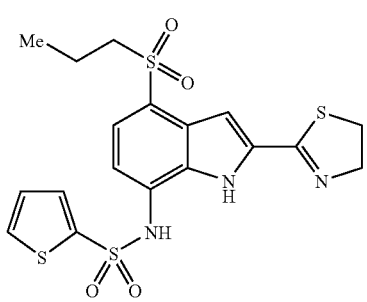 [SMILES: CCCS(=O)(=O)c1ccc(NS(=O)(=O)c2cccs2)c2[nH]c(C3=NCCS3)cc12]

A mixture of triphenylphosphine oxide (1.8 g), trifluoromethanesulfonic anhydride (0.55 mL) and dichloromethane (25 mL) was stirred for 15 min under ice-cooling. 4-(Propylsulfonyl)-7-[(2-thienylsulfonyl)amino]-N-[2-(tritylthio)ethyl]-1H-indole-2-carboxamide (0.68 g) was added, and the mixture was stirred for 3 hr under ice-cooling. The reaction mixture was poured into aqueous sodium hydrogencarbonate solution and extracted with dichloromethane. The aqueous layer was extracted with dichloromethane, and the combined dichloromethane layer was dried over anhydrous magnesium sulfate, and concentrated under reduced pressure. The obtained residue was subjected to silica gel column chromatography (ethyl acetate:hexane=3:7-5:5), and the obtained crystals were recrystallized from ethyl acetate-hexane to give the title compound (359 mg, yield 82%) as colorless prism crystals. melting point 101-102° C.

Example 70

Ethyl 6-methyl-7-[(2-thienylsulfonyl)amino]-1H-indole-2-carboxylate

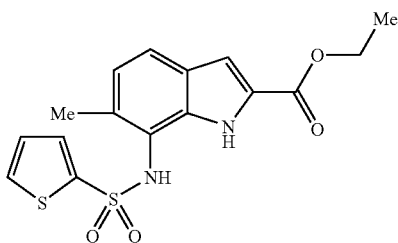 [SMILES: CCOC(=O)c1cc2ccc(C)c(NS(=O)(=O)c3cccs3)c2[nH]1]

To a mixed solution of ethyl 7-amino-6-methyl-1H-indole-2-carboxylate (0.50 g) and pyridine (10 mL) was added 2-thiophenesulfonyl chloride (0.54 g) under ice-cooling, and the mixture was stirred at room temperature for 15 hr. The reaction mixture was concentrated under reduced pressure, and the residue was diluted with ethyl acetate, washed with aqueous citric acid solution, aqueous sodium hydrogencarbonate solution and brine, dried over anhydrous magnesium sulfate, and concentrated under reduced pressure. The obtained residue was subjected to silica gel column chromatography (ethyl acetate:hexane=1:9-1:3), and the obtained crystals were recrystallized from ethyl acetate-hexane to give the title compound (677 mg, yield 81%) as colorless needle crystals. melting point 184-185° C.

Example 71

6-Methyl-7-[(2-thienylsulfonyl)amino]-1H-indole-2-carboxylic acid

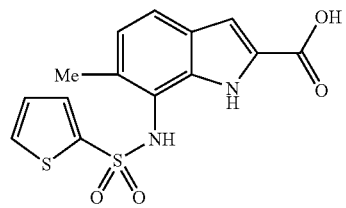 [SMILES: Cc1ccc2cc(C(=O)O)[nH]c2c1NS(=O)(=O)c1cccs1]

To a mixed solution of ethyl 6-methyl-7-[(2-thienylsulfonyl)amino]-1H-indole-2-carboxylate (0.48 g) in tetrahydrofuran (10 mL)-methanol (10 mL) was added aqueous solution (5 mL) of 85% potassium hydroxide (0.35 g), and the mixture was stirred at room temperature for 15 hr. Aqueous citric acid solution was added to the reaction mixture, and the mixture was extracted with ethyl acetate, washed with saturated brine, dried over anhydrous magnesium sulfate, and concentrated under reduced pressure. The obtained crystals were washed with ethyl acetate-hexane to give the title compound (390 mg, yield 88%) as pale-yellow prism crystals. melting point>280° C. (decomposition).

Example 72

6-Methyl-7-[(2-thienylsulfonyl)amino]-N-[2-(tritylthio)ethyl]-1H-indole-2-carboxamide

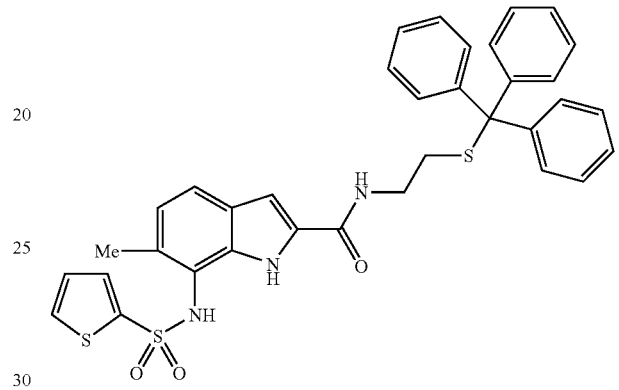

To a mixture of 2-(tritylthio)ethylamine hydrochloride (0.44 g), triethylamine (0.17 mL) and N,N-dimethylformamide (15 mL) were added 6-methyl-7-[(2-thienylsulfonyl)amino]-1H-indole-2-carboxylic acid (0.34 g), 1H-1,2,3-benzotriazol-1-ol (0.21 g) and N-[3-(dimethylamino)propyl]-N'-ethylcarbodiimide hydrochloride (0.26 g) under ice-cooling, and the mixture was stirred at room temperature for 2 days. The reaction mixture was diluted with ethyl acetate, washed with aqueous citric acid solution, aqueous sodium hydrogencarbonate solution and saturated brine, dried over anhydrous magnesium sulfate, and concentrated under reduced pressure. The obtained oil was crystallized from ethyl acetate-hexane to give the title compound (585 mg, yield 91%) as colorless prism crystals. melting point 245-246° C.

Example 73

N-[2-(4,5-Dihydro-1,3-thiazol-2-yl)-6-methyl-1H-indol-7-yl]thiophene-2-sulfonamide

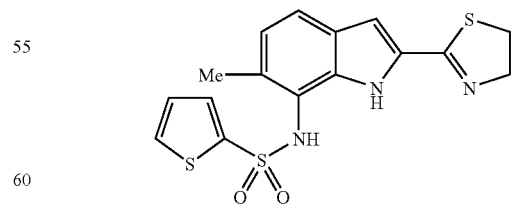

A mixture of triphenylphosphine oxide (1.5 g), trifluoromethanesulfonic anhydride (0.46 mL) and dichloromethane (25 mL) was stirred for 15 min under ice-cooling. 6-Methyl-7-[(2-thienylsulfonyl)amino]-N-[2-(tritylthio) ethyl]-1H-indole-2-carboxamide (0.57 g) was added, and the mixture was stirred for 4 hr under ice-cooling. The reaction mixture was poured into aqueous sodium hydrogencarbonate solution and extracted with dichloromethane. The aqueous layer was extracted with dichloromethane, and the combined dichloromethane layer was dried over anhydrous magnesium sulfate, and concentrated under reduced pressure. The obtained crystals were suspended in ethyl acetate-hexane, and the insoluble material was filtered off. The filtrate was concentrated under reduced pressure. The obtained residue was subjected to silica gel column chromatography (ethyl acetate:hexane=1:9-1:3), and the obtained crystals were recrystallized from ethyl acetate-hexane to give the title compound (251 mg, yield 74%) as colorless prism crystals. melting point 183-184° C.

Example 74

Ethyl 5-methoxy-7-[(2-thienylsulfonyl)amino]-1H-indole-2-carboxylate

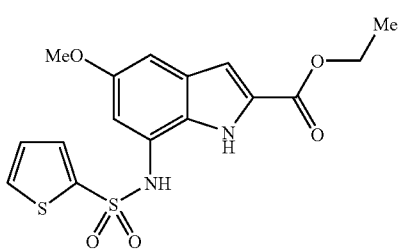 [SMILES: CCOC(=O)c1cc2cc(OC)cc(NS(=O)(=O)c3cccs3)c2[nH]1]

To a mixed solution of ethyl 7-amino-5-methoxy-1H-indole-2-carboxylate (0.40 g) and pyridine (10 mL) was added 2-thiophenesulfonyl chloride (0.38 g) under ice-cooling, and the mixture was stirred at room temperature for 14 hr. The reaction mixture was concentrated under reduced pressure, and the residue was diluted with ethyl acetate, washed with aqueous citric acid solution, aqueous sodium hydrogencarbonate solution and brine, dried over anhydrous magnesium sulfate, and concentrated under reduced pressure. The obtained residue was subjected to silica gel column chromatography (ethyl acetate:hexane=15:85-35:65), and the obtained crystals were recrystallized from ethyl acetate-hexane to give the title compound (370 mg, yield 57%) as colorless needle crystals. melting point 158-159° C.

Example 75

5-Methoxy-7-[(2-thienylsulfonyl)amino]-1H-indole-2-carboxylic acid

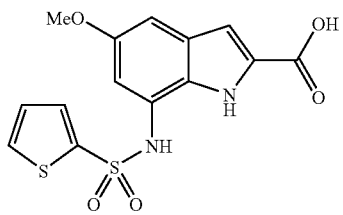 [SMILES: COc1cc(NS(=O)(=O)c2cccs2)c2[nH]c(C(=O)O)cc2c1]

To a mixed solution of ethyl 5-methoxy-7-[(2-thienylsulfonyl)amino]-1H-indole-2-carboxylate (0.34 g) in tetrahydrofuran (10 mL)-methanol (10 mL) was added aqueous solution (5 mL) of 85% potassium hydroxide (0.20 g), and the mixture was stirred at room temperature for 15 hr. Aqueous citric acid solution was added to the reaction mixture, and the mixture was extracted with ethyl acetate, washed with saturated brine, dried over anhydrous magnesium sulfate, and concentrated under reduced pressure. The obtained crystals were washed with ethyl acetate-hexane to give the title compound (300 mg, yield 96%) as pale-yellow crystals. melting point>240° C. (decomposition).

Example 76

5-Methoxy-7-[(2-thienylsulfonyl)amino]-N-[2-(tritylthio)ethyl]-1H-indole-2-carboxamide

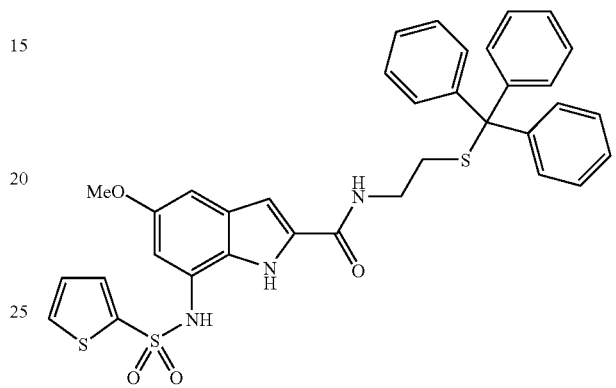

To a mixture of 2-(tritylthio)ethylamine hydrochloride (0.32 g), triethylamine (0.126 mL) and N,N-dimethylformamide (10 mL) were added 5-methoxy-7-[(2-thienylsulfonyl)amino]-1H-indole-2-carboxylic acid (265 mg), 1H-1,2,3-benzotriazol-1-ol (0.15 g) and N-[3-(dimethylamino)propyl]-N'-ethylcarbodiimide hydrochloride (188 mg) under ice-cooling, and the mixture was stirred at room temperature for 15 hr. The reaction mixture was diluted with ethyl acetate, washed with aqueous citric acid solution, aqueous sodium hydrogencarbonate solution and saturated brine, dried over anhydrous magnesium sulfate, and concentrated under reduced pressure. The obtained oil was crystallized from dichloromethane-hexane to give the title compound (465 mg, yield 95%) as pale-yellow crystals. melting point 128-129° C.

Example 77

N-[2-(4,5-Dihydro-1,3-thiazol-2-yl)-5-methoxy-1H-indol-7-yl]thiophene-2-sulfonamide

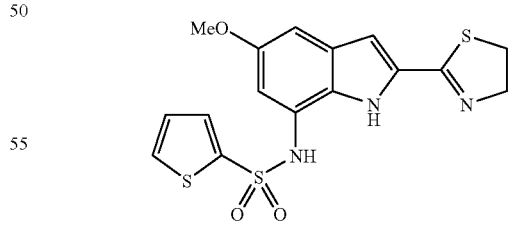

A mixture of triphenylphosphine oxide (1.15 g), trifluoromethanesulfonic anhydride (0.35 mL) and dichloromethane (12 mL) was stirred for 15 min under ice-cooling. 5-Methoxy-7-[(2-thienylsulfonyl)amino]-N-[2-(tritylthio)ethyl]-1H-indole-2-carboxamide (0.45 g) was added, and the mixture was stirred for 2 hr under ice-cooling. The reaction mixture was poured into aqueous sodium hydrogencarbonate solution and extracted with dichloromethane. The aqueous layer was extracted with dichloromethane, and the combined dichloromethane layer was dried over anhydrous magnesium sulfate, and concentrated under reduced pressure. The obtained crystals were suspended in ethyl acetate-hexane, and the insoluble material was filtered off. The filtrate was concentrated under reduced pressure. The obtained residue was subjected to silica gel column chromatography (ethyl acetate:hexane=25:75-40:60), and the obtained oil was crystallized from ethyl acetate-hexane to give the title compound (114 mg, yield 42%) as pale-yellow prism crystals. melting point 188-189° C.

Example 78

Ethyl 7-[(2-thienylcarbonyl)amino]-1H-indole-2-carboxylate

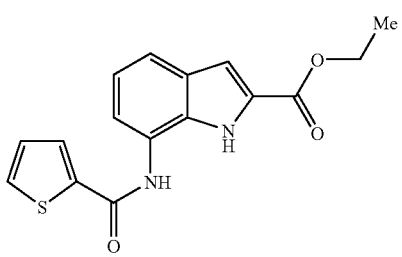 [SMILES: CCOC(=O)c1cc2cccc(NC(=O)c3cccs3)c2[nH]1]

A mixture of ethyl 7-amino-1H-indole-2-carboxylate (0.40 g), thiophene-2-carboxylic acid (0.28 g), ethyldiisopropylamine (0.75 mL), O-(7-azabenzotriazol-1-yl)-N,N,N',N'-tetramethyluronium hexafluorophosphate (0.82 g) and N,N-dimethylformamide (10 mL) was stirred at 60° C. for 18 hr. The reaction mixture was diluted with ethyl acetate, washed with aqueous citric acid solution, aqueous sodium hydrogencarbonate solution and saturated brine, dried over anhydrous magnesium sulfate, and concentrated under reduced pressure. The obtained residue was subjected to silica gel column chromatography (ethyl acetate:hexane=3:97-3:7) to give the title compound (510 mg, yield 83%) as a pale-yellow amorphous solid.

$^1$H-NMR (CDCl$_3$) δ:1.42 (3H, t, J=7.2 Hz), 4.42 (2H, q, J=7.2 Hz), 6.98-7.28 (4H, m), 7.54-7.64 (2H, m), 7.72 (1H, dd, J=4.0, 1.0 Hz), 7.97 (1H, brs), 10.23 (1H, brs).

Example 79

7-[(2-Thienylcarbonyl)amino]-1H-indole-2-carboxylic acid

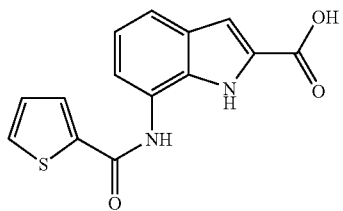 [SMILES: O=C(O)c1cc2cccc(NC(=O)c3cccs3)c2[nH]1]

To a mixed solution of ethyl 7-[(2-thienylcarbonyl)amino]-1H-indole-2-carboxylate (410 mg) in tetrahydrofuran (6 mL)-methanol (6 mL) was added aqueous solution (3 mL) of 85% potassium hydroxide (400 mg), and the mixture was stirred at room temperature for 7 hr. Aqueous citric acid solution was added to the reaction mixture, and the mixture was extracted with ethyl acetate, washed with saturated brine, dried over anhydrous magnesium sulfate, and concentrated under reduced pressure. The obtained crystals were washed with ethyl acetate-hexane to give the title compound (325 mg, yield 87%) as pale-yellow crystals. melting point>268° C. (decomposition).

Example 80

7-[(2-Thienylcarbonyl)amino]-1H-indole-2-carboxamide

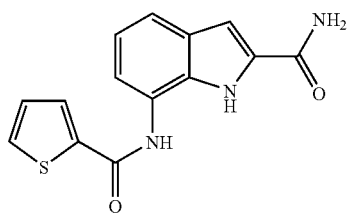 [SMILES: NC(=O)c1cc2cccc(NC(=O)c3cccs3)c2[nH]1]

To a mixture of 7-[(2-thienylcarbonyl)amino]-1H-indole-2-carboxylic acid (100 mg), 1H-1,2,3-benzotriazol-1-ol-ammonia complex (63 mg) and N,N-dimethylformamide (5 mL) was added N-[3-(dimethylamino)propyl]-N'-ethylcarbodiimide hydrochloride (80 mg) at 4° C., and the mixture was stirred at room temperature for 18 hr. The reaction mixture was diluted with ethyl acetate, washed with aqueous sodium hydrogencarbonate solution, water and saturated brine, dried over anhydrous magnesium sulfate, and concentrated under reduced pressure. The obtained crystals were washed with ethyl acetate-hexane to give the title compound (97 mg, yield 98%) as pale-brown crystals. melting point 289-290° C.

Example 81

Ethyl 7-({3,5-bis[(2-fluorobenzyl)oxy]benzoyl}amino)-1H-indole-2-carboxylate

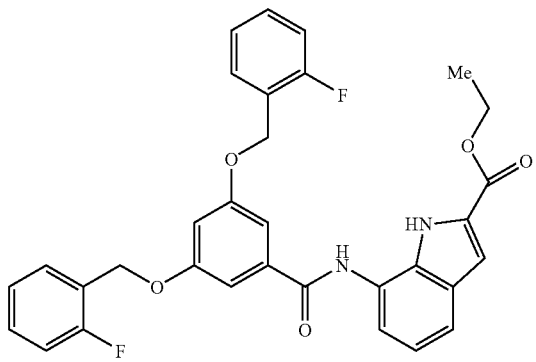 [SMILES: CCOC(=O)c1cc2cccc(NC(=O)c3cc(OCc4ccccc4F)cc(OCc4ccccc4F)c3)c2[nH]1]

A mixture of ethyl 7-amino-1H-indole-2-carboxylate (210 mg), 3,5-bis[(2-fluorobenzyl)oxy]benzoic acid (380 mg), ethyldiisopropylamine (0.47 mL), 0-(7-azabenzotriazol-1-yl)-N,N,N',N'-tetramethyluronium hexafluorophosphate (510 mg) and N,N-dimethylformamide (8 mL) was stirred at 60° C. for 18 hr. The reaction mixture was diluted with ethyl acetate, washed with aqueous citric acid solution, aqueous sodium hydrogencarbonate solution and saturated brine, dried over anhydrous magnesium sulfate, and concentrated under reduced pressure. The obtained crystals were washed with ethyl acetate-hexane and dissolved in ethyl acetate (50 mL). Activated carbon was added, and the mixture was stirred at 60° C. for 30 min. The activated carbon was filtered off, and the filtrate was concentrated under reduced pressure. The obtained crystals were washed with ethyl acetate-hexane to give the title compound (284 mg, yield 50%) as colorless crystals. melting point 157-158° C.

Example 82

7-({3,5-bis[(2-Fluorobenzyl)oxy]benzoyl}amino)-1H-indole-2-carboxylic acid

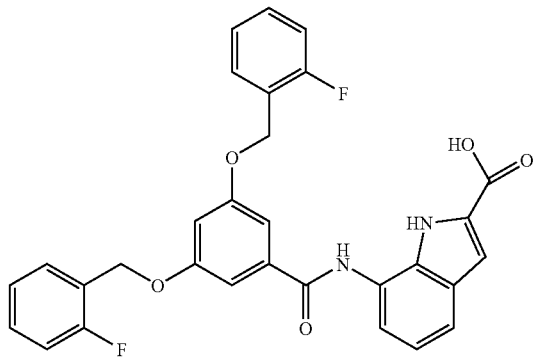 [SMILES: O=C(Nc1cccc2cc(C(=O)O)[nH]c12)c1cc(OCc2ccccc2F)cc(OCc2ccccc2F)c1]

To a mixed solution of ethyl 7-({3,5-bis[(2-fluorobenzyl)oxy]benzoyl}amino)-1H-indole-2-carboxylate (170 mg) in tetrahydrofuran (8 mL)-methanol (8 mL) was added aqueous solution (5 mL) of 85% potassium hydroxide (150 mg), and the mixture was stirred at room temperature for 18 hr. Aqueous citric acid solution was added to the reaction mixture, and the mixture was extracted with ethyl acetate, washed with saturated brine, dried over anhydrous magnesium sulfate, and concentrated under reduced pressure. The obtained crystals were washed with ethyl acetate-hexane to give the title compound (147 mg, yield 91%) as colorless crystals. melting point 271-273° C.

Example 83

Ethyl 7-[methyl(2-thienylsulfonyl)amino]-1H-indole-2-carboxylate

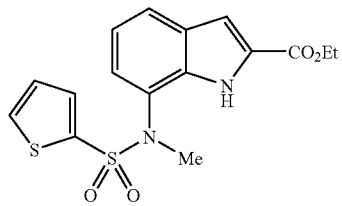 [SMILES: CCOC(=O)c1cc2cccc(N(C)S(=O)(=O)c3cccs3)c2[nH]1]

A mixture of ethyl 1-(methoxymethyl)-7-[methyl(2-thienylsulfonyl)amino]-1H-indole-2-carboxylate (1.06 g), concentrated hydrochloride (1 mL) and ethanol (5 mL) was heated under reflux overnight. Water was added to the reaction mixture, and the obtained crystals were filtrated, washed with water and dried. The obtained crystals were subjected to silica gel column chromatography and the title compound (0.43 g, yield 46%) was obtained as colorless crystals from a fraction eluted with ethyl acetate-hexane (2:1, volume ratio). The crystals were recrystallized from ethyl acetate-hexane. melting point 164-165° C.

Example 84

7-[Methyl (2-thienylsulfonyl)amino]-1H-indole-2-carboxylic acid

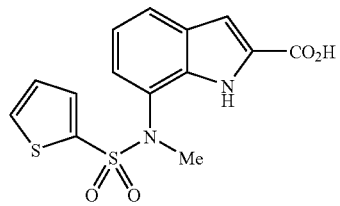 [SMILES: CN(c1cccc2cc(C(=O)O)[nH]c12)S(=O)(=O)c1cccs1]

A mixture of ethyl 7-[methyl(2-thienylsulfonyl)amino]-1H-indole-2-carboxylate (0.40 g), 8N aqueous sodium hydroxide solution (0.40 mL), tetrahydrofuran (5 mL) and methanol (5 mL) was stirred at 60° C. for 1 hr. The reaction mixture was concentrated, and water was added to the residue. The mixture was acidified with 10% aqueous citric acid solution, and the resulting crystals were filtrated, washed with water, and dried to give the title compound (0.35 g, yield 91%) as colorless crystals. melting point>240° C. (decomposition).

Example 85

7-[Methyl(2-thienylsulfonyl)amino]-N-[2-(tritylthio)ethyl]-1H-indole-2-carboxamide

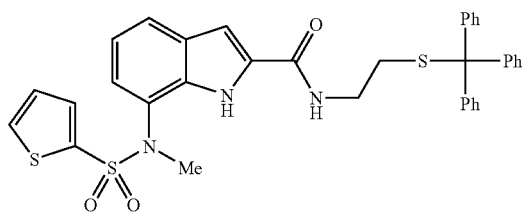 [SMILES: CN(c1cccc2cc(C(=O)NCCSC(c3ccccc3)(c3ccccc3)c3ccccc3)[nH]c12)S(=O)(=O)c1cccs1]

To a mixture of 7-[methyl(2-thienylsulfonyl)amino]-1H-indole-2-carboxylic acid (0.31 g), 2-(tritylthio)ethylamine hydrochloride (0.33 g), 1H-1,2,3-benzotriazol-1-ol (0.15 g), triethylamine (0.15 mL) and N,N-dimethylformamide (8 mL) was added N-[3-(dimethylamino)propyl]-N'-ethylcarbodiimide hydrochloride (0.21 g) at 0° C., and the mixture was stirred at room temperature overnight. Water was added to the reaction mixture, and the obtained crystals were filtrated, washed with water and dried. The obtained crystals were subjected to silica gel column chromatography and the title compound (0.54 g, yield 92%) was obtained as colorless crystals from a fraction eluted with ethyl acetate. melting point>188° C. (decomposition).

Example 86

N-[2-(4,5-Dihydro-1,3-thiazol-2-yl)-1H-indol-7-yl]-N-methylthiophene-2-sulfonamide

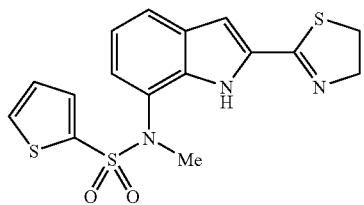 [SMILES: CN(c1cccc2cc(C3=NCCS3)[nH]c12)S(=O)(=O)c1cccs1]

To a solution of triphenylphosphine oxide (1.42 g) in dichloromethane (20 mL) was slowly added trifluoromethanesulfonic anhydride (0.43 mL) at 0° C. The mixture was stirred for 10 min, and 7-[methyl(2-thienylsulfonyl)amino]-N-[2-(tritylthio)ethyl]-1H-indole-2-carboxamide (0.54 g) was added. The reaction mixture was stirred at room temperature for 3 hr and concentrated. Saturated aqueous sodium hydrogen carbonate was added, and the mixture was extracted with ethyl acetate. The ethyl acetate layer was washed with saturated brine, dried (MgSO$_4$) and concentrated. The residue was subjected to silica gel column chromatography and the title compound (0.25 g, yield 78%) was obtained as colorless crystals from a fraction eluted with ethyl acetate-hexane (1:1, volume ratio). melting point 192-193° C.

Example 87

N-Methyl-N-[2-(1,2,4-thiadiazol-5-yl)-1H-indol-7-yl]thiophene-2-sulfonamide

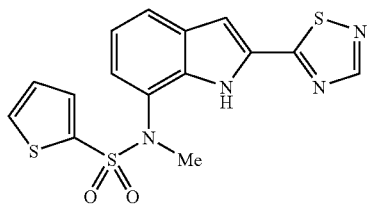 [SMILES: CN(c1cccc2cc(-c3ncns3)[nH]c12)S(=O)(=O)c1cccs1]

A mixture of 7-[(2-thienylsulfonyl)amino]-1H-indole-2-carbothioamide (0.40 g) and N,N-dimethylformamide dimethyl acetal (8 mL) was stirred at 80° C. for 1 hr. The reaction mixture was concentrated, and to a mixture of the obtained residue, pyridine (0.20 mL), tetrahydrofuran (4 mL) and ethanol (5 mL) was added hydroxylamine-O-sulfonic acid (0.15 g). The mixture was stirred at room temperature for 1 hr. Water was added to the reaction mixture, and the mixture was extracted with ethyl acetate. The ethyl acetate layer was washed with saturated brine, dried (MgSO$_4$) and concentrated. The residue was subjected to silica gel column chromatography and the title compound (0.11 g, yield 24%) was obtained as colorless crystals from a fraction eluted with tetrahydrofuran-hexane (2:3, volume ratio). The crystals were recrystallized from ethyl acetate-hexane. melting point>207° C. (decomposition).

Example 88

N-Methyl-N-[2-(1,2,4-oxadiazol-5-yl)-1H-indol-7-yl]thiophene-2-sulfonamide

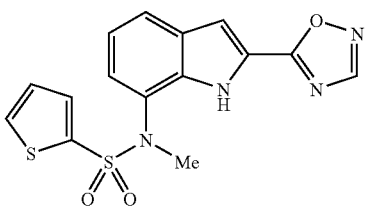

A mixture of 7-[(2-thienylsulfonyl)amino]-1H-indole-2-carboxamide (1.00 g) and N,N-dimethylformamide dimethyl acetal (5 mL) was heated under reflux for 3 hr. The reaction mixture was concentrated, and a mixture of the obtained residue, sodium acetate (0.77 g), hydroxylamine hydrochloride (0.65 g) and acetic acid (5 mL) was stirred at 100° C. for 1 hr. Water was added to the reaction mixture, and the mixture was extracted with ethyl acetate. The ethyl acetate layer was washed with saturated brine, dried (MgSO$_4$) and concentrated. The residue was subjected to silica gel column chromatography and the title compound (0.04 g, yield 3%) was obtained as colorless crystals from a fraction eluted with ethyl acetate-hexane (1:1, volume ratio). The crystals were recrystallized from ethyl acetate. melting point>224° C. (decomposition).

Example 89

7-{[2-(Methylsulfonyl)phenylsulfonyl]amino}-1H-indole-2-carboxylic acid

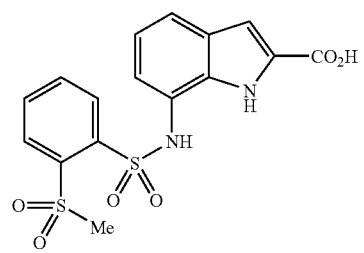 [SMILES: CS(=O)(=O)c1ccccc1S(=O)(=O)Nc1cccc2cc(C(=O)O)[nH]c12]

A mixture of ethyl 7-{[2-(methylsulfonyl)phenylsulfonyl]amino}-1H-indole-2-carboxylate (1.84 g), 8N aqueous sodium hydroxide solution (2.50 mL), tetrahydrofuran (5 mL) and methanol (5 mL) was stirred at 60° C. for 2 hr. The reaction mixture was concentrated, and water was added to the residue. The mixture was acidified with 10% aqueous citric acid solution, and the resulting crystals were filtrated, washed with water, and dried to give the title compound (1.67 g, yield 97%) as yellow crystals. melting point>304° C. (decomposition).

Example 90

7-{[2-(Methylsulfonyl)phenylsulfonyl]amino}-N-[2-(tritylthio)ethyl]-1H-indole-2-carboxamide

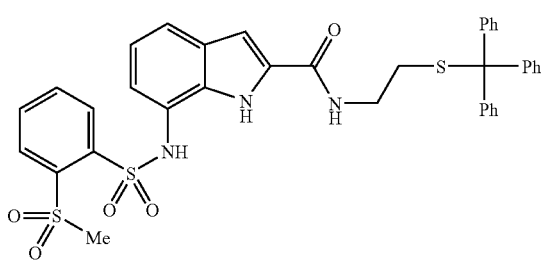 [SMILES: CS(=O)(=O)c1ccccc1S(=O)(=O)Nc1cccc2cc(C(=O)NCCSC(c3ccccc3)(c3ccccc3)c3ccccc3)[nH]c12]

To a mixture of 7-{[2-(methylsulfonyl)phenylsulfonyl]amino}-1H-indole-2-carboxylic acid (1.00 g), 2-(tritylthio)ethylamine hydrochloride (0.92 g), 1H-1,2,3-benzotriazol-1-ol (0.41 g), triethylamine (0.42 mL) and N,N-dimethylformamide (15 mL) was added N-[3-(dimethylamino)propyl]-N'-ethylcarbodiimide hydrochloride (0.58 g) at 0° C., and the mixture was stirred at room temperature overnight. Water was added to the reaction mixture, and the obtained crystals were filtered, washed with water and dried. The obtained crystals were subjected to silica gel column chromatography and the title compound (1.78 g, quantitative) was obtained as colorless crystals from a fraction eluted with ethyl acetate. melting point 91-93° C.

Example 91

N-[2-(4,5-Dihydro-1,3-thiazol-2-yl)-1H-indol-7-yl]-2-(methylsulfonyl)benzenesulfonamide

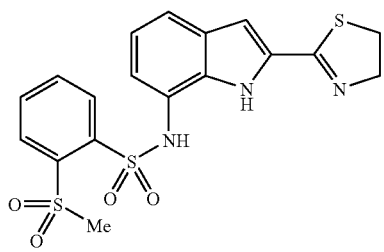 [SMILES: CS(=O)(=O)c1ccccc1S(=O)(=O)Nc1cccc2cc(C3=NCCS3)[nH]c12]

To a solution of triphenylphosphine oxide (4.27 g) in dichloromethane (20 mL) was slowly added trifluoromethanesulfonic anhydride (1.30 mL) at 0° C. The mixture was stirred for 10 min, and 7-{[2-(methylsulfonyl)phenylsulfonyl]amino}-N-[2-(tritylthio)ethyl]-1H-indole-2-carboxamide (1.78 g) was added. The reaction mixture was stirred at room temperature for 3 hr and concentrated. Saturated aqueous sodium hydrogen carbonate was added, and the mixture was extracted with ethyl acetate. The ethyl acetate layer was washed with saturated brine, dried (MgSO$_4$) and concentrated. The residue was subjected to silica gel column chromatography and the title compound (0.69 g, yield 63%) was obtained as colorless crystals from a fraction eluted with ethyl acetate-hexane (1:1, volume ratio). The crystals were recrystallized from ethyl acetate-hexane. melting point 211-212° C.

Example 92

N-[2-(2H-Tetrazol-5-yl)-1H-indol-7-yl]thiophene-2-sulfonamide

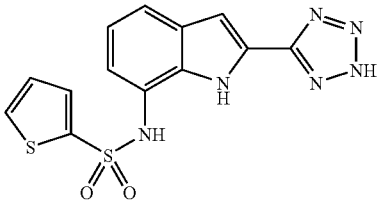 [SMILES: O=S(=O)(Nc1cccc2cc(-c3nn[nH]n3)[nH]c12)c1cccs1]

A mixture of N-(2-cyano-1H-indol-7-yl)thiophene-2-sulfonamide (0.40 g), trimethylsilylazide (0.35 mL), dibutyltin oxide (33 mg) and tetrahydrofuran (15 mL) was heated under reflux overnight. To the reaction mixture was added ethyl acetate, the mixture was ice-cooled, and the resulting crystals were filtrated, washed with cold ethyl acetate, and dried to give the title compound (0.09 g, yield 23%) as pale-yellow crystals. The crystals were recrystallized from ethyl acetate-hexane. melting point 274-275° C. (decomposition).

Example 93

N-[2-(1H-1,2,4-Triazol-3-yl)-1H-indol-7-yl]thiophene-2-sulfonamide

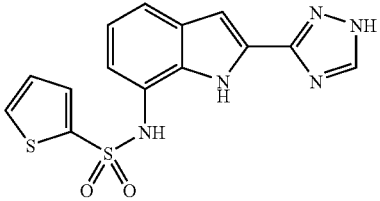 [SMILES: O=S(=O)(Nc1cccc2cc(-c3nc[nH]n3)[nH]c12)c1cccs1]

A mixture of N-(methoxymethyl)-N-[1-(methoxymethyl)-2-(1H-1,2,4-triazol-3-yl)-1H-indol-7-yl]thiophene-2-sulfonamide (0.40 g), concentrated hydrochloride (1 mL) and methanol (10 mL) was heated under reflux for 3 hr. Water was added to the reaction mixture, and the obtained crystals were filtrated, washed with water and dried to give the title compound (0.19 g, yield 60%) as colorless crystals. The crystals were recrystallized from ethyl acetate. melting point>280° C. (decomposition).

Example 94

N-[2-(1-Methyl-1H-1,2,4-triazol-5-yl)-1H-indol-7-yl]thiophene-2-sulfonamide

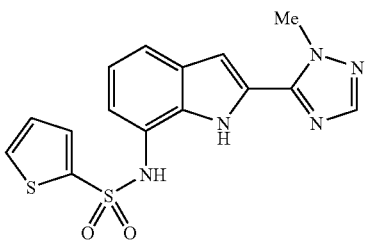 [SMILES: Cn1ncnc1-c1cc2cccc(NS(=O)(=O)c3cccs3)c2[nH]1]

N-(Methoxymethyl)-N-[1-(methoxymethyl)-2-(1-methyl-1H-1,2,4-triazol-5-yl)-1H-indol-7-yl]thiophene-2-sulfonamide (0.42 g), concentrated hydrochloride (1 mL) and methanol (6 mL) were heated under reflux for 6 hr. The reaction mixture was neutralized with aqueous sodium bicarbonate, and the resulting crystals were filtrated, washed with water, and dried to give the title compound (0.07 g, yield 20%) as colorless crystals. The crystals were recrystallized from ethyl acetate-hexane. melting point>271° C. (decomposition).

Example 95

N-[2-(1-Methyl-1H-1,2,4-triazol-3-yl)-1H-indol-7-yl]thiophene-2-sulfonamide

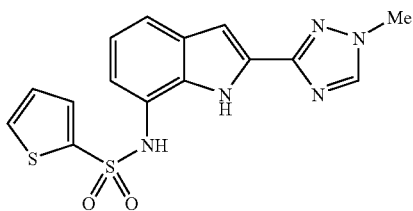 [SMILES: Cn1cnc(-c2cc3cccc(NS(=O)(=O)c4cccs4)c3[nH]2)n1]

N-(Methoxymethyl)-N-[1-(methoxymethyl)-2-(1-methyl-1H-1,2,4-triazol-3-yl)-1H-indol-7-yl]thiophene-2-sulfonamide (0.42 g), concentrated hydrochloric acid (1 mL) and methanol (6 mL) were heated under reflux for 6 hr. The reaction mixture was neutralized with aqueous sodium bicarbonate, and the resulting crystals were filtrated, washed with water, and dried to give the title compound (0.07 g, yield 20%) as colorless crystals. The crystals were recrystallized from ethyl acetate. melting point>161° C. (decomposition).

Example 96

N-[2-(1,2,4-Thiadiazol-5-yl)-1H-indol-7-yl]thiophene-2-sulfonamide

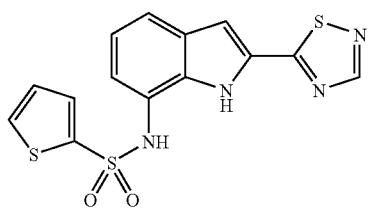 [SMILES: O=S(=O)(Nc1cccc2cc(-c3ncns3)[nH]c12)c1cccs1]

To a mixture of 2-(1,2,4-thiadiazol-5-yl)-1H-indole-7-amine (0.35 g) and pyridine (8 ml) was added thiophene-2-sulfonyl chloride (0.34 g) at 0° C., and the mixture was stirred at room temperature overnight. The reaction mixture was concentrated, 10% aqueous citric acid solution was added, and the resulting crystals were filtrated, washed with water and dried. The obtained crystals were subjected to silica gel column chromatography, and eluted with ethyl acetate. The eluate was treated with activated carbon and concentrated to give the title compound (0.25 g, yield 43%) as colorless crystals. The crystals were recrystallized from ethyl acetate-hexane. melting point 232-233° C.

Example 97

N-Methyl-N-[2-(1,3-thiazol-2-yl)-1H-indol-7-yl]thiophene-2-sulfonamide

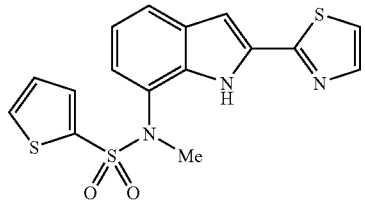 [SMILES: CN(c1cccc2cc(-c3nccs3)[nH]c12)S(=O)(=O)c1cccs1]

A mixture of N-[1-(methoxymethyl)-2-(1,3-thiazol-2-yl)-1H-indol-7-yl]thiophene-2-sulfonamide (0.40 g), methyl iodide (0.12 mL), potassium carbonate (0.20 g) and N,N-dimethylformamide (8 mL) was stirred at room temperature overnight. Water was added to the reaction mixture, and the mixture was extracted with ethyl acetate. The ethyl acetate layer was washed with saturated brine, dried (MgSO$_4$) and concentrated. The obtained residue was subjected to silica gel column chromatography and a yellow oil (0.40 g) was obtained from a fraction eluted with ethyl acetate-hexane (2:3, volume ratio).

A mixture of the obtained yellow oil, concentrated hydrochloride (1 mL) and ethanol (10 mL) was stirred at 60° C. for 6 hr. The reaction mixture was neutralized with aqueous sodium bicarbonate, and extracted with ethyl acetate. The ethyl acetate layer was washed with saturated brine, dried (MgSO$_4$) and concentrated. The obtained residue was subjected to silica gel column chromatography and the title compound (0.16 g, yield 43%) was obtained as colorless crystals from a fraction eluted with ethyl acetate-hexane (1:1, volume ratio). The crystals were recrystallized from ethyl acetate-hexane. melting point 201-202° C.

Example 98

N-Propyl-N-[2-(1,3-thiazol-2-yl)-1H-indol-7-yl]thiophene-2-sulfonamide

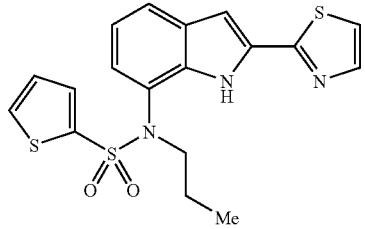

A mixture of N-[1-(methoxymethyl)-2-(1,3-thiazol-2-yl)-1H-indol-7-yl]thiophene-2-sulfonamide (0.40 g), 1-iodopropane (0.15 mL), potassium carbonate (0.20 g) and N,N-dimethylformamide (8 mL) was stirred at room temperature overnight. Water was added to the reaction mixture, and the mixture was extracted with ethyl acetate. The ethyl acetate layer was washed with saturated brine, dried (MgSO$_4$) and concentrated. The obtained residue was subjected to silica gel column chromatography and a yellow oil (0.42 g) was obtained from a fraction eluted with ethyl acetate-hexane (2:3, volume ratio).

A mixture of the obtained yellow oil, concentrated hydrochloride (1 mL) and ethanol (10 mL) was stirred at 60° C. for 6 hr. The reaction mixture was neutralized with aqueous sodium bicarbonate, and extracted with ethyl acetate. The ethyl acetate layer was washed with saturated brine, dried (MgSO$_4$) and concentrated. The obtained residue was subjected to silica gel column chromatography and the title compound (0.19 g, yield 47%) was obtained as colorless crystals from a fraction eluted with ethyl acetate-hexane (2:3, volume ratio). The crystals were recrystallized from ethyl acetate-hexane. melting point 130-131° C.

Example 99

N-(2-Methoxyethyl)-N-[2-(1,3-thiazol-2-yl)-1H-indol-7-yl]thiophene-2-sulfonamide

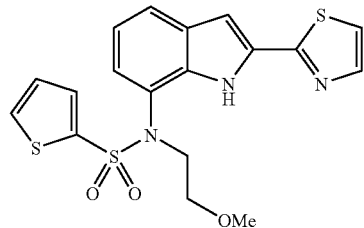

A mixture of N-[1-(methoxymethyl)-2-(1,3-thiazol-2-yl)-1H-indol-7-yl]thiophene-2-sulfonamide (0.40 g), 1-bromo-2-methoxyethane (0.14 mL), potassium carbonate (0.20 g) and N,N-dimethylformamide (8 mL) was stirred at 70° C. overnight. Water was added to the reaction mixture, and the mixture was extracted with ethyl acetate. The ethyl acetate layer was washed with saturated brine, dried (MgSO$_4$) and concentrated. The obtained residue was subjected to silica gel column chromatography and a yellow oil (0.41 g) was obtained from a fraction eluted with ethyl acetate-hexane (2:3, volume ratio).

A mixture of the obtained yellow oil, concentrated hydrochloric acid (1 mL) and ethanol (10 mL) was stirred at 60° C. for 6 hr. The reaction mixture was neutralized with aqueous sodium bicarbonate, and extracted with ethyl acetate. The ethyl acetate layer was washed with saturated brine, dried (MgSO$_4$) and concentrated. The obtained residue was subjected to silica gel column chromatography and the title compound (0.26 g, yield 63%) was obtained as colorless crystals from a fraction eluted with ethyl acetate-hexane (1:1, volume ratio). The crystals were recrystallized from ethyl acetate-hexane. melting point 113-114° C.

Example 100

N-[2-(Morpholin-4-yl)ethyl]-N-[2-(1,3-thiazol-2-yl)-1H-indol-7-yl]thiophene-2-sulfonamide

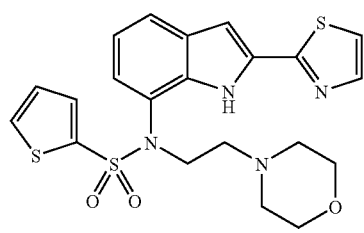 [SMILES: O=S(=O)(c1cccs1)N(CCN1CCOCC1)c1cccc2cc(-c3nccs3)[nH]c12]

A mixture of N-[1-(methoxymethyl)-2-(1,3-thiazol-2-yl)-1H-indol-7-yl]thiophene-2-sulfonamide (0.40 g), 4-(2-chloroethyl)morpholine hydrochloride (0.24 g), potassium carbonate (0.36 g) and N,N-dimethylformamide (8 mL) was stirred at 70° C. overnight. Water was added to the reaction mixture, and the mixture was extracted with ethyl acetate. The ethyl acetate layer was washed with saturated brine, dried (MgSO$_4$) and concentrated. The obtained residue was subjected to silica gel column chromatography and a yellow oil (0.49 g) was obtained from a fraction eluted with ethyl acetate.

A mixture of the obtained yellow oil, concentrated hydrochloric acid (1 mL) and ethanol (10 mL) was stirred at 60° C. for 6 hr. The reaction mixture was neutralized with aqueous sodium bicarbonate, and the resulting crystals were filtrated, washed with water, and dried to give the title compound (0.21 g, yield 44%) as pale-yellow crystals. The crystals were recrystallized from ethyl acetate-hexane. melting point 192-193° C.

Example 101

Ethyl 7-[ethyl(2-thienylsulfonyl)amino]-1H-indole-2-carboxylate

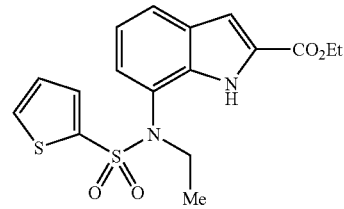 [SMILES: CCOC(=O)c1cc2cccc(N(CC)S(=O)(=O)c3cccs3)c2[nH]1]

A mixture of ethyl 1-(methoxymethyl)-7-[(2-thienylsulfonyl)amino]-1H-indole-2-carboxylate (1.00 g), ethyl iodide (0.40 mL), potassium carbonate (0.53 g) and N,N-dimethylformamide (8 mL) was stirred at room temperature overnight. Water was added to the reaction mixture, and the mixture was extracted with ethyl acetate. The ethyl acetate layer was washed with saturated brine, dried (MgSO$_4$) and concentrated. The obtained residue was subjected to silica gel column chromatography and a yellow oil (1.02 g) was obtained from a fraction eluted with ethyl acetate-hexane (2:3, volume ratio).

A mixture of the obtained yellow oil, concentrated hydrochloric acid (1 mL) and ethanol (10 mL) was stirred at 60° C. for 6 hr. The reaction mixture was neutralized with aqueous sodium bicarbonate, and extracted with ethyl acetate. The ethyl acetate layer was washed with saturated brine, dried (MgSO$_4$) and concentrated. The obtained residue was subjected to silica gel column chromatography and the title compound (0.54 g, yield 55%) was obtained as colorless crystals from a fraction eluted with ethyl acetate-hexane (3:2, volume ratio). melting point 124-125° C.

Example 102

7-[Ethyl(2-thienylsulfonyl)amino]-1H-indole-2-carboxylic acid

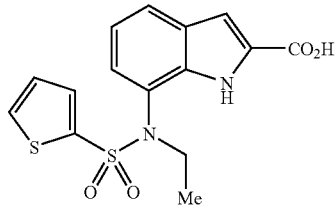 [SMILES: CCN(c1cccc2cc(C(=O)O)[nH]c12)S(=O)(=O)c1cccs1]

A mixture of ethyl 7-[ethyl(2-thienylsulfonyl)amino]-1H-indole-2-carboxylate (0.54 g), 2N aqueous sodium hydroxide solution (2.2 mL), tetrahydrofuran (4 mL) and methanol (4 mL) was stirred at 50° C. for 1 hr. The reaction mixture was concentrated, and water was added to the residue. The mixture was acidified with 10% aqueous citric acid solution, and the resulting crystals were filtrated, washed with water, and dried to give the title compound (0.43 g, yield 86%) as colorless crystals. melting point>222° C. (decomposition).

Example 103

7-[Ethyl(2-thienylsulfonyl)amino]-N-[2-(tritylthio)ethyl]-1H-indole-2-carboxamide

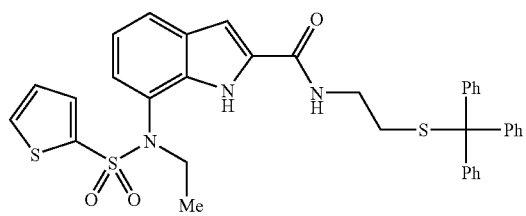 [SMILES: CCN(c1cccc2cc(C(=O)NCCSC(c3ccccc3)(c3ccccc3)c3ccccc3)[nH]c12)S(=O)(=O)c1cccs1]

To a mixture of 7-[ethyl(2-thienylsulfonyl)amino]-1H-indole-2-carboxylic acid (0.43 g), 2-(tritylthio)ethylamine hydrochloride (0.47 g), 1H-1,2,3-benzotriazol-1-ol (0.19 g), triethylamine (0.20 mL) and N,N-dimethylformamide (10 mL) was added N-[3-(dimethylamino)propyl]-N'-ethylcarbodiimide hydrochloride (0.28 g) at 0° C., and the mixture was stirred at 50° C. for 1 hr. Water was added to the reaction mixture, and the obtained crystals were filtrated, washed with water and dried to give the title compound (0.89 g, quantitative) as colorless crystals. melting point 58-61° C.

Example 104

N-[2-(4,5-Dihydro-1,3-thiazol-2-yl)-1H-indol-7-yl]-N-ethylthiophene-2-sulfonamide

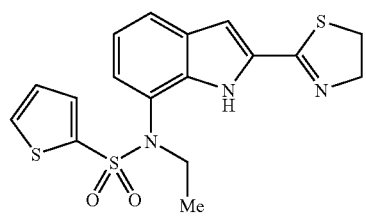 [SMILES: CCN(c1cccc2cc(C3=NCCS3)[nH]c12)S(=O)(=O)c1cccs1]

To a solution of triphenylphosphine oxide (2.34 g) in dichloromethane (25 mL) was slowly added trifluoromethanesulfonic anhydride (0.71 mL) at 0° C. The mixture was stirred for 10 min, and 7-[ethyl(2-thienylsulfonyl)amino]-N-[2-(tritylthio)ethyl]-1H-indole-2-carboxamide (0.89 g) was added. The reaction mixture was stirred at room temperature for 3 hr and concentrated. Saturated aqueous sodium hydrogen carbonate was added, and the mixture was extracted with ethyl acetate. The ethyl acetate layer was washed with saturated brine, dried (MgSO$_4$) and concentrated. The residue was subjected to silica gel column chromatography and the title compound (0.18 g, yield 33%) was obtained as colorless crystals from a fraction eluted with ethyl acetate-hexane (1:1, volume ratio). melting point 206-207° C.

Example 105

Ethyl 7-[(2-methoxyethyl) (2-thienylsulfonyl)amino]-1H-indole-2-carboxylate

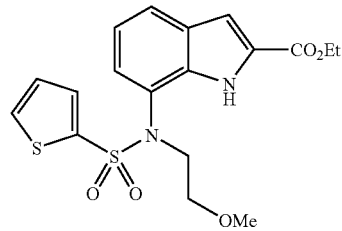 [SMILES: CCOC(=O)c1cc2cccc(N(CCOC)S(=O)(=O)c3cccs3)c2[nH]1]

A mixture of ethyl 1-(methoxymethyl)-7-[(2-thienylsulfonyl)amino]-1H-indole-2-carboxylate (0.82 g), 1-bromo-2-methoxyethane (0.29 mL), potassium carbonate (0.44 g) and N,N-dimethylformamide (8 mL) was stirred at 70° C. overnight. Water was added to the reaction mixture, and the mixture was extracted with ethyl acetate. The ethyl acetate layer was washed with saturated brine, dried (MgSO$_4$) and concentrated. The obtained residue was subjected to silica gel column chromatography and a colorless oil (0.85 g) was obtained from a fraction eluted with ethyl acetate-hexane (2:3, volume ratio).

A mixture of the obtained colorless oil, concentrated hydrochloric acid (1 mL) and ethanol (10 mL) was stirred at 60° C. for 6 hr. The reaction mixture was neutralized with aqueous sodium bicarbonate, and extracted with ethyl acetate. The ethyl acetate layer was washed with saturated brine, dried (MgSO$_4$) and concentrated. The obtained residue was subjected to silica gel column chromatography and the title compound (0.54 g, yield 68%) was obtained as a colorless oil from a fraction eluted with ethyl acetate-hexane (3:2, volume ratio).

$^1$H-NMR (CDCl$_3$) δ:1.42 (3H, t, J=7.1 Hz), 3.35 (3H, s), 3.47 (2H, t, J=5.5 Hz), 3.91 (2H, brs), 4.41 (2H, q, J=7.1 Hz), 6.80 (1H, dd, J=7.5, 0.9 Hz), 6.97-7.09 (2H, m), 7.22 (1H, d, J=2.2 Hz), 7.42 (1H, dd, J=3.9, 1.3 Hz), 7.60 (1H, dd, J=4.9, 1.3 Hz), 7.66 (1H, d, J=8.2 Hz), 9.69 (1H, brs).

Example 106

7-[(2-Methoxyethyl) (2-thienylsulfonyl)amino]-1H-indole-2-carboxylic acid

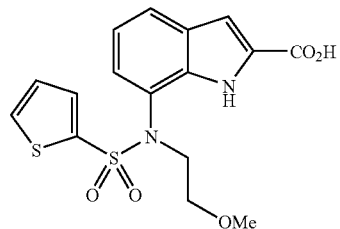 [SMILES: COCCN(c1cccc2cc(C(=O)O)[nH]c12)S(=O)(=O)c1cccs1]

A mixture of ethyl 7-[(2-methoxyethyl)(2-thienylsulfonyl)amino]-1H-indole-2-carboxylate (0.54 g), 2N aqueous sodium hydroxide solution (2.2 mL), tetrahydrofuran (4 mL) and methanol (4 mL) was stirred at 50° C. for 1 hr. The reaction mixture was concentrated, and water was added to the residue. The mixture was acidified with 10% aqueous citric acid solution, and the resulting crystals were filtrated, washed with water, and dried to give the title compound (0.46 g, yield 92%) as colorless crystals. melting point 216-217° C.

Example 107

7-[(2-Methoxyethyl) (2-thienylsulfonyl)amino]-N-[2-(tritylthio)ethyl]-1H-indole-2-carboxamide

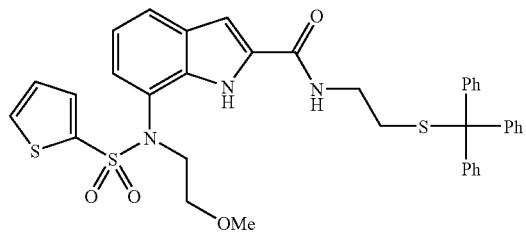 [SMILES: COCCN(c1cccc2cc(C(=O)NCCSC(c3ccccc3)(c3ccccc3)c3ccccc3)[nH]c12)S(=O)(=O)c1cccs1]

To a mixture of 7-[(2-methoxyethyl)(2-thienylsulfonyl)amino]-1H-indole-2-carboxylic acid (0.46 g), 2-(tritylthio)ethylamine hydrochloride (0.47 g), 1H-1,2,3-benzotriazol-1-ol (0.19 g), triethylamine (0.20 mL) and N,N-dimethylformamide (10 mL) was added N-[3-(dimethylamino)propyl]-N'-ethylcarbodiimide hydrochloride (0.28 g) at 0° C., and the mixture was stirred at 50° C. for 1 hr. Water was added to the reaction mixture, and the obtained crystals were filtrated, washed with water and dried to give the title compound (0.90 g, quantitative) as colorless crystals. melting point 65-66° C.

Example 108

N-[2-(4,5-Dihydro-1,3-thiazol-2-yl)-1H-indol-7-yl]-N-(2-methoxyethyl)-2-sulfonamide

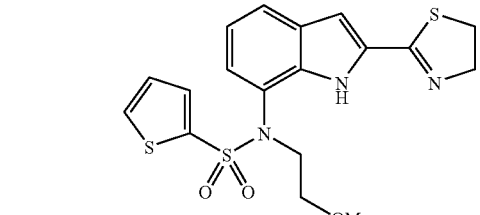

To a solution of triphenylphosphine oxide (2.34 g) in dichloromethane (25 mL) was slowly added trifluoromethanesulfonic anhydride (0.71 mL) at 0° C. The mixture was stirred for 10 min, and 7-[(2-methoxyethyl)(2-thienylsulfonyl)amino]-N-[2-(tritylthio)ethyl]-1H-indole-2-carboxamide (0.90 g) was added. The reaction mixture was stirred at room temperature for 3 hr and concentrated. Saturated aqueous sodium hydrogen carbonate was added, and the mixture was extracted with ethyl acetate. The ethyl acetate layer was washed with saturated brine, dried (MgSO$_4$) and concentrated. The residue was subjected to silica gel column chromatography and the title compound (0.17 g, yield 31%) was obtained as colorless crystals from a fraction eluted with ethyl acetate-hexane (1:1, volume ratio). melting point 153-154° C.

Example 109

N-{2-[(2-Acetylhydrazino)carbonyl]-1H-indol-7-yl}thiophene-2-sulfonamide

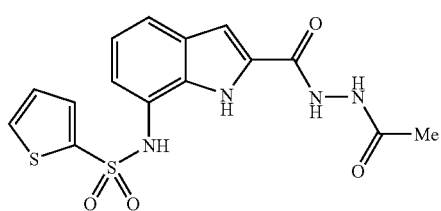 [SMILES: CC(=O)NNC(=O)c1cc2cccc(NS(=O)(=O)c3cccs3)c2[nH]1]

To a mixture of 7-[(2-thienylsulfonyl)amino]-1H-indole-2-carboxylic acid (0.70 g), 1H-1,2,3-benzotriazol-1-ol (0.36 g) and N,N-dimethylformamide (8 mL) was added N-[3-(dimethylamino)propyl]-N'-ethylcarbodiimide hydrochloride (0.51 g) at room temperature. The mixture was stirred for 10 min and acetohydrazide (0.33 g) was added. The reaction mixture was stirred at room temperature for 2 hr, and water was added. The resulting crystals were filtrated, washed with water, and dried to give the title compound (0.65 g, yield 77%) as colorless crystals. melting point 254-256° C.

Example 110

N-[2-(5-Methyl-1,3,4-thiadiazol-2-yl)-1H-indol-7-yl]thiophene-2-sulfonamide

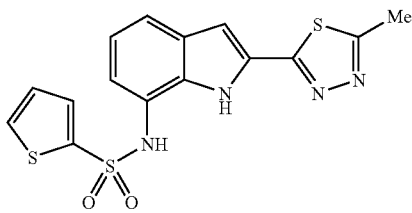 [SMILES: Cc1nnc(-c2cc3cccc(NS(=O)(=O)c4cccs4)c3[nH]2)s1]

A mixture of N-{2-[(2-acetylhydrazino)carbonyl]-1H-indol-7-yl}thiophene-2-sulfonamide (0.65 g), Lawesson's reagent (0.76 g) and tetrahydrofuran (30 mL) was stirred at 50° C. overnight. The resulting crystals were filtrated, washed with tetrahydrofuran, and dried to give the title compound (0.45 g, yield 71%) as colorless crystals. melting point 308-309° C.

Example 111

Ethyl 2-{7-[(2-thienylsulfonyl)amino]-1H-indol-2-yl}-1,3-thiazole-4-carboxylate

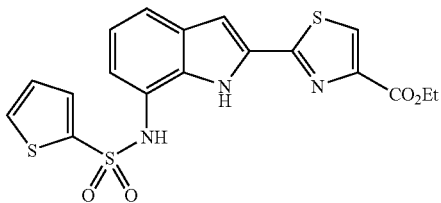

A mixture of 7-[(2-thienylsulfonyl)amino]-1H-indole-2-carbothioamide (0.30 g), ethyl bromopyruvate (0.21 g), ethanol (2 mL) and N,N-dimethylacetamide (2 mL) was stirred at 80° C. for 4 hr. Water was added to the reaction mixture, and the obtained crystals were filtrated, washed with water and dried. The obtained crystals were recrystallized from ethyl acetate to give the title compound (0.14 g, yield 36%) as pale-yellow crystals. melting point 240-241° C.

Example 112

N-[2-(4-Methyl-1,3-thiazol-2-yl)-1H-indol-7-yl]thiophene-2-sulfonamide

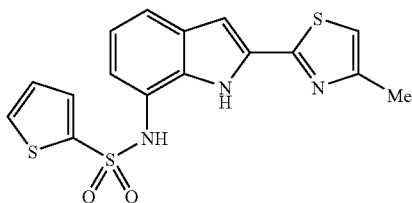 [SMILES: Cc1csc(-c2cc3cccc(NS(=O)(=O)c4cccs4)c3[nH]2)n1]

A mixture of 7-[(2-thienylsulfonyl)amino]-1H-indole-2-carbothioamide (0.30 g), bromoacetone (0.10 mL), ethanol (2 mL) and N,N-dimethylacetamide (2 mL) was stirred at 80° C. for 4 hr. Water was added to the reaction mixture, and the mixture was extracted with ethyl acetate. The ethyl acetate layer was washed with saturated sodium brine, dried (MgSO$_4$) and concentrated. The obtained residue was subjected to silica gel column chromatography and the title compound (0.24 g, yield 72%) was obtained as colorless crystals from a fraction eluted with ethyl acetate-hexane (2:3, volume ratio). The crystals were recrystallized from ethyl acetate-hexane. melting point 181-183° C.

Example 113

Ethyl N-[2-(1,3-thiazol-2-yl)-1H-indol-7-yl]-N-(2-thienylsulfonyl)aminoacetate

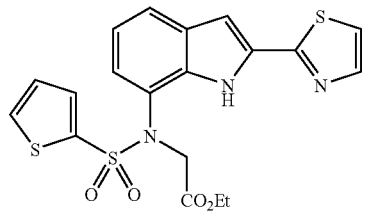 [SMILES: CCOC(=O)CN(c1cccc2cc(-c3nccs3)[nH]c12)S(=O)(=O)c1cccs1]

A mixture of ethyl N-[1-(methoxymethyl)-2-(1,3-thiazol-2-yl)-1H-indol-7-yl]-N-(2-thienylsulfonyl)aminoacetate (0.31 g), concentrated hydrochloric acid (0.5 mL) and ethanol (6 mL) was stirred at 70° C. for 6 hr. The reaction mixture was neutralized with aqueous sodium bicarbonate, and extracted with ethyl acetate. The ethyl acetate layer was washed with saturated brine, dried (MgSO$_4$) and concentrated. The obtained residue was subjected to silica gel column chromatography and the title compound (0.17 g, yield 60%) was obtained as colorless crystals from a fraction eluted with ethyl acetate-hexane (1:1, volume ratio). The crystals were recrystallized from ethyl acetate-hexane. melting point 135-137° C.

Example 114

Ethyl 4-methyl-2-{7-[(2-thienylsulfonyl)amino]-1H-indol-2-yl}-1,3-thiazole-5-carboxylate

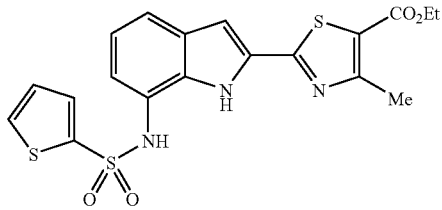 [SMILES: CCOC(=O)c1sc(-c2cc3cccc(NS(=O)(=O)c4cccs4)c3[nH]2)nc1C]

A mixture of 7-[(2-thienylsulfonyl)amino]-1H-indole-2-carbothioamide (0.50 g), ethyl 2-chloro-3-oxobutyrate (0.40 mL), ethanol (4 mL) and N,N-dimethylacetamide (4 mL) was stirred at 90° C. overnight. Water was added to the reaction mixture, and the obtained crystals were filtrated, washed with water and dried. The obtained crystals were subjected to silica gel column chromatography and the title compound (0.47 g, yield 73%) was obtained as pale-yellow crystals from a frac-

Example 115

N-[2-(1,3-Benzothiazol-2-yl)-1H-indol-7-yl]
thiophene-2-sulfonamide

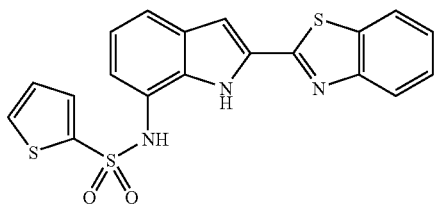 [SMILES: O=S(=O)(Nc1cccc2cc(-c3nc4ccccc4s3)[nH]c12)c1cccs1]

A mixture of 7-[(2-thienylsulfonyl)amino]-1H-indole-2-carbothioamide (0.30 g), 2-aminothiophenol (0.10 mL), concentrated hydrochloric acid (0.5 mL) and ethylene glycol (6 mL) was stirred at 100° C. overnight. Water was added to the reaction mixture, and the obtained crystals were filtrated, washed with water and dried. The obtained crystals were subjected to silica gel column chromatography and the title compound (0.14 g, yield 38%) was obtained as colorless crystals from a fraction eluted with ethyl acetate-hexane (2:3, volume ratio). The crystals were recrystallized from ethyl acetate-hexane. melting point 201-202° C.

Example 116

N-(2-Hydroxyethyl)-N-[2-(1,3-thiazol-2-yl)-1H-indol-7-yl]thiophene-2-sulfonamide

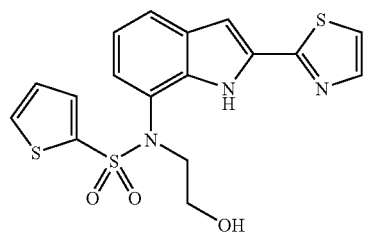 [SMILES: O=S(=O)(c1cccs1)N(CCO)c1cccc2cc(-c3nccs3)[nH]c12]

To a mixture of ethyl N-[1-(methoxymethyl)-2-(1,3-thiazol-2-yl)-1H-indol-7-yl]-N-(2-thienylsulfonyl)aminoacetate (0.49 g) and tetrahydrofuran (8 mL) was added lithium aluminum hydride (0.05 g) at 0° C., and the mixture was stirred at 0° C. for 20 min. To the reaction mixture was added ethanol (2 mL), and then saturated aqueous ammonium chloride solution (0.3 mL) was added. The resulting inorganic salt was removed by filtration, and the filtrate was concentrated. The residue was subjected to silica gel column chromatography, and a colorless amorphous form (0.45 g) was obtained from a fraction eluted with ethyl acetate.

A mixture of the obtained colorless amorphous form, concentrated hydrochloric acid (1 mL) and ethanol (10 mL) was stirred at 70° C. for 6 hr. The reaction mixture was neutralized with aqueous sodium bicarbonate, and the mixture was extracted with ethyl acetate. The ethyl acetate layer was washed with saturated brine, dried (MgSO₄) and concentrated. The obtained residue was subjected to silica gel column chromatography and the title compound (0.72 g, yield 72%) was obtained as colorless crystals from a fraction eluted with ethyl acetate-hexane (2:1, volume ratio). The crystals were recrystallized from ethyl acetate-hexane. melting point 170-171° C.

Example 117

4-Methyl-2-{7-[(2-thienylsulfonyl)amino]-1H-indol-2-yl}-1,3-thiazole-5-carboxylic acid

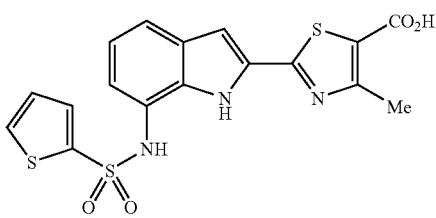 [SMILES: Cc1nc(-c2cc3cccc(NS(=O)(=O)c4cccs4)c3[nH]2)sc1C(=O)O]

A mixture of ethyl 4-methyl-2-{7-[(2-thienylsulfonyl)amino]-1H-indol-2-yl}-1,3-thiazole-5-carboxylate (0.42 g), 8N aqueous sodium hydroxide solution (0.4 mL), tetrahydrofuran (6 mL) and methanol (6 mL) was stirred at 60° C. for 1 hr. The reaction mixture was concentrated, and water was added to the residue. The mixture was acidified with 10% aqueous citric acid solution, and the resulting crystals were filtrated, washed with water and dried. The obtained crystals were dissolved in tetrahydrofuran, treated with activated carbon, and concentrated to give the title compound (0.17 g, yield 44%) as yellow crystals. The crystals were recrystallized from ethyl acetate-hexane. melting point>253° C. (decomposition).

Example 118

Ethyl [2-({7-[methyl (2-thienylsulfonyl)amino]-1H-indol-2-yl}carbonyl)hydrazino](oxo)acetate

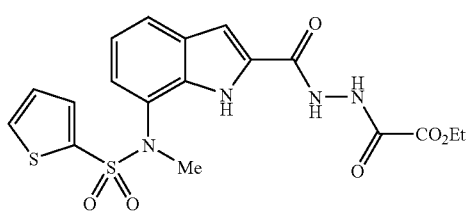 [SMILES: CCOC(=O)C(=O)NNC(=O)c1cc2cccc(N(C)S(=O)(=O)c3cccs3)c2[nH]1]

To a mixture of 7-[methyl(2-thienylsulfonyl)amino]-1H-indole-2-carboxylic acid (0.50 g), 1H-1,2,3-benzotriazol-1-ol (0.24 g) and N,N-dimethylformamide (10 mL) was added N-[3-(dimethylamino)propyl]-N'-ethylcarbodiimide hydrochloride (0.30 g) at room temperature. The mixture was stirred for 10 min, and ethyl hydrazino(oxo)acetate (0.33 g) was added. The reaction mixture was stirred at room temperature for 2 hr, water was added, and the mixture was extracted with ethyl acetate. The ethyl acetate layer was washed with saturated brine, dried (MgSO₄) and concentrated. The obtained residue was subjected to silica gel column chromatography and the title compound (0.43 g, yield 63%) was

Example 119

Ethyl 5-{7-[methyl(2-thienylsulfonyl)amino]-1H-indol-2-yl}-1,3,4-thiadiazole-2-carboxylate

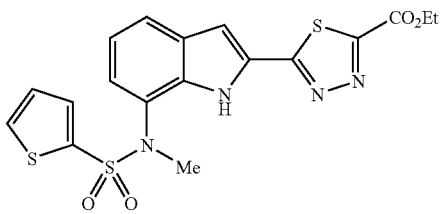 [SMILES: CCOC(=O)c1nnc(-c2cc3cccc(N(C)S(=O)(=O)c4cccs4)c3[nH]2)s1]

A mixture of ethyl [2-({7-[methyl(2-thienylsulfonyl)amino]-1H-indol-2-yl}carbonyl)hydrazino](oxo)acetate (0.43 g), Lawesson's reagent (0.42 g) and tetrahydrofuran (10 mL) was stirred at 50° C. overnight. The reaction mixture was concentrated, and the residue was subjected to silica gel column chromatography, and the title compound (0.29 g, yield 68%) was obtained as colorless crystals from a fraction eluted with ethyl acetate-hexane (2:3, volume ratio). The crystals were recrystallized from ethyl acetate-hexane. melting point 176-177° C.

Example 120

N-(2-{[2-(Methoxyacetyl)hydrazino]carbonyl}-1H-indol-7-yl)-N-methylthiophene-2-sulfonamide

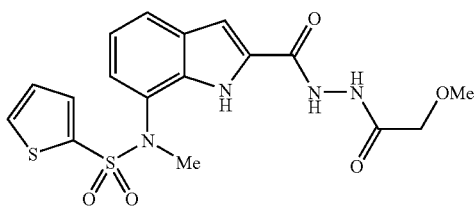 [SMILES: COCC(=O)NNC(=O)c1cc2cccc(N(C)S(=O)(=O)c3cccs3)c2[nH]1]

To a mixture of 7-[methyl(2-thienylsulfonyl)amino]-1H-indole-2-carboxylic acid (0.40 g), 1H-1,2,3-benzotriazol-1-ol (0.19 g) and N,N-dimethylformamide (10 mL) was added N-[3-(dimethylamino)propyl]-N'-ethylcarbodiimide hydrochloride (0.28 g) at room temperature. The mixture was stirred for 10 min, and methoxyacetohydrazide (0.19 g) was added. The reaction mixture was stirred at room temperature for 2 hr, water was added, and the mixture was extracted with ethyl acetate. The ethyl acetate layer was washed with saturated brine, dried ($MgSO_4$) and concentrated. The obtained residue was subjected to silica gel column chromatography and the title compound (0.29 g, yield 58%) was obtained as colorless crystals from a fraction eluted with ethyl acetate. melting point 148-149° C.

Example 121

N-{2-[5-(Methoxymethyl)-1,3,4-thiadiazol-2-yl]-1H-indol-7-yl}-N-methylthiophene-2-sulfonamide

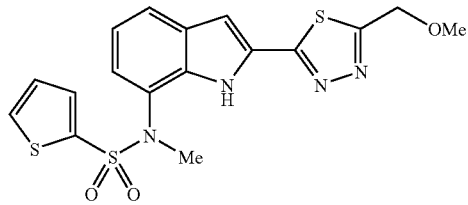 [SMILES: COCc1nnc(-c2cc3cccc(N(C)S(=O)(=O)c4cccs4)c3[nH]2)s1]

A mixture of N-(2-{[2-(methoxyacetyl)hydrazino]carbonyl}-1H-indol-7-yl)-N-methylthiophene-2-sulfonamide (0.29 g), Lawesson's reagent (0.31 g) and tetrahydrofuran (10 mL) was stirred at 50° C. overnight. The reaction mixture was concentrated, and methanol was added to the residue. The resulting crystals were filtrated, washed with methanol, and dried to give the title compound (0.18 g, yield 62%) as pale-yellow crystals. melting point>238° C. (decomposition).

Example 122

2-{7-[(2-Thienylsulfonyl)amino]-1H-indol-2-yl}-1,3-thiazole-4-carboxylic acid

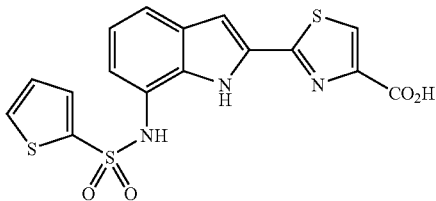 [SMILES: O=C(O)c1csc(-c2cc3cccc(NS(=O)(=O)c4cccs4)c3[nH]2)n1]

A mixture of ethyl 2-{7-[(2-thienylsulfonyl)amino]-1H-indol-2-yl}-1,3-thiazole-4-carboxylate (0.30 g), 8N aqueous sodium hydroxide solution (0.3 mL), tetrahydrofuran (4 mL) and methanol (4 mL) was stirred at 60° C. for 1 hr. The reaction mixture was concentrated, and water was added to the residue. The mixture was acidified with 10% aqueous citric acid solution, and the resulting crystals were filtrated, washed with water and dried. The obtained crystals were dissolved in tetrahydrofuran, treated with activated carbon, and concentrated to give the title compound (0.20 g, yield 71%) as yellow crystals. melting point>273° C. (decomposition).

Example 123

N-Methyl-N-[2-(1,3,4-thiadiazol-2-yl)-1H-indol-7-yl]thiophene-2-sulfonamide

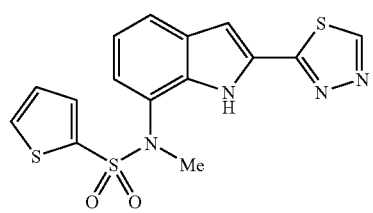 [SMILES: CN(c1cccc2cc(-c3nncs3)[nH]c12)S(=O)(=O)c1cccs1]

A mixture of ethyl 5-{7-[methyl(2-thienylsulfonyl)amino]-1H-indol-2-yl}-1,3,4-thiadiazole-2-carboxylate (0.20 g), 8N aqueous sodium hydroxide solution (0.14 mL), tetrahydrofuran (6 mL) and methanol (6 mL) was stirred at 50° C. for 2 hr. The reaction mixture was concentrated, and water was added to the residue. The mixture was acidified with 10% aqueous citric acid solution, and the resulting crystals were filtrated, washed with water and dried. The obtained crystals were dissolved in tetrahydrofuran, treated with activated carbon, and concentrated to give the title compound (0.13 g, yield 78%) as yellow crystals. melting point 270-271° C.

Example 124

N-{2-[4-(Hydroxymethyl)-1,3-thiazol-2-yl]-1H-indol-7-yl}thiophene-2-sulfonamide

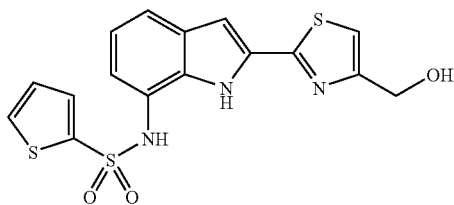 [SMILES: O=S(=O)(Nc1cccc2cc(-c3nc(CO)cs3)[nH]c12)c1cccs1]

To a mixture of ethyl 2-{7-[(2-thienylsulfonyl)amino]-1H-indol-2-yl}-1,3-thiazole-4-carboxylate (0.35 g) and tetrahydrofuran (15 mL) was added lithium aluminum hydride (0.11 g) at 0° C., and the mixture was stirred at 0° C. for 30 min. To the reaction mixture was added ethanol (5 mL) and then saturated aqueous ammonium chloride solution (5 mL) was added. The resulting inorganic salt was removed by filtration, and the filtrate was concentrated. The obtained crystals were dissolved in tetrahydrofuran, treated with activated carbon, and concentrated. Ethyl acetate was added to the obtained residue, and the resulting crystals were collected by filtration and dried to give the title compound (0.10 g, yield 32%) as yellow crystals. melting point>233° C. (decomposition).

Example 125

N-[3-Chloro-2-(1,3-thiazol-2-yl)-1H-indol-7-yl]-N-methylthiophene-2-sulfonamide

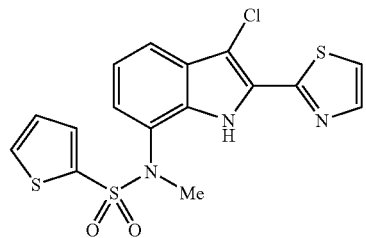 [SMILES: CN(c1cccc2c(Cl)c(-c3nccs3)[nH]c12)S(=O)(=O)c1cccs1]

A mixture of N-[3-chloro-1-(methoxymethyl)-2-(1,3-thiazol-2-yl)-1H-indol-7-yl]thiophene-2-sulfonamide (0.36 g), methyl iodide (0.10 mL), potassium carbonate (0.17 g) and N,N-dimethylformamide (8 mL) was stirred at room temperature for 4 hr. Water was added to the reaction mixture, and the mixture was extracted with ethyl acetate. The ethyl acetate layer was washed with saturated brine, dried (MgSO$_4$) and concentrated. The obtained residue was subjected to silica gel column chromatography and a yellow oil (0.34 g) was obtained from a fraction eluted with ethyl acetate-hexane (1:2, volume ratio).

A mixture of the obtained yellow oil, concentrated hydrochloric acid (1 mL) and ethanol (10 mL) was stirred at 60° C. for 6 hr. Water was added to the reaction mixture, and the obtained crystals were filtrated, washed with water and dried to give the title compound (0.22 g, yield 66%) as yellow crystals. The crystals were recrystallized from ethyl acetate-hexane. melting point 222-223° C.

Example 126

N-[2-(1,3-Thiazol-2-yl)-1H-indol-7-yl]-N-(2,2,2-trifluoroethyl)thiophene-2-sulfonamide

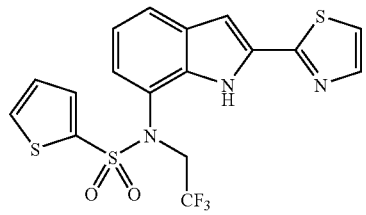 [SMILES: O=S(=O)(c1cccs1)N(CC(F)(F)F)c1cccc2cc(-c3nccs3)[nH]c12]

A mixture of N-[1-(methoxymethyl)-2-(1,3-thiazol-2-yl)-1H-indol-7-yl]thiophene-2-sulfonamide (0.30 g), 2,2,2-trifluoroethyl trifluoromethanesulfonate (0.16 mL), potassium carbonate (0.15 g) and N,N-dimethylformamide (6 mL) was stirred at room temperature overnight. Water was added to the reaction mixture, and the mixture was extracted with ethyl acetate. The ethyl acetate layer was washed with saturated brine, dried (MgSO$_4$) and concentrated. The obtained residue was subjected to silica gel column chromatography and a colorless oil (0.34 g) was obtained from a fraction eluted with ethyl acetate-hexane (1:3, volume ratio).

A mixture of the obtained colorless oil, concentrated hydrochloric acid (1 mL) and ethanol (10 mL) was heated under reflux for 8 hr. The reaction mixture was neutralized with aqueous sodium bicarbonate, and extracted with ethyl acetate. The ethyl acetate layer was washed with saturated brine, dried (MgSO$_4$) and concentrated. The obtained residue was subjected to silica gel column chromatography and the title compound (0.17 g, yield 51%) was obtained as colorless crystals from a fraction eluted with ethyl acetate-hexane (1:3, volume ratio). The crystals were recrystallized from ethyl acetate-hexane. melting point 194-195° C.

Example 127

Ethyl (2-{7-[(2-thienylsulfonyl)amino]-1H-indol-2-yl}-1,3-thiazol-4-yl)acetate

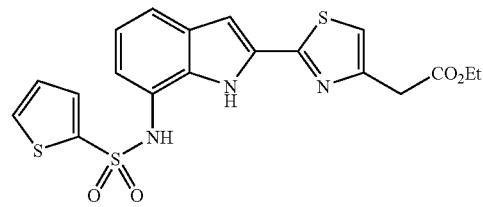 [SMILES: CCOC(=O)Cc1csc(-c2cc3cccc(NS(=O)(=O)c4cccs4)c3[nH]2)n1]

A mixture of 7-[(2-thienylsulfonyl)amino]-1H-indole-2-carbothioamide (0.30 g), ethyl 4-chloro-3-oxobutyrate (0.22 g), ethanol (6 mL) and N,N-dimethylacetamide (6 mL) was stirred at 80° C. overnight. Water was added to the reaction mixture, and the mixture was extracted with ethyl acetate. The ethyl acetate layer was washed with saturated brine, dried (MgSO$_4$) and concentrated. The obtained residue was subjected to silica gel column chromatography and the title compound (0.25 g, yield 63%) was obtained as colorless crystals from a fraction eluted with ethyl acetate-hexane (2:3, volume ratio). The crystals were recrystallized from ethyl acetate-hexane. melting point 161-162° C.

Example 128

(2-{7-[(2-Thienylsulfonyl)amino]-1H-indol-2-yl}-1,3-thiazol-4-yl)acetic acid

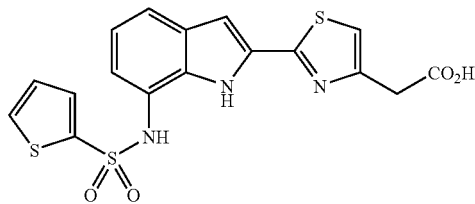 [SMILES: O=C(O)Cc1csc(-c2cc3cccc(NS(=O)(=O)c4cccs4)c3[nH]2)n1]

A mixture of ethyl 2-{7-[(2-thienylsulfonyl)amino]-1H-indol-2-yl}-1,3-thiazol-4-yl)acetate (0.20 g), 8N aqueous sodium hydroxide solution (0.22 mL), tetrahydrofuran (4 mL) and methanol (4 mL) was stirred at 60° C. for 1 hr. The reaction mixture was concentrated, and water was added to the residue. The mixture was acidified with 10% aqueous citric acid solution, and the resulting crystals were filtrated, washed with water, and dried to give the title compound (0.16 g, yield 81%) as colorless crystals. The crystals were recrystallized from ethyl acetate-hexane. melting point 228-229° C.

Example 129

N-[2-(1,3-Thiazol-2-yl)-1H-indol-7-yl]-N-(2-thienylsulfonyl)aminoacetic acid

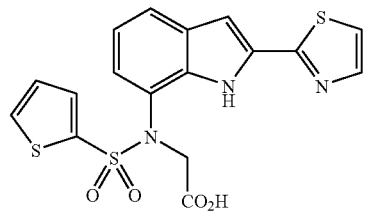 [SMILES: O=C(O)CN(c1cccc2cc(-c3nccs3)[nH]c12)S(=O)(=O)c1cccs1]

A mixture of ethyl N-[2-(1,3-thiazol-2-yl)-1H-indol-7-yl]-N-(2-thienylsulfonyl)aminoacetate (0.29 g), 1N aqueous sodium hydroxide solution (2.0 mL), tetrahydrofuran (5 mL) and methanol (5 mL) was stirred at 60° C. for 1 hr. The reaction mixture was concentrated, and water was added to the residue. The mixture was acidified with 10% aqueous citric acid solution, and the resulting crystals were filtrated, washed with water and dried. The obtained crystals were dissolved in tetrahydrofuran, treated with activated carbon, and concentrated to give the title compound (0.19 g, yield 69%) as colorless crystals. melting point>218° C. (decomposition).

Example 130

N-{2-[5-(Hydroxymethyl)-1,3-thiazol-2-yl]-1H-indol-7-yl}-N-methylthiophene-2-sulfonamide

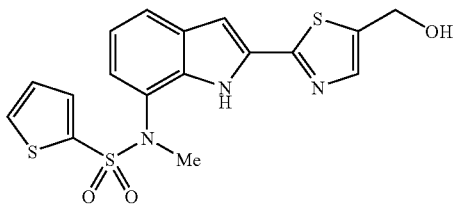

A mixture of N-{2-[5-(hydroxymethyl)-1,3-thiazol-2-yl]-1-(methoxymethyl)-1H-indol-7-yl}-N-methylthiophene-2-sulfonamide (0.20 g), concentrated hydrochloride (0.3 mL) and ethanol (8 mL) was heated under reflux for 8 hr. The reaction mixture was neutralized with aqueous sodium bicarbonate, and extracted with ethyl acetate. The ethyl acetate layer was washed with saturated brine, dried (MgSO$_4$) and concentrated. The obtained residue was subjected to silica gel column chromatography and the title compound (0.09 g, yield 50%) was obtained as colorless crystals from a fraction eluted with ethyl acetate-hexane (3:1, volume ratio). The crystals were recrystallized from ethyl acetate-hexane. melting point 201-202° C.

Example 131

Ethyl [(2-{7-[methyl (2-thienylsulfonyl)amino]-1H-indol-2-yl}-1,3-thiazol-5-yl)methoxy]acetate

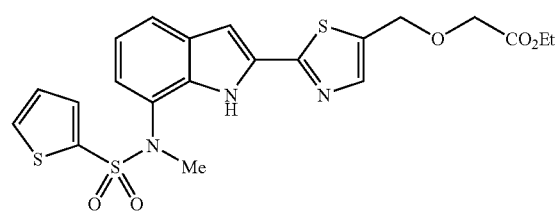 [SMILES: CCOC(=O)COCc1cnc(-c2cc3cccc(N(C)S(=O)(=O)c4cccs4)c3[nH]2)s1]

To a suspension of sodium hydride (60% in oil, 0.02 g) in N,N-dimethylformamide (4 mL) was slowly added N-{2-[5-(hydroxymethyl)-1,3-thiazol-2-yl]-1-(methoxymethyl)-1H-indol-7-yl}-N-methylthiophene-2-sulfonamide (0.20 g) at 0° C., and the mixture was stirred for 15 min. To the reaction mixture was added ethyl bromoacetate (0.06 mL) at 0° C. and the mixture was stirred at room temperature for 1 hr. Water was added to the reaction mixture, and the mixture was extracted with ethyl acetate. The ethyl acetate layer was washed with saturated brine, dried (MgSO$_4$) and concentrated.

A mixture of the obtained residue, 6N hydrochloric acid (0.5 mL) and ethanol (8 mL) was heated under reflux for 8 hr. Water was added to the reaction mixture, and the mixture was extracted with ethyl acetate. The ethyl acetate layer was washed with saturated brine, dried (MgSO$_4$) and concentrated. The obtained residue was subjected to silica gel column chromatography and the title compound (0.08 g, yield 45%) was obtained as a colorless oil from a fraction eluted with ethyl acetate-hexane (1:1, volume ratio).

$^1$H-NMR (CDCl$_3$) δ:1.31 (3H, t, J=7.1 Hz), 3.34 (3H, s), 4.14 (2H, s), 4.25 (2H, q, J=7.1 Hz), 4.87 (2H, s), 6.54 (1H, dd, J=7.8, 0.9 Hz), 6.96 (1H, t, J=7.8 Hz), 6.99 (1H, d, J=2.1 Hz), 7.10 (1H, dd, J=5.1, 3.9 Hz), 7.39 (1H, dd, J=3.9, 1.5 Hz), 7.56 (1H, d, J=7.8 Hz), 7.62 (1H, dd, J=5.1, 1.5 Hz), 7.71 (1H, t, J=0.8 Hz), 9.65 (1H, brs).

Example 132

[(2-{7-[Methyl(2-thienylsulfonyl)amino]-1H-indol-2-yl}-1,3-thiazol-5-yl)methoxy]acetic acid

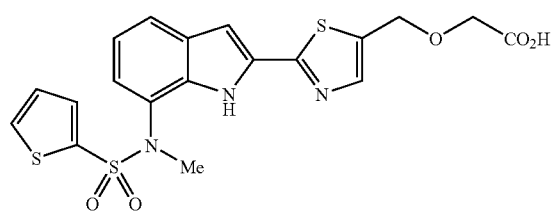 [SMILES: CN(c1cccc2cc(-c3ncc(COCC(=O)O)s3)[nH]c12)S(=O)(=O)c1cccs1]

A mixture of ethyl [(2-{7-[methyl(2-thienylsulfonyl)amino]-1H-indol-2-yl}-1,3-thiazol-5-yl)methoxy]acetate (0.08 g), 1N aqueous sodium hydroxide solution (0.30 mL), tetrahydrofuran (4 mL) and methanol (4 mL) was stirred at 60° C. for 1 hr. The reaction mixture was concentrated, and water was added to the residue. The mixture was acidified with 10% aqueous citric acid solution, and the resulting crystals were filtrated, washed with water, and dried to give the title compound (0.04 g, yield 45%) as pale-yellow crystals. melting point 197-198° C.

Example 133

N-{2-[5-(Cyanomethyl)-1,3-thiazol-2-yl]-1H-indol-7-yl}-N-methylthiophene-2-sulfonamide

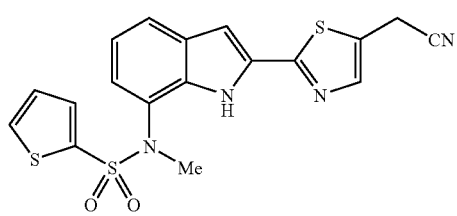 [SMILES: CN(c1cccc2cc(-c3ncc(CC#N)s3)[nH]c12)S(=O)(=O)c1cccs1]

To a mixture of N-{2-[5-(hydroxymethyl)-1,3-thiazol-2-yl]-1-(methoxymethyl)-1H-indol-7-yl}-N-methylthiophene-2-sulfonamide (0.40 g), acetone cyanhydrin (0.27 mL), tributylphosphine (0.44 mL) and tetrahydrofuran (30 ml) was added 1,1'-azodicarbonyldipiperidine (0.45 g) at room temperature and the mixture was stirred overnight. The reaction solution was concentrated, and the residue was subjected to silica gel column chromatography, and a brown oil (0.10 g) was obtained from a fraction eluted with ethyl acetate-hexane (2:3, volume ratio).

A mixture of the obtained brown oil, 6N hydrochloric acid (1.0 mL), ethanol (6 mL) was stirred at 70° C. for 8 hr. Water was added to the reaction mixture, and the mixture was extracted with ethyl acetate. The ethyl acetate layer was washed with saturated brine, dried (MgSO$_4$) and concentrated. The obtained residue was subjected to silica gel column chromatography and the title compound (0.02 g, yield 23%) was obtained as brown crystals from a fraction eluted with ethyl acetate-hexane (1:1, volume ratio). melting point 186-187° C.

Example 134

7-[Methyl(2-thienylsulfonyl)amino]-1H-indole-2-carboxamide

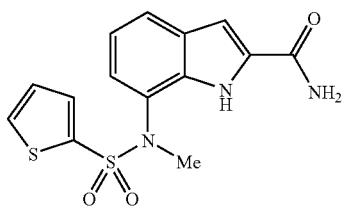

To a mixture of 7-[methyl(2-thienylsulfonyl)amino]-1H-indole-2-carboxylic acid (17.20 g), 1H-1,2,3-benzotriazol-1-ol (8.29 g) and N,N-dimethylformamide (150 mL) was added N-[3-(dimethylamino)propyl]-N'-ethylcarbodiimide hydrochloride (11.8 g) at room temperature, and the mixture was stirred at 50° C. for 20 min. The mixture was allowed to warm to room temperature and 28% aqueous ammonia (3.4 mL) was added. The reaction mixture was stirred at room temperature for 2 hr, and water was added. The mixture was acidified with 10% aqueous citric acid solution, and the resulting crystals were filtrated, washed with water and cold ethyl acetate, and dried to give the title compound (11.47 g, yield 67%) as colorless crystals. melting point 244-245° C.

Example 135

Ethyl 3-(2-{7-[methyl(2-thienylsulfonyl)amino]-1H-indol-2-yl}-1,3-thiazol-5-yl)propanate

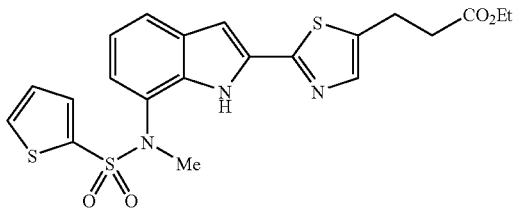 [SMILES: CCOC(=O)CCc1cnc(-c2cc3cccc(N(C)S(=O)(=O)c4cccs4)c3[nH]2)s1]

A mixture of 7-[methyl(2-thienylsulfonyl)amino]-1H-indole-2-carbothioamide (4.00 g), ethyl 4-bromo-5-oxopentanoate (3.80 g) and N,N-dimethylacetamide (25 mL) was stirred at 90° C. for 2 hr. Water was added to the reaction mixture, and the mixture was extracted with ethyl acetate. The ethyl acetate layer was washed with saturated brine, dried (MgSO$_4$) and concentrated. The obtained residue was subjected to silica gel column chromatography and the title compound (3.79 g, yield 70%) was obtained as yellow crystals from a fraction eluted with tetrahydrofuran-hexane (2:3, volume ratio). melting point 126-127° C.

Example 136

3-(2-{7-[Methyl(2-thienylsulfonyl)amino]-1H-indol-2-yl}-1,3-thiazol-5-yl)propanoic acid

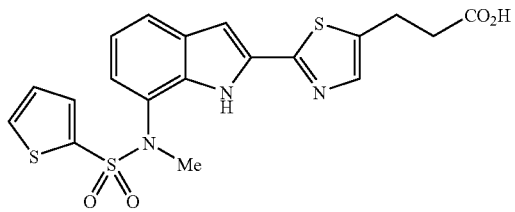 [SMILES: CN(c1cccc2cc(-c3ncc(CCC(=O)O)s3)[nH]c12)S(=O)(=O)c1cccs1]

A mixture of ethyl 3-(2-{7-[methyl(2-thienylsulfonyl)amino]-1H-indol-2-yl}-1,3-thiazol-5-yl)propanate (3.58 g), 2N aqueous sodium hydroxide solution (10.0 mL), tetrahydrofuran (10 mL) and methanol (10 mL) was stirred at 60° C. for 1 hr. The reaction mixture was concentrated, and water was added to the residue. The mixture was acidified with 10% aqueous citric acid solution, and the resulting crystals were filtrated, washed with water, and dried to give the title compound (3.34 g, yield 99%) as pale-yellow crystals. melting point 234-235° C.

Example 137

Ethyl (2-{7-[methyl(2-thienylsulfonyl)amino]-1H-indol-2-yl}-1,3-thiazol-5-yl)acetate

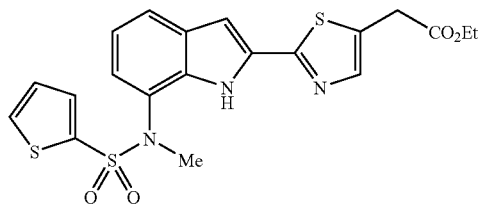 [SMILES: CCOC(=O)Cc1cnc(-c2cc3cccc(N(C)S(=O)(=O)c4cccs4)c3[nH]2)s1]

A mixture of 7-[methyl(2-thienylsulfonyl)amino]-1H-indole-2-carbothioamide (0.40 g), ethyl 3-bromo-4-oxobutyrate (0.48 g) and N,N-dimethylacetamide (25 mL) was stirred at 90° C. for 2 hr. Water was added to the reaction mixture, and the mixture was extracted with ethyl acetate. The ethyl acetate layer was washed with saturated brine, dried (MgSO$_4$) and concentrated. The obtained residue was subjected to silica gel column chromatography and the title compound (0.28 g, yield 55%) was obtained as pale-yellow crystals from a fraction eluted with ethyl acetate-hexane (2:3, volume ratio). melting point 126-127° C.

Example 138

(2-{7-[Methyl(2-thienylsulfonyl)amino]-1H-indol-2-yl}-1,3-thiazol-5-yl)acetic acid

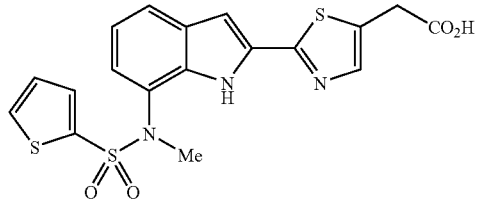 [SMILES: CN(c1cccc2cc(-c3ncc(CC(=O)O)s3)[nH]c12)S(=O)(=O)c1cccs1]

A mixture of ethyl 2-{7-[methyl(2-thienylsulfonyl)amino]-s 1H-indol-2-yl}-1,3-thiazol-5-yl)acetate (0.21 g), 1N aqueous sodium hydroxide solution (1.3 mL), tetrahydrofuran (4 mL) and methanol (4 mL) was stirred at 60° C. for 1 hr. The reaction mixture was concentrated, and water was added to the residue. The mixture was acidified with 10% aqueous citric acid solution, and the resulting crystals were filtrated, washed with water, and dried to give the title compound (0.16 g, yield 82%) as pale-yellow crystals. melting point 242-243° C. (decomposition).

Example 139

N-{2-[4-(Chloromethyl)-1,3-thiazol-2-yl]-1H-indol-7-yl}-N-methylthiophene-2-sulfonamide

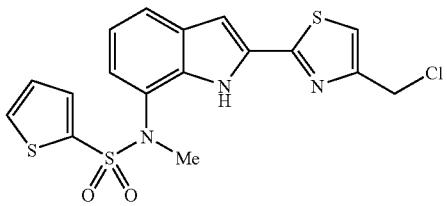 [SMILES: CN(c1cccc2cc(-c3nc(CCl)cs3)[nH]c12)S(=O)(=O)c1cccs1]

A mixture of 7-[methyl(2-thienylsulfonyl)amino]-1H-indole-2-carbothioamide (0.46 g), 1,3-dichloro-2-propanone (0.33 g) and N,N-dimethylacetamide (6 mL) was stirred at 80° C. for 2 hr. Water was added to the reaction mixture, and the mixture was extracted with ethyl acetate. The ethyl acetate layer was washed with saturated brine, dried (MgSO$_4$) and concentrated. The obtained residue was subjected to silica gel column chromatography and the title compound (0.45 g, yield 85%) was obtained as colorless crystals from a fraction eluted with ethyl acetate-hexane (2:3, volume ratio). melting point 153-154° C.

Example 140

Diethyl [(2-{7-[methyl(2-thienylsulfonyl)amino]-1H-indol-2-yl}-1,3-thiazol-4-yl)methyl]malonate

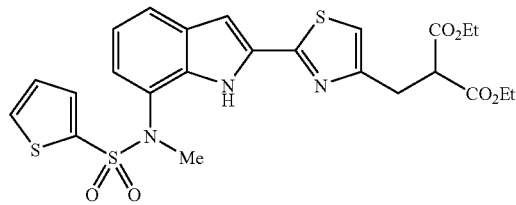 [SMILES: CCOC(=O)C(Cc1csc(-c2cc3cccc(N(C)S(=O)(=O)c4cccs4)c3[nH]2)n1)C(=O)OCC]

To a suspension of sodium hydride (60% in oil, 0.15 g) in N,N-dimethylformamide (10 mL) was added diethyl malonate (0.53 g) at 0° C., and the mixture was stirred for 30 min. To the reaction mixture was added N-{2-[4-(chloromethyl)-1,3-thiazol-2-yl]-1H-indol-7-yl}-N-methylthiophene-2-sulfonamide (0.45 g) at 0° C., and the mixture was stirred at room temperature for 3 hr. To the reaction mixture was added 10% citric acid was added, and the mixture was extracted with ethyl acetate. The ethyl acetate layer was washed with saturated brine, dried (MgSO₄) and concentrated. The obtained residue was subjected to silica gel column chromatography and the title compound (0.43 g, yield 72%) was obtained as a colorless oil from a fraction eluted with ethyl acetate-hexane (2:3, volume ratio).

¹H-NMR (CDCl₃) δ:1.27 (6H, t, J=7.1 Hz), 3.36 (3H, s), 3.41 (2H, d, J=7.5 Hz), 4.04 (1H, t, J=7.5 Hz), 4.18-4.29 (4H, m), 6.53 (1H, d, J=7.8 Hz), 6.92-7.00 (3H, m), 7.12 (1H, dd, J=4.8, 3.6 Hz), 7.40 (1H, dd, J=3.6, 1.2 Hz), 7.55 (1H, d, J=8.1 Hz), 7.64 (1H, dd, J=4.8, 1.2 Hz), 9.50 (1H, brs).

Example 141

3-(2-{7-[Methyl(2-thienylsulfonyl)amino]-1H-indol-2-yl}-1,3-thiazol-4-yl)propanoic acid

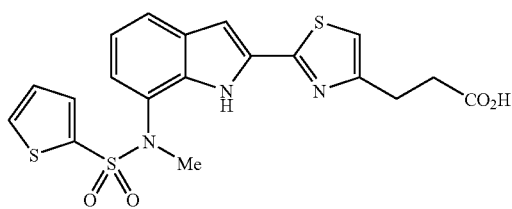 [SMILES: CN(c1cccc2cc(-c3nc(CCC(=O)O)cs3)[nH]c12)S(=O)(=O)c1cccs1]

A mixture of diethyl [(2-{7-[methyl(2-thienylsulfonyl)amino]-1H-indol-2-yl}-1,3-thiazol-4-yl)methyl]malonate (0.43 g), 1N aqueous sodium hydroxide solution (3.2 mL), tetrahydrofuran (4 mL) and methanol (4 mL) was stirred at 50° C. for 2 hr. The reaction mixture was concentrated, 1N hydrochloric acid (3.2 mL) and ethylene glycol (6 mL) were added to the residue, and the mixture was stirred at 140° C. for 1 hr. Water was added to the reaction mixture and the resulting crystals were collected by filtration, washed with water and dried. The obtained crystals were subjected to silica gel column chromatography and the title compound (0.13 g, yield 37%) was obtained as colorless crystals from a fraction eluted with tetrahydrofuran-hexane (1:1, volume ratio). The crystals were recrystallized from ethyl acetate-hexane. melting point 200-201° C.

Example 142

3-(2-{7-[Methyl(2-thienylsulfonyl)amino]-1H-indol-2-yl}-1,3-thiazol-4-yl)propanamide

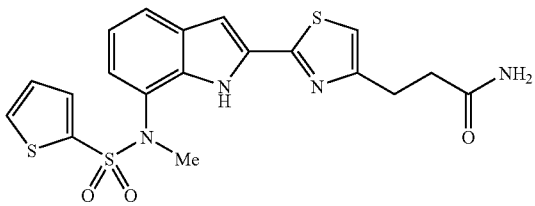 [SMILES: CN(c1cccc2cc(-c3nc(CCC(N)=O)cs3)[nH]c12)S(=O)(=O)c1cccs1]

To a mixture of 3-(2-{7-[methyl(2-thienylsulfonyl)amino]-1H-indol-2-yl}-1,3-thiazol-4-yl)propanoic acid (0.11 g), 1H-1,2,3-benzotriazol-1-ol (40 mg) and N,N-dimethylformamide (6 mL) was added N-[3-(dimethylamino)propyl]-N'-ethylcarbodiimide hydrochloride (57 mg) at room temperature. The mixture was stirred for 20 min, and 28% aqueous ammonia (0.08 mL) was added. The reaction mixture was stirred at room temperature for 1 hr, and water was added. The resulting crystals were filtrated, washed with water and dried. The obtained crystals were subjected to silica gel column chromatography and the title compound (0.04 g, yield 36%) was obtained as colorless crystals from a fraction eluted with tetrahydrofuran-hexane (4:1, volume ratio). The crystals were recrystallized from ethyl acetate-hexane. melting point 200-201° C.

Example 143

Ethyl (2-{7-[methyl(2-thienylsulfonyl)amino]-1H-indol-2-yl}-1,3-thiazol-4-yl)acetate

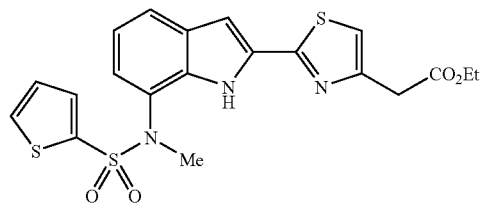 [SMILES: CCOC(=O)Cc1csc(-c2cc3cccc(N(C)S(=O)(=O)c4cccs4)c3[nH]2)n1]

A mixture of 7-[methyl(2-thienylsulfonyl)amino]-1H-indole-2-carbothioamide (0.40 g), ethyl 4-chloro-3-oxobutyrate (0.55 g) and N,N-dimethylacetamide (6 mL) was stirred at 80° C. for 3 hr. Water was added to the reaction mixture, and the mixture was extracted with ethyl acetate. The ethyl acetate layer was washed with saturated brine, dried (MgSO₄) and concentrated. The obtained residue was subjected to silica gel column chromatography and the title compound (0.38 g, yield 75%) was obtained as colorless crystals from a fraction eluted with ethyl acetate-hexane (2:3, volume ratio). melting point 117-118° C.

Example 144

(2-{7-[Methyl(2-thienylsulfonyl)amino]-1H-indol-2-yl}-1,3-thiazol-4-yl)acetic acid

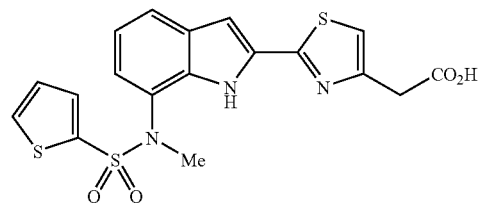 [SMILES: CN(c1cccc2cc(-c3nc(CC(=O)O)cs3)[nH]c12)S(=O)(=O)c1cccs1]

A mixture of ethyl (2-{7-[methyl(2-thienylsulfonyl)amino]-1H-indol-2-yl}-1,3-thiazol-4-yl)acetate (0.31 g), 1N aqueous sodium hydroxide solution (2.0 mL), tetrahydrofuran (6 mL) and methanol (6 mL) was stirred at 50° C. for 2 hr. To the reaction mixture was added 10% citric acid, and the mixture was extracted with ethyl acetate. The ethyl acetate layer was washed with saturated brine, dried (MgSO₄) and concentrated. The obtained residue was subjected to silica gel column chromatography and the title compound (0.18 g, yield 63%) was obtained as pale-yellow crystals from a fraction eluted with tetrahydrofuran-hexane (2:1, volume ratio). The crystals were recrystallized from ethyl acetate-hexane. melting point 214-215° C.

Example 145

N-Methyl-N-(2-{5-[(methylsulfonyl)methyl]-1,3-thiazol-2-yl}-1H-indol-7-yl)thiophene-2-sulfonamide

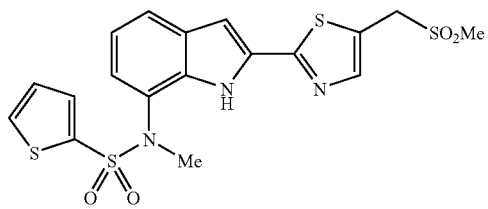 [SMILES: CN(c1cccc2cc(-c3ncc(CS(C)(=O)=O)s3)[nH]c12)S(=O)(=O)c1cccs1]

To a mixture of N-{2-[5-(hydroxymethyl)-1,3-thiazol-2-yl]-1H-indol-7-yl}-N-methylthiophene-2-sulfonamide (0.40 g), methanesulfonyl chloride (0.30 mL) and tetrahydrofuran (15 ml) was added triethylamine (0.54 mL), and the mixture was stirred at 50° C. for 2 hr. Water was added to the reaction mixture, and the mixture was extracted with ethyl acetate. The ethyl acetate layer was washed with saturated brine, dried (MgSO$_4$) and concentrated to give brown crude crystals.

A mixture of the obtained crystals, sodium methylsulfinate (0.40 g), potassium carbonate (0.14 g) and N,N-dimethylformamide (8 mL) was stirred at room temperature for 2 hr. Water was added to the reaction mixture, and the obtained crystals were filtered, washed with water and dried. The obtained crystals were subjected to silica gel column chromatography and the title compound (0.22 g, yield 47%) was obtained as yellow crystals from a fraction eluted with tetrahydrofuran-hexane (2:1, volume ratio). The crystals were recrystallized from ethanol. melting point 242-243° C.

Example 146

N-Methyl-N-{2-[5-(morpholin-4-ylmethyl)-1,3-thiazol-2-yl]-1H-indol-7-yl}thiophene-2-sulfonamide

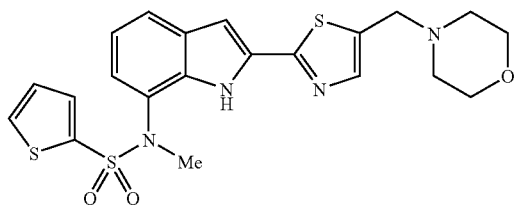 [SMILES: CN(c1cccc2cc(-c3ncc(CN4CCOCC4)s3)[nH]c12)S(=O)(=O)c1cccs1]

To a mixture of N-{2-[5-(hydroxymethyl)-1,3-thiazol-2-yl]-1H-indol-7-yl}-N-methylthiophene-2-sulfonamide (0.20 g), methanesulfonyl chloride (0.15 mL) and tetrahydrofuran (10 ml) was added triethylamine (0.27 mL) and the mixture was stirred at 50° C. for 2 hr. Water was added to the reaction mixture, and the mixture was extracted with ethyl acetate. The ethyl acetate layer was washed with saturated brine, dried (MgSO$_4$) and concentrated to give brown crude crystals.

A mixture of the obtained crystals, morpholine (0.15 g) and N,N-dimethylformamide (8 mL) was stirred at 50° C. for 3 hr. Water was added to the reaction mixture, and the mixture was extracted with ethyl acetate. The ethyl acetate layer was washed with saturated brine, dried (MgSO$_4$) and concentrated. The residue was subjected to silica gel column chromatography and the title compound (0.09 g, yield 39%) was obtained as colorless crystals from a fraction eluted with tetrahydrofuran-hexane (2:1, volume ratio). The crystals were recrystallized from ethyl acetate-hexane. melting point 181-182° C.

Example 147

N-[2-(Hydrazinocarbonyl)-1H-indol-7-yl]-N-methylthiophene-2-sulfonamide

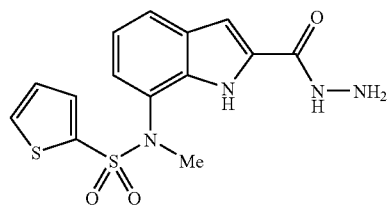 [SMILES: CN(c1cccc2cc(C(=O)NN)[nH]c12)S(=O)(=O)c1cccs1]

To a mixture of 7-[methyl(2-thienylsulfonyl)amino]-1H-indole-2-carboxylic acid (1.00 g), 1H-1,2,3-benzotriazol-1-ol (0.48 g) and N,N-dimethylformamide (10 mL) was added N-[3-(dimethylamino)propyl]-N'-ethylcarbodiimide hydrochloride (0.68 g) at room temperature. The mixture was stirred at 50° C. for 30 min, and hydrazine monohydrate (0.74 g) was added. The reaction mixture was stirred at room temperature for 1 hr, and water was added. The resulting crystals were filtered, washed with water, and dried to give the title compound (0.88 g, yield 84%) as colorless crystals. melting point 273-274° C. (decomposition).

Example 148

Ethyl 3-[2-({7-[methyl(2-thienylsulfonyl)amino]-1H-indol-2-yl}carbonyl)hydrazino]-3-oxopropanoate

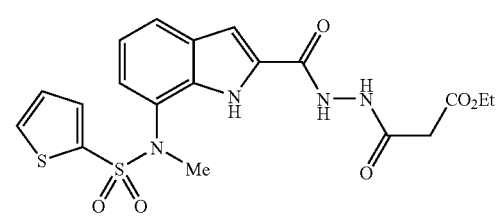 [SMILES: CCOC(=O)CC(=O)NNC(=O)c1cc2cccc(N(C)S(=O)(=O)c3cccs3)c2[nH]1]

To a solution of N-[2-(hydrazinocarbonyl)-1H-indol-7-yl]-N-methylthiophene-2-sulfonamide (0.88 g) in N,N-dimethylacetamide (16 mL) was added ethyl 3-chloro-3-oxopropanoate (0.35 mL) at 0° C., and the mixture was stirred at room temperature for 1 hr. Water was added to the reaction mixture, and the mixture was extracted with ethyl acetate. The ethyl acetate layer was washed with saturated brine, dried (MgSO$_4$) and concentrated. Diethyl ether was added to the obtained oil, and the resulting crystals were filtered, washed

Example 149

Ethyl (5-{7-[methyl(2-thienylsulfonyl)amino]-1H-indol-2-yl}-1,3,4-thiadiazol-2-yl)acetate

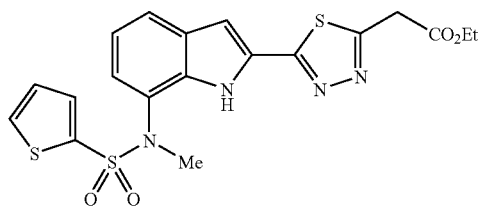

A mixture of ethyl 3-[2-({7-[methyl(2-thienylsulfonyl)amino]-1H-indol-2-yl}carbonyl)hydrazino]-3-oxopropanoate (0.96 g), Lawesson's reagent (0.97 g) and tetrahydrofuran (20 mL) was stirred at 50° C. for 2 hr. The reaction mixture was concentrated, and the residue was subjected to silica gel column chromatography, and the title compound (0.70 g, yield 71%) was obtained as colorless crystals from a fraction eluted with ethyl acetate-hexane (1:1, volume ratio). The crystals were recrystallized from ethyl acetate-hexane. melting point 201-202° C.

Example 150

N-Methyl-N-(2-{5-[3-(morpholin-4-yl)-3-oxopropyl]-1,3-thiazol-2-yl}-1H-indol-7-yl)thiophene-2-sulfonamide

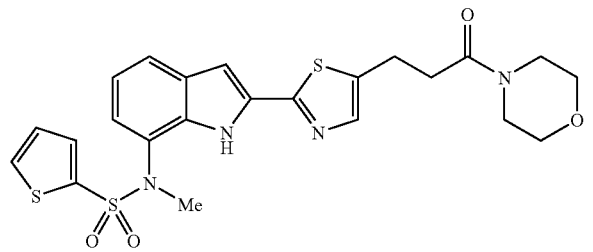 [SMILES: CN(c1cccc2cc(-c3ncc(CCC(=O)N4CCOCC4)s3)[nH]c12)S(=O)(=O)c1cccs1]

To a mixture of 3-(2-{7-[methyl(2-thienylsulfonyl)amino]-1H-indol-2-yl}-1,3-thiazol-5-yl)propanoic acid (0.30 g), 1H-1,2,3-benzotriazol-1-ol (0.11 g) and N,N-dimethylformamide (8 mL) was added N-[3-(dimethylamino)propyl]-N'-ethylcarbodiimide hydrochloride (0.15 g) at room temperature. The mixture was stirred at room temperature for 2 hr, and morpholine (0.30 g) was added. The reaction mixture was stirred at room temperature overnight, and water was added. The resulting crystals were collected by filtration and dried. The obtained crystals were subjected to silica gel column chromatography and the title compound (0.24 g, yield 69%) was obtained as yellow crystals from a fraction eluted with tetrahydrofuran-hexane (2:1, volume ratio). The crystals were recrystallized from ethyl acetate-hexane. melting point 160-161° C.

Example 151

N-{2-[5-(2-Cyanoethyl)-1,3-thiazol-2-yl]-1H-indol-7-yl}-N-methylthiophene-2-sulfonamide

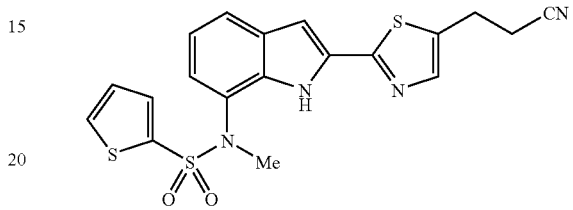

To a mixture of 3-(2-{7-[methyl(2-thienylsulfonyl)amino]-1H-indol-2-yl}-1,3-thiazol-5-yl)propanamide (1.32 g) and pyridine (15 mL) was added trifluoroacetic anhydride (0.90 mL) at 0° C. over 15 min. The reaction mixture was stirred at room temperature for 2 hr and concentrated. 10% Aqueous citric acid solution was added to the residue. The resulting crystals were collected by filtration, washed with water and dried. The obtained crystals were subjected to silica gel column chromatography and the title compound (1.20 g, yield 95%) was obtained as yellow crystals from a fraction eluted with tetrahydrofuran-hexane (2:1, volume ratio). melting point 207-208° C.

Example 152

3-(2-{7-[Methyl(2-thienylsulfonyl)amino]-1H-indol-2-yl}-1,3-thiazol-5-yl)propanamide

To a mixture of 3-(2-{7-[methyl(2-thienylsulfonyl)amino]-1H-indol-2-yl}-1,3-thiazol-5-yl)propanoic acid (1.15 g), 1H-1,2,3-benzotriazol-1-ol (0.54 g) and N,N-dimethylformamide (14 mL) was added N-[3-(dimethylamino)propyl]-N'-ethylcarbodiimide hydrochloride (0.77 g) at room temperature. The mixture was stirred at room temperature for 1 hr, and 28% aqueous ammonia (1.0 mL) was added. The reaction mixture was stirred at room temperature overnight, and water was added. The resulting crystals were filtrated,

Example 153

4-Oxo-N-[2-(1,3-thiazol-2-yl)-1H-indol-7-yl]-4-(2-thienyl)butanamide

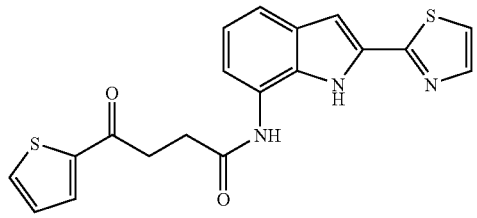 [SMILES: O=C(CCC(=O)c1cccs1)Nc1cccc2cc(-c3nccs3)[nH]c12]

To a mixture of 2-(1,3-thiazol-2-yl)-1H-indole-7-amine (0.31 g), 4-oxo-4-(2-thienyl)butanoic acid (0.89 g), 1H-1,2,3-benzotriazol-1-ol (0.75 g) and N,N-dimethylformamide (20 mL) was added N-[3-(dimethylamino)propyl]-N'-ethylcarbodiimide hydrochloride (1.06 g), and the mixture was stirred at room temperature overnight. Water was added to the reaction mixture, and the mixture was extracted with ethyl acetate. The ethyl acetate layer was washed with saturated brine, dried ($MgSO_4$) and concentrated. The residue was subjected to silica gel column chromatography and the title compound (1.21 g, yield. 69%) was obtained as colorless crystals from a fraction eluted with ethyl acetate-hexane (3:1, volume ratio). melting point 140-141° C.

Example 154

4-Hydroxy-N-[2-(1,3-thiazol-2-yl)-1H-indol-7-yl]-4-(2-thienyl)butanamide

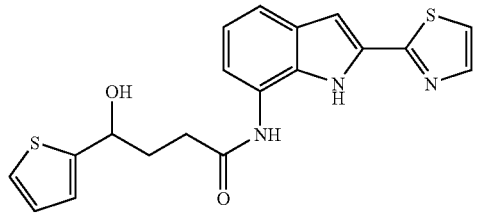 [SMILES: O=C(CCC(O)c1cccs1)Nc1cccc2cc(-c3nccs3)[nH]c12]

To a mixture of 4-oxo-N-[2-(1,3-thiazol-2-yl)-1H-indol-7-yl]-4-(2-thienyl)butanamide (1.43 g), tetrahydrofuran (10 ml) and methanol (10 ml) was added sodium borohydride (0.16 g) at 0° C., and the mixture was stirred at the same temperature for 1 hr. To the reaction mixture was added 10% aqueous citric acid solution, and the mixture was extracted with ethyl acetate. The ethyl acetate layer was washed with saturated brine, dried ($MgSO_4$) and concentrated. The residue was subjected to silica gel column chromatography and the title compound (1.21 g, yield 84%) was obtained as colorless crystals from a fraction eluted with ethyl acetate. melting point 155-157° C.

Example 155

N-Methyl-N-(2-{5-[2-(2H-tetrazol-5-yl)ethyl]-1,3-thiazol-2-yl}-1H-indol-7-yl)thiophene-2-sulfonamide

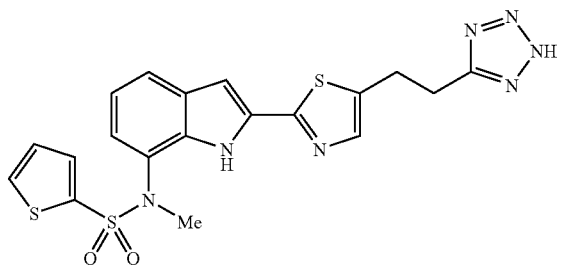 [SMILES: CN(c1cccc2cc(-c3ncc(CCc4nn[nH]n4)s3)[nH]c12)S(=O)(=O)c1cccs1]

A mixture of N-{2-[5-(2-cyanoethyl)-1,3-thiazol-2-yl]-1H-indol-7-yl}-N-methylthiophene-2-sulfonamide (0.30 g), dibutyltin oxide (35 mg), trimethylsilylazide (0.74 mL) and tetrahydrofuran (10 mL) was heated under reflux for 3 days. The reaction mixture was concentrated. The residue was subjected to silica gel column chromatography, and the title compound (0.22 g, yield 67%) was obtained as yellow crystals from a fraction eluted with tetrahydrofuran-methanol (9:1, volume ratio). The crystals were recrystallized from ethyl acetate. melting point 211-212° C.

Example 156

N-{2-[5-(3-Hydrazino-3-oxopropyl)-1,3-thiazol 2-yl]-1H-indol-7-yl}-N-methylthiophene-2-sulfonamide

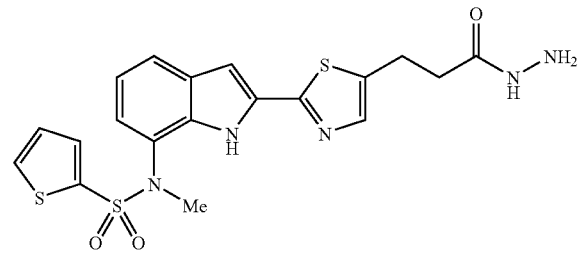 [SMILES: CN(c1cccc2cc(-c3ncc(CCC(=O)NN)s3)[nH]c12)S(=O)(=O)c1cccs1]

To a mixture of 3-(2-{7-[methyl(2-thienylsulfonyl)amino]-1H-indol-2-yl}-1,3-thiazol-5-yl)propanoic acid (0.50 g), 1H-1,2,3-benzotriazol-1-ol (0.18 g) and N,N-dimethylformamide (15 mL) was added N-[3-(dimethylamino)propyl]-N'-ethylcarbodiimide hydrochloride (0.26 g) at room temperature. The mixture was stirred at room temperature for 1 hr and hydrazine monohydrate (0.28 g) was added. The reaction mixture was stirred at room temperature overnight, and water was added. The resulting crystals were filtrated,

Example 157

N-Methyl-N-(2-{5-[2-(5-oxo-4,5-dihydro-1,3,4-oxadiazol-2-yl)ethyl]-1,3-thiazol-2-yl}-1H-indol-7-yl)thiophene-2-sulfonamide

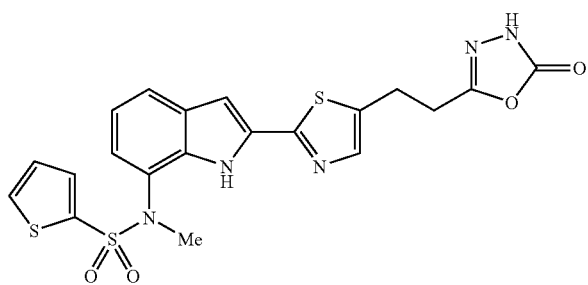 [SMILES: CN(c1cccc2cc(-c3ncc(CCc4n[nH]c(=O)o4)s3)[nH]c12)S(=O)(=O)c1cccs1]

A mixture of N-{2-[5-(3-hydrazino-3-oxopropyl)-1,3-thiazol-2-yl]-1H-indol-7-yl}-N-methylthiophene-2-sulfonamide (0.29 g), 1,1'-carbonylbis-1H-imidazole (0.22 g) and N,N-dimethylacetamide (15 mL) was stirred at room temperature for 2 hr. Water was added to the reaction mixture and the resulting crystals were collected by filtration, washed with water and dried. The obtained crystals were subjected to silica gel column chromatography and the title compound (0.20 g, yield 65%) was obtained as yellow crystals from a fraction eluted with tetrahydrofuran-hexane (2:1, volume ratio). The crystals were recrystallized from ethyl acetate. melting point 255-256° C.

Example 158

N-Methyl-N-(2-{5-[2-(5-oxo-4,5-dihydro-1,2,4-oxadiazol-3-yl)ethyl]-1,3-thiazol-2-yl}-1H-indol-7-yl)thiophene-2-sulfonamide

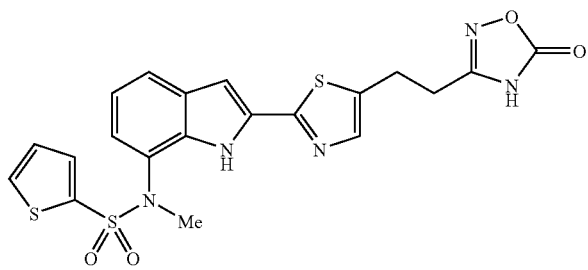 [SMILES: CN(c1cccc2cc(-c3ncc(CCc4noc(=O)[nH]4)s3)[nH]c12)S(=O)(=O)c1cccs1]

A mixture of N-{2-[5-(2-cyanoethyl)-1,3-thiazol-2-yl]-1H-indol-7-yl}-N-methylthiophene-2-sulfonamide (0.30 g), hydroxylamine hydrochloride (0.29 g), triethylamine (0.68 mL), methanol (6 mL) and tetrahydrofuran (4 mL) was heated under reflux overnight. The reaction mixture was concentrated, and water was added. The resulting crystals were collected by filtration, washed with water, and dried to give yellow crude crystals (0.31 g).

A mixture of the obtained crude crystals, 1,1'-carbonylbis-1H-imidazole (0.23 g) and N,N-dimethylacetamide (8 mL) was stirred at room temperature for 1 hr, and then stirred at 90° C. for 2 hr. To the reaction mixture was added 10% aqueous citric acid solution, and the mixture was extracted with ethyl acetate. The ethyl acetate layer was washed with saturated brine, dried (MgSO₄) and concentrated. The residue was subjected to silica gel column chromatography and the title compound (0.05 g, yield 14%) was obtained as colorless crystals from a fraction eluted with tetrahydrofuran-hexane (2:1, volume ratio). melting point>220° C. (decomposition).

Example 159

N-(Methylsulfonyl)-3-(2-{7-[methyl(2-thienylsulfonyl)amino]-1H-indol-2-yl}-1,3-thiazol-5-yl)propanamide

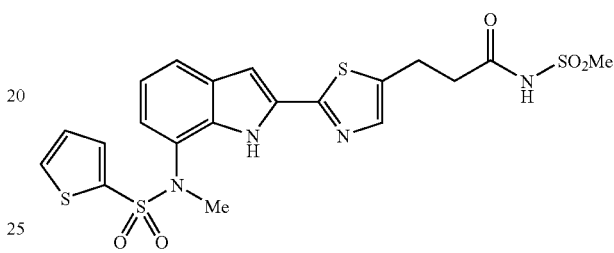

A mixture of 3-(2-{7-[methyl(2-thienylsulfonyl)amino]-1H-indol-2-yl}-1,3-thiazol-5-yl)propanoic acid (0.3.0 g), 1,1'-carbonylbis-1H-imidazole (0.27 g) and tetrahydrofuran (10 mL) was heated under reflux for 2 hr. The reaction mixture was cooled to room temperature, methanesulfonamide (0.32 g) and 1,8-diazabicyclo[5.4.0]-7-undecene (0.50 mL) were added, and the mixture was stirred at room temperature overnight. The reaction mixture was concentrated and 10% aqueous citric acid solution was added. The resulting crystals were collected by filtration, washed with water and dried. The obtained crystals were subjected to silica gel column chromatography and the title compound (0.21 g, yield 60%) was obtained as yellow crystals from a fraction eluted with tetrahydrofuran-hexane (3:1, volume ratio). The crystals were recrystallized from ethyl acetate. melting point 217-218° C.

Example 160

N-[2-(4,5-Dimethyl-1,3-thiazol-2-yl)-1H-indol-7-yl]thiophene-2-sulfonamide

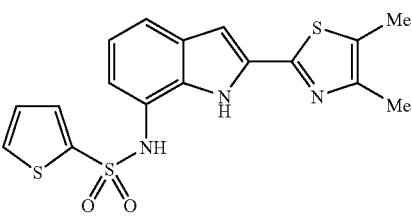 [SMILES: Cc1nc(-c2cc3cccc(NS(=O)(=O)c4cccs4)c3[nH]2)sc1C]

To a mixture of 2-(4,5-dimethyl-1,3-thiazol-2-yl)-1H-indole-7-amine (0.10 g) and pyridine (8 mL) was added thiophene-2-sulfonyl chloride (0.090 g) at 4° C., and the mixture was stirred at room temperature for 15 hr. The reaction solution was concentrated. The obtained residue was diluted with ethyl acetate, washed with aqueous citric acid solution and saturated brine, dried over-anhydrous magnesium sulfate, and concentrated under reduced pressure. The washed with water, and dried to give the title compound (0.29 g, yield 57%) as yellow crystals. melting point 224-226° C.

Example 161

5-Fluoro-7-[(2-thienylsulfonyl)amino]-1H-indole-2-carboxylic acid

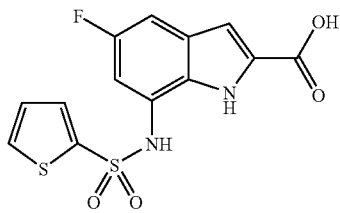 [SMILES: O=C(O)c1cc2cc(F)cc(NS(=O)(=O)c3cccs3)c2[nH]1]

To a mixed solution of ethyl 5-fluoro-7-[(2-thienylsulfonyl)amino]-1H-indole-2-carboxylate (0.24 g) in tetrahydrofuran (10 mL)-methanol (10 mL) was added aqueous solution (5 mL) of 85% potassium hydroxide (0.20 g), and the mixture was stirred at room temperature for 18 hr. The reaction solution was concentrated under reduced pressure, and aqueous citric acid solution was added to the obtained residue. The mixture was extracted with ethyl acetate, washed with saturated brine, dried over anhydrous magnesium sulfate, and concentrated under reduced pressure to give the title compound (205 mg, yield 93%) as pale-pink crystals. MS:341 (MH+).

Example 162

N-[2-(Benzylthio)-2-methylpropyl]-5-fluoro-7-[(2-thienylsulfonyl)amino]-1H-indole-2-carboxamide

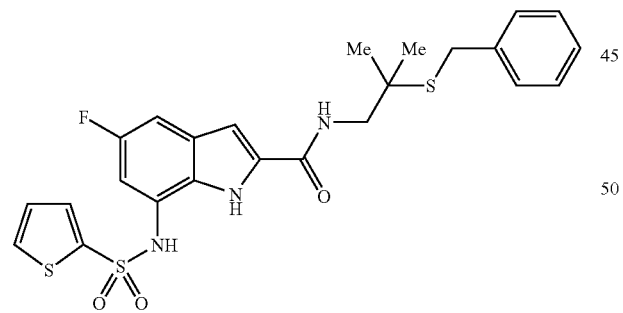

To a mixture of 5-fluoro-7-[(2-thienylsulfonyl)amino]-1H-indole-2-carboxylic acid (0.20 g), 2-(benzylthio)-2-methylpropylamine (0.13 g), 1H-1,2,3-benzotriazol-1-ol (0.11 g) and N,N-dimethylformamide (10 mL) was added N-[3-(dimethylamino)propyl]-N'-ethylcarbodiimide hydrochloride (0.14 g) at 4° C., and the mixture was stirred at room temperature for 18 hr. The reaction solution was diluted with ethyl acetate, washed with aqueous citric acid solution, aqueous sodium hydrogencarbonate solution and saturated brine, dried over anhydrous magnesium sulfate, and concentrated under reduced pressure. The obtained residue was subjected to silica gel column chromatography (ethyl acetate:hexane=2:8-4:6) to give the title compound (220 mg, crude yield 72%) as pale-purple crystals.

Example 163

N-[2-(5,5-Dimethyl-4,5-dihydro-1,3-thiazol-2-yl)-5-fluoro-1H-indol-7-yl]thiophene-2-sulfonamide

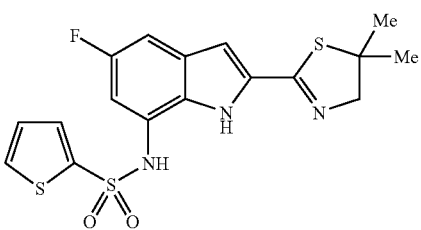 [SMILES: CC1(C)CN=C(c2cc3cc(F)cc(NS(=O)(=O)c4cccs4)c3[nH]2)S1]

A mixture of triphenylphosphine oxide (0.71 g), trifluoromethanesulfonic anhydride (0.22 mL), and dichloromethane (20 mL) was stirred for 15 min under ice-cooling. Then, N-[2-(benzylthio)-2-methylpropyl]-5-fluoro-7-[(2-thienylsulfonyl)amino]-1H-indole-2-carboxamide (0.23 g) was added, and the mixture was stirred for 5 hr under ice-cooling. The reaction solution was poured into aqueous sodium hydrogencarbonate solution and the mixture was extracted with dichloromethane. The aqueous layer was extracted with dichloromethane, and the combined dichloromethane layer was dried over anhydrous magnesium sulfate, and concentrated under reduced pressure. The obtained residue was subjected to silica gel column chromatography (ethyl acetate:hexane=1:9-3:7), and the obtained oil was crystallized from diethyl ether-hexane to give the title compound (23 mg, yield 13%) as colorless prism crystals. melting point 175-176° C.

Example 164

5-Fluoro-7-[methyl(2-thienylsulfonyl)amino]-N-[2-(tritylthio)ethyl]-1H-indole-2-carboxamide

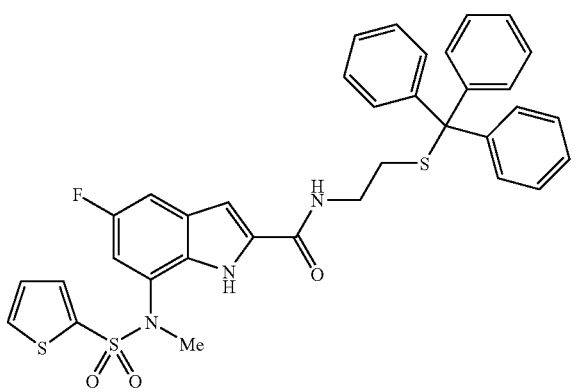 [SMILES: CN(c1cc(F)cc2cc(C(=O)NCCSC(c3ccccc3)(c3ccccc3)c3ccccc3)[nH]c12)S(=O)(=O)c1cccs1]

A mixed solution of ethyl 5-fluoro-1-(methoxymethyl)-7-[methyl(2-thienylsulfonyl)amino]-1H-indole-2-carboxylate (0.20 g), 6N hydrochloric acid (6 mL) and tetrahydrofuran (10 mL) was stirred at 60° C. for 18 hr. The reaction solution was concentrated under reduced pressure. Ethyl acetate was added to the obtained residue, and the mixture was washed with water and saturated brine, dried over anhydrous magnesium sulfate, and concentrated under reduced pressure. aqueous solution (5 mL) of 85% potassium hydroxide (0.12 g) was added to a mixed solution of the obtained residue in tetrahydrofuran (8 mL)-methanol (8 mL), and the mixture was stirred at room temperature for 18 hr. Aqueous citric acid solution was added to the reaction solution, and the mixture was extracted with ethyl acetate, washed with saturated brine, dried over anhydrous magnesium sulfate, and concentrated under reduced pressure.

The obtained crystals were added to a mixture of 2-(tritylthio)ethylamine hydrochloride (0.20 g), triethylamine (0.080 mL) and N,N-dimethylformamide (10 mL) under ice-cooling. Furthermore, 1H-1,2,3-benzotriazol-1-ol (0.094 g) and N-[3-(dimethylamino)propyl]-N'-ethylcarbodiimide hydrochloride (0.12 g) were added, and the mixture was stirred at room temperature for 15 hr. The reaction solution was diluted with ethyl acetate, washed with aqueous citric acid solution, aqueous sodium hydrogencarbonate solution and saturated brine, dried over anhydrous magnesium sulfate, and concentrated under reduced pressure. The obtained residue was subjected to silica gel column chromatography (ethyl acetate:hexane=1:4-2:3) to give the title compound (0.205 g, yield 67%) as colorless prism crystals.

$^1$H-NMR (CDCl$_3$) δ:2.55 (2H, t, J=6.4 Hz), 3.24-3.38 (2H, m), 3.30 (3H, s), 6.24-6.34 (1H, m), 6.40 (1H, dd, J=2.2, 9.8 Hz), 6.75 (1H, d, J=2.2 Hz), 7.12-7.48 (18H, m), 7.66 (1H, dd, J=1.2, 5.0 Hz), 9.48 (1H, brs).

Example 165

N-[2-(4,5-Dihydro-1,3-thiazol-2-yl)-5-fluoro-1H-indol-7-yl]-N-methylthiophene-2-sulfonamide

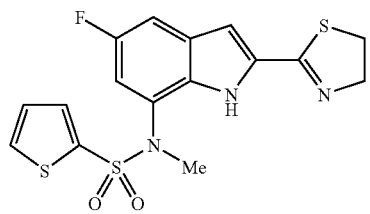 [SMILES: CN(c1cc(F)cc2cc(C3=NCCS3)[nH]c12)S(=O)(=O)c1cccs1]

A mixture of triphenylphosphine oxide (522 mg), trifluoromethanesulfonic anhydride (0.158 mL), and dichloromethane (10 mL) was stirred for 15 min under ice-cooling. Then, 5-fluoro-7-[methyl(2-thienylsulfonyl)amino]-N-[2-(tritylthio)ethyl]-1H-indole-2-carboxamide (205 mg) was added, and the mixture was stirred for 3 hr under ice-cooling. The reaction solution was poured into aqueous sodium hydrogencarbonate solution and extracted with dichloromethane. The aqueous layer was extracted with dichloromethane, and the combined dichloromethane layer was dried over anhydrous magnesium sulfate, and concentrated under reduced pressure. The obtained residue was subjected to silica gel column chromatography (ethyl acetate:hexane=2:8-5:5), and the obtained crystals were recrystallized from ethyl acetate-hexane to give the title compound (92 mg, yield 75%) as colorless prism crystals. melting point 188-189° C.

Example 166

Ethyl 7-[(2-thienylsulfonyl)amino]-5-(trifluoromethoxy)-1H-indole-2-carboxylate

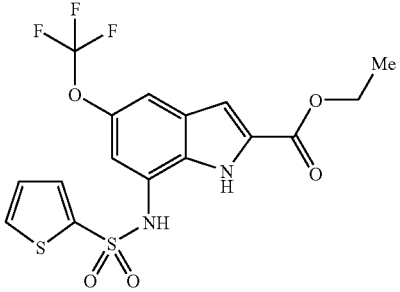 [SMILES: CCOC(=O)c1cc2cc(OC(F)(F)F)cc(NS(=O)(=O)c3cccs3)c2[nH]1]

A mixed solution of ethyl 1-(methoxymethyl)-7-[(2-thienylsulfonyl)amino]-5-(trifluoromethoxy)-1H-indole-2-carboxylate (105 mg), 6N hydrochloric acid (4 mL) and ethanol (4 mL) was stirred at 80° C. for 3 hr. The reaction solution was diluted with ethyl acetate, washed with water and saturated brine, dried over anhydrous magnesium sulfate, and concentrated under reduced pressure. The obtained colorless crystals were suspended in dichloromethane (10 mL), and thionyl chloride (0.20 mL) and N,N-dimethylformamide (1 drop) were added. The mixture was stirred at 50° C. for 2 hr. Ethanol (2 mL) and triethylamine (1 mL) were added to the reaction solution, and the mixture was stirred at 50° C. for 2 hr. The reaction solution was concentrated under reduced pressure. The obtained residue was diluted with ethyl acetate, washed with aqueous citric acid solution and saturated brine, dried over anhydrous magnesium sulfate, and concentrated under reduced pressure. The obtained residue was subjected to silica gel column chromatography (ethyl acetate:hexane=1:9-2:8), and the obtained oil was crystallized from diethyl ether-hexane to give the title compound (41 mg, yield 43%) as colorless crystals. melting point 192-193° C.

Example 167

7-[Methyl(2-thienylsulfonyl)amino]-5-(trifluoromethoxy)-1H-indole-2-carboxylic acid

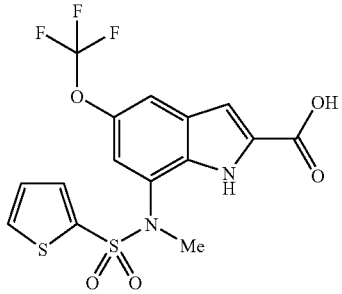 [SMILES: CN(c1cc(OC(F)(F)F)cc2cc(C(=O)O)[nH]c12)S(=O)(=O)c1cccs1]

A mixed solution of ethyl 1-(methoxymethyl)-7-[methyl(2-thienylsulfonyl)amino]-5-(trifluoromethoxy)-1H-indole-2-carboxylate (0.75 g), 6N hydrochloric acid (15 mL), tetrahydrofuran (4 mL) and ethanol (16 mL) was stirred at 80° C. for 18 hr. The reaction solution was concentrated under reduced pressure. The obtained residue was diluted with ethyl acetate, washed with saturated brine, dried over anhydrous magnesium sulfate, and concentrated under reduced pressure. The obtained colorless solid was dissolved in a mixed solution of tetrahydrofuran (10 mL) and methanol (10 mL). aqueous solution (5 mL) of 85% potassium hydroxide (0.35 g) was added, and the mixture was stirred at room temperature for 18 hr. Aqueous citric acid solution was added to the reaction solution, and the mixture was extracted with ethyl acetate, washed with saturated brine, dried over anhydrous magnesium sulfate, and concentrated under reduced pressure to give the title compound (0.65 g, yield 100%) as pale-pink crystals. The obtained crystals were washed with ethyl acetate-hexane to give colorless prism crystals. MS:421 (MH$^+$). melting point 245-246° C.

Example 168

7-[Methyl(2-thienylsulfonyl)amino]-N-[2-(tritylthio) ethyl]-5-(trifluoromethoxy)-1H-indole-2-carboxamide

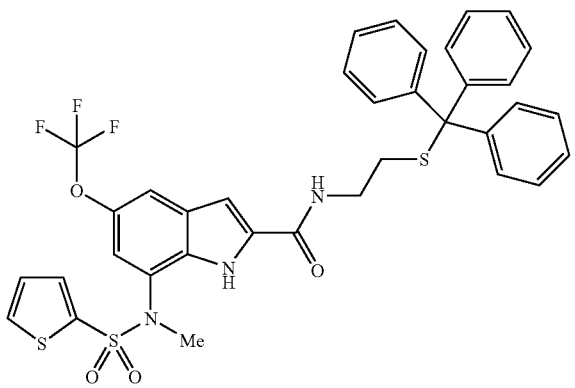 [SMILES: CN(c1cc(OC(F)(F)F)cc2cc(C(=O)NCCSC(c3ccccc3)(c3ccccc3)c3ccccc3)[nH]c12)S(=O)(=O)c1cccs1]

To a mixture of 7-[methyl(2-thienylsulfonyl)amino]-5-(trifluoromethoxy)-1H-indole-2-carboxylic acid (0.30 g), 2-(tritylthio)ethylamine hydrochloride (0.32 g), triethylamine (0.13 mL) and N,N-dimethylformamide (10 mL) were added 1H-1,2,3-benzotriazol-1-ol (0.15 g) and N-[3-(dimethylamino)propyl]-N'-ethylcarbodiimide hydrochloride (0.19 g) under ice-cooling, and the mixture was stirred at room temperature for 18 hr. The reaction solution was diluted with ethyl acetate, washed with water, aqueous sodium hydrogencarbonate solution and saturated brine, dried over anhydrous magnesium sulfate, and concentrated under reduced pressure. The obtained residue was subjected to silica gel column chromatography (ethyl acetate:hexane=5:95-20:80), and the obtained crystals were washed with diethyl ether-hexane to give the title compound (160 mg, yield 31%) as colorless crystals. melting point 222-223° C.

Example 169

N-[2-(4,5-Dihydro-1,3-thiazol-2-yl)-5-(trifluoromethoxy)-1H-indol-7-yl]-N-methylthiophene-2-sulfonamide

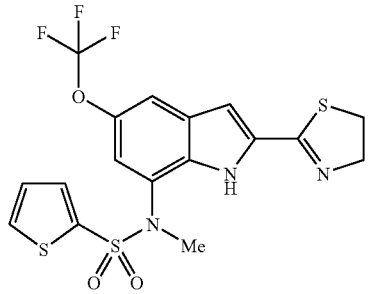 [SMILES: CN(c1cc(OC(F)(F)F)cc2cc(C3=NCCS3)[nH]c12)S(=O)(=O)c1cccs1]

A mixture of triphenylphosphine oxide (0.37 g), trifluoromethanesulfonic anhydride (0.11 mL), and dichloromethane (5 mL) was stirred for 15 min under ice-cooling. Then, 7-[methyl(2-thienylsulfonyl)amino]-N-[2-(tritylthio) ethyl]-5-(trifluoromethoxy)-1H-indole-2-carboxamide (0.16 g) was added, and the mixture was stirred for 3 hr under ice-cooling. The reaction solution was poured into aqueous sodium hydrogencarbonate solution and extracted with dichloromethane. The aqueous layer was extracted with dichloromethane, and the combined dichloromethane layer was dried over anhydrous magnesium sulfate, and concentrated under reduced pressure. The obtained residue was subjected to silica gel column chromatography (ethyl acetate:hexane=1:4-1:2), and the obtained crystals were washed with diethyl ether-hexane to give the title compound (84 mg, yield 82%) as colorless crystals. melting point 179-180° C.

Example 170

N-[(1R)-1-[(Benzylthio)methyl]-2-oxo-2-(propylamino)ethyl]-7-[(2-thienylsulfonyl)amino]-1H-indole-2-carboxamide

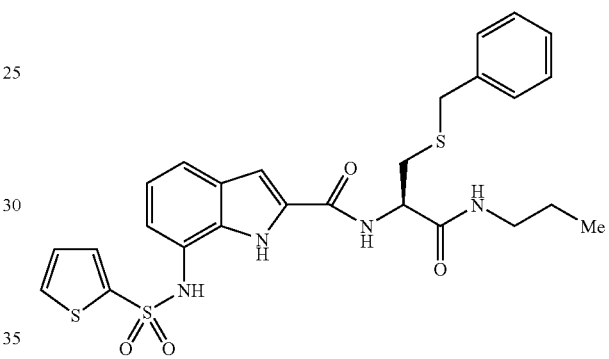

To a mixture of 7-[(2-thienylsulfonyl)amino]-1H-indole-2-carboxylic acid (0.34 g), S-benzyl-N-propyl-L-cysteinamide (0.27 g), 1H-1,2,3-benzotriazol-1-ol (0.22 g) and N,N-dimethylformamide (15 ml) was added N-[3-(dimethylamino)propyl]-N'-ethylcarbodiimide hydrochloride (0.27 g) at 4° C., and the mixture was stirred at room temperature for 18 hr. The reaction solution was diluted with ethyl acetate, washed with water, aqueous sodium hydrogencarbonate solution and saturated brine, dried over anhydrous magnesium sulfate, and concentrated under reduced pressure. The obtained residue was subjected to silica gel column chromatography (ethyl acetate:hexane=1:9-1:1), and the obtained crystals were washed with ethyl acetate-hexane to give the title compound (285 mg, yield 49%) as colorless crystals. melting point 124-125° C.

Example 171

Methyl 7-[(2-thienylsulfonyl)amino]-1H-pyrrolo[2,3-c]pyridine-2-carboxylate

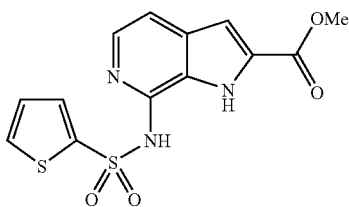 [SMILES: COC(=O)c1cc2ccnc(NS(=O)(=O)c3cccs3)c2[nH]1]

A mixed solution of methyl 7-amino-1H-pyrrolo[2,3-c]pyridine-2-carboxylate (0.40 g), thiophene-2-sulfonyl chloride (0.48 g) and N,N-dimethylacetamide (20 ml) was stirred at 120° C. for 18 hr. The reaction solution was diluted with ethyl acetate, washed with aqueous sodium hydrogencarbonate solution, water and saturated brine, dried over anhydrous magnesium sulfate, and concentrated under reduced pressure. The obtained residue was subjected to silica gel column chromatography (ethyl acetate:hexane=2:8-1:1) to give the title compound (10.5 mg, yield 1.5%) as pale-yellow crystals. melting point 159-160° C.

Example 172

N-[2-(2-Chloroacetyl)-1H-indol-7-yl]-N-methylthiophene-2-sulfonamide

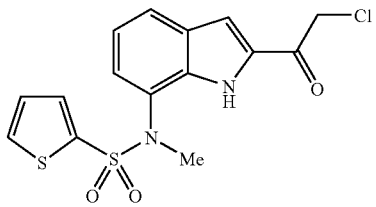 [SMILES: CN(c1cccc2cc(C(=O)CCl)[nH]c12)S(=O)(=O)c1cccs1]

A mixed solution of 7-[(2-thienylsulfonyl)amino]-1H-indole-2-carboxylic acid (0.50 g), thionyl chloride (0.50 mL), tetrahydrofuran (6 mL) and toluene (10 mL) was stirred at 80° C. for 2 hr. The reaction solution was concentrated under reduced pressure. The obtained residue was dissolved in a mixed solution of tetrahydrofuran and toluene, and concentration again under reduced pressure. The obtained solid was dissolved in tetrahydrofuran (10 mL) and ice-cooled. A solution (0.082 M, 50 mL) of diazomethane in ether was added by small portions. The solution was stirred at room temperature for 18 hr, and the reaction solution was ice-cooled. Then, 4N hydrogen chloride-ethyl acetate solution (1 mL) was added, and the mixture was stirred at the same temperature for 3 hr. The reaction solution was diluted with ethyl acetate, washed with water, aqueous sodium hydrogencarbonate solution and saturated brine, dried over anhydrous magnesium sulfate, and concentrated under reduced pressure to give the title compound (575 mg, crude yield 100%) as a pale-yellow solid. MS:369 (MH$^+$).

Example 173

N-Methyl-N-[2-(2-methyl-1,3-thiazol-4-yl)-1H-indol-7-yl]thiophene-2-sulfonamide

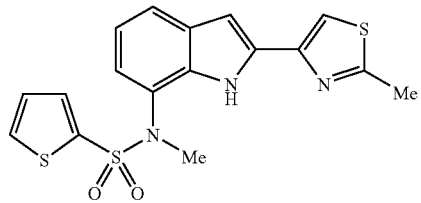 [SMILES: Cc1nc(-c2cc3cccc(N(C)S(=O)(=O)c4cccs4)c3[nH]2)cs1]

A mixed solution of N-[2-(2-chloroacetyl)-1H-indol-7-yl]-N-methylthiophene-2-sulfonamide (570 mg), thioacetamide (0.20 g) and N,N-dimethylacetamide (15 ml) was stirred at 80° C. for 2 hr. The reaction solution was diluted with ethyl acetate, washed with water, aqueous sodium hydrogencarbonate solution and saturated brine, dried over anhydrous magnesium sulfate, and concentrated under reduced pressure. The obtained residue was subjected to silica gel column chromatography (ethyl acetate:hexane=1:9-4:6), the obtained crude product was purified by preparative HPLC, and the obtained oil was crystallized from ethyl acetate-hexane to give the title compound (64 mg, yield 11%) as colorless needle crystals. melting point 161-162° C. MS:390 (MH$^+$).

Example 174

N-Methyl-N-{2-[2-(methylamino)-1,3-thiazol-4-yl]-1H-indol-7-yl}thiophene-2-sulfonamide

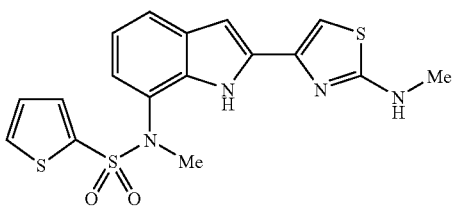 [SMILES: CNc1nc(-c2cc3cccc(N(C)S(=O)(=O)c4cccs4)c3[nH]2)cs1]

A mixed solution of N-[2-(2-chloroacetyl)-1H-indol-7-yl]-N-methylthiophene-2-sulfonamide (100 mg), N-methylthiourea (30 mg) and N,N-dimethylacetamide (6 ml) was stirred at 60° C. for 5 hr. The reaction solution was diluted with ethyl acetate, washed with water and saturated brine, dried over anhydrous magnesium sulfate, and concentrated under reduced pressure. The obtained residue was subjected to silica gel column chromatography (ethyl acetate:hexane=1:3-1:1), and the obtained oil was crystallized from ethyl acetate-hexane to give the title compound (84 mg, yield 77%) as pale-yellow prism crystals. melting point 162-163° C. MS:405 (MH$^+$).

Example 175

4-Methyl-7-[methyl (2-thienylsulfonyl)amino]-1H-indole-2-carboxylic acid

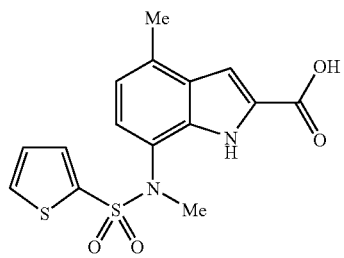 [SMILES: Cc1ccc(N(C)S(=O)(=O)c2cccs2)c2[nH]c(C(=O)O)cc12]

A mixed solution of ethyl 1-(methoxymethyl)-4-methyl-7-[methyl(2-thienylsulfonyl)amino]-1H-indole-2-carboxylate (4.0 g), 6N hydrochloric acid (20 mL), tetrahydrofuran (20 mL) and ethanol (60 mL) was stirred at 80° C. for 4 hr. The reaction solution was concentrated under reduced pressure. The obtained residue was diluted with ethyl acetate, washed with saturated brine, dried over anhydrous magnesium sulfate, and concentrated under reduced pressure. The obtained solid was dissolved in a mixed solution of tetrahydrofuran (40 mL) and methanol (40 mL), aqueous solution (20 mL) of 85% potassium hydroxide (2.2 g) was added, and the mixture was stirred at room temperature for 18 hr. The reaction solution was concentrated under reduced pressure, and the obtained residue was acidified with aqueous citric acid solution. The precipitated crystals were collected by filtration, thoroughly washed with water, and dried to give the title compound (3.3 g, yield 99%) as colorless crystals. MS:351 (MH$^+$). melting point 223-225° C.

Example 176

4-Methyl-7-[methyl(2-thienylsulfonyl)amino]-1H-indole-2-carboxamide

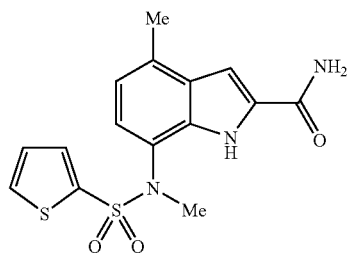

A mixture of 4-methyl-7-[methyl(2-thienylsulfonyl)amino]-1H-indole-2-carboxylic acid (2.2 g), 1H-1,2,3-benzotriazol-1-ol (1.2 g), N-[3-(dimethylamino)propyl]-N'-ethylcarbodiimide hydrochloride (1.5 g) and N,N-dimethylformamide (30 ml) was stirred at room temperature for 1 hr, and the mixture was further stirred at 60° C. for 1 hr. Then, 28% aqueous ammonia (2.0 mL) was added, and the mixture was stirred at room temperature for 3 hr. The reaction solution was concentrated under reduced pressure. The obtained residue was diluted with ethyl acetate, washed with water, aqueous sodium hydrogencarbonate solution and saturated brine, dried over anhydrous magnesium sulfate, and concentrated under reduced pressure. The obtained oil was crystallized from ethyl acetate-hexane to give the title compound (1.84 g, yield 84%) as colorless prism crystals. melting point 221-222° C.

Example 177

N-Methyl-N-[4-methyl-2-(1,3-thiazol-2-yl)-1H-indol-7-yl]thiophene-2-sulfonamide

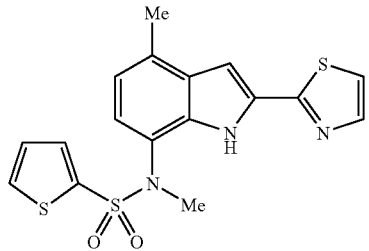 [SMILES: Cc1ccc(N(C)S(=O)(=O)c2cccs2)c2[nH]c(-c3nccs3)cc12]

A mixed solution of 4-methyl-7-[methyl(2-thienylsulfonyl)amino]-1H-indole-2-carbothioamide (0.20 g), 1-bromo-2,2-diethoxyethane (0.23 mL) and N,N-dimethylacetamide (10 ml) was stirred at 100° C. for 6 hr. The reaction solution was diluted with ethyl acetate, washed with water and saturated brine, dried over anhydrous magnesium sulfate, and concentrated under reduced pressure. The obtained residue was subjected to silica gel column chromatography (ethyl acetate:hexane=25:75-35:65), and the obtained oil was crystallized from ethyl acetate-hexane to give the title compound (92 mg, yield 43%) as pale-yellow prism crystals. melting point 159-160° C.

MS:390 (MH$^+$).

Example 178

Ethyl 2-{4-methyl-7-[methyl(2-thienylsulfonyl)amino]-1H-indol-2-yl}-1,3-thiazole-4-carboxylate

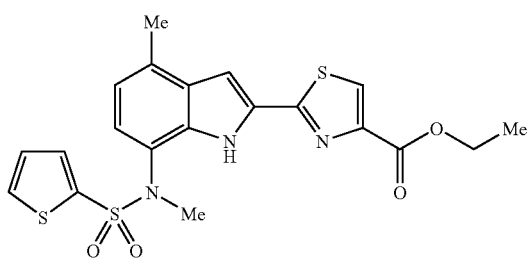 [SMILES: CCOC(=O)c1csc(-c2cc3c(C)ccc(N(C)S(=O)(=O)c4cccs4)c3[nH]2)n1]

A mixed solution of 4-methyl-7-[methyl(2-thienylsulfonyl)amino]-1H-indole-2-carbothioamide (0.50 g), ethyl bromopyruvate (0.36 mL) and N,N-dimethylacetamide (14 ml) was stirred at 100° C. for 3 hr. The reaction solution was diluted with ethyl acetate, washed with water and saturated brine, dried over anhydrous magnesium sulfate, and concentrated under reduced pressure. The obtained crystals were washed with ethyl acetate-hexane to give the title compound (403 mg, yield 64%) as pale-brown crystals. MS:462 (MH$^+$).

Example 179

2-{4-Methyl-7-[methyl(2-thienylsulfonyl)amino]-1H-indol-2-yl}-1,3-thiazole-4-carboxylic acid

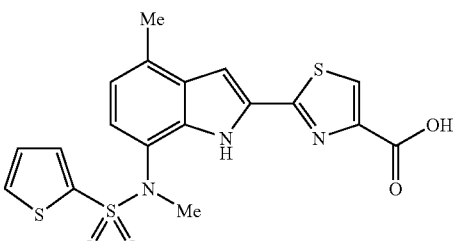

Ethyl 2-{4-methyl-7-[methyl(2-thienylsulfonyl)amino]-1H-indol-2-yl}-1,3-thiazole-4-carboxylate (0.40 g) was dissolved in a mixed solution of tetrahydrofuran (15 mL) and methanol (15 mL), aqueous solution (5 mL) of 85% potassium hydroxide (0.20 g) was added, and the mixture was stirred at room temperature for 18 hr. The reaction solution was diluted with ethyl acetate, washed with aqueous citric acid solution and saturated brine, dried over anhydrous magnesium sulfate, and concentrated under reduced pressure to give the title compound (368 mg, yield 98%) as pale-yellow crystals. MS:434 (MH$^+$).

Example 180 tert-Butyl (2-{4-methyl-7-[methyl(2-thienylsulfonyl)amino]-1H-indol-2-yl}-1,3-thiazol-4-yl)carbamate, and Example 181

N-[2-(4-Amino-1,3-thiazol-2-yl)-4-methyl-1H-indol-7-yl]-N-methylthiophene-2-sulfonamide

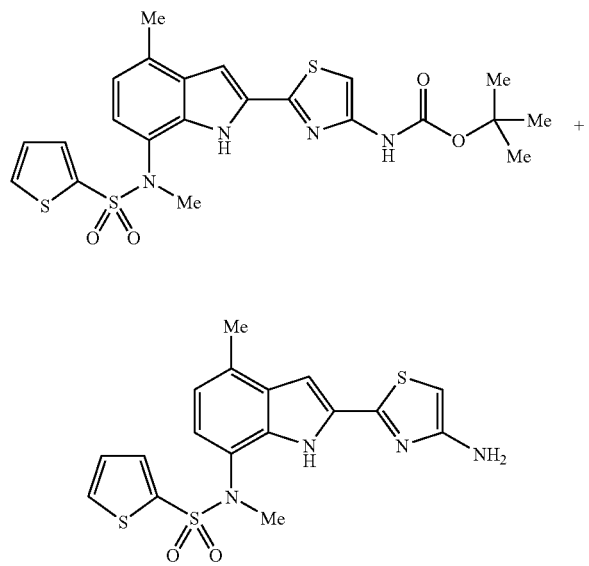

A mixed solution of 2-{4-methyl-7-[methyl(2-thienylsulfonyl)amino]-1H-indol-2-yl}-1,3-thiazole-4-carboxylic acid (367 mg), diphenylphosphoryl azide (0.20 mL), triethylamine (0.20 mL) and tert-butanol (15 mL) was stirred for 2 hr with heating under reflux. The reaction solution was diluted with ethyl acetate, washed with water and saturated brine, dried over anhydrous magnesium sulfate, and concentrated under reduced pressure. The obtained residue was subjected to silica gel column chromatography (ethyl acetate:hexane=2:8-4:6).

tert-Butyl (2-{4-methyl-7-[methyl(2-thienylsulfonyl)amino]-1H-indol-2-yl}-1,3-thiazol-4-yl)carbamate (260 mg, 61%) was obtained as a pale-yellow amorphous solid.

MS:505 (MH$^+$).

In addition, N-[2-(4-amino-1,3-thiazol-2-yl)-4-methyl-1H-indol-7-yl]-N-methylthiophene-2-sulfonamide (47 mg) was obtained as a crude product. The obtained crude product was purified by preparative HPLC to give pale-brown crystals (7.2 mg, 2.1%). melting point 178-180° C.

Example 182

N-[4-Fluoro-2-(1,3-thiazol-2-yl)-1H-indol-7-yl]-N-methylthiophene-2-sulfonamide

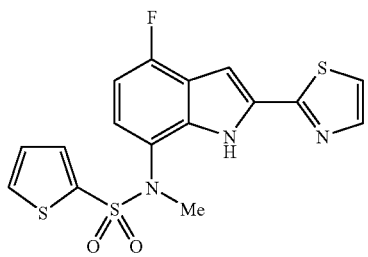 [SMILES: CN(c1ccc(F)c2cc(-c3nccs3)[nH]c12)S(=O)(=O)c1cccs1]

A mixed solution of N-[4-fluoro-1-(methoxymethoxy)-2-(1,3-thiazol-2-yl)-1H-indol-7-yl]-N-methylthiophene-2-sulfonamide (165 mg), 6N hydrochloric acid (6 mL), tetrahydrofuran (2 mL) and ethanol (4 mL) was stirred at 80° C. for 7 hr. The reaction solution was diluted with ethyl acetate, washed with water, aqueous sodium hydrogencarbonate solution and saturated brine, dried over anhydrous magnesium sulfate, and concentrated under reduced pressure. The obtained residue was subjected to silica gel column chromatography (ethyl acetate:hexane=1:9-3:7), and the obtained crystals were recrystallized from ethyl acetate-hexane to give the title compound (73 mg, yield 49%) as colorless needle crystals. melting point 197-198° C.

MS:394 (MH$^+$).

Example 183

N-[2-(4,5-Dihydro-1,3-thiazol-2-yl)-1H-indol-7-yl]-5-methyl-2-(trifluoromethyl)furan-3-sulfonamide

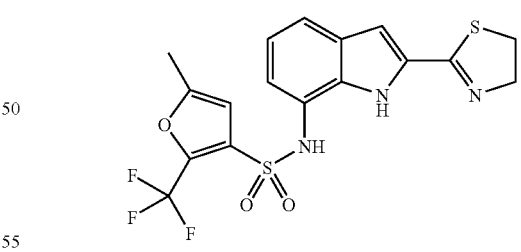

To a mixture of 2-(4,5-dihydro-1,3-thiazol-2-yl)-1H-indole-7-amine (100 mg) and pyridine (3 mL) was added 5-methyl-2-trifluoromethylfuran-3-sulfonyl chloride (150 mg) at 0° C., and the mixture was stirred at room temperature for 2 hr. The reaction mixture was concentrated, 1N hydrochloric acid was added, and the mixture was extracted with ethyl acetate. The ethyl acetate layer was washed with saturated brine, dried (MgSO$_4$) and concentrated. The residue was subjected to silica gel column chromatography (ethyl acetate:

hexane=1:1) to give the title compound (90 mg, yield 46%) as pale-yellow crystals. M+1=430.

Example 184

N-[2-(4,5-Dihydro-1,3-thiazol-2-yl)-1H-indol-7-yl]-2,5-dimethylthiophene-3-sulfonamide

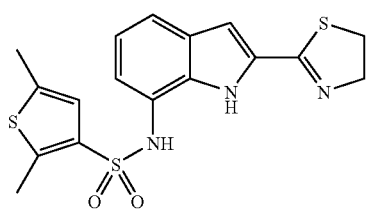 [SMILES: Cc1cc(S(=O)(=O)Nc2cccc3cc(C4=NCCS4)[nH]c23)c(C)s1]

The title compound (176 mg, yield 98%) was obtained as pale-yellow crystals from 2-(4,5-dihydro-1,3-thiazol-2-yl)-1H-indole-7-amine (100 mg) and 2,5-dimethylthiophene-3-sulfonyl chloride (110 mg) in the same manner as in Example 183. M+1=392.

Example 185

N-[2-(4,5-Dihydro-1,3-thiazol-2-yl)-1H-indol-7-yl]-1-methyl-1H-pyrazole-4-sulfonamide

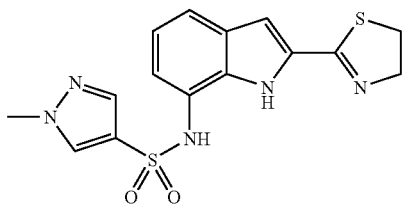 [SMILES: Cn1cc(S(=O)(=O)Nc2cccc3cc(C4=NCCS4)[nH]c23)cn1]

The title compound (62 mg, yield 38%) was obtained as pale-yellow crystals from 2-(4,5-dihydro-1,3-thiazol-2-yl)-1H-indole-7-amine (100 mg) and 1-methyl-1H-pyrazole-4-sulfonyl chloride (110 mg) in the same manner as in Example 183. M+1=362.

Example 186

N-[2-(4,5-Dihydro-1,3-thiazol-2-yl)-1H-indol-7-yl]-5-(1,3-oxazol-5-yl)thiophene-2-sulfonamide

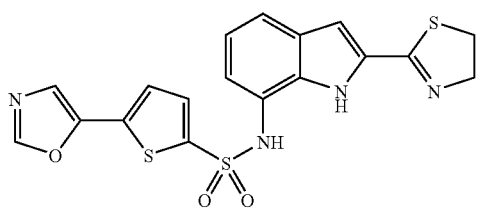 [SMILES: O=S(=O)(Nc1cccc2cc(C3=NCCS3)[nH]c12)c1ccc(-c2cnco2)s1]

The title compound (110 mg, yield 57%) was obtained as pale-yellow crystals from 2-(4,5-dihydro-1,3-thiazol-2-yl)-1H-indole-7-amine (100 mg) and 5-(1,3-oxazol-5-yl) thiophene-2-sulfonyl chloride (130 mg) in the same manner as in Example 183. M+1=431.

Example 187

N-[2-(4,5-Dihydro-1,3-thiazol-2-yl)-1H-indol-7-yl]-1,3,5-trimethyl-1H-pyrazole-4-sulfonamide

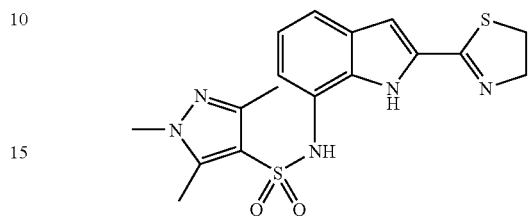

The title compound (107 mg, yield 61%) was obtained as pale-yellow crystals from 2-(4,5-dihydro-1,3-thiazol-2-yl)-1H-indole-7-amine (100 mg) and 1,3,5-trimethyl-1H-pyrazole-4-sulfonyl chloride (110 mg) in the same manner as in Example 183. M+1=390.

Example 188

6-Chloro-N-[2-(4,5-dihydro-1,3-thiazol-2-yl)-1H-indol-7-yl]imidazo[2,1-b][1,3]thiazole-5-sulfonamide

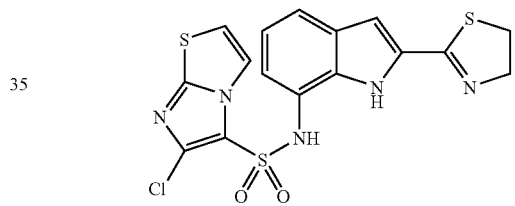

The title compound (102 mg, yield 52%) was obtained as pale-yellow crystals from 2-(4,5-dihydro-1,3-thiazol-2-yl)-1H-indole-7-amine (100 mg) and 6-chloroimidazo[2,1-b][1,3]thiazole-5-sulfonyl chloride (150 mg) in the same manner as in Example 183. M+1=438.

Example 189

N-[2-(4,5-Dihydro-1,3-thiazol-2-yl)-1H-indol-7-yl]-2,4-dimethyl-1,3-thiazole-5-sulfonamide

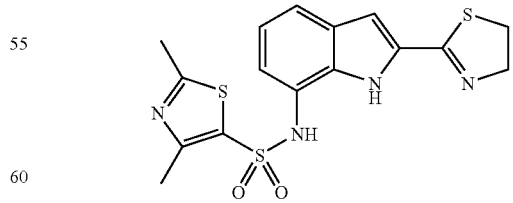

The title compound (87 mg, yield 49%) was obtained as pale-yellow crystals from 2-(4,5-dihydro-1,3-thiazol-2-yl)-1H-indole-7-amine (100 mg) and 2,4-dimethyl-1,3-thiazole-5-sulfonyl chloride (110 mg) in the same manner as in Example 183. M+1=393.

Example 190

4-Bromo-N-[2-(4,5-dihydro-1,3-thiazol-2-yl)-1H-indol-7-yl]thiophene-3-sulfonamide

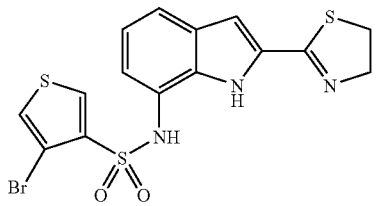 [SMILES: O=S(=O)(Nc1cccc2cc(C3=NCCS3)[nH]c12)c1cscc1Br]

The title compound (82 mg, yield 41%) was obtained as pale-yellow crystals from 2-(4,5-dihydro-1,3-thiazol-2-yl)-1H-indole-7-amine (100 mg) and 4-bromothiophene-3-sulfonyl chloride (150 mg) in the same manner as in Example 183. M+1=443.

Example 191

N-[2-(4,5-Dihydro-1,3-thiazol-2-yl)-1H-indol-7-yl]-3-(methylsulfonyl)-N-{[3-(methylsulfonyl)phenyl]sulfonyl}benzenesulfonamide

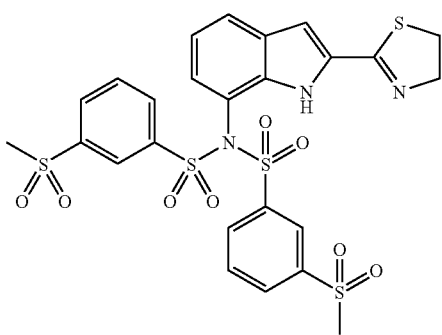 [SMILES: CS(=O)(=O)c1cccc(S(=O)(=O)N(c2cccc3cc(C4=NCCS4)[nH]c23)S(=O)(=O)c2cccc(S(C)(=O)=O)c2)c1]

To a mixture of 2-(4,5-dihydro-1,3-thiazol-2-yl)-1H-indole-7-amine (100 mg) and pyridine (3 mL) was added 3-(methylsulfonyl)benzenesulfonyl chloride (140 mg) at 0° C., and the mixture was stirred at room temperature for 2 hr. The reaction mixture was concentrated, and the residue was subjected to silica gel column chromatography (ethyl acetate:hexane=1:1) to give the title compound (41 mg, yield 14%) as pale-yellow crystals. M+1=654.

Example 192

N-[2-(4,5-Dihydro-1,3-thiazol-2-yl)-1H-indol-7-yl]-3-(methylsulfonyl)benzenesulfonamide

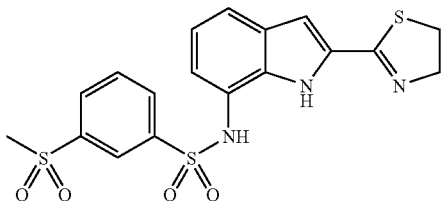 [SMILES: CS(=O)(=O)c1cccc(S(=O)(=O)Nc2cccc3cc(C4=NCCS4)[nH]c23)c1]

The title compound (41 mg, yield 20%) was obtained as pale-yellow crystals by silica gel column chromatography from the fraction (ethyl acetate:hexane=1:1) after elution of the compound of Example 191. M+1=436.

Example 193

Methyl 3-({[2-(4,5-Dihydro-1,3-thiazol-2-yl)-1H-indol-7-yl]amino}sulfonyl)benzoate

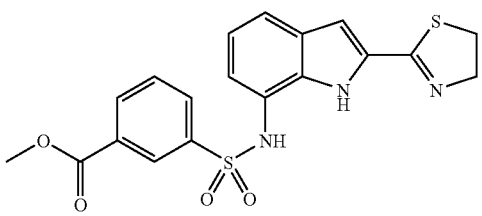 [SMILES: COC(=O)c1cccc(S(=O)(=O)Nc2cccc3cc(C4=NCCS4)[nH]c23)c1]

The title compound (79 mg, yield 42%) was obtained as pale-yellow crystals from 2-(4,5-dihydro-1,3-thiazol-2-yl)-1H-indole-7-amine (100 mg) and methyl 3-(chlorosulfonyl)benzoate (130 mg) in the same manner as in Example 183. M+1=416.

Example 194

5-({[2-(4,5-Dihydro-1,3-thiazol-2-yl)-1H-indol-7-yl]amino}sulfonyl)-2-methoxybenzoic acid

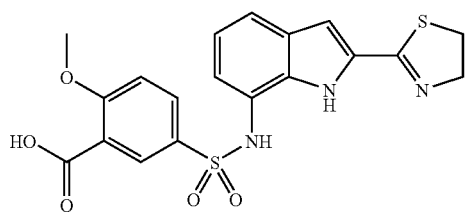 [SMILES: COc1ccc(S(=O)(=O)Nc2cccc3cc(C4=NCCS4)[nH]c23)cc1C(=O)O]

The title compound (13 mg, yield 7%) was obtained as pale-yellow crystals from 2-(4,5-dihydro-1,3-thiazol-2-yl)-1H-indole-7-amine (100 mg) and 5-(chlorosulfonyl)-2-methoxybenzoic acid (130 mg) in the same manner as in Example 183. M+1=432.

Example 195

N-[2-(4,5-Dihydro-1,3-thiazol-2-yl)-1H-indol-7-yl]-3-(trifluoromethyl)-N-{[3-(trifluoromethyl)phenyl]sulfonyl}benzenesulfonamide

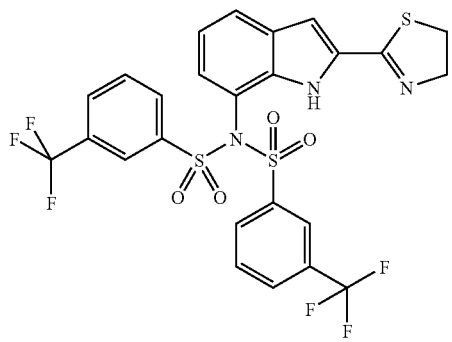 [SMILES: O=S(=O)(c1cccc(C(F)(F)F)c1)N(c1cccc2cc(C3=NCCS3)[nH]c12)S(=O)(=O)c1cccc(C(F)(F)F)c1]

To a mixture of 2-(4,5-dihydro-1,3-thiazol-2-yl)-1H-indole-7-amine (100 mg) and pyridine (3 mL) was added 3-(trifluoromethyl)benzenesulfonyl chloride (140 mg) at 0° C., and the mixture was stirred at room temperature for 2 hr. The reaction mixture was concentrated, and the residue was subjected to silica gel column chromatography (ethyl acetate:hexane=1:1) to give the title compound (93 mg, yield 32%) as pale-yellow crystals. M+1=634.

Example 196

N-[2-(4,5-Dihydro-1,3-thiazol-2-yl)-1H-indol-7-yl]-3-(trifluoromethyl)benzenesulfonamide

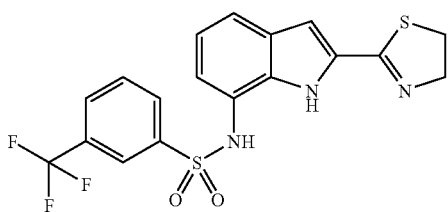 [SMILES: O=S(=O)(Nc1cccc2cc(C3=NCCS3)[nH]c12)c1cccc(C(F)(F)F)c1]

The title compound (93 mg, yield 32%) was obtained as pale-yellow crystals by silica gel column chromatography from the fraction (ethyl acetate:hexane=1:1) after elution of the compound of Example 195. M+1=426.

Example 197

N-[2-(4,5-Dihydro-1,3-thiazol-2-yl)-1H-indol-7-yl]-1-methyl-1H-imidazole-4-sulfonamide

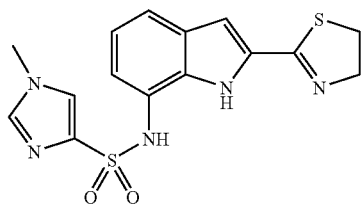 [SMILES: Cn1cnc(S(=O)(=O)Nc2cccc3cc(C4=NCCS4)[nH]c23)c1]

The title compound (83 mg, yield 51%) was obtained as pale-yellow crystals from 2-(4,5-dihydro-1,3-thiazol-2-yl)-1H-indole-7-amine (100 mg) and 1-methyl-1H-imidazole-4-sulfonyl chloride (110 mg) in the same manner as in Example 183. M+1=362.

Example 198

N-[2-(4,5-dihydro-1,3-thiazol-2-yl)-1H-indol-7-yl]thiophene-3-sulfonamide

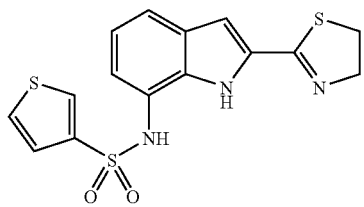 [SMILES: O=S(=O)(Nc1cccc2cc(C3=NCCS3)[nH]c12)c1ccsc1]

The title compound (62 mg, yield 38%) was obtained as pale-yellow crystals from 2-(4,5-dihydro-1,3-thiazol-2-yl)-1H-indole-7-amine (100 mg) and thiophene-3-sulfonyl chloride (110 mg) in the same manner as in Example 183. M+1=364.

Example 199

Ethyl 7-[methyl(2-thienylcarbonyl)amino]-1H-indole-2-carboxylate

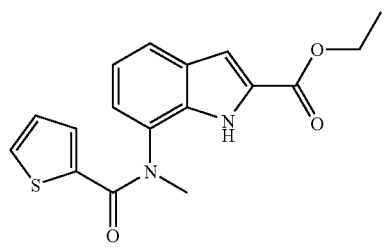 [SMILES: CCOC(=O)c1cc2cccc(N(C)C(=O)c3cccs3)c2[nH]1]

To a solution of ethyl 7-(methylamino)-1H-indole-2-carboxylate (54 mg) in tetrahydrofuran (3 mL) were added triethylamine (42 µL) and 2-thenoylchloride (44 mg), and the mixture was stirred at room temperature for 1 hr. The reaction mixture was concentrated, and the obtained residue was subjected to silica gel column chromatography (ethyl acetate:hexane=1:3) to give colorless crystals (71 mg, yield 87%). melting point 193° C.

Example 200

N-[2-(4,5-Dihydro-1,3-thiazol-2-yl)-1H-indol-7-yl]-N-methylmethanesulfonamide

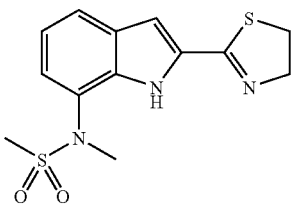 [SMILES: CN(c1cccc2cc(C3=NCCS3)[nH]c12)S(C)(=O)=O]

The title compound (78 mg, yield 65%) was obtained as pale-yellow crystals from 2-(4,5-dihydro-1,3-thiazol-2-yl)-N-methyl-1H-indole-7-amine (90 mg) and methanesulfonyl chloride (70 mg) in the same manner as in Example 183. melting point 212° C.

Example 201

N-[2-(4,5-Dihydro-1,3-thiazol-2-yl)-1H-indol-7-yl]-2,2,2-trifluoro-N-methylethanesulfonamide

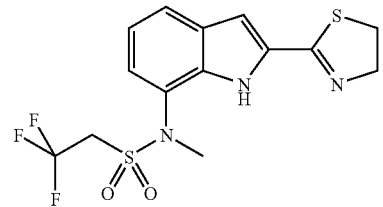 [SMILES: CN(c1cccc2cc(C3=NCCS3)[nH]c12)S(=O)(=O)CC(F)(F)F]

The title compound (44 mg, yield 30%) was obtained as pale-yellow crystals from 2-(4,5-dihydro-1,3-thiazol-2-yl)-

N-methyl-1H-indole-7-amine (90 mg) and 2,2,2-trifluoroethanesulfonyl chloride (110 mg) in the same manner as in Example 183. melting point 200° C.

Example 202

N-[2-(4,5-Dihydro-1,3-thiazol-2-yl)-1H-indol-7-yl]-N-methyl-1-phenylmethanesulfonamide

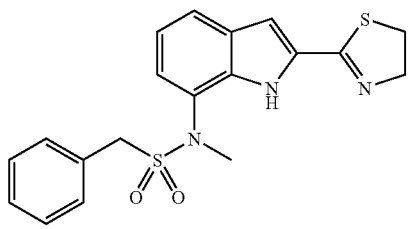 [SMILES: CN(c1cccc2cc(C3=NCCS3)[nH]c12)S(=O)(=O)Cc1ccccc1]

The title compound (11 mg, yield 7%) was obtained as pale-yellow crystals from 2-(4,5-dihydro-1,3-thiazol-2-yl)-N-methyl-1H-indole-7-amine (90 mg) and phenylmethanesulfonyl chloride (110 mg) in the same manner as in Example 183. melting point 194° C.

Example 203

N-[2-(4,5-Dihydro-1,3-thiazol-2-yl)-1H-indol-7-yl]-N-methylpropane-2-sulfonamide

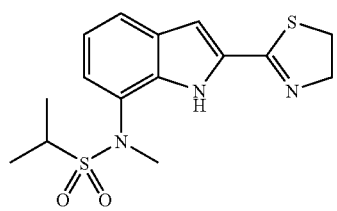 [SMILES: CC(C)S(=O)(=O)N(C)c1cccc2cc(C3=NCCS3)[nH]c12]

The title compound (7 mg, yield 5%) was obtained as pale-yellow crystals from 2-(4,5-dihydro-1,3-thiazol-2-yl)-N-methyl-1H-indole-7-amine (90 mg) and propane-2-sulfonyl chloride (90 mg) in the same manner as in Example 183. melting point 154° C.

Example 204

N,1,2-Trimethyl-N-[2-(1,3-thiazol-2-yl)-1H-indol-7-yl]-1H-imidazole-4-sulfonamide

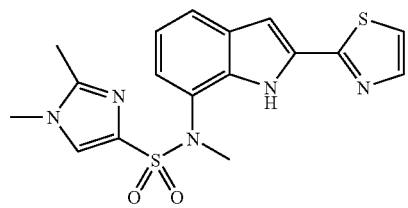 [SMILES: Cc1nc(S(=O)(=O)N(C)c2cccc3cc(-c4nccs4)[nH]c23)cn1C]

The title compound (104 mg, yield 82%) was obtained as pale-yellow crystals from N-methyl-2-(1,3-thiazol-2-yl)-1H-indole-7-amine hydrochloride (90 mg) and 1,2-dimethyl-1H-imidazole-4-sulfonyl chloride (78 mg) in the same manner as in Example 183. melting point 255° C.

Example 205

5-Chloro-N,1,3-trimethyl-N-[2-(1,3-thiazol-2-yl)-1H-indol-7-yl]-1H-pyrazole-4-sulfonamide

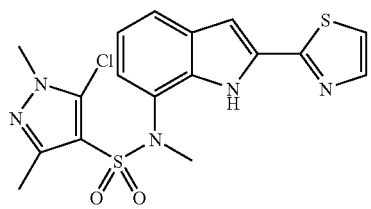 [SMILES: Cc1nn(C)c(Cl)c1S(=O)(=O)N(C)c1cccc2cc(-c3nccs3)[nH]c12]

The title compound (125 mg, yield 69%) was obtained as pale-yellow crystals from N-methyl-2-(1,3-thiazol-2-yl)-1H-indole-7-amine hydrochloride (114 mg) and 5-chloro-1,3-dimethyl-1H-pyrazole-4-sulfonyl chloride (130 mg) in the same manner as in Example 183. melting point 164° C.

Example 206

6-Chloro-N-methyl-N-[2-(1,3-thiazol-2-yl)-1H-indol-7-yl]pyridine-2-sulfonamide

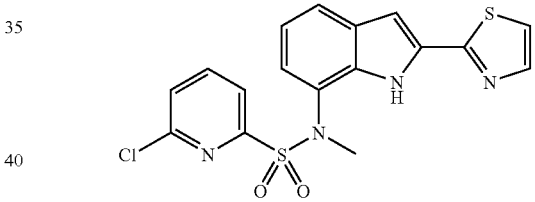

The title compound (130 mg, yield 76%) was obtained as pale-yellow crystals from N-methyl-2-(1,3-thiazol-2-yl)-1H-indole-7-amine hydrochloride (113 mg) and 6-chloropyridine-2-sulfonyl chloride (105 mg) in the same manner as in Example 183. melting point 184° C.

Example 207

N-Methyl-N-[2-(1,3-thiazol-2-yl)-1H-indol-7-yl]pyridine-2-sulfonamide

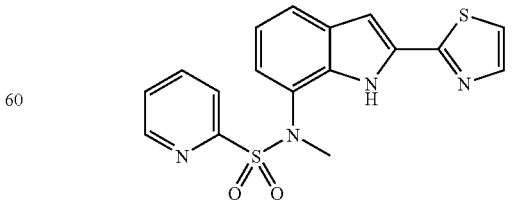

The title compound (147 mg, yield 80%) was obtained as pale-yellow crystals from N-methyl-2-(1,3-thiazol-2-yl)-1H- indole-7-amine hydrochloride (132 mg) and pyridine-2-sulfonyl chloride (100 mg) in the same manner as in Example 183. melting point 152° C.

Example 208

N-Methyl-N-[2-(1,3-thiazol-2-yl)-1H-indol-7-yl]pyridine-3-sulfonamide

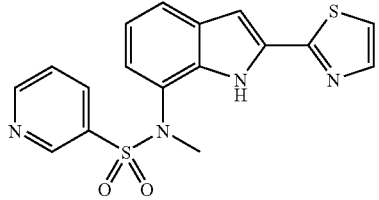 [SMILES: CN(c1cccc2cc(-c3nccs3)[nH]c12)S(=O)(=O)c1cccnc1]

The title compound (136 mg, yield 75%) was obtained as pale-yellow crystals from N-methyl-2-(1,3-thiazol-2-yl)-1H-indole-7-amine hydrochloride (132 mg) and pyridine-3-sulfonyl chloride hydrochloride (120 mg) in the same manner as in Example 183. melting point 203° C.

Example 209

N,1-Dimethyl-N-[2-(1,3-thiazol-2-yl)-1H-indol-7-yl]-1H-imidazole-2-sulfonamide

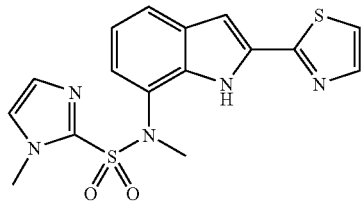 [SMILES: CN(c1cccc2cc(-c3nccs3)[nH]c12)S(=O)(=O)c1nccn1C]

To a solution of 1-methyl-1H-imidazole-2-thiol (2 g) in concentrated sulfuric acid (50 mL) was added dropwise sodium hypochlorite solution (5%, 265 mL) under ice-cooling. The reaction mixture was stirred for 30 min. Water (100 mL) was added to the reaction mixture and the mixture was extracted with dichloromethane. The dichloromethane layer was washed with saturated brine, dried (MgSO$_4$) and concentrated. The obtained residue was added to a solution of N-methyl-2-(1,3-thiazol-2-yl)-1H-indole-7-amine hydrochloride (132 mg) in pyridine (5 mL) under ice-cooling, and the mixture was stirred at room temperature for 2 hr. The reaction mixture was concentrated, 1N hydrochloric acid was added, and the mixture was extracted with ethyl acetate. The ethyl acetate layer was washed with saturated brine, dried (MgSO$_4$) and concentrated. The residue was subjected to silica gel column chromatography (ethyl acetate:hexane=1:3) to give the title compound (12 mg, yield 6%) as a pale-yellow amorphous. M+1=374.

Example 210

N-Methyl-2-(methylsulfonyl)-N-[2-(1,3-thiazol-2-yl)-1H-indol-7-yl]benzenesulfonamide

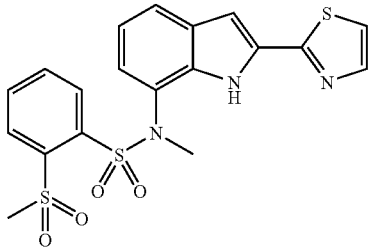 [SMILES: CN(c1cccc2cc(-c3nccs3)[nH]c12)S(=O)(=O)c1ccccc1S(C)(=O)=O]

The title compound (86 mg, yield 38%) was obtained as colorless crystals from N-methyl-2-(1,3-thiazol-2-yl)-1H-indole-7-amine hydrochloride (132 mg) and 2-(methylsulfonyl)benzenesulfonyl chloride (130 mg) in the same manner as in Example 183. melting point 150° C.

Example 211

Methyl 3-({methyl[2-(1,3-thiazol-2-yl)-1H-indol-7-yl]amino}sulfonyl)thiophene-2-carboxylate

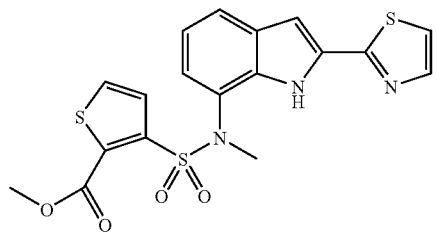 [SMILES: COC(=O)c1sccc1S(=O)(=O)N(C)c1cccc2cc(-c3nccs3)[nH]c12]

The title compound (1.72 g, yield 75%) was obtained as pale-yellow crystals from N-methyl-2-(1,3-thiazol-2-yl)-1H-indole-7-amine hydrochloride (1.4 g) and methyl 3-(chlorosulfonyl)thiophene-2-carboxylate (1.5 g) in the same manner as in Example 183. melting point 114° C.

Example 212

3-({Methyl[2-(1,3-thiazol-2-yl)-1H-indol-7-yl]amino}sulfonyl)thiophene-2-carboxylic acid

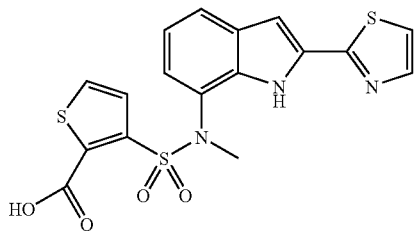 [SMILES: CN(c1cccc2cc(-c3nccs3)[nH]c12)S(=O)(=O)c1ccsc1C(=O)O]

To a solution of methyl 3-({methyl[2-(1,3-thiazol-2-yl)-1H-indol-7-yl]amino}sulfonyl)thiophene-2-carboxylate (300 mg) in methanol (2 mL) and tetrahydrofuran (2 mL) was added 1N aqueous sodium hydroxide solution (2 mL) at room temperature, and the mixture was stirred for 3 hr. The reaction mixture was concentrated, and 1N hydrochloric acid (5 mL) was added to the residue. The precipitated crystals were col-

Example 213

3-({Methyl[2-(1,3-thiazol-2-yl)-1H-indol-7-yl]amino}sulfonyl)thiophene-2-carboxamide

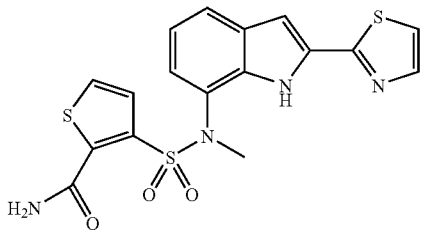 [SMILES: CN(c1cccc2cc(-c3nccs3)[nH]c12)S(=O)(=O)c1ccsc1C(N)=O]

To a solution of 3-({methyl[2-(1,3-thiazol-2-yl)-1H-indol-7-yl]amino}sulfonyl)thiophene-2-carboxylic acid (100 mg), 1H-1,2,3-benzotriazol-1-ol (46 mg) and N-[3-(dimethylamino)propyl]-N'-ethylcarbodiimide hydrochloride (58 mg) in N,N-dimethylformamide (2 mL) was added 28% aqueous ammonia (1 mL), and the mixture was stirred at room temperature for 12 hr. To the reaction mixture was added 1N hydrochloric acid was added, and extracted with ethyl acetate. The ethyl acetate layer was washed with saturated brine, dried (MgSO$_4$) and concentrated. The obtained residue was crystallized from diethyl ether-hexane to give the title compound (57 mg, yield 57%) as colorless crystals. melting point 269° C.

Example 214

N-Methyl-2-(morpholin-4-ylcarbonyl)-N-[2-(1,3-thiazol-2-yl)-1H-indol-7-yl]thiophene-3-sulfonamide

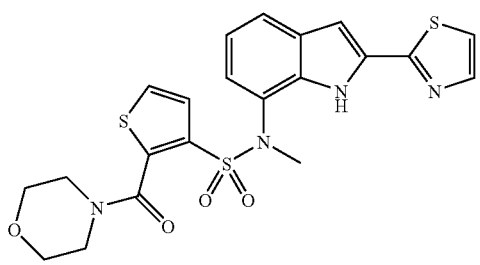 [SMILES: CN(c1cccc2cc(-c3nccs3)[nH]c12)S(=O)(=O)c1ccsc1C(=O)N1CCOCC1]

To a solution of 3-({methyl[2-(1,3-thiazol-2-yl)-1H-indol-7-yl]amino}sulfonyl)thiophene-2-carboxylic acid (100 mg), 1H-1,2,3-benzotriazol-1-ol (46 mg) and N-[3-(dimethylamino)propyl]-N'-ethylcarbodiimide hydrochloride (58 mg) in N,N-dimethylformamide (2 mL) was added morpholine (100 μL), and the mixture was stirred at room temperature for 12 hr. To the reaction mixture was added 1N hydrochloric acid, and the mixture was extracted with ethyl acetate. The ethyl acetate layer was washed with saturated brine, dried (MgSO$_4$) and concentrated. The obtained residue was crystallized from diethyl ether-hexane to give the title compound (61 mg, yield 52%) as colorless crystals. melting point 190° C.

Example 215

2-(Hydroxymethyl)-N-methyl-N-[2-(1,3-thiazol-2-yl)-1H-indol-7-yl]thiophene-3-sulfonamide

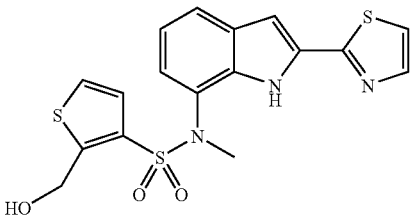 [SMILES: CN(c1cccc2cc(-c3nccs3)[nH]c12)S(=O)(=O)c1ccsc1CO]

To a suspension of lithium aluminum hydride (260 mg) in tetrahydrofuran (10 mL) was added dropwise a solution of methyl 3-({methyl[2-(1,3-thiazol-2-yl)-1H-indol-7-yl]amino}sulfonyl)thiophene-2-carboxylate (1.4 g) in tetrahydrofuran (5 mL) under ice-cooling, and the mixture was stirred at room temperature for 4 hr. To the reaction mixture were added water (260 μL), 15% aqueous sodium hydroxide solution (260 μL) and water (780 μL) in this order and the mixture was stirred at room temperature for 2 hr. The insoluble material was filtered off, and the filtrate was concentrated. The residue was subjected to silica gel column chromatography (ethyl acetate:hexane=1:1) to give the title compound (701 mg, yield 54%) as pale-yellow crystals. melting point 192° C.

Example 216

2-(Chloromethyl)-N-methyl-N-[2-(1,3-thiazol-2-yl)-1H-indol-7-yl]thiophene-3-sulfonamide

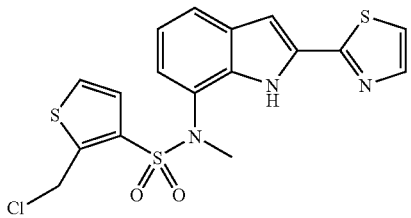 [SMILES: CN(c1cccc2cc(-c3nccs3)[nH]c12)S(=O)(=O)c1ccsc1CCl]

To a solution of 2-(hydroxymethyl)-N-methyl-N-[2-(1,3-thiazol-2-yl)-1H-indol-7-yl]thiophene-3-sulfonamide (405 mg) and triethylamine (167 μL) in tetrahydrofuran (5 mL) was added methanesulfonyl chloride (93 μL). The reaction mixture was stirred at room temperature for 10 hr. Water was added to the reaction mixture, and the mixture was extracted with ethyl acetate. The ethyl acetate layer was washed with saturated brine, dried (MgSO$_4$) and concentrated. The obtained residue was crystallized from diethyl ether-hexane

Example 217

2-[(4-Acetylpiperazin-1-yl)methyl]-N-methyl-N-[2-(1,3-thiazol-2-yl)-1H-indol-7-yl]thiophene-3-sulfonamide

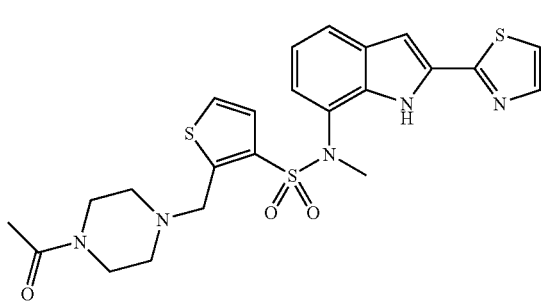 [SMILES: CC(=O)N1CCN(Cc2sccc2S(=O)(=O)N(C)c2cccc3cc(-c4nccs4)[nH]c23)CC1]

To a solution of 2-(chloromethyl)-N-methyl-N-[2-(1,3-thiazol-2-yl)-1H-indol-7-yl]thiophene-3-sulfonamide (110 mg) and triethylamine (150 μL) in tetrahydrofuran (5 mL) was added N-acetylpiperazine (33 mg). The reaction mixture was stirred at room temperature for 10 hr. The reaction mixture was concentrated, and the obtained residue was subjected to silica gel column chromatography (ethyl acetate:hexane=1:1) to give the title compound (108 mg, yield 81%) as pale-yellow crystals. melting point 242° C.

Example 218

N-Methyl-2-[(2-oxo-1-oxa-3,8-diazaspiro[4.5]dec-8-yl)methyl]-N-[2-(1,3-thiazol-2-yl)-1H-indol-7-yl]thiophene-3-sulfonamide

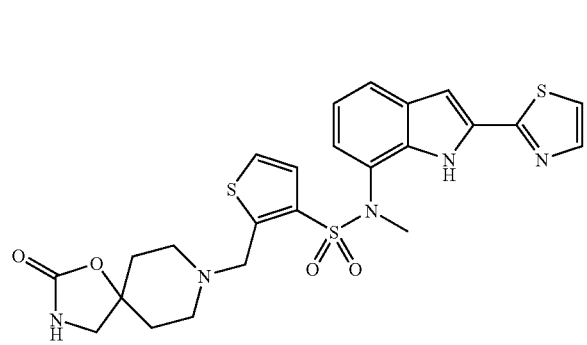 [SMILES: CN(c1cccc2cc(-c3nccs3)[nH]c12)S(=O)(=O)c1ccsc1CN1CCC2(CC1)CNC(=O)O2]

The title compound (67 mg, yield 47%) was obtained as pale-yellow crystals from 2-(chloromethyl)-N-methyl-N-[2-(1,3-thiazol-2-yl)-1H-indol-7-yl]thiophene-3-sulfonamide (110 mg) and 1-oxa-3,8-diazaspiro[4.5]decan-2-one (41 mg) in the same manner as in Example 217. melting point 236° C.

Example 219

N-Methyl-2-[(4-oxohexahydropyrazino[2,1-c][1,4]oxazin-8(1H)-yl)methyl]-N-[2-(1,3-thiazol-2-yl)-1H-indol-7-yl]thiophene-3-sulfonamide

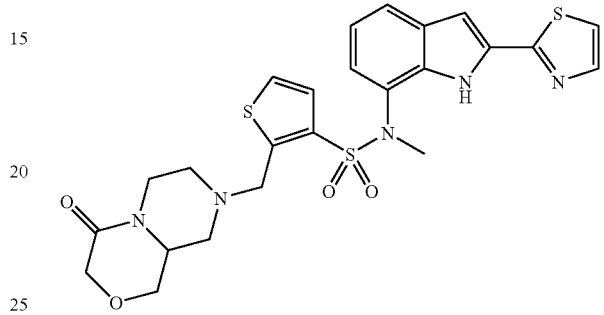

The title compound (81 mg, yield 57%) was obtained as pale-yellow crystals from 2-(chloromethyl)-N-methyl-N-[2-(1,3-thiazol-2-yl)-1H-indol-7-yl]thiophene-3-sulfonamide (110 mg) and hexahydropyrazino[2,1-c][1,4]oxazin-4(3H)-one (50 mg) in the same manner as in Example 217. melting point 219° C.

Example 220

2-{[bis(2-Methoxyethyl)amino]methyl}-N-methyl-N-[2-(1,3-thiazol-2-yl)-1H-indol-7-yl]thiophene-3-sulfonamide

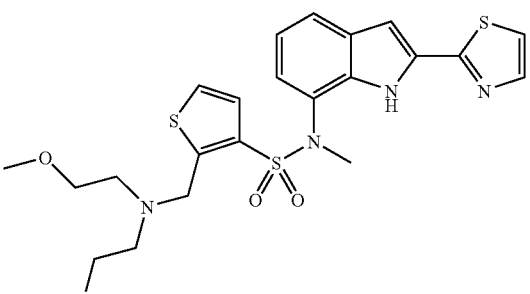

The title compound (39 mg, yield 32%) was obtained as a pale-yellow amorphous form from 2-(chloromethyl)-N-methyl-N-[2-(1,3-thiazol-2-yl)-1H-indol-7-yl]thiophene-3-sulfonamide (64 mg) and 2-methoxy-N-(2-methoxyethyl)ethylamine (40 mg) in the same manner as in Example 217.

M+1=521.

Example 221

2{-[(2-Methoxyethyl)(methyl)amino]methyl}-N-methyl-N-[2-(1,3-thiazol-2-yl)-1H-indol-7-yl]thiophene-3-sulfonamide

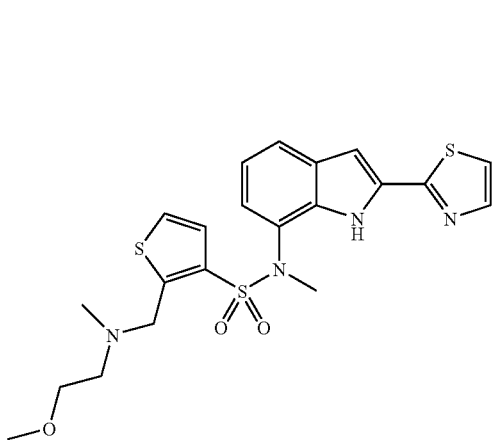 [SMILES: COCCN(C)Cc1sccc1S(=O)(=O)N(C)c1cccc2cc(-c3nccs3)[nH]c12]

The title compound (75 mg, yield 33%) was obtained as pale-yellow crystals from 2-(chloromethyl)-N-methyl-N-[2-(1,3-thiazol-2-yl)-1H-indol-7-yl]thiophene-3-sulfonamide (200 mg) and 2-methoxy-N-methylethylamine (50 mg) in the same manner as in Example 217. melting point 106° C.

Example 222

N-Methyl-2-({[2-(morpholin-4-yl)ethyl]amino}methyl)-N-[2-(1,3-thiazol-2-yl)-1H-indol-7-yl]thiophene-3-sulfonamide

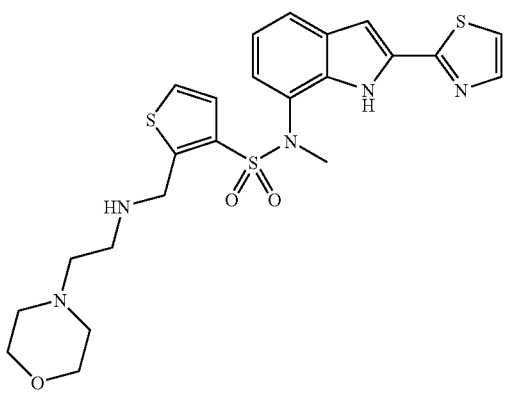 [SMILES: CN(c1cccc2cc(-c3nccs3)[nH]c12)S(=O)(=O)c1ccsc1CNCCN1CCOCC1]

The title compound (66 mg, yield 27%) was obtained as pale-yellow crystals from 2-(chloromethyl)-N-methyl-N-[2-(1,3-thiazol-2-yl)-1H-indol-7-yl]thiophene-3-sulfonamide (64 mg) and 2-(morpholin-4-yl)ethylamine (70 mg) in the same manner as in Example 217. melting point 125° C.

Example 223

N-Methyl-2-({methyl[2-(methylsulfonyl)ethyl]amino}methyl)-N-[2-(1,3-thiazol-2-yl)-1H-indol-7-yl]thiophene-3-sulfonamide

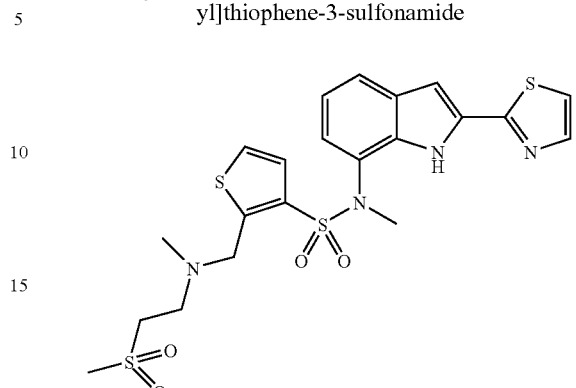

The title compound (95 mg, yield 39%) was obtained as pale-yellow crystals from 2-(chloromethyl)-N-methyl-N-[2-(1,3-thiazol-2-yl)-1H-indol-7-yl]thiophene-3-sulfonamide (64 mg) and N-methyl-2-(methylsulfonyl)ethylamine (70 mg) in the same manner as in Example 217. melting point 145° C.

Example 224

Diethyl {[3-({methyl[2-(1,3-thiazol-2-yl)-1H-indol-7-yl]amino}sulfonyl)-2-thienyl]methyl}phosphonate

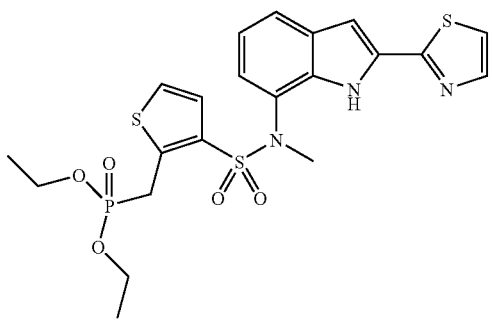 [SMILES: CCOP(=O)(Cc1sccc1S(=O)(=O)N(C)c1cccc2cc(-c3nccs3)[nH]c12)OCC]

A solution of 2-(chloromethyl)-N-methyl-N-[2-(1,3-thiazol-2-yl)-1H-indol-7-yl]thiophene-3-sulfonamide (240 mg) in triethyl phosphite (5 mL) was stirred at 100° C. for 1 hr. The reaction mixture was subjected to silica gel column chromatography (ethyl acetate) to give the title compound (67 mg, yield 25%) as a pale-yellow amorphous. M+1=526.

Example 225

N-Methyl-2-[(methylthio)methyl]-N-[2-(1,3-thiazol-2-yl)-1H-indol-7-yl]thiophene-3-sulfonamide

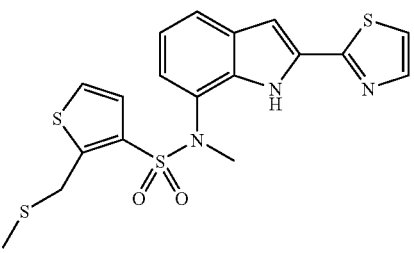 [SMILES: CSCc1sccc1S(=O)(=O)N(C)c1cccc2cc(-c3nccs3)[nH]c12]

A solution of 2-(chloromethyl)-N-methyl-N-[2-(1,3-thiazol-2-yl)-1H-indol-7-yl]thiophene-3-sulfonamide (250 mg) and sodium methanethiolate (50 mg) in tetrahydrofuran (5 mL) was stirred at room temperature for 1 hr. The reaction mixture was concentrated, and the obtained crystals were collected by filtration. The crystals were washed with water and diethyl ether, and dried to give the title compound (256 mg, yield 99%) as pale-brown crystals. melting point 213° C.

Example 226

N-Methyl-2-[(methylsulfonyl)methyl]-N-[2-(1,3-thiazol-2-yl)-1H-indol-7-yl]thiophene-3-sulfonamide

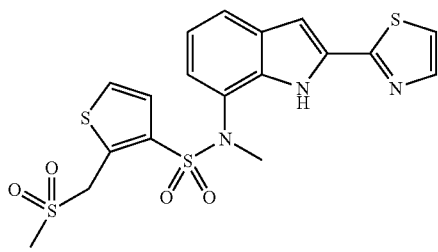 [SMILES: CN(c1cccc2cc(-c3nccs3)[nH]c12)S(=O)(=O)c1ccsc1CS(C)(=O)=O]

To a solution of N-methyl-2-[(methylthio)methyl]-N-[2-(1,3-thiazol-2-yl)-1H-indol-7-yl]thiophene-3-sulfonamide (200 mg) in tetrahydrofuran (5 mL), methanol (8 mL) and water (2 ml) was added oxone (700 mg), and the mixture was stirred with heating under reflux for 1 hr. Water was added to the reaction mixture, and the mixture was extracted with ethyl acetate. The ethyl acetate layer was washed with saturated brine, dried (MgSO$_4$) and concentrated. The obtained residue was subjected to silica gel column chromatography (ethyl acetate:hexane=1:1) to give the title compound (32 mg, yield 15%) as pale-brown crystals. melting point 253° C.

Example 227

Methyl ({[3-({methyl[2-(1,3-thiazol-2-yl)-1H-indol-7-yl]amino}sulfonyl)-2-thienyl]methyl}thio)acetate

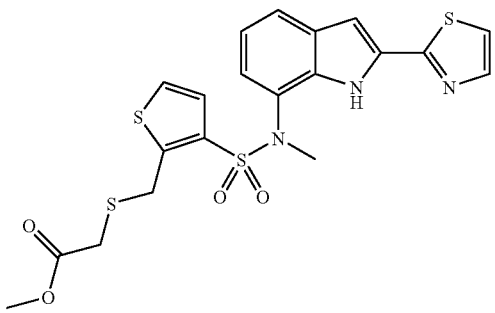 [SMILES: COC(=O)CSCc1sccc1S(=O)(=O)N(C)c1cccc2cc(-c3nccs3)[nH]c12]

To a solution of 2-(chloromethyl)-N-methyl-N-[2-(1,3-thiazol-2-yl)-1H-indol-7-yl]thiophene-3-sulfonamide (450 mg) in N,N-dimethylformamide (5 mL) were added potassium carbonate (150 mg) and methyl mercaptoacetate (130 μL), and the mixture was stirred at 50° C. for 10 hr. Water was added to the reaction mixture, and the mixture was extracted with ethyl acetate. The ethyl acetate layer was washed with saturated brine, dried (MgSO$_4$) and concentrated. The obtained residue was subjected to silica gel column chromatography (ethyl acetate:hexane=1:1) to give the title compound (348 mg, yield 67%) as pale-yellow crystals. melting point 126° C.

Example 228

({[3-({Methyl[2-(1,3-thiazol-2-yl)-1H-indol-7-yl]amino}sulfonyl)-2-thienyl]methyl}thio)acetic acid

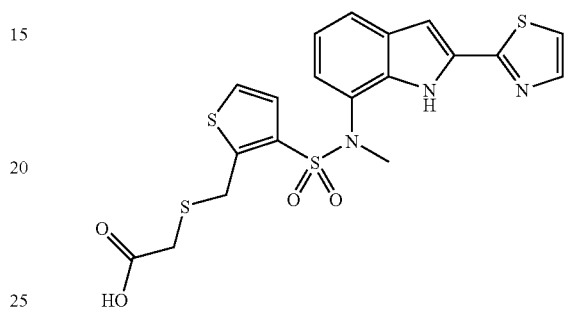

To a solution of methyl ({[3-({methyl[2-(1,3-thiazol-2-yl)-1H-indol-7-yl]amino}sulfonyl)-2-thienyl]methyl}thio)acetate (300 mg) in methanol (2 mL) and tetrahydrofuran (2 mL) was added 1N aqueous sodium hydroxide solution (2 mL) at room temperature, and the mixture was stirred for 3 hr. The reaction mixture was concentrated, and 1N hydrochloric acid (5 mL) was added to the residue. The precipitated crystals were collected by filtration, washed with water, and dried to give the title compound (276 mg, yield 96%) as colorless crystals. melting point 193° C.

Example 229

({[3-({Methyl[2-(1,3-thiazol-2-yl)-1H-indol-7-yl]amino}sulfonyl)-2-thienyl]methyl}sulfonyl)acetic acid

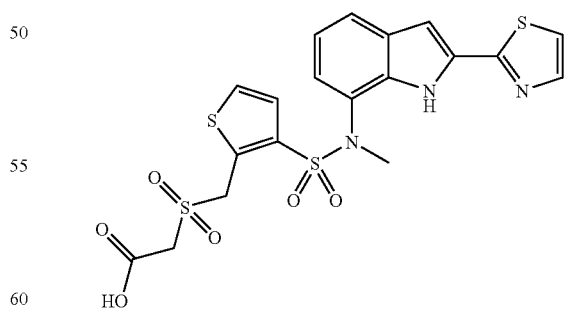

The title compound (56 mg, yield 26%) was obtained as colorless crystals from ({[3-({methyl[2-(1,3-thiazol-2-yl)-1H-indol-7-yl]amino}sulfonyl)-2-thienyl]methyl}thio)acetic acid (200 mg) in the same manner as in Example 226. melting point 193° C.

Example 230

2-(1-Hydroxy-1-methylethyl)-N-methyl-N-[2-(1,3-thiazol-2-yl)-1H-indol-7-yl]thiophene-3-sulfonamide

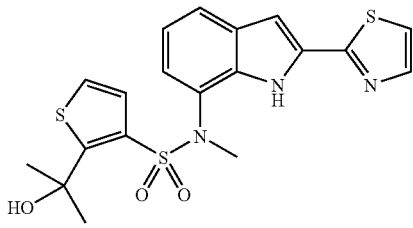 [SMILES: CN(c1cccc2cc(-c3nccs3)[nH]c12)S(=O)(=O)c1ccsc1C(C)(C)O]

To a solution of methyl 3-({methyl[2-(1,3-thiazol-2-yl)-1H-indol-7-yl]amino}sulfonyl)thiophene-2-carboxylate (217 mg) in tetrahydrofuran (5 mL) was added methylmagnesium bromide (3M diethyl ether solution, 1 mL) at room temperature. The reaction mixture was stirred at room temperature for 3 hr. 0.1N Hydrochloric acid was added to the reaction mixture, and the mixture was extracted with ethyl acetate. The ethyl acetate layer was washed with saturated brine, dried (MgSO$_4$) and concentrated. The obtained residue was crystallized from diethyl ether-hexane to give the title compound (150 mg, yield 70%) as colorless crystals. melting point 153° C.

Example 231

N-Methyl-N-[2-(1,3-thiazol-2-yl)-1H-indol-7-yl]thiophene-2-carboxamide

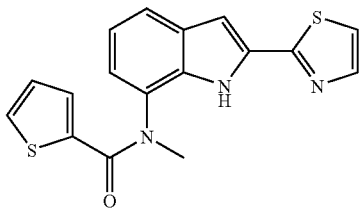 [SMILES: CN(C(=O)c1cccs1)c1cccc2cc(-c3nccs3)[nH]c12]

To a solution of N-methyl-2-(1,3-thiazol-2-yl)-1H-indole-7-amine hydrochloride (200 mg) in tetrahydrofuran (3 mL) were added triethylamine (100 μL) and 2-thenoyl chloride (100 mg), and the mixture was stirred at room temperature for 1 hr. The reaction mixture was concentrated, and the obtained residue was subjected to silica gel column chromatography (ethyl acetate:hexane=1:3) to give the title compound (273 mg, yield 92%) as colorless crystals. melting point 250° C.

Example 232

N-Methyl-2-(1,3-thiazol-2-yl)-N-(2-thienylmethyl)-1H-indole-7-amine

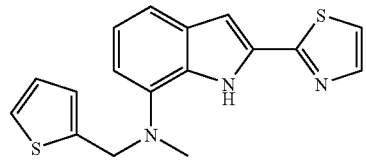 [SMILES: CN(Cc1cccs1)c1cccc2cc(-c3nccs3)[nH]c12]

To a solution of N-methyl-N-[2-(1,3-thiazol-2-yl)-1H-indol-7-yl]thiophene-2-carboxamide (150 mg) in tetrahydrofuran (10 mL) was added borane-tetrahydrofuran complex (1.0 M tetrahydrofuran solution, 10 mL). The reaction mixture was stirred with heating under reflux for 1 hr. The reaction mixture was cooled to room temperature, and methanol (5 mL) was added. The reaction mixture was stirred with heating under reflux for 1 hr, and the reaction mixture was concentrated. The obtained residue was subjected to silica gel column chromatography (ethyl acetate:hexane=1:3) to give the title compound (55 mg, yield 38%) as a yellow oil. M+1=326.

Example 233

N-methyl-N-[2-(1,3-thiazol-2-yl)-1H-indol-7-yl]-N'-3-thienylurea

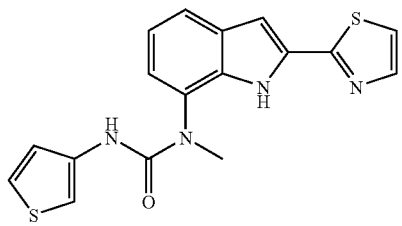 [SMILES: CN(C(=O)Nc1ccsc1)c1cccc2cc(-c3nccs3)[nH]c12]

To a solution of N-methyl-2-(1,3-thiazol-2-yl)-1H-indole-7-amine hydrochloride (50 mg) and triethylamine (35 mL) in tetrahydrofuran (3 mL) was added 3-isocyanatothiophene (26 mg). The reaction mixture was stirred at 50° C. for 1 hr. The reaction mixture was concentrated, and the obtained residue was subjected to silica gel column chromatography (ethyl acetate:hexane=1:1) to give the title compound (74 mg, yield 99%) as yellow crystals. melting point 266° C.

Example 234

N'-Isopropyl-N-methyl-N-[2-(1,3-thiazol-2-yl)-1H-indol-7-yl]urea

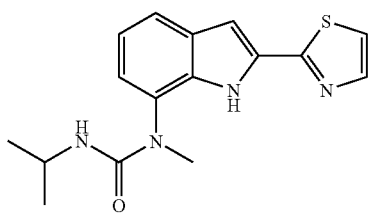 [SMILES: CC(C)NC(=O)N(C)c1cccc2cc(-c3nccs3)[nH]c12]

The title compound (55 mg, yield 92%) was obtained as colorless crystals from N-methyl-2-(1,3-thiazol-2-yl)-1H-indole-7-amine hydrochloride (50 mg) and 2-isocyanatopropane (25 mg) in the same manner as in Example 233. melting point 211° C.

Example 235

N,N,N'-Trimethyl-N'-[2-(1,3-thiazol-2-yl)-1H-indol-7-yl]sulfamide

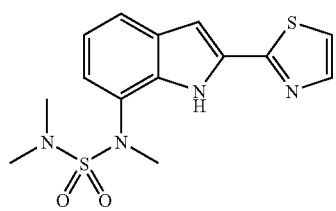 [SMILES: CN(C)S(=O)(=O)N(C)c1cccc2cc(-c3nccs3)[nH]c12]

To a solution of N-methyl-2-(1,3-thiazol-2-yl)-1H-indole-7-amine hydrochloride (100 mg) in pyridine (3 mL) was added dimethylsulfamoyl chloride (200 μL). The reaction mixture was stirred at room temperature for 3 hr. The reaction mixture was concentrated, and the obtained residue was subjected to silica gel column chromatography (ethyl acetate:hexane=1:1) to give. the title compound (88 mg, yield 69%) as yellow crystals. melting point 123° C.

Example 236

N-methyl-N-[2-(1,3-thiazol-2-yl)-1H-indol-7-yl]pyrrolidine-1-sulfonamide

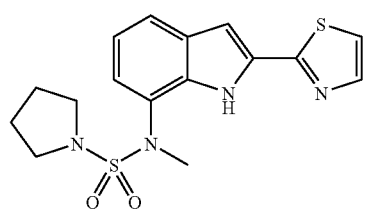 [SMILES: CN(c1cccc2cc(-c3nccs3)[nH]c12)S(=O)(=O)N1CCCC1]

To a solution of sulfuryl chloride (803 μL) in toluene (6 mL) was added pyrrolidine (835 μL) at −30° C. The reaction mixture was stirred at −30° C. for 2 hr. Toluene (6 mL) was added to the reaction mixture, and the mixture was washed with water and 2N hydrochloric acid. The toluene layer was washed with saturated brine, dried (MgSO$_4$) and concentrated. The obtained residue was dissolved in dichloromethane (10 mL), and N-methyl-2-(1,3-thiazol-2-yl)-1H-indole-7-amine hydrochloride (265 mg) and triethylamine (210 μL) were added under ice-cooling. The reaction mixture was stirred at room temperature for 10 hr. The reaction mixture was washed with water and saturated brine, dried (MgSO$_4$) and concentrated. The obtained residue was subjected to silica gel column chromatography (ethyl acetate:hexane=1:1) to give the title compound (128 mg, yield 35%) as yellow crystals. melting point 108° C.

Example 237

N-Methyl-N-[2-(1,3-thiazol-2-yl)-1H-indol-7-yl]pyrrolidine-1-carboxamide

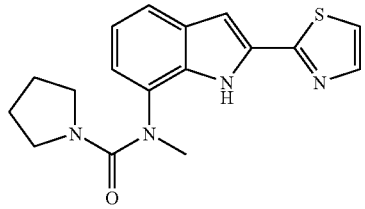 [SMILES: CN(C(=O)N1CCCC1)c1cccc2cc(-c3nccs3)[nH]c12]

To a solution of N-methyl-2-(1,3-thiazol-2-yl)-1H-indole-7-amine hydrochloride (133 mg) and triethylamine (105 μL) in tetrahydrofuran (5 mL) was added pyrrolidine-1-carbonylchloride (100 mg). The reaction mixture was stirred at room temperature for 1 hr. Saturated aqueous sodium hydrogencarbonate solution was added to the reaction solution, and the mixture was extracted with ethyl acetate. The ethyl acetate layer was washed with saturated brine, dried (MgSO$_4$) and concentrated. The obtained residue was subjected to silica gel column chromatography (ethyl acetate:hexane=1:1) to give yellow crystals (8.2 mg, yield 5%). melting point 182° C.

Example 238

N-Methyl-N-[2-(1,3-thiazol-2-yl)-1H-indol-7-yl]morpholine-4-carboxamide

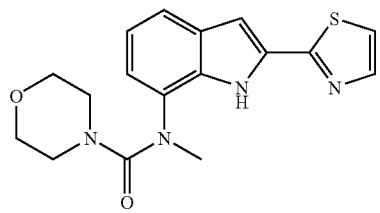 [SMILES: CN(C(=O)N1CCOCC1)c1cccc2cc(-c3nccs3)[nH]c12]

The title compound (91 mg, yield 53%) was obtained as colorless crystals from N-methyl-2-(1,3-thiazol-2-yl)-1H-indole-7-amine hydrochloride (133 mg) and morpholine-4-carbonyl chloride (80 mg) in the same manner as in Example 237. melting point 179° C.

Example 239

Ethyl 1-({methyl[2-(1,3-thiazol-2-yl)-1H-indol-7-yl]amino}carbonyl)cyclobutanecarboxylate

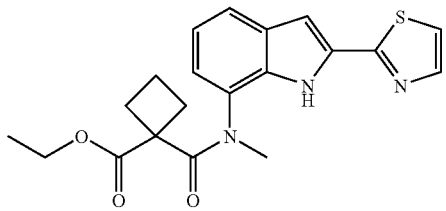 [SMILES: CCOC(=O)C1(C(=O)N(C)c2cccc3cc(-c4nccs4)[nH]c23)CCC1]

A solution of 1-(ethoxycarbonyl)cyclobutanecarboxylic acid (860 mg) in thionyl chloride solution was stirred at 50° C. for 30 min. The reaction mixture was concentrated, and N-methyl-2-(1,3-thiazol-2-yl)-1H-indole-7-amine hydrochloride (665 mg), triethylamine (1.4 mL) and tetrahydrofuran (10 mL) were added. The reaction mixture was stirred at room temperature for 1 hr. Saturated aqueous sodium hydrogencarbonate solution was added to the reaction solution, and the mixture was extracted with ethyl acetate. The ethyl acetate layer was washed with saturated brine, dried (MgSO$_4$) and concentrated. The obtained residue was crystallized from diethyl ether-hexane to give colorless crystals (980 mg, yield 99%). melting point 197° C.

Example 240

1-({Methyl[2-(1,3-thiazol-2-yl)-1H-indol-7-yl]amino}carbonyl)cyclobutanecarboxylic acid

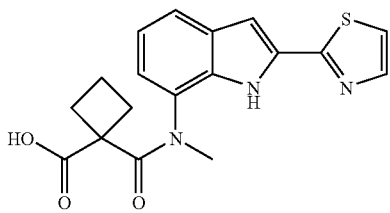 [SMILES: CN(C(=O)C1(C(=O)O)CCC1)c1cccc2cc(-c3nccs3)[nH]c12]

The title compound (654 mg, yield 76%) was obtained as colorless crystals from ethyl 1-({methyl[2-(1,3-thiazol-2-yl)-1H-indol-7-yl]amino}carbonyl)cyclobutanecarboxylate (930 mg) in the same manner as in Example 212. melting point 169° C.

Example 241

N-Methyl-N-[4-[(1-methyl-1H-tetrazol-5-yl)thio]-2-(1,3-thiazol-2-yl)-1H-indol-7-yl]thiophene-2-sulfonamide

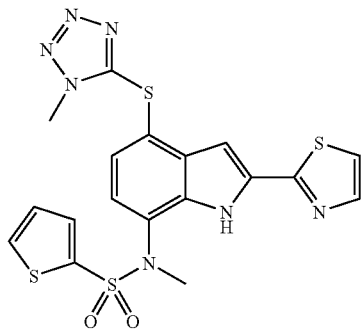 [SMILES: CN(c1ccc(Sc2nnnn2C)c2cc(-c3nccs3)[nH]c12)S(=O)(=O)c1cccs1]

The title compound (168 mg, yield 78%) was obtained as colorless crystals from N-methyl-4-[(1-methyl-1H-tetrazol-5-yl)thio]-2-(1,3-thiazol-2-yl)-1H-indole-7-amine (150 mg) and thiophene-2-sulfonyl chloride (100 mg) in the same manner as in Example 183. melting point 160° C.

Example 242

{[3-({Methyl[2-(1,3-thiazol-2-yl)-1H-indol-7-yl]amino}sulfonyl)-2-thienyl]methoxy}acetic acid

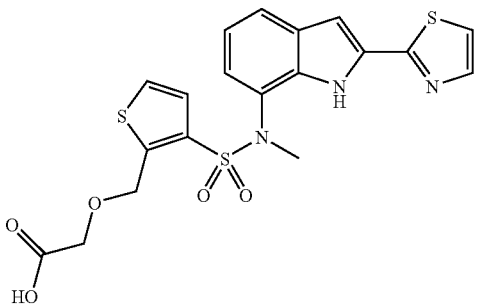 [SMILES: CN(c1cccc2cc(-c3nccs3)[nH]c12)S(=O)(=O)c1ccsc1COCC(=O)O]

To a solution of 2-(hydroxymethyl)-N-[1-(methoxymethyl)-2-(1,3-thiazol-2-yl)-1H-indol-7-yl]-N-methylthiophene-3-sulfonamide (480 mg) and bromoacetic acid (178 mg) in tetrahydrofuran (10 mL) was added sodium hydride (60% in oil, 95 mg), and the mixture was stirred at 80° C. for 12 hr. Hydrochloric acid (3 mL) was added to the reaction mixture, and the mixture was stirred at 80° C. for 5 hr. Water was added to the reaction mixture, and the mixture was extracted with ethyl acetate. The ethyl acetate layer was washed with saturated brine, dried (MgSO$_4$) and concentrated. The obtained residue was subjected to silica gel column chromatography (ethyl acetate) to give the title compound (98 mg, yield 22%) as pale-yellow crystals. melting point 189° C.

Example 243

N,5-Dimethyl-N-[2-(1,3-thiazol-2-yl)-1H-indol-7-yl]isoxazole-4-sulfonamide

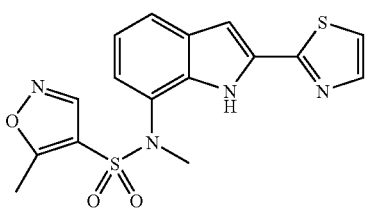 [SMILES: Cc1oncc1S(=O)(=O)N(C)c1cccc2cc(-c3nccs3)[nH]c12]

The title compound (14 mg, yield 20%) was obtained as colorless crystals from N-methyl-2-(1,3-thiazol-2-yl)-1H-indole-7-amine hydrochloride (50 mg) and 5-methylisoxazole- 4-sulfonyl chloride (40 mg) in the same manner as in Example 183. melting point 161° C.

Example 244

N-Methyl-N-[2-(1,3-thiazol-2-yl)-1H-indol-7-yl]furan-2-sulfonamide

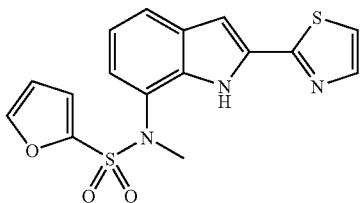 [SMILES: CN(c1cccc2cc(-c3nccs3)[nH]c12)S(=O)(=O)c1ccco1]

The title compound (130 mg, yield 73%) was obtained as colorless crystals from N-methyl-2-(1,3-thiazol-2-yl)-1H-indole-7-amine hydrochloride (133 mg) and furan-2-sulfonyl chloride (100 mg) in the same manner as in Example 183. melting point 174° C.

Example 245

N-{2-[5-(Hydroxymethyl)-1,3-thiazol-2-yl]-4-methyl-1H-indol-7-yl}-N-methylthiophene-2-sulfonamide

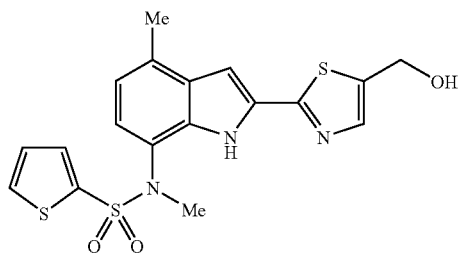 [SMILES: Cc1ccc(N(C)S(=O)(=O)c2cccs2)c2[nH]c(-c3ncc(CO)s3)cc12]

A mixed solution of 4-methyl-7-[methyl(2-thienylsulfonyl)amino]-1H-indole-2-carbothioamide (0.95 g), bromomalonaldehyde (0.78 g) and N,N-dimethylacetamide (15 ml) was stirred at 80° C. for 3 hr. The reaction solution was diluted with ethyl acetate, washed twice with water, and concentrated under reduced pressure. The obtained residue was washed with toluene to give yellow crystals (857 mg). The mother liquor was concentrated, and the residue was subjected to silica gel column chromatography (ethyl acetate:hexane=1:2-1:1) to further give yellow crystals (80 mg). The above-mentioned crystals were combined, dissolved in a mixed solvent of tetrahydrofuran (20 mL) and methanol (20 mL), and ice-cooled. Sodium borohydride (0.10 g) was added, and the mixture was stirred for 2 hr under ice-cooling. Aqueous citric acid solution was added to the reaction solution, and the organic solvent was evaporated under reduced pressure. The obtained residue was extracted with ethyl acetate, washed with saturated brine, dried over anhydrous sodium sulfate, and concentrated under reduced pressure. The obtained residue was subjected to silica gel column chromatography (ethyl acetate:hexane=1:2-2:1-1:0) and washed with ethyl acetate-hexane to give the title compound (0.56 g, yield 60%) as pale-yellow crystals. melting point 184-185° C.

MS:420 (MH$^+$).

Example 246

Ethyl 7-[ethyl(2-thienylsulfonyl)amino]-4-methyl-1H-indole-2-carboxylate

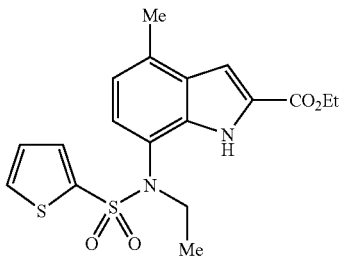 [SMILES: CCOC(=O)c1cc2c(C)ccc(N(CC)S(=O)(=O)c3cccs3)c2[nH]1]

To a mixture of ethyl 7-[(2-thienylsulfonyl)amino]-4-methyl-1H-indole-2-carboxylate (2.89 g), potassium carbonate (1.2 g) and N,N-dimethylformamide (25 mL) was added dropwise a solution of ethyl iodide (0.67 mL) in N,N-dimethylformamide (2 mL) under ice-cooling. The mixture was stirred from under ice-cooling to room temperature for 2 days. The reaction solution was diluted with ethyl acetate, washed successively with aqueous citric acid solution, water and saturated brine, dried over anhydrous magnesium sulfate, and concentrated under reduced pressure. The obtained yellow oil was crystallized from ethyl acetate-hexane and washed with ethyl acetate-hexane to give the title compound (2.16 g, yield 70%) as colorless prism crystals. melting point 148-149° C.

MS:393 (MH$^+$).

Example 247

7-[Ethyl(2-thienylsulfonyl)amino]-4-methyl-1H-indole-2-carboxamide

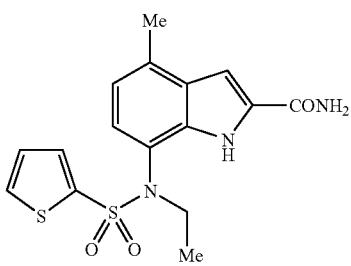 [SMILES: CCN(c1ccc(C)c2cc(C(N)=O)[nH]c12)S(=O)(=O)c1cccs1]

To a mixed solution of ethyl 7-[ethyl(2-thienylsulfonyl)amino]-4-methyl-1H-indole-2-carboxylate (2.12 g) in tetrahydrofuran (15 mL)-methanol (15 mL) was added aqueous solution (5 mL) of 85% potassium hydroxide (1.0 g), and the mixture was stirred at room temperature for 15 hr. The reaction solution was acidified with aqueous citric acid solution, extracted with ethyl acetate, washed with water and saturated brine, dried over anhydrous magnesium sulfate, and concentrated under reduced pressure to give 7-[ethyl(2-thienylsulfonyl)amino]-4-methyl-1H-indole-2-carboxylic acid (2.0 g, yield: quantitative) as a colorless amorphous solid. To a mixture of the obtained solid (2.0 g), 1H-1,2,3-benzotriazol-1-ol-ammonia complex (1.0 g) and N,N-dimethylformamide (20 mL) was added N-[3-(dimethylamino)propyl]-N'-ethylcarbodiimide hydrochloride (1.3 g) under ice-cooling, and the mixture was stirred at room temperature for 2 days. The reaction solution was diluted with ethyl acetate, washed successively with aqueous sodium hydrogencarbonate solution, water and saturated brine, dried over anhydrous magnesium sulfate, and concentrated under reduced pressure. The obtained residue was subjected to silica gel column chromatography (ethyl acetate:hexane=1:1-3:1) to give the title compound (2.0 g, yield: quantitative) as a colorless amorphous solid.

MS:364 (MH$^+$).

Example 248

N-Ethyl-N-[2-(5-formyl-1,3-thiazol-2-yl)-4-methyl-1H-indol-7-yl]thiophene-2-sulfonamide

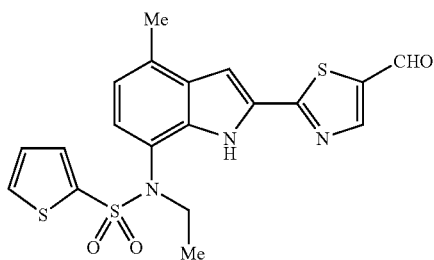 [SMILES: CCN(c1ccc(C)c2cc(-c3ncc(C=O)s3)[nH]c12)S(=O)(=O)c1cccs1]

A mixture of 7-[ethyl(2-thienylsulfonyl)amino]-4-methyl-1H-indole-2-carboxamide (1.9 g), Lawesson's reagent (2.1 g) and tetrahydrofuran (100 mL) was stirred at 40° C. for 4 hr. The reaction solution was concentrated under reduced pressure. The obtained oil was crystallized from dichloromethane-toluene and washed with toluene to give 7-[ethyl(2-thienylsulfonyl)amino]-4-methyl-1H-indole-2-carbothioamide (2.0 g, yield:quantitative) as pale-yellow crystals. A mixed solution of the obtained crystals (2.0 g), bromomalonaldehyde (2.4 g) and N,N-dimethylacetamide (50 mL) was stirred at 70° C. for 3 hr. The reaction solution was diluted with ethyl acetate, washed successively with water and saturated brine, dried over anhydrous magnesium sulfate, and concentrated under reduced pressure. The obtained oil was crystallized from dichloromethane-toluene to give the title compound (1.6 g, yield 70%) as pale-yellow crystals.

MS:432 (MH$^+$).

Example 249

N-Ethyl-N-{2-[5-(1-hydroxyethyl)-1,3-thiazol-2-yl]-4-methyl-1H-indol-7-yl}thiophene-2-sulfonamide

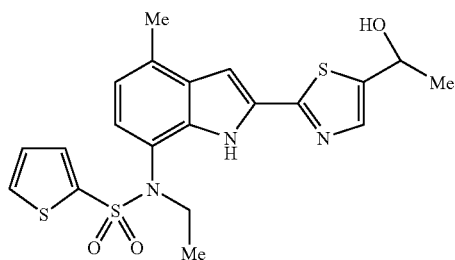 [SMILES: CCN(c1ccc(C)c2cc(-c3ncc(C(C)O)s3)[nH]c12)S(=O)(=O)c1cccs1]

To a mixed solution of N-ethyl-N-[2-(5-formyl-1,3-thiazol-2-yl)-4-methyl-1H-indol-7-yl]thiophene-2-sulfonamide (0.30 g) and tetrahydrofuran (30 mL) was added ether solution (0.60 mL) of 3M-methylmagnesium bromide under ice-cooling, and the mixture was stirred at the same temperature for 4 hr. The reaction mixture was diluted with ethyl acetate, washed successively with aqueous citric acid solution and saturated brine, dried over anhydrous magnesium sulfate, and concentrated under reduced pressure. The obtained residue was subjected to silica gel column chromatography (ethyl acetate:hexane=1:2-2:1), and the obtained pale-yellow oil was crystallized from ethyl acetate-hexane to give the title compound (201 mg, yield 65%) as pale-yellow prism crystals. melting point 152-153° C.

MS:448 (MH$^+$).

Example 250

N-Ethyl-N-{2-[5-(hydroxymethyl)-1,3-thiazol-2-yl]-4-methyl-1H-indol-7-yl}thiophene-2-sulfonamide

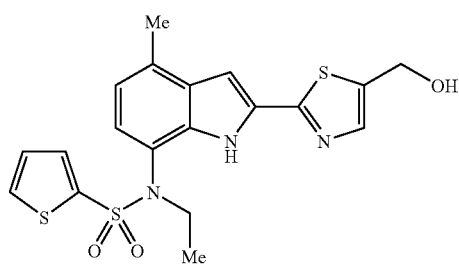 [SMILES: CCN(c1ccc(C)c2cc(-c3ncc(CO)s3)[nH]c12)S(=O)(=O)c1cccs1]

To a mixed solution of N-ethyl-N-[2-(5-formyl-1,3-thiazol-2-yl)-4-methyl-1H-indol-7-yl]thiophene-2-sulfonamide (1.3 g), methanol (15 mL) and tetrahydrofuran (40 mL) was added sodium borohydride (0.14 g) under ice-cooling, and the mixture was stirred at the same temperature for 2 hr. Aqueous citric acid solution was added to the reaction mixture, and the mixture was extracted with ethyl acetate, washed with saturated brine, dried over anhydrous magnesium sulfate, and concentrated under reduced pressure. The obtained crystals were washed with ethyl acetate-hexane to give the title compound (0.74 g) as pale-yellow crystals. The mother liquor was concentrated, and the residue was subjected to silica gel column chromatography (ethyl acetate:hexane=3:7-6:4) to further give the title compound (0.20 g) as pale-yellow crystals. total yield 0.94 g (yield 72%). melting point 166-167° C.

MS:434 (MH$^+$).

Example 251

Ethyl 7-[ethyl(2-thienylsulfonyl)amino]-4,5-dimethyl-1H-indole-2-carboxylate

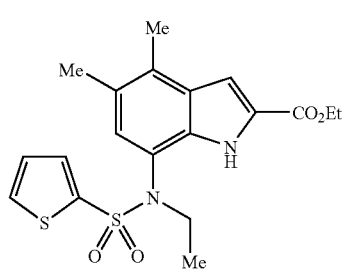 [SMILES: CCOC(=O)c1cc2c(C)c(C)cc(N(CC)S(=O)(=O)c3cccs3)c2[nH]1]

To a mixture of ethyl 7-[(2-thienylsulfonyl)amino]-4,5-dimethyl-1H-indole-2-carboxylate (0.35 g), potassium carbonate (0.13 g) and N,N-dimethylformamide (8 mL) was added dropwise ethyl iodide (0.074 mL) under ice-cooling. The mixture was stirred at from under ice-cooling to room temperature for 18 hr. The reaction solution was diluted with ethyl acetate, washed successively with aqueous citric acid solution, water and saturated brine, dried over anhydrous magnesium sulfate, and concentrated under reduced pressure. The obtained residue was subjected to silica gel column chromatography (ethyl acetate:hexane=1:9-2:8), and the obtained colorless crystals were recrystallized from ethyl acetate-hexane to give the title compound (253 mg, yield 67%) as colorless prism crystals. melting point 134-135° C.

MS:407 (MH$^+$).

Example 252

7-[Ethyl(2-thienylsulfonyl)amino]-4,5-dimethyl-1H-indole-2-carboxamide

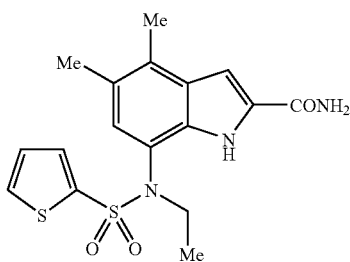 [SMILES: CCN(c1cc(C)c(C)c2cc(C(N)=O)[nH]c12)S(=O)(=O)c1cccs1]

To a mixed solution of ethyl 7-[ethyl(2-thienylsulfonyl)amino]-4,5-dimethyl-1H-indole-2-carboxylate (210 mg) in tetrahydrofuran (8 ml)-methanol (8 mL) was added aqueous solution (5 mL) of 85% potassium hydroxide (100 mg), and the mixture was stirred at room temperature for 6 hr. The reaction solution was acidified with aqueous citric acid solution, extracted with ethyl acetate, washed with saturated brine, dried over anhydrous magnesium sulfate, and concentrated under reduced pressure to give 7-[ethyl(2-thienylsulfonyl)amino]-4,5-dimethyl-1H-indole-2-carboxylic acid (200 mg, yield:quantitative) as colorless crystals. To a mixture of the obtained crystals (200 mg), 1H-1,2,3-benzotriazol-1-ol-ammonia complex (100 mg) and N,N-dimethylformamide (8 mL) was added N-[3-(dimethylamino)propyl]-N'-ethylcarbodiimide hydrochloride (130 mg) under ice-cooling, and the mixture was stirred at room temperature for 2 days. The reaction mixture was diluted with ethyl acetate, washed successively with aqueous sodium hydrogencarbonate solution, water and saturated brine, dried over anhydrous magnesium sulfate, and concentrated under reduced pressure. The obtained residue was subjected to silica gel column chromatography (ethyl acetate:hexane=2:1) to give the title compound (200 mg, yield: quantitative) as colorless prism crystals.

MS:378 (MH$^+$).

Example 253

N-Ethyl-N-[2-(5-formyl-1,3-thiazol-2-yl)-4,5-dimethyl-1H-indol-7-yl]thiophene-2-sulfonamide

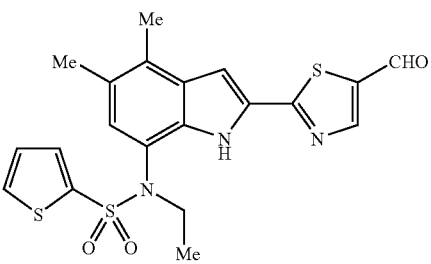 [SMILES: CCN(c1cc(C)c(C)c2cc(-c3ncc(C=O)s3)[nH]c12)S(=O)(=O)c1cccs1]

A mixture of 7-[ethyl(2-thienylsulfonyl)amino]-4,5-dimethyl-1H-indole-2-carboxamide (0.20 g), Lawesson's reagent (0.22 g) and tetrahydrofuran (10 mL) was stirred at 40° C. for 5 hr. The reaction solution was concentrated under reduced pressure. The obtained residue was subjected to silica gel column chromatography(ethyl acetate:hexane=1:9-ethyl acetate) to give 7-[ethyl(2-thienylsulfonyl)amino]-4,5-dimethyl-1H-indole-2-carbothioamide (0.16 g, yield 77%) as pale-yellow crystals. A mixed solution of the obtained crystals (0.16 g), bromomalonaldehyde (0.13 g) and N,N-dimethylacetamide (8 mL) was stirred at 80° C. for 3 hr. The reaction solution was diluted with ethyl acetate, washed successively with water and saturated brine, dried over anhydrous magnesium sulfate, and concentrated under reduced pressure. The obtained residue was subjected to silica gel column chromatography (ethyl acetate:hexane=1:9-1:3) to give the title compound (85 mg, yield 47%) as pale-yellow crystals.

MS:446 (MH$^+$).

Example 254

N-Ethyl-N-{2-[5-(hydroxymethyl)-1,3-thiazol-2-yl]-4,5-dimethyl-1H-indol-7-yl}thiophene-2-sulfonamide

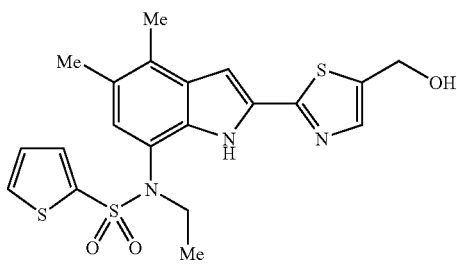 [SMILES: CCN(c1cc(C)c(C)c2cc(-c3ncc(CO)s3)[nH]c12)S(=O)(=O)c1cccs1]

A mixed solution of N-ethyl-N-[2-(5-formyl-1,3-thiazol-2-yl)-4,5-dimethyl-1H-indol-7-yl]thiophene-2-sulfonamide (85 mg), methanol (10 mL) and tetrahydrofuran (15 mL) was added sodium borohydride (10 mg) under ice-cooling, and the mixture was stirred at the same temperature for 2 hr. Aqueous citric acid solution was added to the reaction mixture, and the organic solvent was evaporated under reduced pressure. The obtained mixture was extracted with ethyl acetate, washed with saturated brine, dried over anhydrous magnesium sulfate, and concentrated under reduced pressure.

The obtained crystals were washed with ethyl acetate-hexane to give the title compound (84 mg, yield 99%) as pale-yellow crystals, melting point 189-190° C.

MS:448 (MH$^+$).

Example 255

7-{[(1-Methyl-1H-imidazol-2-yl)thio]methyl}-2-(1,3-thiazol-2-yl)-1H-indole,

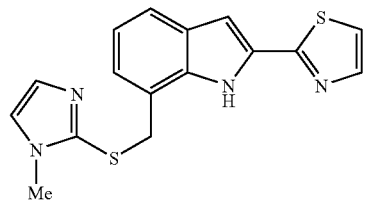 [SMILES: Cn1ccnc1SCc1cccc2cc(-c3nccs3)[nH]c12]

A solution of [2-(1,3-thiazol-2-yl)-1H-indol-7-yl]methanol (0.095 g), 1-methyl-1H-imidazole-2-thiol (0.047 g) and tributylphosphine (0.251 g) in tetrahydrofuran (7 mL) was stirred, 1,1'-(azodicarbonyl)dipiperidine (0.312 g) was added, and the mixture was stirred at room temperature for 2 hr. Water was added to the reaction mixture, and the mixture was extracted with ethyl acetate. The extract was washed successively with water and saturated brine, dried over anhydrous magnesium sulfate, and concentrated under reduced pressure. The residue was purified by silica gel column chromatography (ethyl acetate:hexane=30:70-70:30) to give the title compound (0.089 g, yield 66%) as colorless crystals.

MS m/z 327 (M+H$^+$).

Example 256

7-{[(1-Methyl-1H-imidazol-2-yl) sulfinyl]methyl}-2-(1,3-thiazol-2-yl)-1H-indole

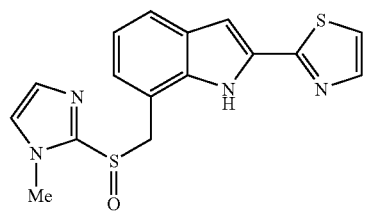 [SMILES: Cn1ccnc1S(=O)Cc1cccc2cc(-c3nccs3)[nH]c12]

To a solution of 7-{[(1-methyl-1H-imidazol-2-yl)thio]methyl}-2-(1,3-thiazol-2-yl)-1H-indole (0.087 g) in ethyl acetate was added m-chloroperbenzoic acid (0.070 g) under ice-cooling, and the mixture was stirred at 0° C. for 1 hr. Saturated aqueous sodium hydrogencarbonate solution was added to the reaction mixture, and the mixture was extracted with ethyl acetate. The extract was washed successively with water and saturated brine, dried over anhydrous magnesium sulfate, and concentrated under reduced pressure. The residue was purified by silica gel column chromatography (ethyl acetate:hexane=50:50-100:0) to give the title compound (0.028 g, yield 31%) as colorless crystals.

MS m/z 343 (M+H$^+$).

Example 257

7-{1-[(1-Methyl-1H-imidazol-2-yl)thio]ethyl}-2-(1,3-thiazol-2-yl)-1H-indole

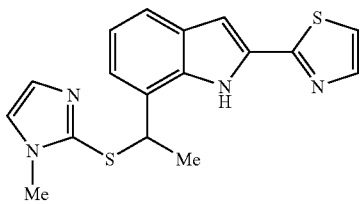 [SMILES: CC(Sc1nccn1C)c1cccc2cc(-c3nccs3)[nH]c12]

A solution of 1-[2-(1,3-thiazol-2-yl)-1H-indol-7-yl]ethanol (0.089 g), 1-methyl-1H-imidazole-2-thiol (0.046 g) and tributylphosphine (0.458 g) in tetrahydrofuran (7 mL) was stirred, 1,1'-(azodicarbonyl)dipiperidine (0.584 g) was added, and the mixture was stirred at room temperature for 1 hr. Water was added to the reaction mixture, and the mixture was extracted with ethyl acetate. The extract was washed successively with water and saturated brine, dried over anhydrous magnesium sulfate, and concentrated under reduced pressure. The residue was purified by silica gel column chromatography (ethyl acetate:hexane=30:70-70:30) to give the title compound (0.110 g, yield 89%) as colorless crystals.

MS m/z 341 (M+H$^+$).

Example 258

7-{1-[(1-Methyl-1H-imidazol-2-yl) sulfonyl]ethyl}-2-(1,3-thiazol-2-yl)-1H-indole

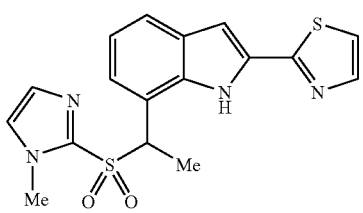 [SMILES: CC(c1cccc2cc(-c3nccs3)[nH]c12)S(=O)(=O)c1nccn1C]

To a mixed solution of 7-{1-[(1-methyl-1H-imidazol-2-yl)thio]ethyl}-2-(1,3-thiazol-2-yl)-1H-indole (0.089 g) in acetonitrile (5 mL) and water (5 mL) was added sodium carbonate-1.5 hydrogen peroxide complex (0.530 g), and the mixture was stirred at room temperature for 4 hr. Saturated aqueous sodium hydrogencarbonate solution and 1N aqueous sodium thiosulfate solution were added, and the mixture was extracted with ethyl acetate. The extract was washed successively with water and saturated brine, dried over anhydrous magnesium sulfate, and concentrated under reduced pressure. The residue was purified by silica gel column chromatography (ethyl acetate:hexane=50:50-100:0) to give the title compound (0.077 g, yield 64%) as colorless crystals.

MS m/z 373 (M+H$^+$).

Example 259

N-Methyl-N-{2-[5-(2-morpholin-4-yl-2-oxoethyl)-1,3-thiazol-2-yl]-1H-indol-7-yl}thiophene-2-sulfonamide

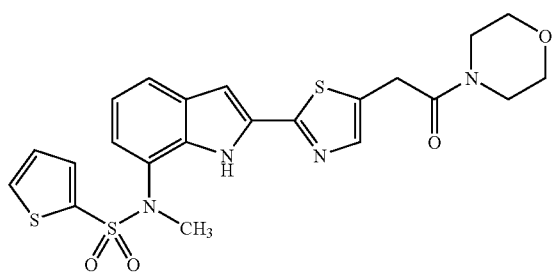 [SMILES: CN(c1cccc2cc(-c3ncc(CC(=O)N4CCOCC4)s3)[nH]c12)S(=O)(=O)c1cccs1]

To a mixture of (2-{7-[methyl(2-thienylsulfonyl)amino]-1H-indol-2-yl}-1,3-thiazol-5-yl)acetic acid (0.38 g), morpholine (0.16 g), 1H-1,2,3-benzotriazol-1-ol (0.18 g) and N,N-dimethylformamide (10 mL) was added N-[3-(dimethylamino)propyl]-N'-ethylcarbodiimide-hydrochloride (0.26 g) at 0° C., and the mixture was stirred at room temperature for 4 hr. Water was added to the reaction mixture, and the obtained crystals were filtrated, washed with water and dried. A solution of the obtained crystals in tetrahydrofuran was treated with activated carbon and concentrated to give the title compound (0.37 g, yield 83%) as colorless crystals. The crystals were recrystallized from ethyl acetate. melting point 199-200° C.

Example 260

4-Chloro-7-[methyl(2-thienylsulfonyl)amino]-1H-indole-2-carboxamide

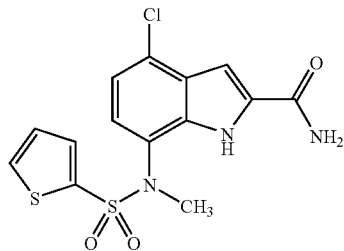 [SMILES: CN(c1ccc(Cl)c2cc(C(N)=O)[nH]c12)S(=O)(=O)c1cccs1]

A mixture of ethyl 4-chloro-1-(methoxymethyl)-7-[methyl(2-thienylsulfonyl)amino]-1H-indole-2-carboxylate (1.10 g), 6N hydrochloric acid (5 mL), tetrahydrofuran (20 mL) and ethanol (10 mL) was heated under reflux overnight. Water was added to the reaction mixture, and the mixture was extracted with ethyl acetate. The ethyl acetate layer was washed with saturated brine and concentrated. A mixture of the obtained residue, 4N aqueous sodium hydroxide solution (1.2 mL), tetrahydrofuran (10 mL) and methanol (10 mL) was stirred at 60° C. for 1 hr. The mixture was acidified with 10% aqueous citric acid solution, and extracted with ethyl acetate. The ethyl acetate layer was washed with saturated brine, dried (MgSO$_4$) and concentrated. To a mixture of the obtained residue, 1H-1,2,3-benzotriazol-1-ol (0.40 g) and N,N-dimethylformamide (10 mL) was added N-[3-(dimethylamino)propyl]-N'-ethylcarbodiimide-hydrochloride (0.57 g) at room temperature, and the mixture was stirred at 50° C. for 30 min, allowed to warm to room temperature and 28% aqueous ammonia (0.75 mL) was added. The reaction mixture was stirred at room temperature for 2 hr, and water was added. The mixture was acidified with 10% aqueous citric acid solution, and extracted with ethyl acetate. The ethyl acetate layer was washed with saturated brine, dried (MgSO$_4$) and concentrated. The residue was subjected to silica gel column chromatography and the title compound (0.25 g, yield 78%) was obtained as pale-yellow crystals from a fraction eluted with tetrahydrofuran-hexane (2:1, volume ratio). melting point 252-254° C.

Example 261

N-{4-Chloro-2-[5-(hydroxymethyl)-1,3-thiazol-2-yl]-1H-indol-7-yl}-N-methylthiophene-2-sulfonamide

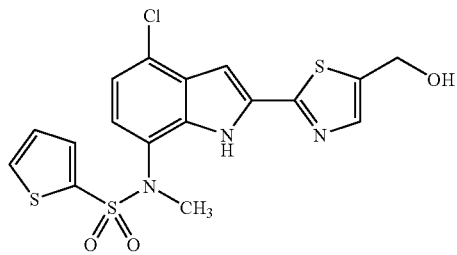 [SMILES: CN(c1ccc(Cl)c2cc(-c3ncc(CO)s3)[nH]c12)S(=O)(=O)c1cccs1]

A mixture of 4-chloro-7-[methyl(2-thienylsulfonyl)amino]-1H-indole-2-carbothioamide (0.51 g), bromomalonaldehyde (0.30 g) and N,N-dimethylacetamide (15 mL) was stirred at 90° C. for 4 hr. Water was added to the reaction mixture, and the obtained crystals were filtrated, washed with water and dried. To a mixture of the obtained crystals, tetrahydrofuran (5 mL) and methanol (5 mL) was added sodium borohydride (55 mg) at 0° C., and the mixture was stirred at the same temperature for 1 hr. To the reaction mixture was added 10% aqueous citric acid solution, and the mixture was extracted with ethyl acetate. The ethyl acetate layer was washed with saturated brine, dried (MgSO$_4$) and concentrated. The residue was subjected to silica gel column chromatography and the title compound (0.30 g, yield 52%) was obtained as pale-yellow crystals from a fraction eluted with tetrahydrofuran-hexane (2:1, volume ratio). melting point 225-226° C.

Example 262

N-{2-[5-(Hydroxymethyl)-1,3-thiazol-2-yl]-1H-indol-7-yl}thiophene-2-sulfonamide

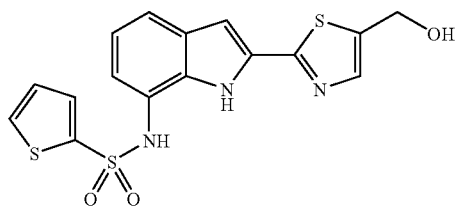 [SMILES: O=S(=O)(Nc1cccc2cc(-c3ncc(CO)s3)[nH]c12)c1cccs1]

A mixture of 7-[(2-thienylsulfonyl)amino]-1H-indole-2-carbothioamide (1.12 g), bromomalonaldehyde (0.90 g) and N,N-dimethylacetamide (15 mL) was stirred at 90° C. for 1 hr. Water was added to the reaction mixture, and the obtained crystals were filtrated, washed with water and dried. To a mixture of the obtained crystals, tetrahydrofuran (10 mL) and methanol (10 mL) was added sodium borohydride (0.13 g) at 0° C., and the mixture was stirred at the same temperature for 1 hr. To the reaction mixture was added 10% aqueous citric acid solution was added, and the mixture was extracted with ethyl acetate. The ethyl acetate layer was washed with saturated brine, dried (MgSO$_4$) and concentrated. The residue was subjected to silica gel column chromatography and the title compound (0.70 g, yield 60%) was obtained as pale-yellow crystals from a fraction eluted with tetrahydrofuran-hexane (3:1, volume ratio). melting point 209-210° C.

Example 263

Ethyl 6-chloro-7-[(2-thienylsulfonyl)amino]-1H-indole-2-carboxylate

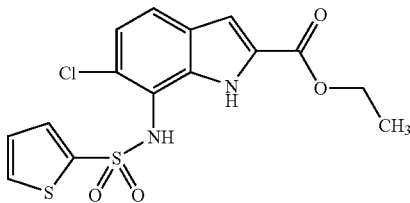 [SMILES: CCOC(=O)c1cc2ccc(Cl)c(NS(=O)(=O)c3cccs3)c2[nH]1]

To a mixture of ethyl 7-amino-6-chloro-1H-indole-2-carboxylate (1.59 g) and pyridine (10 mL) was added thiophene-2-sulfonyl chloride (1.46 g) and the mixture was stirred at 50° C. for 3 hr. The reaction mixture was concentrated, 10% aqueous citric acid solution was added, and the mixture was extracted with ethyl acetate. The ethyl acetate layer was washed with saturated brine, dried (MgSO$_4$) and concentrated. The obtained residue was subjected to silica gel column chromatography and the title compound (2.17 g, yield 85%) was obtained as colorless crystals from a fraction eluted with tetrahydrofuran-hexane (1:2, volume ratio). The crystals were recrystallized from ethyl acetate. melting point 191-192° C.

Example 264

6-Chloro-7-[(2-thienylsulfonyl)amino]-1H-indole-2-carboxylic acid

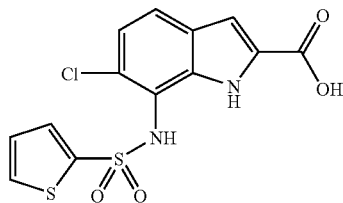 [SMILES: O=C(O)c1cc2ccc(Cl)c(NS(=O)(=O)c3cccs3)c2[nH]1]

A mixture of ethyl 6-chloro-7-[(2-thienylsulfonyl)amino]-1H-indole-2-carboxylate (1.00 g), 4N aqueous sodium hydroxide solution (2.3 mL), tetrahydrofuran (5 mL) and methanol (5 mL) was stirred at 50° C. for 2 hr. The reaction mixture was concentrated and acidified with 10% aqueous citric acid solution. The resulting crystals were filtrated, washed with water, and dried to give the title compound (0.88 g, yield 95%) as colorless crystals. melting point>290° C. (decomposition).

Example 265

6-Chloro-7-[(2-thienylsulfonyl)amino]-1H-indole-2-carboxamide

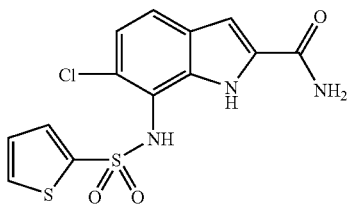 [SMILES: NC(=O)c1cc2ccc(Cl)c(NS(=O)(=O)c3cccs3)c2[nH]1]

To a mixture of 6-chloro-7-[(2-thienylsulfonyl)amino]-1H-indole-2-carboxylic acid (0.83 g), 1H-1,2,3-benzotriazol-1-ol (0.38 g) and N,N-dimethylformamide (10 mL) was added N-[3-(dimethylamino)propyl]-N'-ethylcarbodiimide-hydrochloride (0.54 g) at room temperature, and the mixture was stirred at 50° C. for 20 min. The mixture was allowed to warm to room temperature, and 28% aqueous ammonia (0.30 mL) was added. The reaction mixture was stirred at room temperature for 1 hr and acidified with 10% aqueous citric acid solution. The resulting crystals were filtrated, washed with water, and dried to give the title compound (0.80 g, yield 96%) as colorless crystals. melting point>300° C. (decomposition).

Example 266

N-{6-Chloro-2-[5-(hydroxymethyl)-1,3-thiazol-2-yl]-1H-indol-7-yl}thiophene-2-sulfonamide

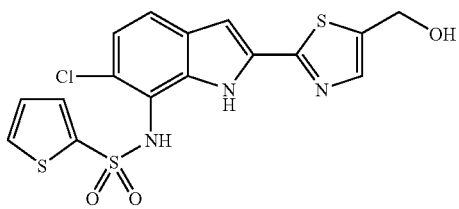 [SMILES: O=S(=O)(Nc1c(Cl)ccc2cc(-c3ncc(CO)s3)[nH]c12)c1cccs1]

A mixture of 6-chloro-7-[(2-thienylsulfonyl)amino]-1H-indole-2-carbothioamide (0.75 g), bromomalonaldehyde (0.45 g) and N,N-dimethylacetamide (10 mL) was stirred at 90° C. for 3 hr. Water was added to the reaction mixture, and the obtained crystals were filtrated, washed with water and dried. To a mixture of the obtained crystals, tetrahydrofuran (10 mL) and methanol (5 mL) was added sodium borohydride (84 mg) at 0° C., and the mixture was stirred at the same temperature for 30 min. To the reaction mixture was added 10% aqueous citric acid solution, and the mixture was extracted with ethyl acetate. The ethyl acetate layer was washed with saturated brine, dried (MgSO$_4$) and concentrated. The residue was subjected to silica gel column chromatography and the title compound (0.46 g, yield 55%) was

Example 267

Ethyl 6-chloro-7-[methyl(2-thienylsulfonyl)amino]-1H-indole-2-carboxylate

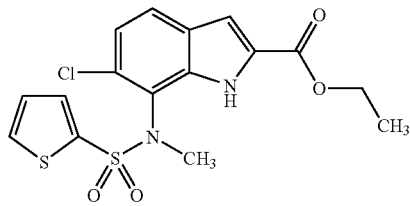 [SMILES: CCOC(=O)c1cc2ccc(Cl)c(N(C)S(=O)(=O)c3cccs3)c2[nH]1]

A mixture of ethyl 6-chloro-7-[(2-thienylsulfonyl)amino]-1H-indole-2-carboxylate (1.00 g), methyl iodide (0.17 mL), potassium carbonate (0.36 g) and N,N-dimethylformamide (10 mL) was stirred at room temperature overnight. Water was added to the reaction mixture, and the obtained crystals were filtrated, washed with water and dried. The obtained crystals were subjected to NH silica gel column chromatography and the title compound (0.80 g, yield 77%) was obtained as colorless crystals from a fraction eluted with ethyl acetate-hexane (1:2, volume ratio). melting point 156-157° C.

Example 268

6-Chloro-7-[methyl (2-thienylsulfonyl)amino]-1H-indole-2-carboxylic acid

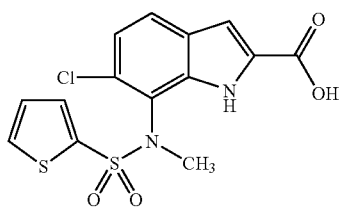 [SMILES: CN(c1c(Cl)ccc2cc(C(=O)O)[nH]c12)S(=O)(=O)c1cccs1]

A mixture of ethyl 6-chloro-7-[methyl(2-thienylsulfonyl)amino]-1H-indole-2-carboxylate (0.74 g), 4N aqueous sodium hydroxide solution (1.2 mL), tetrahydrofuran (6 mL) and methanol (4 mL) was stirred at 60° C. for 2 hr. The reaction mixture was concentrated and acidified with 10% aqueous citric acid solution. The resulting crystals were filtrated, washed with water, and dried to give the title compound (0.69 g, quantitative) as colorless crystals. melting point 286-288° C.

Example 269

6-Chloro-7-[methyl(2-thienylsulfonyl)amino]-1H-indole-2-carboxamide

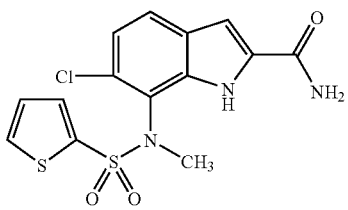 [SMILES: CN(c1c(Cl)ccc2cc(C(N)=O)[nH]c12)S(=O)(=O)c1cccs1]

To a mixture of 6-chloro-7-[methyl(2-thienylsulfonyl)amino]-1H-indole-2-carboxylic acid (0.69 g), 1H-1,2,3-benzotriazol-1-ol (0.31 g) and N,N-dimethylformamide (10 mL) was added N-[3-(dimethylamino)propyl]-N'-ethylcarbodiimide-hydrochloride (0.44 g) at room temperature, and the mixture was stirred at 50° C. for 20 min. The mixture was allowed to warm to room temperature, and 28% aqueous ammonia (0.30 mL) was added. The reaction mixture was stirred at room temperature for 2 hr, and acidified with 10% aqueous citric acid solution. The resulting crystals were filtrated, washed with water, and dried to give the title compound (0.70 g, quantitative) as colorless crystals. melting point 225-226° C. (decomposition).

Example 270

N-{6-Chloro-2-[5-(hydroxymethyl)-1,3-thiazol-2-yl]-1H-indol-7-yl}-N-methylthiophene-2-sulfonamide

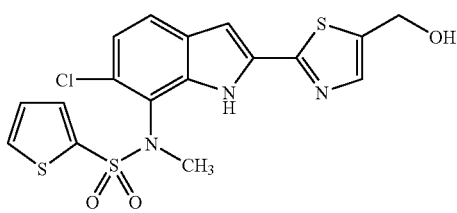 [SMILES: CN(c1c(Cl)ccc2cc(-c3ncc(CO)s3)[nH]c12)S(=O)(=O)c1cccs1]

A mixture of 6-chloro-7-[methyl(2-thienylsulfonyl)amino]-1H-indole-2-carbothioamide (0.60 g), bromomalonaldehyde (0.38 g) and N,N-dimethylacetamide (10 mL) was stirred at 90° C. for 3 hr. Water was added to the reaction mixture, and the obtained crystals were filtrated, washed with water and dried. To a mixture of the obtained crystals, tetrahydrofuran (10 mL) and methanol (5 mL) was added sodium borohydride (70 mg) at 0° C., and the mixture was stirred at the same temperature for 30 min. To the reaction mixture was added 10% aqueous citric acid solution, and the mixture was extracted with ethyl acetate. The ethyl acetate layer was washed with saturated brine, dried (MgSO$_4$) and concentrated. The residue was subjected to silica gel column chromatography and the title compound (0.38 g, yield 45%) was obtained as pale-yellow crystals from a fraction eluted with tetrahydrofuran-hexane (2:1, volume ratio). melting point 214-215° C.

Example 271

2-Chloro-N-methyl-N-[2-(1,3-thiazol-2-yl)-1H-indol-7-yl]pyridine-3-sulfonamide

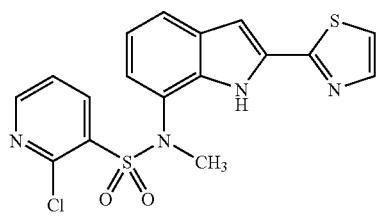 [SMILES: CN(c1cccc2cc(-c3nccs3)[nH]c12)S(=O)(=O)c1cccnc1Cl]

To a solution of N-methyl-2-(1,3-thiazol-2-yl)-1H-indole-7-amine monohydrochloride (132 mg) in pyridine (3 mL) was added 2-chloropyridine-3-sulfonyl chloride (120 mg) at 0° C., and the mixture was stirred at room temperature for 2 hr. The reaction mixture was concentrated, water was added, and the mixture was extracted with ethyl acetate. The ethyl acetate layer was washed with saturated brine, dried (MgSO$_4$) and concentrated. The residue was subjected to silica gel column chromatography (ethyl acetate:hexane=1:1) to give the title compound (126 mg, yield 62%) as pale-yellow crystals. melting point 203° C.

Example 272

2-Formyl-N-methyl-N-[2-(1,3-thiazol-2-yl)-1H-indol-7-yl]thiophene-3-sulfonamide

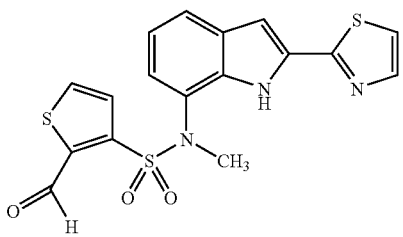 [SMILES: CN(c1cccc2cc(-c3nccs3)[nH]c12)S(=O)(=O)c1ccsc1C=O]

To a solution of 2-(hydroxymethyl)-N-methyl-N-[2-(1,3-thiazol-2-yl)-1H-indol-7-yl]thiophene-3-sulfonamide (1.75 g) in acetonitrile (50 mL) was added Dess-Martin reagent (2.1 g). The reaction mixture was stirred at room temperature for 16 hr. Saturated aqueous sodium hydrogencarbonate solution was added, and the mixture was extracted with ethyl acetate. The ethyl acetate layer was washed with saturated brine, dried (MgSO$_4$) and concentrated. The residue was subjected to silica gel column chromatography (ethyl acetate:hexane=1:1) to give the title compound (790 mg, yield 46%) as pale-yellow crystals.

$^1$H-NMR (DMSO-d$_6$) δ:6.52 (1H, d, J=6.9 Hz), 6.94 (1H, t, J=7.8 Hz), 7.13 (1H, d, J=2.1 Hz), 7.50 (1H, d, J=5.4 Hz), 7.62 (1H, d, J=7.8 Hz), 7.83 (1H, d, J=3.3 Hz), 7.97 (1H, d, J=3.3 Hz), 8.29 (1H, dd, J=1.2 Hz, 4.8 Hz), 9.31 (1H, s),12.02 (1H, brs).

Example 273

2-(1-Hydroxyethyl)-N-methyl-N-[2-(1,3-thiazol-2-yl)-1H-indol-7-yl]thiophene-3-sulfonamide

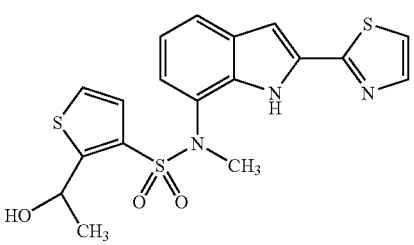 [SMILES: CC(O)c1sccc1S(=O)(=O)N(C)c1cccc2cc(-c3nccs3)[nH]c12]

To a solution of 2-formyl-N-methyl-N-[2-(1,3-thiazol-2-yl)-1H-indol-7-yl]thiophene-3-sulfonamide (790 mg) in tetrahydrofuran (20 mL) was added methylmagnesium bromide (3.0 M, 1.5 mL), and the mixture was stirred at room temperature for 1 hr. Water was added to the reaction mixture, and the mixture was extracted with ethyl acetate. The ethyl acetate layer was washed with saturated brine, dried (MgSO$_4$) and concentrated. The residue was subjected to silica gel column chromatography (ethyl acetate:hexane=1:1) to give the title compound (272 mg, yield 33%) as white crystals. melting point 193° C.

Example 274

2-Acetyl-N-methyl-N-[2-(1,3-thiazol-2-yl)-1H-indol-7-yl]thiophene-3-sulfonamide

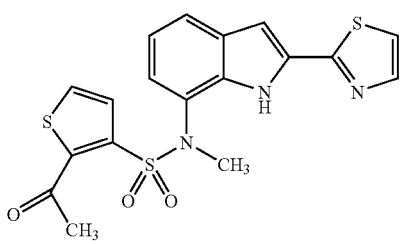 [SMILES: CC(=O)c1sccc1S(=O)(=O)N(C)c1cccc2cc(-c3nccs3)[nH]c12]

To a solution of 2-(1-hydroxyethyl)-N-methyl-N-[2-(1,3-thiazol-2-yl)-1H-indol-7-yl]thiophene-3-sulfonamide (180 mg) in acetonitrile (10 mL) was added Dess-Martin reagent (212 mg), and the mixture was stirred at room temperature for 16 hr. Saturated aqueous sodium hydrogencarbonate solution was added to the reaction mixture, and the mixture was extracted with ethyl acetate. The ethyl acetate layer was washed with saturated brine, dried (MgSO$_4$) and concentrated. The residue was subjected to silica gel column chro-

Example 275

N-(Cyclopropylmethyl)-N-{2-[5-(hydroxymethyl)-1,3-thiazol-2-yl]-1H-indol-7-yl}thiophene-2-sulfonamide

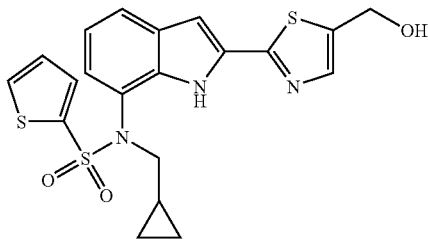 [SMILES: O=S(=O)(c1cccs1)N(CC1CC1)c1cccc2cc(-c3ncc(CO)s3)[nH]c12]

A mixture of 7-[(cyclopropylmethyl)(2-thienylsulfonyl)amino]-1H-indole-2-carbothioamide (225 mg), bromomalonaldehyde (182 mg) and N,N-dimethylacetamide (3 mL) was stirred at 90° C. for 1 hr. Water was added and the obtained precipitate was washed with water, and then with hexane. The solid was dissolved in a mixture of tetrahydrofuran (5 mL) and methanol (5 mL), and the mixture was cooled in an ice bath. Sodium borohydride (20 mg) was added and the mixture was stirred at room temperature for 3 days. The reaction mixture was concentrated, and the residue was diluted with a mixture of tetrahydrofuran-ethyl acetate (1:1) and washed with saturated brine and aqueous sodium bicarbonate. The organic layer was dried over magnesium sulfate, filtrated, and the filtrate was concentrated. The residue was subjected to silica gel column chromatography and eluted with a mixture of ethyl acetate-hexane. The obtained solid was washed with a mixture of hexane-ether to give the title compound (100 mg, yield 50%) as crystals. melting point 174° C.

Example 276

N-{2-[5-(Hydroxymethyl)-1,3-thiazol-2-yl]-1H-indol-7-yl}-N-isopropylthiophene-2-sulfonamide

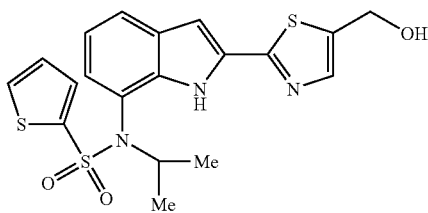 [SMILES: CC(C)N(c1cccc2cc(-c3ncc(CO)s3)[nH]c12)S(=O)(=O)c1cccs1]

A mixture of 7-[isopropyl(2-thienylsulfonyl)amino]-1H-indole-2-carbothioamide (123 mg), bromomalonaldehyde (103 mg) and N,N-dimethylacetamide (3 mL) was stirred at 90° C. for 2 hr. To the reaction mixture was added water, and the obtained solid was washed with water, and then with hexane. To a mixture of the solid, tetrahydrofuran (5 mL) and methanol (5 mL) was added sodium borohydride (15 mg), and the mixture was stirred at room temperature for 14 hr. The reaction mixture was concentrated under reduced pressure, and ethyl acetate was added to the residue. The mixture was washed with aqueous sodium bicarbonate and saturated brine, and the ethyl acetate layer was dried over magnesium sulfate, and filtrated. The filtrate was concentrated. The residue was subjected to silica gel column chromatography, and eluted with a mixture of ethyl acetate-hexane (2:1) to give the title compound (124 mg, yield 88%) as crystals. melting point 209° C.

Example 277

N-(2-Ethoxyethyl)-N-{2-[5-(hydroxymethyl)-1,3-thiazol-2-yl]-1H-indol-7-yl}thiophene-2-sulfonamide

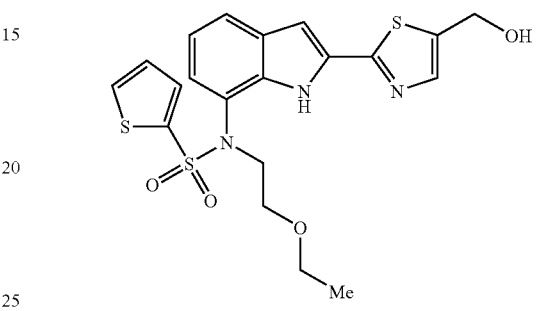

7-[(2-Ethoxyethyl) (2-thienylsulfonyl)amino]-1H-indole-2-carbothioamide (3.00 g), bromomalonaldehyde (2.32 g) and N,N-dimethylacetamide (50 mL) were stirred at 95° C. for 3 hr. The reaction mixture was diluted with ethyl acetate and water, and the ethyl acetate layer was washed successively with saturated brine and aqueous sodium bicarbonate, dried over magnesium sulfate and filtrated. The filtrate was concentrated, subjected to silica gel column chromatography and eluted with a mixture of ethyl acetate-hexane (1:1) to give a solid. The solid was dissolved in tetrahydrofuran (50 mL) and methanol (20 mL), sodium borohydride (176 mg) was added and the mixture was stirred at room temperature for 3 days. The reaction mixture was diluted with ethyl acetate and washed with saturated brine. The organic layer was dried over magnesium sulfate and filtrated. The filtrate was concentrated, subjected to silica gel column chromatography and eluted with a mixture of ethyl acetate-hexane (2:1) to give the title compound (1.00 g, yield 29%) as an amorphous form.

MS m/z 464 (M+H$^+$).

Example 278

N-Ethyl-N-{2-[5-(hydroxymethyl)-1,3-thiazol-2-yl]-1H-indol-7-yl}thiophene-2-sulfonamide

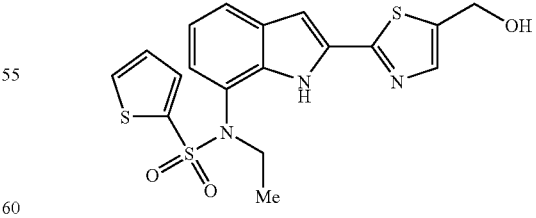

A mixture of 7-[ethyl(2-thienylsulfonyl)amino]-1H-indole-2-carbothioamide (4.10 g), bromomalonaldehyde (3.55 g) and N,N-dimethylacetamide (30 mL) was stirred at 95° C. for 1.5 hr. To the reaction mixture was added water, and the obtained precipitate was dissolved in tetrahydrofuran (30 mL) and methanol (30 mL). After cooling in an ice bath, sodium borohydride (508 mg) was added, and the mixture was stirred at room temperature for 16 hr. The reaction mixture was concentrated and diluted with a mixture of ethyl acetate-tetrahydrofuran and washed successively with aqueous sodium bicarbonate and saturated brine. The organic layer was dried over magnesium sulfate and filtrated. The filtrate was concentrated, subjected to silica gel column chromatography, and eluted with an ethyl acetate-hexane (2:1) mixture to give the title compound (800 mg, yield 17%) as a solid.

MS m/z 420 (M+H$^+$).

Example 279

Methyl 4-[(2-{7-[ethyl(2-thienylsulfonyl)amino]-1H-indol-2-yl}-1,3-thiazol-5-yl)methoxy]benzoate

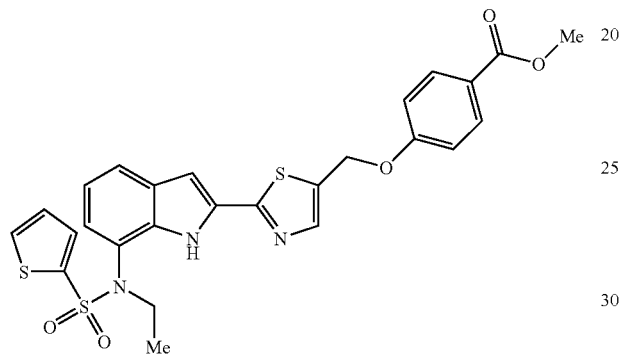

N-ethyl-N-{2-[5-(hydroxymethyl)-1,3-thiazol-2-yl]-1H-indol-7-yl}thiophene-2-sulfonamide (420 mg) and methyl 4-hydroxybenzoate (153 mg) were dissolved in tetrahydrofuran (10 mL), and tri-tert-butylphosphine (263 mg) and 1,1'-(azodicarbonyl)dipiperidine (328 mg) were added. The reaction mixture was stirred at room temperature for 30 min. The reaction mixture was filtrated and the filtrate was concentrated. The residue was subjected to silica gel column chromatography and eluted with a mixture of ethyl acetate-hexane (1:1) to give the title compound (200 mg, yield 36%) as pale-yellow crystals. melting point 191° C.

Example 280

4-[(2-{7-[Ethyl(2-thienylsulfonyl)amino]-1H-indol-2-yl}-1,3-thiazol-5-yl)methoxy]benzoic acid

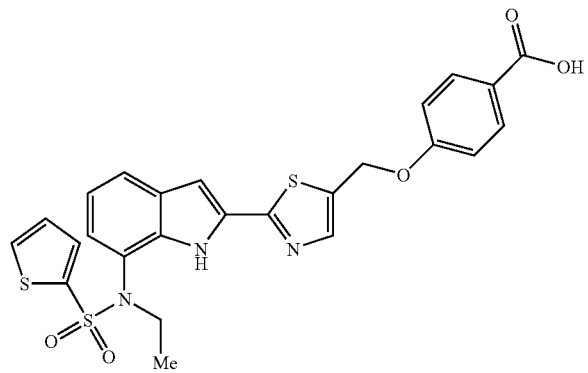 [SMILES: CCN(c1cccc2cc(-c3ncc(COc4ccc(C(=O)O)cc4)s3)[nH]c12)S(=O)(=O)c1cccs1]

Methyl 4-[(2-{7-[ethyl(2-thienylsulfonyl)amino]-1H-indol-2-yl}-1,3-thiazol-5-yl)methoxy]benzoate (98 mg), tetrahydrofuran (2 mL), methanol (2 mL) and 1N aqueous sodium hydroxide solution (2 mL) was stirred at 50° C. for 16 hr. The reaction mixture was acidified with 1N hydrochloride, diluted with ethyl acetate and washed with saturated brine. The organic layer was dried over magnesium sulfate and filtrated. The filtrate was concentrated, and the residue was subjected to silica gel column chromatography and recrystallized from an ethyl acetate-hexane (4:1) mixture to give the title compound (51 mg, yield 54%) as crystals. melting point 188° C.

Example 281

2-{7-[Methyl(2-thienylsulfonyl)amino]-1H-indol-2-yl}-1,3-thiazole-5-carboxylic acid

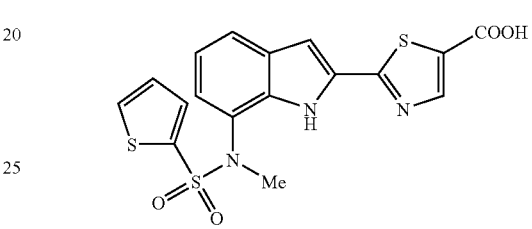

A mixture of 7-[methyl(2-thienylsulfonyl)amino]-1H-indole-2-carbothioamide (1.00 g), potassium (1-chloro-2-ethoxy-1-formyl-2-oxoethyl) (1.18 g), acetic acid (855 mg) and N,N-dimethylacetamide (20 mL) was stirred at 90° C. for 16 hr. The reaction mixture was diluted with ethyl acetate and washed with saturated brine. The organic layer was dried over magnesium sulfate and filtrated. The filtrate was concentrated, and the residue was subjected to silica gel column chromatography and eluted with an ethyl acetate-hexane (1:1) mixture to give a solid. The solid was mixed with tetrahydrofuran (3 mL), ethanol (3 mL) and 1N sodium hydroxide (5 mL), and the mixture was stirred at 60° C. for 3 days. The reaction mixture was acidified with 1N hydrochloric acid, diluted with ethyl acetate and washed with saturated brine. The organic layer was washed with sodium sulfate, filtrated, and the filtrate was concentrated. The residue was subjected to silica gel column chromatography and eluted with a methanol.ethyl acetate (1:5) mixture. The obtained solid was recrystallized from a methanol-ethyl acetate (1:10) mixed solvent to give the title compound (32 mg, yield 2.7%) as crystals. melting point 258-260° C.

For Examples 282-288, the following purification and analysis conditions were employed.

LC-MS Measurement Conditions

In the following Examples, HPLC-mass spectrum (LC-MS) was measured under the following conditions.

measurement tool: Micromass Co., Ltd. Quattro Micro, Agilent Technologies, Inc. HP1100, or Waters Corporation MUX system (Micromass Co., Ltd., ZQ)

column: Shiseido Co., Ltd. Capcelpak C18 UG-120, 1.5× 35 mm solvent: SOLUTION A; 5 mM ammonium acetate/2% acetonitrile/water, SOLUTION B; 5 mM ammonium acetate/95% acetonitrile/water gradient cycle: 0.00 min (SOLUTION A 100%), 2.00 min (SOLUTION B 100%), 3.00 min (SOLUTION B 100%), 3.01 min (SOLUTION A 100%), 3.80 min (SOLUTION A 100%)

flow rate: 0.5 ml/min detection method: UV 220 nm ionization method: electron impact ionization method (Electron Spray Ionization: ESI)

Preparative HPLC Conditions

In the following Examples, the purification conditions by preparative HPLC were as followings.

Tool: Gilson, Inc. high throughput purification system column: Shiseido Co., Ltd. Capcelpak C18 UG-120, S-5 µM, 20×50 mm solvent: SOLUTION A; 0.1% trifluoroacetic acid-containing water, SOLUTION B; 0.1% trifluoroacetic acid-containing aqueous acetonitrile gradient cycle: 0.00 min (SOLUTION A/SOLUTION B=95/5), 1.10 min (SOLUTION A/SOLUTION B=95/5), 5.00 min (SOLUTION A/SOLUTION B=0/100), 6.40 min (SOLUTION A/SOLUTION B=0/100), 6.50 min (SOLUTION A/SOLUTION B=95/5)

flow rate: 20 ml/min, detection method: UV 220 nm

Example 282

N-(2-Ethoxyethyl)-N-[2-(5-{[(2-hydroxyethyl)thio]methyl}-1,3-thiazol-2-yl)-1H-indol-7-yl]thiophene-2-sulfonamide

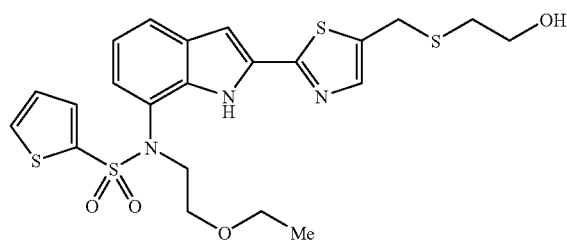 [SMILES: CCOCCN(c1cccc2cc(-c3ncc(CSCCO)s3)[nH]c12)S(=O)(=O)c1cccs1]

A solution (2 mL) of N-{2-[5-(chloromethyl)-1,3-thiazol-2-yl]-1H-indol-7-yl}-N-(2-ethoxyethyl)thiophene-2-sulfonamide (18 mg) and triethylamine (14 mg), 2-mercaptoethanol (10 mg) in N,N-dimethylformamide was stirred at room temperature for 18 hr. The reaction mixture was diluted with water, and extracted with ethyl acetate. The extract was concentrated, and the residue was purified by preparative HPLC to give the title compound (5.9 mg, yield 30%).

HPLC purity 100%.

MS m/z 524 (M+H$^+$).

$^1$H-NMR (CDCl$_3$) δ:1.13 (3H, t, J=7.0 Hz), 2.75 (2H, t, J=5.9 Hz), 3.43 (2H, q, J=7.0 Hz), 3.51 (2H, t, J=5.8 Hz), 3.79 (2H, t, J=5.8 Hz), 3.80 (2H, brs), 3.98 (2H, s), 6.66 (1H, d, J=7.5 Hz), 6.94-7.02 (2H, m), 7.07 (1H, dd, J=4.9, 3.8 Hz), 7.43 (1H, dd, J=3.7, 1.2 Hz), 7.57-7.62 (3H, m), 9.81 (1H, brs).

Example 283

2-{[(2-{7-[Methyl (2-thienylsulfonyl)amino]-1H-indol-2-yl}-1,3-thiazol-5-yl)methyl]thio}acetamide

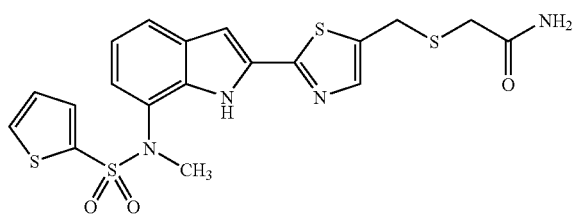 [SMILES: CN(c1cccc2cc(-c3ncc(CSCC(N)=O)s3)[nH]c12)S(=O)(=O)c1cccs1]

The title compound (1.2 mg, yield 5%) was obtained from N-{2-[5-(chloromethyl)-1,3-thiazol-2-yl]-1H-indol-7-yl}-N-methylthiophene-2-sulfonamide (23 mg) and 2-mercaptoacetamide (15 mg) in the same manner as in Example 282.

HPLC purity 100%.

MS m/z 479 (M+H$^+$).

Example 284

N-[2-(5-{[(2-Hydroxyethyl)thio]methyl}-1,3-thiazol-2-yl)-1H-indol-7-yl]-N-methylthiophene-2-sulfonamide

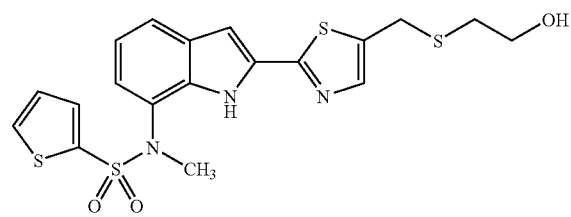 [SMILES: CN(c1cccc2cc(-c3ncc(CSCCO)s3)[nH]c12)S(=O)(=O)c1cccs1]

The title compound (6.2 mg, yield 25%) was obtained from N-{2-[5-(chloromethyl)-1,3-thiazol-2-yl]-1H-indol-7-yl}-N-methylthiophene-2-sulfonamide (23 mg) and 2-mercaptoethanol (13 mg) in the same manner as in Example 282.

HPLC purity 93%.

MS m/z 466 (M+H$^+$).

Example 285

N-Ethyl-N-[2-(5-{[(2-hydroxyethyl)thio]methyl}-1,3-thiazol-2-yl)-1H-indol-7-yl]thiophene-2-sulfonamide

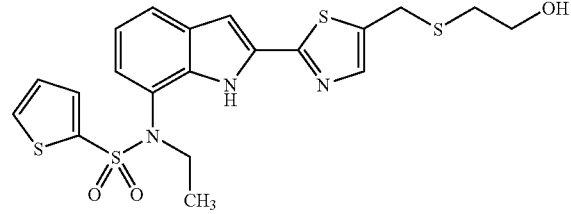 [SMILES: CCN(c1cccc2cc(-c3ncc(CSCCO)s3)[nH]c12)S(=O)(=O)c1cccs1]

The title compound (4.2 mg, yield 19%) was obtained from N-{-2-[5-(chloromethyl)-1,3-thiazol-2-yl]-1H-indol-7-yl}-

N-ethylthiophene-2-sulfonamide (21 mg) and 2-mercaptoethanol (11 mg) in the same manner as in Example 282.

HPLC purity 95%.

MS m/z 480 (M+H$^+$).

Example 286

N-(Cyclopropylmethyl)-N-[2-(5-{[(2-hydroxyethyl)thio]methyl}-1,3-thiazol-2-yl)-1H-indol-7-yl]thiophene-2-sulfonamide

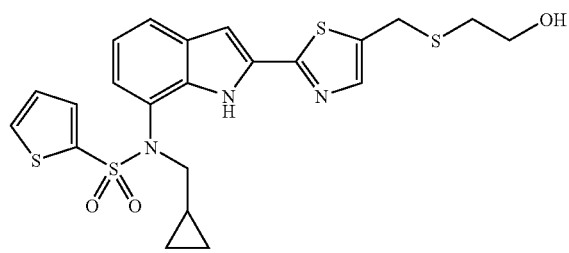 [SMILES: O=S(=O)(c1cccs1)N(CC1CC1)c1cccc2cc(-c3ncc(CSCCO)s3)[nH]c12]

The title compound (6.5 mg, yield 29%) was obtained from N-{2-[5-(chloromethyl)-1,3-thiazol-2-yl]-1H-indol-7-yl}-N-(cyclopropylmethyl)thiophene-2-sulfonamide (21 mg) and 2-mercaptoethanol (10 mg) in the same manner as in Example 282.

HPLC purity 100%.

MS m/z 506 (M+H$^+$).

Example 287

N-[2-(5-{[(2-Hydroxyethyl) thio]methyl}-1,3-thiazol-2-yl)-1H-indol-7-yl]-N-isopropylthiophene-2-sulfonamide

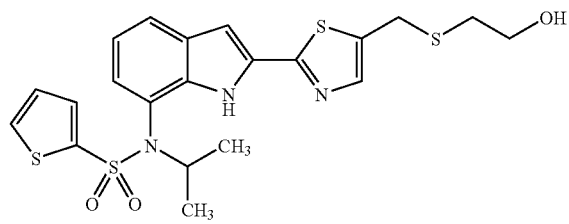 [SMILES: CC(C)N(c1cccc2cc(-c3ncc(CSCCO)s3)[nH]c12)S(=O)(=O)c1cccs1]

The title compound (4.4 mg, yield 19%) was obtained from N-{2-[5-(chloromethyl)-1,3-thiazol-2-yl]-1H-indol-7-yl}-N-isopropylthiophene-2-sulfonamide (22 mg) and 2-mercaptoethanol (11 mg) in the same manner as in Example 282.

HPLC purity 100%.

MS m/z 494 (M+H$^+$).

Example 288

2-{[(2-{7-[(2-Ethoxyethyl) (2-thienylsulfonyl)amino]-1H-indol-2-yl}-1,3-thiazol-5-yl)methyl]thio}acetamide

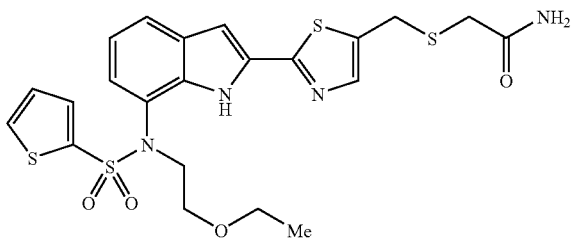 [SMILES: CCOCCN(c1cccc2cc(-c3ncc(CSCC(N)=O)s3)[nH]c12)S(=O)(=O)c1cccs1]

The title compound (1.2 mg, yield 6%) was obtained from N-{2-[5-(chloromethyl)-1,3-thiazol-2-yl]-1H-indol-7-yl}-N-(2-ethoxyethyl)thiophene-2-sulfonamide (18 mg) and 2-mercaptoacetamide (10 mg) in the same manner as in Example 282.

HPLC purity 100%.

MS m/z 537 (M+H$^+$).

Experimental Example

Determination of GK Activity Value

A solution (5 µL) of test compound in 50% dimethyl sulfoxide was added to each well of 384 well black plate (Nalge Nunc International K.K.). Then, a solution (35 µL) obtained by diluting GST-hLGK1 obtained in Reference Example 2A with measurement buffer (containing 50 mM HEPES (pH 7.4), 200 mM KCl, 5 mM MgCl$_2$, 2.5 mM DTT and 50 µM 2'-(or -3')-O—(N-methylanthraniloyl)adenosine 5'-triphosphate (Mant-ATP) (Jena Bioscience GmbH)) to 6 µg/mL was added to each well.

Each well was stood at 37° C. for 10 min, and 25 mM D-glucose solution (10 µL) was added to start the reaction.

Each well after the reaction was stood at 37° C. for 60 min, and the reaction was quenched by adding 25 µL of a quenching solution (containing 200 mM HEPES (pH 7.4), 20 mM MgCl$_2$, 200 mM EDTA, 0.03% Triton-X 100, 0.3% Coating 3 reagent (Caliper Life Sciences, Inc.)).

Mant-ATP (substrate) and Mant-ADP (reaction resultant product) were separated from each well after the reaction by a microchip type capillary electrophoresis apparatus 250 HTS (Caliper Life Sciences, Inc.). The reaction rate [(reaction resultant product peak height)/(reaction resultant product peak height+substrate peak height)×100(%)] was calculated from the ratio of the substrate peak height and reaction resultant product peak height obtained by fluorescence detection (excitation wavelength 355 nm, measurement wavelength 460 nm) and used as the index of GK activity.

As a control group, the reaction rate was calculated in the same manner as above except that "solution in 50% dimethyl sulfoxide" was used instead of "solution of test compound in 50% dimethyl sulfoxide".

The percentage obtained by dividing the reaction rate of the well added with the test compound (test compound addition group) by the reaction rate of the well added with 50% solution in dimethyl sulfoxide alone (control group) was taken as the GK activity value of the test compound, and the concentration of the test compound necessary for activating 50% of the maximum value of the activity value is shown as EC$_{50}$ value. The results are shown in Table 1.

TABLE 1

| test compound (Ex. No.) | EC$_{50}$ value (μM) |
| --- | --- |
| 3 | 0.11 |
| 5 | 1.2 |
| 7 | 0.24 |
| 8 | 1.5 |
| 11 | 1.4 |
| 17 | 4.8 |
| 23 | 2.7 |
| 26 | 1.7 |
| 52 | 2 |
| 65 | 0.39 |
| 86 | 0.027 |
| 97 | 0.077 |
| 104 | 0.034 |
| 137 | 0.048 |
| 146 | 0.180 |
| 151 | 0.080 |
| 165 | 0.028 |
| 169 | 0.022 |
| 182 | 0.029 |
| 209 | 0.510 |
| 261 | 0.019 |
| 280 | 0.035 |

Formulation Example 1

Production of Capsule

| | |
| --- | --- |
| 1) compound of Example 1 | 30 mg |
| 2) finely divided powder cellulose | 10 mg |
| 3) lactose | 19 mg |
| 4) magnesium stearate | 1 mg |
| total | 60 mg |

1), 2), 3) and 4) are mixed and filled in a gelatin capsule.

Formulation Example 2

Production of Tablet

| | |
| --- | --- |
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3), and 30 g of 4) are kneaded with water, vacuum dried and sized. The sized powder is mixed with 14 g of 4) and 1 g of 5), and the mixture is punched by a tabletting machine. In this way, 1000 tablets containing 30 mg of the compound of Example 1 per tablet are obtained.

INDUSTRIAL APPLICABILITY

The glucokinase activator of the present invention has a superior activity and is useful as a pharmaceutical agent such as an agent for the prophylaxis or treatment of diabetes, obesity and the like, and the like.

This application is based on patent application Nos. 2005-123018 and 2005-359656 filed in Japan, the contents of which are incorporated in full herein by this reference.

---

The invention claimed is:

1. A glucokinase activator comprising a compound represented by formula (I):

$$R^3-Y-W-\underset{H}{\underset{|}{A}}\begin{array}{c}R^1\\ \diagup\\ \diagdown\\ N\end{array}R^2\text{—}Z \quad (I)$$

wherein
ring A is an optionally substituted benzene ring,
W is O, S(O)$_m$ (m is 0, 1 or 2), CR$^5$R$^6$ (R$^5$ and R$^6$ are each independently a hydrogen atom or a C$_{1-6}$ alkyl group) or NR$^7$ (R$^7$ is a hydrogen atom or a C$_{1-6}$ alkyl group),
Y is a bond, CO, SO$_2$ or CR$^8$R$^9$ (R$^8$ and R$^9$ are each independently a hydrogen atom or a C$_{1-6}$ alkyl group),
R$^3$ is an optionally substituted heterocyclic group,
Z is a bond,
R$^1$ is a hydrogen atom, and
R$^2$ is 2-pyridyl, 1,3-thiazol-2-yl, or optionally substituted imidazol[4,5-b]pyrazine,
or a salt thereof.

2. A compound represented by the formula (II):

$$R^3-Ya-Wa-\underset{H}{\underset{|}{A'}}\begin{array}{c}R^1\\ \diagup\\ \diagdown\\ N\end{array}R^{2a} \quad (II)$$

wherein
ring A' is an optionally substituted benzene ring,
Wa is O, S(O)$_m$ (m is 0, 1 or 2) or NR$^7$ (R$^7$ is a hydrogen atom or R$^{3'}$-Y'— (R$^{3'}$ is an optionally substituted hydrocarbon group, an optionally substituted hydroxy group, an optionally substituted mercapto group, an optionally substituted amino group or an optionally substituted heterocyclic group, and Y' is a bond, CO, S(O)$_q$ (q is 0, 1 or 2) or CR$^{8'}$R$^{9'}$ (R$^{8'}$ and R$^{9'}$ are each independently a hydrogen atom or a C$_{1-6}$ alkyl group))), Ya is CO, S(O)$_{pa}$ (pa is 0, 1 or 2) or CR$^8$R$^9$ (R$^8$ and R$^9$ are each independently a hydrogen atom or a C$_{1-6}$ alkyl group),
R$^3$ is an optionally substituted heterocyclic group,
R$^1$ is a hydrogen atom, and
R$^{2a}$ is 2-pyridyl, 1,3-thiazol-2-yl, or optionally substituted imidazol[4,5-b]pyrazine,
or a salt thereof.

3. The compound of claim 2, wherein R$^7$ is a hydrogen atom or a C$_{1-6}$ alkyl group, and Ya is CO, SO$_2$ or CR$^8$R$^9$ (R$^8$ and R$^9$ are each independently a hydrogen atom or a C$_{1-6}$ alkyl group).

4. The compound of claim 2, wherein Wa is NR$^7$ (R$^7$ is a hydrogen atom or R$^{3'}$-Y'— (R$^{3'}$ is an optionally substituted hydrocarbon group, an optionally substituted hydroxy group, an optionally substituted mercapto group, an optionally substituted amino group or an optionally substituted heterocyclic group, and Y' is a bond, CO, S(O)$_q$ (q is 0, 1 or 2) or CR$^{8'}$R$^{9'}$ (R$^{8'}$ and R$^{9'}$ are each independently a hydrogen atom or a C$_{1-6}$ alkyl group))).

5. The compound of claim 2, wherein Ya is SO$_2$.

6. N-[4-Fluoro-2-(1,3-thiazol-2-yl)-1H-indol-7-yl]-N-methylthiophene-2-sulfonamide, or a salt thereof.

7. A pharmaceutical composition comprising the compound of claim 2 or a salt thereof, and a pharmacologically acceptable carrier.

8. A method of activating a glucokinase in a mammal, which comprises administering a compound represented by formula (I):

$$R^3-Y-W-\underset{H}{\underset{|}{A}}\begin{array}{c}R^1\\ \diagup\\ \diagdown\\ N\end{array}R^2\text{—}Z \quad (I)$$

wherein
ring A is an optionally substituted benzene ring,
W is O, S(O)$_m$ (m is 0, 1 or 2), CR$^5$R$^6$ (R$^5$ and R$^6$ are each independently a hydrogen atom or a C$_{1-6}$ alkyl group) or NR$^7$ (R$^7$ is a hydrogen atom or a C$_{1-6}$ alkyl group),
Y is a bond, CO, SO$_2$ or CR$^8$R$^9$ (R$^8$ and R$^9$ are each independently a hydrogen atom or a C$_{1-6}$ alkyl group),
R$^3$ is an optionally substituted heterocyclic group, Z is a bond,
R$^1$ is a hydrogen atom, and
R$^2$ is 2-pyridyl, 1,3-thiazol-2-yl, or optionally substituted imidazol[4,5-b]pyrazine,
or a salt thereof, to the mammal.

9. A method for the treatment of diabetes or obesity comprising administering an effective amount of the compound of claim 2 or a salt thereof to a patient in need thereof.

* * * * *